US011492400B2

(12) United States Patent
Jefferies et al.

(10) Patent No.: US 11,492,400 B2
(45) Date of Patent: Nov. 8, 2022

(54) ANTIBODIES TO L-TYPE VOLTAGE GATED CHANNELS AND RELATED METHODS

(71) Applicant: The University of British Columbia, Vancouver (CA)

(72) Inventors: Wilfred Arthur Jefferies, Surrey (CA); Kyung Bok Choi, Surrey (CA); Shawna Rose Stanwood, Burnaby (CA); Franz Fenninger, Vancouver (CA); Brett Alexander Eyford, Vancouver (CA); Lonna Munro, Vancouver (CA); Cheryl Gurine Pfeifer, Vancouver (CA); Reinhard Gabathuler, Quebec (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 16/751,951

(22) Filed: Jan. 24, 2020

(65) Prior Publication Data
US 2020/0385458 A1 Dec. 10, 2020

Related U.S. Application Data

(63) Continuation of application No. 15/549,912, filed as application No. PCT/US2016/018114 on Feb. 16, 2016, now abandoned.

(60) Provisional application No. 62/280,557, filed on Jan. 19, 2016, provisional application No. 62/115,823, filed on Feb. 13, 2015.

(51) Int. Cl.
*C07K 16/28* (2006.01)
*C07K 16/30* (2006.01)
*C07K 14/705* (2006.01)

(52) U.S. Cl.
CPC ............ *C07K 16/28* (2013.01); *C07K 14/705* (2013.01); *C07K 16/30* (2013.01); *C07K 2317/33* (2013.01); *C07K 2317/34* (2013.01); *C07K 2317/56* (2013.01); *C07K 2317/565* (2013.01); *C07K 2317/73* (2013.01); *C07K 2317/76* (2013.01)

(58) Field of Classification Search
None
See application file for complete search history.

(56) References Cited

U.S. PATENT DOCUMENTS

| | | |
|---|---|---|
| 2002/0165353 A1 | 11/2002 | Malouf et al. |
| 2005/0074850 A1 | 4/2005 | Nadler et al. |
| 2016/0194393 A1 | 7/2016 | Jefferies et al. |

FOREIGN PATENT DOCUMENTS

| | | |
|---|---|---|
| WO | 2002/063000 A2 | 8/2002 |
| WO | 2005/033139 A2 | 4/2005 |
| WO | 2005/060479 A2 | 7/2005 |
| WO | 2013/020235 A1 | 2/2013 |
| WO | 2013/130808 A1 | 9/2013 |
| WO | 2016/131058 A1 | 8/2016 |
| WO | 2017/004435 A1 | 1/2017 |

OTHER PUBLICATIONS

"Cystic fibrosis", www.nhlbi.nih.qov/health/health-topics/topics/cf/; accessed Feb. 3, 2017, 2 paqes.
"Rheumatoid Arthritis", www.ncbi.nlm.nih.gov/pubmedhealth/PMH0050554/#consra2.s6; Nov. 20, 2012, 11 paqes.
"Human Immunodeficiency Virus (HIV)", "cystic fibrosis", www.nhlbi.nih.gov/health/health-topics/topics/cf/; accessed Feb. 3, 2017, 3 pages.
Badou, A. et al, "Critical role for the beta regulatory subunits of Cav channels in T lymphocyte function," PNAS USA (2006); 103(42):15529-15534.
Burgess, D. L. et al., "Mutation of the Ca2+ Channel ? Subunit Gene Cchb4 Is Associated with Ataxia and Seizures in the Letharqic (Ih) Mouse," Cell, 88:385-392 (1997).
Caterall, et al., "Voltage-gated ion channels and gating modifier toxins." Toxicon (2007); 49(2): 124-141.
Davenport, Bennett, et al. "Signature channels of excitability no more: L-type channels in immune cells." Frontiers in Immunology (2015); 6:1-13.
Davies and Padlan, "Antibody-antigen complexes." Annu Rev Biochem. (1990); 59: 439-473.
Devereux, J., et al., "A comprehensive set of seguence analysis programs for the VAX." Nucleic Acids Research (1984); 12(1 Part 1): 387-395.
Elgert, K. Immunology: Understanding the immune system. New York: Wiley-Liss, 1996, p. 323, 3 paqes.
Fenninger et al. "P.A.02.02: Receptor editing leading to B lymphocyte tolerance is governed by the L-type calcium channel Cav1.4," Abstracts of the 4th European Congress of Immunology, Sep. 7, 2015 (Sep. 7, 2015), p. 47. Retrieved from the Internet: <www.eci-vienna2015.org/images/docs/ECI2015_Abstract-Book-v2.pdf> on Sep. 13, 2016 (Sep. 13, 2016). entire document.
Goodwin, Leslie 0., et al. "Alternative splicing of exons in the alpha1 subunit of the rat testis L-type voltage-dependent calcium channel generates germ line-specific dihydropyridine binding sites." Molecular Human Reproduction (1998); 4.3: 215-226.
Grafton, G. et al., "A non-voltage-gated calcium channel with L-type characteristics activated by B cell receptor liqation," Biochem. Pharmacol., 66:2001-2009 (2003).
Grafton, G. et al., "Calcium channels in lymphocytes," Immunoloqy, 104(2): 119-126 (2001).

(Continued)

*Primary Examiner* — Christine J Saoud
*Assistant Examiner* — Jon M Lockard
(74) *Attorney, Agent, or Firm* — Snell & Wilmer L.L.P.

(57) ABSTRACT

Provided are antibodies, and antigen-binding fragments thereof, which specifically bind to an extracellular poor loop of an alpha 1a subunit of L-type voltage gated calcium channel, and related compositions, kits, and methods of use thereof, for instance, administration to a subject in need thereof to modify an immune response, for example, in the treatment of cancer.

1 Claim, 17 Drawing Sheets
Specification includes a Sequence Listing.

(56) References Cited

OTHER PUBLICATIONS

Healy, et al., "Different Nuclear Signals Are Activated by the B Cell Receptor during Positive Versus Negative Signaling." Immunity (1997); 6(4): 419-428.
Heng et al., "The Immunological Genome Project: networks of gene expression in immune cells." Nat Immunol (2008); 9: 1091-1094.
Hoek, Kristen L., et al. "Transitional B cell fate is associated with developmental stage-specific regulation of diacylglycerol and calcium signaling upon B cell receptor engagement." The Journal of Immunology (2006); 177.8: 5405-5413.
International Preliminary Report on Patentability for International Application No. PCT/CA2012/050542, dated Feb. 11, 2014, 9 pages.
International Search Report and Written Opinion for International Application No. PCT/CA2012/050542, dated Dec. 3, 2012, 13 pages.
International Search Report and Written Opinion for International Application No. PCT/US2016/018114, dated May 17, 2016, 10 paqes.
International Search Report and Written Opinion for International Application No. PCT/US2016/040517, dated Oct. 11, 2016, 9 pages.
International Preliminary Report on Patentability for International Application No. PCT/US2016/018114, dated Aug. 15, 2017, 6 pages.
Jha, M. K. et al., "Defective survival of naiive CD8(+) T lymphocytes in the absence of the beta3 regulatory subunit of voltage-gated calcium channels," Nature Immunology, 10( 12): 1275-1282 (2009).
Kotturi, M. F. et al, "Identification and Functional Characterization of Voltage-dependent Calcium Channels in T Lymphocytes," J Biol Chem., 278(47):46949-46960 (2003).
Kotturi, M. F. et al, "Roles of CRAC and CaV-like channels in T cells: more than one gatekeeper?," Trends Pharmacol Sci., 27(7):360-367 (2006).
Kotturi, M. F. et al., "Molecular characterization of L-type calcium channel splice variants expressed in human T lymphocytes," Molecular Immunology, 42(12):1461-1474 (2005).
Lipscombe, D. et al., "L-type calcium channels: the low down," J. Neurophysiol. 92(5):2633-2641 (2004).
McRory, J.E. et al., "The CACNA1 F gene encodes an L-type calcium channel with unigue biophysical properties and tissue distribution," J. Neuroscience, 24(7): 1707-1718 (2004).
Mansergh, et al. "Mutation of the calcium channel gene Cacna1f disrupts calcium signaling, synaptic transmission and cellular organization in mouse retina." Human Mol Genet (2005); 14(20): 3035-3046.
Matsumoto, Masanori, et al. "The calcium sensors STIM1 and STIM2 control B cell regulatory function throuqh interleukin-10 production." Immunity (2011 ); 34.5: 703-714.
Oh-Hora, M., "Calcium signaling in the development and function of T-lineage cells," Immunol. Rev., 231(1):210-224 (2009).
Omilusik, K. et al., "The Cav1 .4 calcium channel is a critical regulator of T cell receptor signaling and naive T cell homeostasis," Immunity, 35(3):349-360 (2011).
Omilusik, K.D., et al., "Weft, warp, and weave: the intricate tapestry of calcium channels regulatingT lymphocyte function." Frontiers in Immunology (2013); 4: 164, 12 pages.
Park, C. Y. et al., "The CRAC channel activator STIM1 binds and inhibits L-type voltage-gated calcium channels," Science, 330:101-105 (2010).
Priatel, J. J. et al., "RasGRP1 transduces low-grade TCR signals which are critical for T cell development, homeostasis, and differentiation," Immunity, 17(5):617-627 (2002).
Priatel, J. J. et al., "RasGRPI transmits prodifferentiation TCR signaling that is crucial for CD4 T cell development," The Journal of Immunoloqy 177:1470-1480 (2006).
Priatel, J. Jet al., "Chronic immunodeficiency in mice lacking RasGRP1 results in CD4 T cell immune activation and exhaustion," The Journal of Immunology, 179(4):2143-2152 (2007).
Revy, P. et al., "Functional antigen-independent synapses formed between T cells and dendritic cells," Nat. Immunol., 2(10):925-931 (2001).
Stokes, L. et al., "Non-voltage-gated L-type Ca2+ channels in human T cells: pharmacology and molecular characterization of the major alpha pore-forming and auxiliary beta-subunits," J. Biol. Chem., 279(19): 19566-19573 (2004).
Supplementary European Search Report for European Application No. 12821707.2, dated Feb. 3, 2015, 10 pages.
Suzuki, Y. et al., "L-type Ca2+ channels: A new player in the regulation of Ca2+ signaling, cell activation and cell survival in immune cells," Mol. Immunol., 47:640-648 (2010).
Tyson, J. R. et al., "Molecular nature of voltage-gated calcium channels: Structure and species comparison," WIREs Membr. Transp. Siqnal, 2(5):181-206 (2013).
Wang, Y. et al., "The calcium store sensor, STIMI, reciprocally controls Orai and CaV1 .2 channels," Science, 330: 105-109 (2010).
Wyatt, C. N. et al., "Voltage-dependent binding and calcium channel current inhibition by an anti-a1 D subunit antibody in rat dorsal root ganglion neurons and guinea-pig myocytes," J. Physiol., 502(Pt. 2):307-319 (1997).
Zhang, Zhao, et al. "Functional roles of Cav1. 3 (a1 D) calcium channels in atria insights gained from qene-tarqeted null mutant mice." Circulation (2005); 112.13: 1936-1944.
MacCallum et al. "Antibody-antigen interactions: contact analysis and binding site topography," (1996). J. Mol. Biol. 262:732-745.
De Pascalis et al. ""Abbreviated" Complementarity-Determining Regions Containing Specificity-Determining Residues Essential for Ligand Contact to Engineer a Less Immunogenic Humanized Monoclonal Antibody" (2002). Journal of Immunology. 169:3076-3084.
Gasset et al. (2003). Biochemical and Biophysical Reseaerch Communications. 307: 198-205.
Chen, et al. "Selection and analysis of an optimized anti-VEGF antibody: crystal structure of an affinity-matured Fab in complex with antigen." Journal of Molecular Biology, 1999. 293:865-881.
Wu, et al. "Humanization of a murine monoclonal antibody by simultaneous optimization of framework and CDR residues," Journal of Molecular Biology, 1999. 294:151-162.
Rudikoff et al. "Single amino acid substitution altering antigen-binding specificity," Proceedings of the National Academy of Sciences Mar. 1982, 79 (6) 1979-1983.
USPTO; Non-Final Office Action dated Jul. 29, 2019 in U.S. Appl. No. 15/549,912.
Nakai et al. "Critical roles of the S3 segment and S3-S4 linker of repeat I in activation of L-type calcium channels." Proceedings of the National Academy of Sciences Feb. 1994, 91 (3) 1014-1018.
Adachi-Akahane. "Molecular and pharmacological bases for the gating regulation of I-type voltage-dependent Ca2+ channels." Folia Pharm. Jpn. vol. 123, Issue 3, pp. 197-209 (2004).
Adachi-Akahane, "Molecular and pharmacological bases for the gating regulation of L-type voltage-dependent Ca2+ channels", Folia Pharmacol. Japan, vol. 123, p. 197-209 (2004).
Nakai et al., "Critical roles of the S3 segment and S3-S4 linker of repeat I in activation of L-type calcium channels", Proc. Natl. Acad. Sci. USA, vol. 91, p. 1014-1018 (1994).

| Name | Peptide | Number of mice | Number of lymphocytes harvested | Number of lymphocytes fused | Number of lymphocytes frozen in LN2 |
|---|---|---|---|---|---|
| Cav1.1 | PMQELRHREWVH | 2 | 6.6 x 10E7 | 0.5 x 10E8 | 1.6 x 10E7 |
| Cav1.2 | ATKADGANALGGKGA | 2 | 5.9 x 10E7 | 0.5 x 10E8 | 0.9 x 10E7 |
| Cav1.3 | LTKETEGGNHSSGKSG | 2 | 9.15 x 10E7 | 0.5 x 10E8 | 4.6 x 10E7 |
| Cav1.4 | GPGRPGDAPHTG | 2 | 1 x 10E8 | 0.5 x 10E8 | 5.0 x 10E7 |
| | | Total lymphocytes fused: | 2 x 10E8 | | |
| | | % of fusion: | 200% | | |
| | | % of fused cells plated out: | 100% | | |
| | | % of fused cells frozen in LN2: | 100% | | |

Figure 2

|          | 1A3 | 1B9 | 1B10 | 1B11 | 1C8 | 1C10 | 1D2 | 1E7 | 1F4 | 1F7 | 2B3 | 2D4 |
|----------|-----|-----|------|------|-----|------|-----|-----|-----|-----|-----|-----|
| All Cav1s | +  | +   |      | +    | +   | +    | +   | +   | +   | +   | +   |     |
| Cav1.1   |     |     |      |      |     |      |     | +   | +   |     |     |     |
| Cav1.2   | +   | +   |      |      | +   |      | +   |     |     | +   |     |     |
| Cav1.3   |     | +   | +    | +    | +   |      | +   |     |     |     |     | +   |
| Cav1.4   | +   |     |      |      |     | +    | +   |     |     |     | +   |     |

Figure 3

| Specificity | #thymus | #spleen | Total Hybridomas |
|---|---|---|---|
| $Ca_V1.1$ | 2 | 3 | 3 |
| $Ca_V1.2$ | 9 | 5 | 11 |
| $Ca_V1.3$ | 9 | 15 | 18 |
| $Ca_V1.4$ | 2 | 2 | 4 |

Figure 8

| Target | Gene Symbol | % identity w mouse | Unigene http://www.ncbi.nlm.nih.gov/unigene | biogps.org http://biogps.org/#goto=welcome | Protein Atlas http://www.proteinatlas.org | Zenbu http://fantom.gsc.riken.jp/zenbu/ | cbioportal.org http://www.cbioportal.org | EMBL EBI expression atlas http://www.ebi.ac.uk/gxa/home;jsessionid=542F83A698303FBB | Broad Institute cancer cell lines http://www.broadinstitute.org/ccle/home |
|---|---|---|---|---|---|---|---|---|---|
| Cav1.1 | CACNA1S | 92.50% | 31 cDNA sequences, muscle, larynx, thyroid, prostate; adult; some leukemia | skeletal muscle is highest expression (by far) | skeletal muscle (RNA and protein) | bronchial epithelial cell; smooth muscle cell; other epithelial | mutations and amplifications in many solid tumors,... | skeletal muscle | Burkett lymphoma, medulloblastoma, endometrium. High expression in NCI-H2342 lung carcinoma |
| Cav1.2 | CACNA1C | 98.10% | 181 sequences; more widely expressed in development, cancer; spleen, thymus, mammary gland, uterus, etc. | widely expressed blood, brain... | both protein and RNA in many tissues, smooth muscle..etc. | GM progenitor, heart, smooth muscle..etc. | Often amplified and mutations in many tumors... | brain, colon, heart, smooth muscle, uterus | chondrosarcoma, lymphoma, leukemia, neuroblastoma. High expression in SUP-HD1, Hodgkin lymphoma |
| Cav1.3 | CACNA1D | 97.90% | 105 sequences, more widely expressed, bone, brain, lung, intestine, pituitary, etc, colorectal and prostate cancer etc but mostly adult | some expression in many tissues, most in pancreas, pituitary | some RNA in many tissues, highest adrenal; protein in many tissues, highest in adrenal, kidney, testis | good expression in many cells and cell lines, including bronchial epithelial, GM progenitor, heart... | Abundant mutations (25%) in DESM, others | intestine, lung, adrenal, lung, pituitary | lung small cell, breast.. High expression in ZR-75-30 breast carcinoma |
| Cav1.4 | CACNA1F | 92.30% | 30 sequences, Selectively expressed in eye (different transcript), lung, muscle, thymus, all adult, no embryonic or juvenile expression. | Some pineal gland expression. | Very small amount in lung and small intestine, no antibodies to look at protein level. | Leukocyte cell lines. | Expressed in many cancers and abundant mutated. | Retina and pineal gland; also some in intestine, spleen, lung, lymph node | leukemia, lymphoma, meningioma...High expression in NCI-H524 lung carcinoma |

Figure 10

ANTIBODIES TO L-TYPE VOLTAGE GATED CHANNELS AND RELATED METHODS

CROSS-REFERENCE TO RELATED APPLICATIONS

This application is a continuation of U.S. application Ser. No. 15/549,912, filed on Aug. 9, 2017, now abandoned, which is a national stage entry of PCT/US2016/018114, filed on Feb. 16, 2016, which claims priority under 35 U.S.C. § 119(e) to U.S. application Ser. No. 62/115,823, filed Feb. 13, 2015; and U.S. application Ser. No. 62/280,557, filed Jan. 19, 2016; each of which is incorporated by reference in its entirety.

STATEMENT REGARDING THE SEQUENCE LISTING

The Sequence Listing associated with this application is provided in text format in lieu of a paper copy, and is hereby incorporated by reference into the specification. The name of the text file containing the Sequence Listing is BIMN_005_02WO_ST25.txt. The text file is about 177,000 bytes, was created on Feb. 16, 2016, and is being submitted electronically via EFS-Web.

BACKGROUND

Technical Field

Embodiments of the present invention include antibodies, and antigen-binding fragments thereof, which specifically bind to one or more of the L-type voltage calcium channels Cav1.4, Cav1.3, Cav1.2, and Cav1.1, and related compositions and methods of use thereof.

Description of the Related Art

Immune cells, including T and B lymphocytes, are key mediators of immune responses against pathogens. Elevation of intracellular calcium ion ($Ca^{2+}$) levels is a vital event that regulates cell activation, proliferation, differentiation, and cell death in immune cells. Dysregulated Calcium responses in immune cells have been associated with several immunodeficiency and autoimmune diseases, such as X-linked agammaglobulinemia and systemic lupus erythematosus. While calcium signaling is known to play a role in immune function, the means by which calcium signals are generated in immune cells are not fully characterized. One mechanism of calcium entry into immune cells is through calcium release activated calcium (CRAC) channels. Other candidate plasma membrane calcium channels operating in immune cells include P2X receptors, transient receptor potential (TRP) channels, and voltage-gated calcium channels.

The voltage-gated calcium channels are multi-subunit proteins composed of a pore forming alpha 1 subunit and as well as at least an alpha 2 subunit, delta subunit, and beta subunit, and optionally, a gamma subunit. At least four subtypes of L-type voltage-gated calcium channels (also known as Cav1 channels or Cav1s) have been described: Cav1.1, Cav1.2, Cav1.3, and Cav1.4. These subtypes are categorized by the alpha 1 subunits they contain. These channels open in response to depolarization in the plasma membrane and thereby mediate $Ca^{2+}$ influx into excitable cells, such as neurons, muscle, and endocrine cells. Voltage gated calcium channels are also present in many cells not traditionally considered excitable, including various hematopoietic cells. Notably, expression of L-type voltage gated calcium channels has been observed in mouse and human lymphocytes (Kotturi et al., J. Biol. Chem. 278:46949-46960 (2003); Kotturi and Jefferies, Mol. Immunol. 42:1461-1474 (2005)).

Dysregulation of calcium signaling in immune cells contributes to inflammatory and autoimmune diseases. What are needed in the art are new agents that can bind and modify activity of targets in immune cells that regulate calcium signaling. While inhibitors to L-type voltage-gated calcium channels are presently available, these inhibitors are broadly targeted and produce undesirable side effects. The present invention addresses these needs by providing antibodies and antigen-binding fragments thereof that specifically target L-type voltage-gated calcium channels subtypes.

BRIEF DESCRIPTION OF THE FIGURES

FIG. 2 shows a table summarizing the results of hybridoma generation.

FIG. 3 shows a table displaying representative results of Eliza experiments performed with antibodies. Monoclonal antibodies produced by hybridomas were tested for binding to peptides with amino acid sequences taken from extracellular loops of L-type voltage-gated calcium channels. Wells were coated with BSA and peptides from all subtypes (All Cav1s), or with peptides from Cav1.1, Cav1.2, Cav1.3, or Cav1.4.

FIG. 8 shows a table summarizing characteristics of monoclonal antibodies produced by 31 selected clones with respect to channel specificity and their ability to bind to thymocytes and/or splenocytes.

FIG. 10 illustrates the mutations in CaV1 channels that can be found in cancer.

BRIEF SUMMARY OF THE INVENTION

Figure 1:
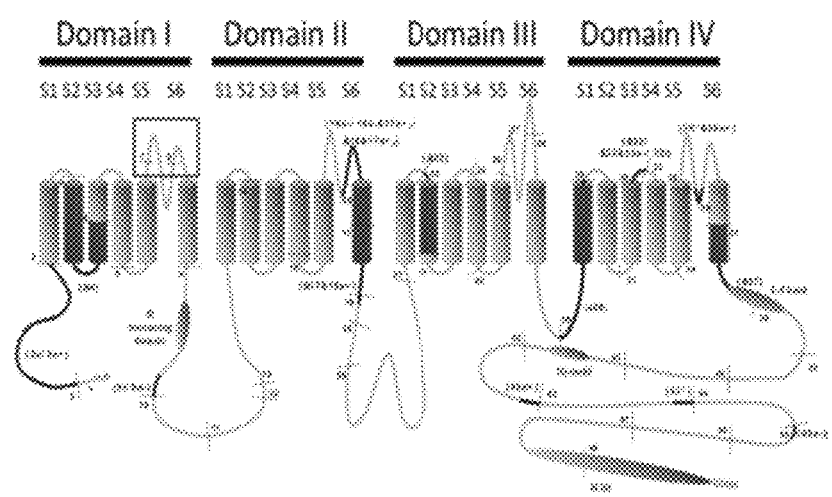
FIG. 1 shows a schematic of an alpha 1 subunit polypeptide of an L-type voltage-gated calcium channel. Transmembrane domains are represented by cylinders. Cytosolic domains are depicted below the transmembrane domains and extracellular domains are depicted above the transmembrane domains. The N-terminal is depicted at the bottom left and the C-terminal is depicted at the bottom right of the figure. Lines bisecting the polypeptide represent the borders of regions encoded by different exons of the messenger RNA. The Box indicates the extracellular domain of a pore loop between transmembrane segments S5 and S6 of domain I of the alpha 1 subunit.

Embodiments of the present disclosure include isolated antibodies, or antigen-binding fragments thereof, which specifically bind to an alpha 1 subunit of an L-type voltage-gated calcium channel, wherein the antibodies or antigen binding fragments thereof, (a) specifically bind to an amino acid sequence of an extracellular domain of a pore loop between transmembrane segments S5 and S6 of motif I of the alpha 1 subunit, or (b) competitively inhibits the binding of (a) to the alpha 1 subunit.

In certain embodiments, the L-type voltage-gated calcium channel is from human or mouse. In certain embodiments, the binding of the antibody or antigen binding fragment thereof to the alpha 1 subunit alters activity of the L-type voltage-gated calcium channel.

In certain embodiments, the L-type voltage-gated calcium channel is Cav1.4. In some embodiments, the amino acid sequence of the extracellular domain is GPGRPGDAPHTG [SEQ ID NO: 1], or is at least 90% identical to GPGRPGDAPHTG [SEQ ID NO: 1].

In certain embodiments, the L-type voltage-gated calcium channel is Cav1.3. In particular embodiments, the amino acid sequence of the extracellular domain is LTKETEGGNHSSGKSG [SEQ ID NO 2] or is at least 90% identical to LTKETEGGNHSSGKSG [SEQ ID NO 2].

In some embodiments, the L-type voltage-gated calcium channel is Cav1.2. In certain embodiments, the amino acid sequence of the extracellular domain is ATKADGANALGGKGA [SEQ ID NO: 3] at least 90% identical to ATKADGANALGGKGA [SEQ ID NO: 3].

In certain embodiments, the L-type voltage-gated calcium channel is Cav1.1. In certain embodiments, the amino acid sequence of the extracellular domain is PMQIELRHREWVH [SEQ ID NO 4] or is at least 90% identical to PMQIELRHREWVH [SEQ ID NO 4].

In some embodiments, the antibody or antigen-binding fragment binds to any of Cav1.4, Cav1.3, Cav1.2, or Cav1.1. In certain embodiments, the antibody or antigen-binding fragment thereof binds to any three of Cav1.4, Cav1.3, Cav1.2, or Cav1.1. In certain embodiments, the antibody or antigen-binding fragment thereof binds to any of Cav1.4, Cav1.3, or Cav1.2. In some embodiments, the antibody or antigen-binding fragment thereof binds to any of Cav1.4, Cav1.3, or Cav1.1. In certain embodiments, the antibody or antigen-binding fragment thereof binds to any of Cav1.4, Cav1.2, or Cav1.1. In certain embodiments, the antibody or antigen-binding fragment thereof binds to any of Cav1.3, Cav1.2, or Cav1.1. In certain embodiments, the antibody or antigen-binding fragment thereof binds to any two of Cav1.4, Cav1.3, Cav1.2, or Cav1.1. In certain embodiments, the antibody or antigen-binding fragment thereof binds Cav1.4 or Cav1.3. In certain embodiments, the antibody or antigen-binding fragment thereof binds Cav1.4 or Cav1.2. In some embodiments, the antibody or antigen-binding fragment thereof binds Cav1.4 or Cav1.1. In some embodiments, the antibody or antigen-binding fragment thereof binds Cav1.3 or Cav1.2. In particular embodiments, the antibody or antigen-binding fragment thereof binds Cav1.3 or Cav1.1. In specific embodiments, the antibody or antigen-binding fragment thereof binds Cav1.2 or Cav1.1. In certain embodiments, the antibody or antigen-binding fragment thereof binds only Cav1.4, that is, it does not significantly bind to Cav1.1, Cav1.2, or Cav1.3. In certain embodiments, the antibody or antigen-binding fragment thereof binds only Cav1.3, that is, it does not significantly bind to Cav1.1, Cav1.2, or Cav1.4. In certain embodiments, the antibody or antigen-binding fragment thereof binds only Cav1.2, that is, it does not significantly bind to Cav1.1, Cav1.3, or Cav1.4. In certain embodiments, the antibody or antigen-binding fragment thereof binds only Cav1.1, that is, it does not significantly bind to Cav1.2, Cav1.3, or Cav1.4.

In some embodiments, the isolated antibody, or antigen-binding fragment thereof, comprises a heavy chain variable region ($V_H$) that comprises $V_H$CDR1, $V_H$CDR2 and $V_H$CDR3 amino acid sequences; and/or a light chain variable region ($L_H$) that comprises $V_L$CDR1, $V_L$CDR2 and $V_L$CDR3 amino acid sequences, which are selected from:

(A) (i) $V_H$CDR1, $V_H$CDR2 and $V_H$CDR3 comprise, respectively, the amino acid sequences of SEQ ID NOS:14-16; and (ii) $V_L$CDR1, $V_L$CDR2 and $V_L$CDR3 comprise, respectively, the amino acid sequences of (i) SEQ ID NOS: 18-20; including variants thereof where at least one of said $V_H$CDR or $V_L$CDR amino acid sequences is modified by about 1, 2, or 3 amino acid substitutions, additions, or deletions;

(B) (i) $V_H$CDR1, $V_H$CDR2 and $V_H$CDR3 comprise, respectively, the amino acid sequences of SEQ ID NOS:22-24; and (ii) $V_L$CDR1, $V_L$CDR2 and $V_L$CDR3 comprise, respectively, the amino acid sequences of (i) SEQ ID NOS: 26-28; including variants thereof where at least one of said $V_H$CDR or $V_L$CDR amino acid sequences is modified by about 1, 2, or 3 amino acid substitutions, additions, or deletions;

(C) (i) $V_H$CDR1, $V_H$CDR2 and $V_H$CDR3 comprise, respectively, the amino acid sequences of SEQ ID NOS:30-32; and (ii) $V_L$CDR1, $V_L$CDR2 and $V_L$CDR3 comprise, respectively, the amino acid sequences of (i) SEQ ID NOS: 34-36; including variants thereof where at least one of said $V_H$CDR or $V_L$CDR amino acid sequences is modified by about 1, 2, or 3 amino acid substitutions, additions, or deletions;

(D) (i) $V_H$CDR1 and $V_H$CDR2 comprise, respectively, the amino acid sequences of SEQ ID NOS:38-39; and (ii) $V_L$CDR1, $V_L$CDR2 and $V_L$CDR3 comprise, respectively, the amino acid sequences of (i) SEQ ID NOS:42-44; including variants thereof where at least one of said $V_H$CDR or $V_L$CDR amino acid sequences is modified by about 1, 2, or 3 amino acid substitutions, additions, or deletions;

(E) (i) $V_H$CDR1, $V_H$CDR2 and $V_H$CDR3 comprise, respectively, the amino acid sequences of SEQ ID NOS:46-48; and (ii) $V_L$CDR1, $V_L$CDR2 and $V_L$CDR3 comprise, respectively, the amino acid sequences of (i) SEQ ID NOS:

50-52; including variants thereof where at least one of said $V_H$CDR or $V_L$CDR amino acid sequences is modified by about 1, 2, or 3 amino acid substitutions, additions, or deletions;

(F) (i) $V_H$CDR1 and $V_H$CDR2 comprise, respectively, the amino acid sequences of SEQ ID NOS:54-55; and (ii) $V_L$CDR1, $V_L$CDR2 and $V_L$CDR3 comprise, respectively, the amino acid sequences of (i) SEQ ID NOS:58-60; including variants thereof where at least one of said $V_H$CDR or $V_L$CDR amino acid sequences is modified by about 1, 2, or 3 amino acid substitutions, additions, or deletions;

(G) (i) $V_H$CDR1, $V_H$CDR2 and $V_H$CDR3 comprise, respectively, the amino acid sequences of SEQ ID NOS:62-64; including variants thereof where at least one of said $V_H$CDR or $V_L$CDR amino acid sequences is modified by about 1, 2, or 3 amino acid substitutions, additions, or deletions;

(H) (i) $V_H$CDR1, $V_H$CDR2 and $V_H$CDR3 comprise, respectively, the amino acid sequences of SEQ ID NOS:70-72; and (ii) $V_L$CDR1, $V_L$CDR2 and $V_L$CDR3 comprise, respectively, the amino acid sequences of (i) SEQ ID NOS: 74-76; including variants thereof where at least one of said $V_H$CDR or $V_L$CDR amino acid sequences is modified by about 1, 2, or 3 amino acid substitutions, additions, or deletions;

(I) (i) $V_H$CDR1, $V_H$CDR2 and $V_H$CDR3 comprise, respectively, the amino acid sequences of SEQ ID NOS:78-80; and (ii) $V_L$CDR1, $V_L$CDR2 and $V_L$CDR3 comprise, respectively, the amino acid sequences of (i) SEQ ID NOS: 82-84; including variants thereof where at least one of said $V_H$CDR or $V_L$CDR amino acid sequences is modified by about 1, 2, or 3 amino acid substitutions, additions, or deletions;

(J) (i) $V_H$CDR1, $V_H$CDR2 and $V_H$CDR3 comprise, respectively, the amino acid sequences of SEQ ID NOS:86-88; and (ii) $V_L$CDR1, $V_L$CDR2 and $V_L$CDR3 comprise, respectively, the amino acid sequences of (i) SEQ ID NOS: 90-92; including variants thereof where at least one of said $V_H$CDR or $V_L$CDR amino acid sequences is modified by about 1, 2, or 3 amino acid substitutions, additions, or deletions;

(K) (i) $V_L$CDR1, $V_L$CDR2 and $V_L$CDR3 comprise, respectively, the amino acid sequences of (i) SEQ ID NOS: 98-100; including variants thereof where at least one of said $V_H$CDR or $V_L$CDR amino acid sequences is modified by about 1, 2, or 3 amino acid substitutions, additions, or deletions; and (L) (i) $V_L$CDR1, $V_L$CDR2 and $V_L$CDR3 comprise, respectively, the amino acid sequences of (i) SEQ ID NOS: 106-108; including variants thereof where at least one of said $V_H$CDR or $V_L$CDR amino acid sequences is modified by about 1, 2, or 3 amino acid substitutions, additions, or deletions.

In certain embodiments, the antibody, or antigen-binding fragment thereof, comprises a $V_H$ sequence that is at least 90% identical to SEQ ID NO:13, 21, 29, 37, 45, 53, 61, 69, 77, or 85.

In certain embodiments, antibody, or antigen-binding fragment thereof, comprises a $V_L$ sequence that is at least 90% identical to SEQ ID NO:17, 25, 33, 41, 49, 57, 73, 81, 89, 97, or 105.

In some embodiments, the antibody, or antigen-binding fragment thereof, comprises a $V_H$ sequence that is at least 90% identical to SEQ ID NO: 13, 21, 29, 37, 45, 53, 61, 69, 77, or 85, and a $V_L$ sequence that is at least 90% identical to SEQ ID NO: 17, 25, 33, 41, 49, 57, 73, 81, 89, 97, or 105.

In particular embodiments, the antibody, or antigen-binding fragment thereof, comprises a $V_H$ sequence and a $V_L$ sequence selected from:

(A) the $V_H$ sequence of SEQ ID NO:13 and the $V_L$ sequence of SEQ ID NO:17;

(B) the $V_H$ sequence of SEQ ID NO:21 and the $V_L$ sequence of SEQ ID NO:25;

(C) the $V_H$ sequence of SEQ ID NO:29 and the $V_L$ sequence of SEQ ID NO:33;

(D) the $V_H$ sequence of SEQ ID NO:37 and the $V_L$ sequence of SEQ ID NO:41;

(E) the $V_H$ sequence of SEQ ID NO:45 and the $V_L$ sequence of SEQ ID NO:49;

(F) the $V_H$ sequence of SEQ ID NO:53 and the $V_L$ sequence of SEQ ID NO:57;

(G) the $V_H$ sequence of SEQ ID NO:69 and the $V_L$ sequence of SEQ ID NO:73;

(H) the $V_H$ sequence of SEQ ID NO:77 and the $V_L$ sequence of SEQ ID NO:81;

(I) the $V_H$ sequence of SEQ ID NO:85 and the $V_L$ sequence of SEQ ID NO:89; and (J) a variant $V_H$ sequence and a variant $V_L$ sequence that is at least 90% identical to any of (A)-(I).

Also included are polynucleotides that encode the antibodies, or antigen-binding fragments thereof, described herein, vectors that comprise such polynucleotides, and host cells that comprise and optionally express the polynucleotides and/or vectors.

Also included are methods for modulating a function of a cell expressing an L-type voltage-gated calcium channel comprising contacting the cell with an antibody, or antigen-binding fragment thereof, which specifically binds to (a) an amino acid sequence of an extracellular domain of a pore loop between transmembrane segments S5 and S6 of domain 1 of an alpha 1 subunit of the L-type voltage-gated calcium channel, or (b) competitively inhibits the binding of (a) to the alpha 1 subunit, wherein binding of the agent to the alpha I subunit modulates the activity of the L-type voltage-gated calcium channel.

In certain embodiments, the antibody or binding fragment thereof is an antibody or binding fragment described herein. In certain embodiments, the cell is a hematopoietic cell. In certain embodiments, the antibody or antigen binding-fragment thereof inhibits the activity of the L-type voltage-gated calcium channel. In certain embodiments, the antibody or antigen binding-fragment thereof increases the activity of the L-type voltage-gated calcium channel. In certain embodiments, the cell is a hematopoietic cell of the lymphoid lineage.

In certain embodiments, the cell is a T cell. In certain embodiments, the function of the cell comprises T cell maturation. In certain embodiments, the function of the cell comprises antigen binding.

In certain embodiments, the cell is a B cell. In certain embodiments, the function of the cell comprises B cell maturation. In certain embodiments, the function of the cell comprises B cell receptor-induced activation.

In certain embodiments, the L-type voltage-gated calcium channel is Cav1.4. In certain embodiments, the L-type voltage-gated calcium channel is Cav1.3. In certain embodiments, the L-type voltage-gated calcium channel is Cav1.2. In certain embodiments, the L-type voltage-gated calcium channel is Cav1.1.

Some embodiments relate to methods of modulating an immune response in a subject comprising administering to the subject an effective amount of an antibody, or antigen-binding fragment thereof, which specifically binds to (a) an amino acid sequence of an extracellular domain of a pore loop between transmembrane segments S5 and S6 of domain 1 of an alpha 1 subunit of the L-type voltage-gated calcium channel, or (b) competitively inhibits the binding of (a) to the alpha 1 subunit, wherein the L-type voltage-gated calcium channel is expressed in a hematopoietic cell.

In certain embodiments, the antibody or binding fragment thereof is an antibody or binding fragment thereof described herein. In certain embodiments, the hematopoietic cell is of the lymphoid lineage. In certain embodiments, the hematopoietic cell is a T cell or a B cell.

In certain embodiments, the L-type voltage-gated calcium channel is Cav1.4. In certain embodiments, the L-type voltage-gated calcium channel is Cav1.3. In certain embodiments, the L-type voltage-gated calcium channel is Cav1.2. In certain embodiments, the L-type voltage-gated calcium channel is Cav1.1.

Also included are methods of inhibiting an immune response in a subject comprising administering to the subject an effective amount of an antibody, or antigen-binding fragment thereof, which specifically binds to (a) an amino acid sequence of an extracellular domain of a pore loop between transmembrane segments S5 and S6 of domain 1 of an alpha 1 subunit of the L-type voltage-gated calcium channel, or (b) competitively inhibits the binding of (a) to the alpha 1 subunit, wherein the L-type voltage-gated calcium channel is expressed in a hematopoietic cell.

In certain embodiments, the antibody or binding fragment thereof is an antibody or binding fragment thereof described herein. In certain embodiments, the hematopoietic cell is of the lymphoid lineage. In certain embodiments, the hematopoietic cell is a T cell. In certain embodiments, administering the effective amount of the antibody or antigen-binding fragment thereof decreases T cell receptor-induced Ca2+ fluxes. In certain embodiments, administering the effective amount of the antibody or antigen-binding fragment thereof reduces naive T cell survival.

In certain embodiments, administering the effective amount of the antibody or antigen-binding fragment reduces CD3/CD28 induced T cell proliferation. In certain embodiments, the hematopoietic cell is a B cell.

In certain embodiments, administering the effective amount of the antibody or antigen-binding fragment inhibits B cell receptor-induced activation.

In certain embodiments, the L-type voltage-gated calcium channel is Cav1.4. In certain embodiments, the L-type voltage-gated calcium channel is Cav1.3. In certain embodiments, the L-type voltage-gated calcium channel is Cav1.2. In certain embodiments, the L-type voltage-gated calcium channel is Cav1.1.

Also included are methods of treating a disease in a subject comprising administering to the subject an effective amount of an antibody, or antigen-binding fragment thereof, which specifically binds to (a) an amino acid sequence of an extracellular domain of a pore loop between transmembrane segments S5 and S6 of domain 1 of an alpha 1 subunit of the L-type voltage-gated calcium channel, or (b) competitively inhibits the binding of (a) to the alpha 1 subunit.

In certain embodiments, the antibody or binding fragment thereof is an antibody or binding fragment thereof described herein.

In some embodiments, the disease is an inflammatory disease. In particular embodiments, the inflammatory disease is X-linked agammaglobulinemia, systemic lupus erythematosus, inflammatory (rheumatoid) arthritis, Hashimoto's thyroiditis, pernicious anemia, inflammatory bowel disease (Crohn's disease and ulcerative colitis), psoriasis, renal fibroses, pulmonary fibroses, hepatic fibroses, Addison's disease, Type I diabetes, systemic lupus erythematosus (SLE), dermatomyositis, Sjogren's syndrome, multiple sclerosis, myasthenia gravis, Reiter's syndrome, asthma, or Grave's disease.

In some embodiments, the disease is a cancer. In certain embodiments, the cancer is a hematopoietic cancer. In some embodiments, hematopoietic cancer is a lymphoma, leukemia, or multiple myeloma.

In specific embodiments, the lymphoma is a T-cell lymphoma, B-cell lymphoma, small lymphocytic lymphoma, mangle cell lymphoma, anaplastic large cell lymphoma (ALCL), follicular lymphoma, Hodgkin's lymphoma, or non-Hodgkin's lymphoma. In some embodiments, the leukemia is chronic lymphocytic leukemia (CLL), hairy cell leukemia, acute lymphoblastic leukemia, myelocytic leukemia, acute myeloid or myelogenous leukemia, or chronic myelogenous leukemia.

In some embodiments, the cancer is selected from one or more of breast cancer, cervical cancer, prostate cancer, gastrointestinal cancer, lung cancer, ovarian cancer, testicular cancer, head and neck cancer, bladder cancer, kidney cancer (e.g., renal cell carcinoma), soft tissue sarcoma, squamous cell carcinoma, CNS or brain cancer, melanoma, non-melanoma cancer, thyroid cancer, endometrial cancer, an epithelial tumor, and bone cancer.

In some embodiments, the cancer (cell) expresses or overexpresses Cav1.1, Cav1.2, Cav1.3, Cav1.4, or any combination thereof. In particular embodiments, the cancer expresses or overexpresses Cav1.1 and the antibody, or antigen-binding fragment thereof, specifically binds to Cav1.1. In certain embodiments, the cancer expresses or overexpresses Cav1.2 and the antibody, or antigen-binding fragment thereof, specifically binds to Cav1.2. In some embodiments, the cancer expresses or overexpresses Cav1.3 and the antibody, or antigen-binding fragment thereof, specifically binds to Cav1.3. In particular embodiments, the cancer expresses or overexpresses Cav1.4 and the antibody, or antigen-binding fragment thereof, specifically binds to Cav1.4.

DETAILED DESCRIPTION

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below. All of the patent and non-patent literature references listed herein are incorporated by reference in their entireties.

The articles "a" and "an" are used herein to refer to one or to more than one (i.e., to at least one) of the grammatical object of the article. By way of example, "an element" means one element or more than one element.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length.

As used herein, the term "amino acid" is intended to mean both naturally occurring and non-naturally occurring amino acids as well as amino acid analogs and mimetics. Naturally occurring amino acids include the 20 (L)-amino acids utilized during protein biosynthesis as well as others such as 4-hydroxyproline, hydroxylysine, desmosine, isodesmosine, homocysteine, citrulline and ornithine, for example. Non-naturally occurring amino acids include, for example, (D)-amino acids, norleucine, norvaline, p-fluorophenylalanine, ethionine and the like, which are known to a person skilled in the art. Amino acid analogs include modified forms of naturally and non-naturally occurring amino acids. Such modifications can include, for example, substitution or replacement of chemical groups and moieties on the amino acid or by derivatization of the amino acid. Amino acid mimetics include, for example, organic structures which exhibit functionally similar properties such as charge and charge spacing characteristic of the reference amino acid. For example, an organic structure which mimics Arginine (Arg or R) would have a positive charge moiety located in similar molecular space and having the same degree of mobility as the ε-amino group of the side chain of the naturally occurring Arg amino acid. Mimetics also include constrained structures so as to maintain optimal spacing and charge interactions of the amino acid or of the amino acid functional groups. Those skilled in the art know or can determine what structures constitute functionally equivalent amino acid analogs and amino acid mimetics.

Throughout this specification, unless the context requires otherwise, the words "comprise," "comprises," and "comprising" will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The term "biological sample" includes a biological material that can be collected from a subject and used in connection with diagnosis or monitoring of biological states. Biological samples can include clinical samples, including body fluid samples, such as body cavity fluids, urinary fluids, cerebrospinal fluids, blood, and other liquid samples of biological origin; and tissue samples, such as biopsy samples, tumor or suspected tumor samples, and other solid samples of biological origin. Biological samples can also include those that are manipulated in some way after their collection, such as by treatment with reagents, culturing, solubilization, enrichment for certain biological constituents, cultures or cells derived therefrom, and the progeny thereof.

The term "conjugate" includes an entity formed as a result of covalent or non-covalent attachment or linkage of an agent or other molecule, e.g., a detectable entity, a biologically active molecule, PEG or other polymer, to an antibody described herein.

A "control" such as a "control subject" or "control tissue" includes a healthy subject or a healthy tissue sample, for example, which is not pathological or diseased. In certain embodiments, a control includes a non-diseased tissue from a different, healthy subject or the same subject being tested or diagnosed. A control can also include a reference standard, for example, a standard value generated from one or more healthy subjects or tissues.

As used herein, the terms "function" and "functional" and the like refer to a biological, enzymatic, or therapeutic function.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions of the invention can include a single treatment or a series of treatments.

"Homology" refers to the percentage number of amino acids that are identical or constitute conservative substitutions. Homology may be determined using sequence comparison programs such as GAP (Deveraux et al., Nucleic Acids Research. 12, 387-395, 1984), which is incorporated herein by reference. In this way sequences of a similar or substantially different length to those cited herein could be compared by insertion of gaps into the alignment, such gaps being determined, for example, by the comparison algorithm used by GAP.

By "isolated" is meant material that is substantially or essentially free from components that normally accompany it in its native state. For example, an "isolated peptide" or an "isolated polypeptide" and the like, as used herein, includes the in vitro isolation and/or purification of a peptide or polypeptide molecule from its natural cellular environment, and from association with other components of the cell; i.e., it is not significantly associated with in vivo substances. In particular embodiments, the isolated polypeptide is an antibody.

A "decreased" or "reduced" amount is typically a "statistically significant" amount, and may include, for example, a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and ranges in between) relative to a control. Other examples of comparisons and "statistically significant" amounts are described herein. "Decrease," as used herein, can refer to "inhibit," "reduce," "curb," "abate," "diminish," "lessen," "lower," or "weaken."

A "increased" or "enhanced" amount is typically a "statistically significant" amount, and may include, for example, a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% increase. An increased or enhanced amount may also include a 2-fold, 3, fold, 4 fold, 5 fold, 6 fold, 7 fold, 8-fold, 9-fold, 10 fold, 20-fold, 30 fold, 40 fold, 50 fold, 60 fold 70 fold, 80-fold, 90-fold, 100-fold, 200-fold, 300-fold, 400-fold, 500-fold, 1,000-fold, 10,000-fold, or greater than 10,000-fold increase (including all integers and ranges in between) relative to a control. Other examples of comparisons and "statistically significant" amounts are described herein. "Increase," as used herein, can refer to "agonize," "enhance," "inflate," "escalate," expand," "augment," "enlarge," or "raise."

In certain embodiments, the "purity" of any given agent (e.g., an antibody) in a composition may be specifically defined. For instance, certain compositions may comprise an agent that is at least 80%, 85%, 90%, 91%, 92%, 93%, 94%, 95%, 96%, 97%, 98%, 99%, or 100% pure, including all decimals in between, as measured, for example, and by no means limiting, by high performance liquid chromatography (HPLC), a well-known form of column chromatography used frequently in biochemistry and analytical chemistry to separate, identify, and quantify compounds.

The terms "polypeptide" and "protein" are used interchangeably herein to refer to a polymer of amino acid residues and to variants and synthetic analogues of the same. Thus, these terms apply to amino acid polymers in which one or more amino acid residues are synthetic non-naturally occurring amino acids, such as a chemical analogue of a corresponding naturally occurring amino acid, as well as to naturally-occurring amino acid polymers. The polypeptides described herein are not limited to a specific length of the product; thus, peptides, oligopeptides, and proteins are included within the definition of polypeptide, and such terms may be used interchangeably herein unless specifically indicated otherwise. The polypeptides described herein may also comprise post-expression modifications, such as glycosylations, acetylations, phosphorylations and the like, as well as other modifications known in the art, both naturally occurring and non-naturally occurring. A polypeptide may be an entire protein, or a subsequence, fragment, variant, or derivative thereof.

The term "reference sequence" refers generally to a nucleic acid coding sequence, or amino acid sequence, to which another sequence is being compared. All polypeptide and polynucleotide sequences described herein are included as references sequences, including those described by name and those described in the Tables and the Sequence Listing.

The terms "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 97%, 98%, 99% or 100% sequence identity to any of the reference sequences described herein (see, e.g., Sequence Listing), typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity." A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example, disclosed by Altschul et al., Nucl. Acids Res. 25:3389, 1997. A detailed discussion of sequence analysis can be found in Unit 19.3 of Ausubel et al., "Current Protocols in Molecular Biology," John Wiley & Sons Inc, 1994-1998, Chapter 15.

By "significant" or "statistically significant," it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

The term "solubility" refers to the property of an antibody described herein to dissolve in a liquid solvent and form a homogeneous solution. Solubility is typically expressed as a concentration, either by mass of solute per unit volume of solvent (g of solute per kg of solvent, g per dL (100 mL), mg/mL, etc.), molarity, molality, mole fraction or other similar descriptions of concentration. The maximum equilibrium amount of solute that can dissolve per amount of solvent is the solubility of that solute in that solvent under the specified conditions, including temperature, pressure, pH, and the nature of the solvent. In certain embodiments, solubility is measured at physiological pH, or other pH, for example, at pH 5.0, pH 6.0, pH 7.0, or pH 7.4. In certain embodiments, solubility is measured in water or a physiological buffer such as PBS or NaCl (with or without NaP). In specific embodiments, solubility is measured at relatively lower pH (e.g., pH 6.0) and relatively higher salt (e.g., 500 mM NaCl and 10 mM NaP). In certain embodiments, solubility is measured in a biological fluid (solvent) such as blood or serum. In certain embodiments, the temperature can be about room temperature (e.g., about 20, 21, 22, 23, 24, 25° C.) or about body temperature (~37° C.). In certain embodiments, an antibody has a solubility of at least about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 25, or 30 mg/mL at room temperature or at about 37° C.

A "subject," as used herein, includes any animal that exhibits a symptom or condition, or is at risk for or suspected of exhibiting a symptom or condition, which can be diagnosed with an antibody described herein. Suitable subjects (patients) include laboratory animals (such as mouse, rat, rabbit, or guinea pig), farm animals, and domestic animals or pets (such as a cat or dog). Non-human primates and, preferably, human patients, are included.

A "subject subpopulation" or "patient subpopulation," as used herein, includes a subject or patient subset characterized as having one or more distinctive measurable and/or identifiable characteristics that distinguishes the subject or patient subset from others in the broader disease category (e.g., cancer) to which it belongs. Such characteristics include disease subcategories, gender, lifestyle, health history, organs/tissues involved, treatment history, etc. In some embodiments, a patient or subject subpopulation is characterized by the (e.g., reduced) amount or levels of an L-type voltage-gated calcium channel alpha 1 subunit polypeptide in a biological sample, for example, a tumor sample.

"Substantially" or "essentially" means nearly totally or completely, for instance, 95%, 96%, 97%, 98%, 99% or greater of some given quantity.

"Substantially free" refers to the nearly complete or complete absence of a given quantity for instance, less than about 10%, 5%, 4%, 3%, 2%, 1%, 0.5% or less of some given quantity. For example, certain compositions may be "substantially free" of cell proteins, membranes, nucleic acids, endotoxins, or other contaminants.

"Treatment" or "treating," as used herein, includes any desirable effect on the symptoms or pathology of a disease or condition, and may include even minimal changes or improvements in one or more measurable markers of the disease or condition being treated. "Treatment" or "treating" does not necessarily indicate complete eradication or cure of the disease or condition, or associated symptoms thereof. The subject receiving this treatment is any subject in need thereof. Exemplary markers of clinical improvement will be apparent to persons skilled in the art.

The term "wild-type" refers to a gene or gene product that has the characteristics of that gene or gene product when isolated from a naturally-occurring source. A wild-type gene or gene product (e.g., a polypeptide) is that which is most frequently observed in a population and is thus arbitrarily designed the "normal" or "wild-type" form of the gene.

L-Type Voltage-Gated Calcium Channels

Voltage-gated calcium channels mediate calcium influx in response to membrane depolarization and regulate intracellular processes such as contraction, secretion, neurotransmission, and gene expression in many different cell types. Voltage-gated calcium channels couple electrical events that alter membrane potential at the cell surface to physiological processes in the cells. Voltage-gated calcium channels are members of a gene superfamily of transmembrane ion channel proteins that includes voltage-gated potassium and sodium channels.

Calcium currents recorded in different cell types have diverse physiological and pharmacological properties, and so voltage-gated calcium channels are grouped based on the properties of their respective currents. In general, L-type voltage-gated calcium channels open in response to a strong depolarization and produce long-lasting calcium current. L-type voltage-gated calcium channels are blocked by organic L-type calcium channel antagonists, including dihydropyridines, phenylalkylamines, and benzothiazepines. L-type voltage-gated calcium channels generate the main calcium currents recorded in muscle and endocrine cells, where they initiate contraction and secretion. L-type currents activating at lower voltages also exist predominantly in neurons and cardiac pacemaker cells. L-type voltage-gated calcium channels are also expressed in cells that are not considered excitable, including in hematopoietic cells such as T cells and B cells.

The L-type voltage-gated calcium channels are complex proteins composed of four or five distinct subunits that are encoded by multiple genes. The α1 subunit of 190 to 250 kDa is the largest subunit, and it incorporates the conduction pore, the voltage sensor and gating apparatus, and most of the known sites of channel regulation by secondary messengers, drugs, and toxins. A particular L-type voltage-gated channel will take its name (i.e. Cav1.4) from the alpha 1 subunit it contains. Like the alpha subunits of sodium channels, the alpha 1 subunit of voltage gated calcium channels is organized in four homologous domains (I-IV), also called motifs, with six transmembrane segments (S1-S6) in each. The transmembrane segments of each domain are numbered in the order they are arranged from the N-terminal to the C-terminal.

The alpha 1 subunit forms the channel structure of the voltage-gated calcium channel protein. The pore of the calcium channel is formed at the center of a pseudo-symmetric arrangement of the four domains, and the pore loops between S5 and S6 of each domain form the narrow, extracellular end of the channel. These pore loops determine ion conductance and selectivity, and changes of only three specific amino acids in the pore loops in domains I, III, and IV will convert a channel's selectivity from calcium ions to sodium ions. The S4 segments of each domain serve as the channel's voltage sensor. An intracellular beta subunit and a transmembrane, disulfide-linked alpha2 beta subunit complex are components of most types of calcium channels. A gamma subunit has also been found in skeletal muscle calcium channels, and related subunits are expressed in heart and brain. Although these auxiliary subunits modulate the properties of the channel complex, the pharmacological and electrophysiological diversity of calcium channels arises primarily from the α1 subunits.

The opening and closing of the voltage-gated calcium channels are primarily gated by changes in membrane potential, which cause movement of charges across the membrane and drive conformational changes that open and close the pore. The positively charged S4 segments are thought to undergo outward and rotational movement through the protein structure during the gating process, as proposed in the 'sliding helix' and 'helical screw' models of gating (Reviewed in Catterall et al, (2007) Toxicol. 49(2), pp 124-141). This structure suggests that the pore is closed at its intracellular end and discriminates ions at the narrow ion selectivity filter at its extracellular end.

L-type voltage-gated calcium channels are found in populations of cells considered to be excitable. Excitable cells are cells where specific stimulations can trigger changes in the membrane potential globally throughout the cell or locally in a region of the cell. Calcium channels can function to regulate the changes in membrane potential. Additionally, calcium ions that enter the cytosol when calcium channels are open can act as a secondary messenger that can continue to regulate cellular processes after the depolarization event. Expression of L-type voltage calcium channels are also found in cells not considered to be excitable.

At least four subtypes of L-type voltage-gated calcium channels have been described. These subtypes are categorized by the alpha 1 subunits they contain, which are each encoded by separate genes. The gene encoding Cav1.4 is CACNA1F. High levels of Cav1.4 are found in retina, spleen, thymus, and bone marrow. Cav1.3 is encoded by CACNA1D, and is found in brain, pancreas, kidney, ovary, and cochlea. Cav1.2 is encoded by CACNA1C, and shows high expression in heart, smooth muscle, brain, pituitary and adrenal glands. Cav1.1 is encoded by CACNA1S, and has high levels of expression in skeletal muscle.

Data from mouse and human studies demonstrate that each L-type voltage gated calcium channel subtype is found in immune cells (Reviewed in Omilusik et al (2013) Frontiers in Immunology, vol 4:164). Cav1.4 expression has been observed in the human Jurkat T cell line, as well as in human and rat spleen and thymus, and human and mouse T cells. Cav1.3 expression has been observed in the human Jurkat T cell line, and in mouse T cells. Cav1.2 expression has been observed in human peripheral blood T cells, as well as in the human Jurkat, MOLT-4, and CEM T cell lines. Cav1.2 has also been reported in mouse T cells. Cav1.1 has been observed in mouse T cells. The expression profile of these subtypes suggests that L-type voltage-gated calcium channels participate in regulation of calcium signaling in immune cells.

Antibodies

Certain embodiments relate to isolated antibodies which specifically bind to a human or mouse alpha 1 subunit of one or more L-type voltage-gated calcium channels, including those that specifically bind to one or more contiguous or non-contiguous fragments or epitopes thereof. In some embodiments, the antibodies or antigen-binding fragments thereof specifically bind to an extracellular domain of an L-type voltage-gated calcium channel alpha 1 subunit. In particular embodiments, the antibodies or antigen-binding fragments thereof specifically bind to an amino acid sequence of an alpha 1 subunit that resides in an extracellular domain of a pore loop between segments S5 and S6 of a domain in an alpha 1 subunit of an L-type voltage-gated calcium channel. In some embodiments, the pore loop is located in domain I of the alpha 1 subunit. This region is encoded by exons 7 and 8 of the messenger RNA encoding the alpha 1 subunit. In some embodiments, the antibody or antigen-binding fragment thereof prevents the binding of a second antibody to the extracellular pore loop between S5 and S6 of domain I of the alpha 1 subunit of the voltage-gated calcium-channel. In some embodiments, the alpha 1 subunit can be of human or mouse origin. In certain embodiments, the antibody is monoclonal.

In some embodiments, the antibody or antigen-binding fragment thereof described herein modulates the activity of the L-type gated voltage calcium channel. "Modulate," as used herein, can refer to "alter," "modify," "change," "shift," "transform," or "adjust." The alterations may be in the form of an increase or a decrease of channel activity, or a combination of both. An example of altering activity that comprises a combination of increasing and decreasing activity is an antibody that functions as an inverse agonist, where upon the binding of the antibody to the voltage-gated calcium channel would result in an initial brief increase in channel activity, followed by a sustained decrease in channel activity.

"Activity," as used herein, of the L-type voltage-gated calcium channel refers to the calcium conductance of the channel. The L-type voltage-gated calcium channel is considered to be in a closed conformation at resting membrane conditions. "Closed" refers to a conformation of the channel where there is little or no calcium conductance. When the plasma membrane becomes depolarized, the channel adopts an open conformation which allows for calcium conductance. Following the membrane depolarization, the channel remains open for a time before reverting back to a closed conformation. "Open" refers to a conformation where calcium ions are permitted to pass through the channel. An L-type voltage-gated calcium channel can have one or more open and closed conformations. In some embodiments, an antibody or antigen binding fragment thereof specifically binds to the alpha 1 subunit of the voltage gated calcium channel and alters its activity. This effect may be achieved by, for example but not limited to, changing the probability that the channel will be in an open or closed conformation, changing the conditions, such as the degree of membrane depolarization, that changes the conformation of the channel, changing the duration of time that the calcium channel remains in an open or closed state, changing the calcium conductance of the channel when it is in an open or closed state, or any combination thereof. In some embodiments, inhibiting activity of an L-type voltage-gated calcium channel is achieved by reducing the probability that the channel will adopt an open conformation in response to membrane depolarization, increasing the degree of membrane depolarization required to shift the channel into an open conformation, decreasing the duration of time the channel remains in an open conformation following depolarization of the plasma membrane, reducing the calcium conductance of the channel when it is in an open conformation, or any combination thereof.

In some embodiments, the antibody or antigen-binding fragment thereof as described herein specifically binds to an alpha subunit of a specific subtype of an L-type voltage gated channel. The subtypes of the L-type voltage gated calcium channels include Cav1.4, Cav1.3, Cav1.2, and Cav1.1. In particular embodiments, the antibody or antigen-binding fragment thereof specifically binds to an extracellular region of the alpha 1 subunit of Cav1.4, Cav1.3, Cav1.2, or Cav1.1. In some embodiments, the antibody or antigen-binding fragment thereof specifically binds to an amino acid sequence located on the extracellular pore loop between S5 and S6 of domain I of the Cav1.4, Cav 1.3, Cav1.2, or Cav1.1 alpha 1 subunit. In particular embodiments, the amino acid sequence is GPGRPGDAPHTG [SEQ ID NO: 1] of Cav1.4, or is at least 90% identical to GPGRPGDAPHTG [SEQ ID NO: 1]. In some embodiments, the amino acid sequence is LTKETEGGNHSSGKSG [SEQ ID NO 2] of Cav1.3, or is at least 90% identical to LTKETEGGNHSSGKSG [SEQ ID NO 2]. In some embodiments, the amino acid sequence is ATKADGANALGGKGA [SEQ ID NO: 3] of Cav1.2, or is at least 90% identical to ATKADGANALGGKGA [SEQ ID NO: 3] of Cav1.2. In particular embodiments, the amino acid sequence is PMQIELRHREWVH [SEQ ID NO 4] of Cav1.1, or is at least 90% identical to PMQIELRHREWVH [SEQ ID NO 4].

Each L-type voltage-gated calcium channel subtype has several splice variants. Alternative splicing is a regulated process during gene expression that results in a single gene coding for multiple isoforms of the protein. In this process, particular exons of a gene may be included within or excluded from the final, processed messenger RNA (mRNA) produced from that gene. Consequently the proteins translated from alternatively spliced mRNAs will contain differences in their amino acid sequence. Alternative splicing occurs as a normal phenomenon in eukaryotes, and has been described in the genes encoding L-type voltage-gated subunits. As used herein, the term "L-type voltage-gated calcium channel," unless otherwise specified, includes Cav1.1, Cav1.2, Cav1.3, and Cav1.4, and all isoforms of the alpha 1 subunit that result from alternative splicing of mRNA encoding Cav1.1, Cav1.2, Cav1.3, and Cav1.4.

L-type voltage-gated calcium channel subtypes are expressed in different cell types and tissue types throughout the body, and can be expressed as different variants, including variants that result from alternate splicing of message RNA, or different post translational modifications, such as glycosylation or phosphorylation. Different variants of the subtype can be expressed in different tissue or cell types, or alternatively, different variants of the subtype can be expressed in the same tissue or cell type, including in the same cell. In particular embodiments, the antibody or antigen binding fragment thereof specifically binds to all variants of the subtype. In some embodiments, the antibody or antigen binding fragment thereof specifically binds to a subset of the variants of the subtype. In particular embodiments, the antibody or binding fragment thereof specifically binds to the subtype expressed in any cell or tissue. In some embodiments, the antibody or binding fragment thereof specifically binds to the subtype in a subset of cells or tissues of which the subtype is expressed.

In a particular embodiment, the antibody or antigen-binding fragment thereof described herein specifically binds to any one or more of Cav1.4, Cav1.3, Cav1.2, and Cav1.1. In some embodiments, the antibody or antigen-binding fragment thereof specifically binds to any three of Cav1.4, Cav1.3, Cav1.2, and Cav1.1. Such an antibody or antigen-binding fragment thereof may specifically bind to any of Cav1.4, Cav1.3, and Cav1.2; Cav1.4, Cav1.3, and Cav1.1; Cav1.4, Cav1.2, and Cav1.1; or Cav1.3, Cav1.2, and Cav1.1. In some embodiments, the antibody or antigen-binding fragment thereof specifically binds to any two of Cav1.4, Cav1.3, Cav1.2, and Cav1.1. Such an antibody or antigen-binding fragment thereof specifically binds to any of Cav1.4 and Cav1.3; Cav1.4 and Cav1.2; Cav1.4 and Cav1.1; Cav1.3 and Cav1.2; Cav1.3 and Cav1.1; or Cav1.2 and Cav1.1. In some embodiments, the antibody or binding fragment thereof specifically binds to only one subtype of an L-type voltage-gated calcium channel. Such an antibody will only bind to Cav1.4, Cav1.3, Cav1.2, or Cav1.1, relative to the other Cav1 subtypes.

In certain embodiments, an antibody or antigen-binding fragment thereof described herein specifically binds to cells expressing an L-type voltage-gated calcium channel. In some embodiments, the antibody or antigen-binding fragment will bind to any cell expressing the L-type voltage-gated calcium channel. In some embodiments, the antibody or antigen-binding fragment will bind to a subset of cells expressing the L-type voltage-gated calcium channel. In particular embodiments, the antibody or antigen-binding fragment will specifically bind to a subset of cells expressing the L-type voltage-gated calcium channel, but not bind to another subset of cells expressing the L-type voltage-gated calcium channel. In some embodiments, the antibody or antigen-binding fragment will specifically bind any cells expressing one or more of Cav1.4, Cav1.3, Cav1.2, and Cav1.1. In certain embodiments, an antibody or antigen-binding fragment described herein will specifically bind to a subset of cells expressing one or more of Cav1.4, Cav1.3, Cav1.2, and Cav1.1. In particular embodiments, the antibody or antigen-binding fragment will specifically bind to some cell types expressing a particular subtype of an L-type voltage-gated calcium channel, but not bind to other cell types expressing the same subtype of the L-type voltage-gated calcium channel. In particular embodiments, the antibody or antigen-binding fragment thereof specifically binds to some cell types that express a variant of the channel subtype, but not to other cell types that express the same variant of the channel subtype. In certain embodiments, the antibody or antigen-binding fragments thereof specifically binds to cells expressing one or more variants of the channel subtype, but not to cells expressing different variants of the channel subtype.

In some embodiments, the antibodies are defined by the light chain variable region sequences and/or heavy chain variable regions described herein, and/or the complementary determining region (CDR) sequences or antigen-binding regions (ABRs) contained therein, including variants and combinations of these sequences that specifically bind to amino acid sequence on an extracellular pore loop between S5 and S6 of domain I of an alpha one subunit of an L-type voltage-gated calcium channel. Also included are antibodies that competitively inhibit the binding of such antibodies to an extracellular pore loop between S5 and S6 of domain I of an alpha one subunit of an L-type voltage-gated calcium channel.

The term "antigen-binding fragment" as used herein refers to a polypeptide fragment that contains at least one CDR of an immunoglobulin heavy and/or light chains that specifically bind to the antigen of interest. In this regard, an antigen-binding fragment of the herein described antibodies may comprise 1, 2, 3, 4, 5, or all 6 CDRs of a $V_H$ and $V_L$ sequence from antibodies that specifically bind to a therapeutic or diagnostic target such as an extracellular pore loop between S5 and S6 of domain I of an alpha one subunit of an L-type voltage-gated calcium channel, including fragments thereof.

The term "antigen" refers to a molecule or a portion of a molecule capable of being bound by a selective antibody, or an antigen-binding fragment thereof, and additionally capable of being used in an animal to produce antibodies capable of binding to an epitope of that antigen. An antigen may have one or more epitopes.

The term "epitope" includes any determinant, preferably a polypeptide determinant, capable of specific binding to an immunoglobulin or T-cell receptor. An epitope is a region of an antigen that is bound by an antibody. In certain embodiments, epitope determinants include chemically active surface groupings of molecules such as amino acids, sugar side chains, phosphoryl or sulfonyl, and may in certain embodiments have specific three-dimensional structural characteristics, and/or specific charge characteristics. Epitopes can be contiguous or non-contiguous in relation to the primary structure of the antigen.

An antibody or antigen-binding fragment thereof, is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a specific epitope is an antibody that binds that specific epitope with greater affinity, avidity, more readily, and/or with greater duration than it binds to other epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

Immunological binding generally refers to the non-covalent interactions of the type which occur between an immunoglobulin molecule and an antigen for which the immunoglobulin is specific, for example, by way of illustration and not limitation, as a result of electrostatic, ionic, hydrophilic and/or hydrophobic attractions or repulsion, steric forces, hydrogen bonding, van der Waals forces, and other interactions. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and on geometric parameters that equally influence the rate in both directions. Thus, both the "on rate constant" ($k_{on}$) and the "off rate constant" ($k_{off}$) can be determined by calculation of the concentrations and the actual rates of association and dissociation. The ratio of $k_{off}/k_{on}$ enables cancellation of all parameters not related to affinity, and is thus equal to the dissociation constant $K_d$.

Immunological binding properties of antibodies, and antigen-binding fragments thereof, can be quantified using methods well known in the art (see Davies et al., *Annual Rev. Biochem.* 59:439-473, 1990). In some embodiments, an antibody is said to specifically bind an antigen or epitope thereof when the equilibrium dissociation constant is about $\leq 10^{-7}$ or $10^{-8}$ M. In some embodiments, the equilibrium dissociation constant of a protein may be about $\leq 10^{-9}$ M or $\leq 10^{-10}$ M. In certain illustrative embodiments, a protein has an affinity ($K_d$) for an antigen or target described herein (to which it specifically binds) of about, at least about, or no more than about 0.01, 0.05, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, or 50 nM.

As used herein, the terms "L-type Voltage-Gated Calcium Channel" and "CaV1" channels are used interchangeably, and are meant to include Cav1.1, Cav1.2, Cav1.3, and Cav1.4 unless otherwise specified. "L-type Voltage-Gated Calcium Channel" and "CaV1" channels also comprise Cav1.1, Cav1.2, Cav1.3, and Cav1.4 channels that may undergo variations in post-expression modifications, such as glycosylations, acetylations, phosphorylations and the like, and include the entire Cav1.1, Cav1.2, Cav1.3, and Cav1.4 proteins, as well as subsequences, fragments, variants (including but not limited to variants resulting from alternative splicing), or derivatives thereof.

The primary amino acid sequence of human and mouse L-type voltage gated calcium channel alpha 1 subunits are shown in Table 1 below. Of note, mRNAs encoding alpha 1 subunits of L-type voltage-gated calcium channels have splice variants that can result in different isoforms of the polypeptide. Therefore, the amino acid sequences listed in Table 1 are exemplary.

TABLE 1

| | | L-Type Voltage Gated Calcium Channels (CaV1)Alpha Subunits | |
|---|---|---|---|
| Name | Gene Symbol | Amino Acid Sequence | SEQ ID NO: |
| Human CaV1.4 | CACNA1F | mseseggkdttpepspangagpgpewglcpgppavegessgasglgtpk rrnqhskhktvavasaqrspralfcltlanplrrscisivewkpfdili lltifancvalgvyipfpeddsntanhnleqveyvflviftvetvlkiv ayglvlhpsayirngwnlldfiivvglfsvllecopgrpgdaphtggk pggfdvkalrafrvlrplrlvsgvpslhivlnsimkalvpllhiallvl fviiiyaiiglelflgrmhktcyflgsdmeaeedpspcassgsgractl nqtecrgrwpgpnggitnfdnfffamltvfqcvtmegwtdvlywmqdam gyelpwvyfvslvifgsffvlnlvlgvlsgefskerekakargdfqkqr ekqqmeedlrgyldwitqaeeldmedpsaddnlgsmaeegraghrpqla eltnrrrgrlrwfshstrsthstsshaslpasdtgsmtetqgdedeeeg alasctrclnkimktrvcrrlrranrvlrarcrravksnacywavlllv flntltiasehhgqpvwltqiqeyankvllclftvemllklyglgpsay vssffnrfdcfvvcggilettivevgamqplgisvlrcvrllrifkvtr hwaslsnlvasllnsmksiasllllllflfiiifsllgmqlfggkfnfdq thtkrstfdtfpqalltvfqiltgedwnvymydgimaygpffpgmlvc iyfiilficgnyillnvflaiavdnlasgdagtakdkggeksnekdlpq eneglvpgvekeeeegarregadmeeeeeeeeeeeeeegaggvell qevvpkekvvpipegsaffclsqtnplrkgchtlihhhvftnlilvfii lssvslaaedpirahsfrnhilgyfdyaftsiftveillkmtvfgaflh rgsferswfnmldllvvsvslisfgihssaisvvkilrvlrvlrplrai nrakglkhvvqcfvairtignimivttllqfmfacigvqlfkgkfytc tdeakhtpqeckgsflvypdgdvsrplvrerlwvnsdfnfdnvlsamma lftvstfegwpallykaidayaedhgpiynyrveisvffivyiiiiaff mmnifvgfviitfraqgeqeyqnceldknqrqcveyalkaqplrryipk nphqyrvwatvnsaafeylmfllillntvalamqhyeqtapfnyamdil nmvftglftiemvlkiiafkpkhyftdawntfdalivvgsivdiavtev nngghlgessedssrisitffrlfrvmrlvkllskgegirtllwtfiks fqalpyvalliamiffiyavigmqmfgkvalqdgtqinrnnnfqtfpqa vlllfrcatgeawqeimlaslpgnrcdpesdfgpgeeftcgsnfaiayf isffmlcafliinlfvavimdnfdyltrdwsilgphhldefkriwseyd pgakgrikhldvvallrriqpplgfgklcphrvackrlvamnmplnsdg tvtfnatlfalvrtslkiktegnleqanqelrivikkiwkrmkqkllde vippppdeeevtvgkfyatfliqdyfrkfrrrkekgllgndaapstssal qaglrslqdlgpemrqaltedteeeeeeggegveeedekdletnkatmv sqpsarrgsgisyslpvgdrlpdslsfgpsdddrgtptssqpsvpqags nthrrgsgaliftipeegnsqpkgtkgqnkqdedeevpdrlsyldeqag tppcsvllpphraqrymdghlvprrrllpptpagrkpsftiqclqrqgs | 5 |

TABLE 1-continued

L-Type Voltage Gated Calcium Channels (CaV1)Alpha Subunits

| Name | Gene Symbol | Amino Acid Sequence | SEQ ID NO: |
|---|---|---|---|
| | | cedlpipgtyhrgrnsgpnraqgswatppqrgrllyaplllveegaage gylgrssgplrtftclhvpgthsdpshgkrgsadslveavliseglglf ardprfvalakqeiadacrltldemdnaasdllaqgtsslysdeesils rfdeedlgdemacvhal | |
| Human CaV1.3 | CACNL1A2 | mmmmmmmkkmqhqrqqqadhaneanyargtrlplsgegptsqpnsskqt vlswqaaidaarqakaaqtmstsapppvgslsqrkrqqyakskkqgnss nsrparalfclslnnpirracisivewkpfdifillaifancvalaiyi pfpeddsnstnhnlekveyafliiftvetflkiiayglllhpnayvrng wnlldfvivivglfsvileqltketeggnhssgksggfdvkalrafrvl rplrlvsgvpslqvvlnsiikamvpllhiallvlfviiiyaiiglelfi gkmhktcffadsdivaeedpapcafsgngrqctangtecrsgwvgpngg itnfdnfafamltvfqcitmegwtdvlywmndamgfelpwvyfvslvif gsffvlnlvlgvlsgefskerekakargdfqklrekqqleedlkgyldw itqaedidpeneeeggeegkrntsmptsetesvntenvsgegenrgccg slcqaiskskslsrrwrrwnrfnrrrcraavksvtfywlvivlvflntlt issehynqpdwltqiqdiankvllalftcemlvkmyslglqayfvslfn rfdcfvvcggitetilveleimsplgisvfrcvrllrifkvtrhwtsls nlvaslllnsmksiaslllllflfiiifsllgmqlfggkfnfdetqtkrs tfdnfpqalltvfqiltgedwnavmydgimayggpsssgmivciyfiil ficgnyillnvflaiavdnladaeslntaqkeeaaeekerkkiarkesle nkknnkpevnqiansdnkvtiddyreededkdpyppcdvpvgeeeeeee edepevpagprprriselnmkekiapipegsaffilsktnpirvgchkl inhhiftnlilvfimlssaalaaedpirshsfrntilgyfdyaftaift veillkmttfgaflhkgafcrnyfnlldmlvvgvslvsfgiqssaisvv kilrvlrvlrplrainrakglkhvvqcvfvairtignimivttllqfmf acigvqlfkgkfyrctdeaksnpeecrglfilykdgdvdspvvreriwq nsdfnfdnvlsammalftvstfegwpallykaidsngenigpiynhrve isiffiiyiiiivaffmmnifvgfvivtfqeqgekeykncelknqrqcv eyalkarplrryipknpyqykfwyvvnsspfeymmfvlimlntlelamq hyeqskmfndamdilnmvftgvftvemvlkviafkpkgyfsdawntfds livigsiidvalseadptesenvpvptatpgnseesnrisitffrlfrv mrlvkllsrgegirtlllwtfiksfqalpyvalliamlffiyavigmqmf gkvamrdnnqinrnnnfqtfpqavllllfrcatgeawqeimlaclpgklc dpesdynpgeeytcgsnfaivyfisfymlcafliinlfvavimdnfdyl trdwsilgphhldefkriwseydpeakgrikhldvvtllrriqpplgfg klcphrvackrlvamnmpinsdgtvmfnatlfalvrtalkiktegnleq aneelravikkiwkktsmklldqvvppagddevtvgkfyatfliqdyfr kfkkrkeqglvgkypaknttialqaglrtlhdigpeirraiscdlqdde peetkreeeddvfkrngallgnhvnhvnsdrrdslqqtntthrplhvqr psippasdtekplfppagnsvchnhhnhnsigkqvptstnanlnnanms kaahgkrpsignlehvsenghhsshkhdrepqrrssvkrtryyetyirs dsgdeqlpticredpeihgyfrdphclgeqeyfsseecyeddssptwsr qnygyysrypgrnidserprgyhhpqgfledddspvcydsrrsprrrll pptpashrrssfnfeclrrqssqeevpsspifphrtalplhlmqqqima vagldsskaqkyspshstrswatppatppyrdwtpcytpliqveqseal dqvngslpslhrsswytdepdisyrtftpasltvpssfrnknsdkqrsa dslveavliseglgryardpkfvsatkheiadacdltidemesaastll ngnvrprangdvgplshrqdyelqdfgpgysdeepdpgrdeedlademi cittl | 6 |
| Human CaV1.2 | CACNL1A1 | mvnentrmyipeenhqgsnygsprpahanmmnanaaaglapehiptpgaa lswqaaidaarqaklmgsagnatistvsstqrkrqqygkpkkqgsttat rpprallcltlknpirracisivewkpfeiiilltifancvalaiypf peddsnatnsnlrveylflliiftveaflkviaygllfhpnaylrngwn lldfiivvvglfsaileqatkadganalggkgagfdvkalrafrvlrpl rlvsgvpslqvvlnsiikamvpllhiallvlfviiiyaiiglelfmgkm hktcynqegiadvpaeddpspcaletghgrqcqngtvckpgwdgpkhgi tnfdnfafamltvfqcitmegwtdvlywvndavgrdwpwiyfvtliiig sffvlnlvlgvlsgefskerekakargdfqklrekqqleedlkgyldwi tqaedidpenedegmdeekprnmsmptsetesvntenvaggdiegencg arlahriskskfsrywrrwnrfcrrkcraavksnvfywlviflvflntl tiasehynqpnwltevqdtankallalftaemllkmyslglqayfvslf nrfdcfvvcggiletilvetkimsplgisvlrcvrllrifkitrywnsl snlvaslllnsvrsiaslllllflfiiifsllgmqlfggkfnfdemqtrr stfdnfpqslltvfqiltgedwnsvmydgimayggpsfpgmlvciyfii lficgnyillnvflaiavdnladaesltsaqkeeeeekerkklartasp ekkqelvekpavgeskeekielksitadgesppatkinmddlqpnened kspypnpettgeedeeepempvgprprplselhlkekavpmpeasaffi fssnnrfrlqchrivndtiftnlilfflillssislaaedpvqhtsfrnh ilfyfdivfttiftieialkilgnadyvftsiftleiilkmtaygaflh kgsfcrnyfnildllvvsvslisfgiqssainvvkilrvlrvlrplrai nrakglkhvvqcvfvairtigniviivttllqfmfacigvqlfkgklytc sdsskqteaeckgnyitykdgevdhpiiqprswenskfdfdnvlaamma lftvstfegwpellyrsidshtedkgpiynyrveisiffiiyiiiiaff | 7 |

TABLE 1-continued

L-Type Voltage Gated Calcium Channels (CaV1)Alpha Subunits

| Name | Gene Symbol | Amino Acid Sequence | SEQ ID NO: |
|---|---|---|---|
| | | mmnifvgfvivtfqeggeqeykncedldknqrqcveyalkarplrryipk nqhqykvwyvvnstyfeylmfvlillnticlamqhyggsclfkiamnil nmlftglftvemilkliafkpkgyfsdpwnvfdflivigsiidvilset nhyfcdawntfdalivvgsivdiaitevnpaehtqcspsmnaeensris itffrlfrvmrlvkllsrgegirtllwtfiksfqalpyvallivmlffi yavigmqvfgkialndtteinrnnnfqtfpqavllfrcatgeawqdim lacmpgkkcapesepsnstegetpcgssfavfyfisfymlcafliinlf vavimdnfdyltrdwsilgphhldefkriwaeydpeakgrikhldvvtl lrriqpplgfgklcphrvackrlvsmnmplnsdgtvmfnatlfalvrta lriktegnleqaneelraiikkiwkrtsmklldqvvppagddevtvgkf yatfliqeyfrkfkkrkeqglvgkpsqrnalslqaglrtlhdigpeirr aisgdltaeeeldkamkeavsaaseddifrraggfgnhvsyyqsdgrs afpqtfttqrplhinkagssqgdtespsheklvdstftpssysstgsna ninnanntalgrlprpagypstvstveghgpplspairvqevawklssn rerhvpmcedlelrrdsgsagtqahclllrranpsrchsresqaamagq eetsqdetyevkmnhdteacsepsllstemlsyqddenrqltlpeedkr dirqspkrgflrsaslgrrasfhleclkrqkdrggdisqktvlplhlvh hqalavaglspllqrshspasfprpfatppatpgsrgwppqpvptlrle gvesseklnssfpsihcgswaettpggggssaarrvrpvslmvpsqaga pgrqfhgsassllveavliseglgqfaqdpkfievttqeladacdmtiee mesaadnilsggapqspngallpfvncrdagqdraggeedagcvrargr pseeelqdsrvyvssl | |
| Human CaV1.1 | CACNL1A3 | mepsspqdeglrkkqpkpvpeilprppralfcltlenplrkacisive wkpfetiilltifancvalavylpmpeddnnslnlglekleyfflivfs ieaamkiiaygflfhqdaylrsgwnvldftivflgvftvileqvniqs htapmsskgagldvkalrafrvlrplrlvsgvpslqvvlnsifkamlpl fhiallvlfmviiyaiiglelfkgmhktcyfigtdivatveneepspc artgsgrrctingsecrggwpgpnhgithfdnfgfsmltvyqcitmegw tdvlywvndaignewpwiyfvtlillgsffilnlvlgvlsgeftkerek aksrgtfqklrekqqldedlrgymswitqgevmdvedfregklsldegg sdteslyeiaglnkiiqfirhwrqwnrifrwkchdivkskvfywlvili valntlsiasehhnqplwltrlqdianrvllslftteemlmkmyglglrq yfmsifnrfdcfvvcsgileillvesgamtplgisvlrcirllrifkit kywtslsnlvaslnsirsiaslllllflfivifallgmqlfggrydfe dtevrrsnfdnfpqalisvfqvltgedwtsmmyngimayggpsypgmlv ciyfiilfvcgnyillnvflaiavdnlaeaesltsaqkakaeekkrrkm skglpdkseeekstmakkleqkpkgegipttaklkideefesnvnevkdp ypsadfpgddeedepeiplsprprplaelqlkekavpipeassfffisp tnkirvlchrivnatwftnfillfillssaalaaedpiradsmrnqilk hfdigftsvftveivlkmttygaflhkgsfcrnyfnmldllvvavslis mglessaisvvkilrvlrvlrplrainrakglkhvvqcmfvaistigni vlvttllqfmfacigvqlfkgkffrctdlskmteeecrgyyyvykdgdp mqielrhrewvhsdfhfdnvlsammslftvstfegwpqllykaidsnae dvgpiynnrvemaiffiiyiiliaffmmnifvgfvivtfqeqgeteykn celdknqrqcvqyalkarplrcyipknpyqyqvwyivtssyfeylmfal imlnticlgmqhynqseqmnhisdilnvaftiiftlemilklmafkarg yfgdpwnvfdflivigsiidvilseidtflasssgglyclgggcnvdpd esarissaffrlfrvmrlikllsraegvrtllwtfiksfqalpyvalli vmlffiyavigmqmfgkialvdgtqinrnnnfqtfpqavlllfrcatge awqeillacsygklcdpesdyapgeeytcgtnfayyyfisfymlcaflv inlfvavimdnfdyltrdwsilgphhldefkaiwaeydpeakgrikhld vvtllrriqpplgfgkfcphrvackrlvgmnmpinsdgtvtfnatlfal vrtalkiktegnfeqaneelraiikkiwkrtsmklldqvippigddevt vgkfyatfliqehfrkfmkrqeeyygyrpkkdivqiqaglrtieeeaap eicrtvsgdlaaeeeleramveaameegifrrtgglfgqvdnflertns lppvmanqrplqfaeiemeemespvfledfpqdprtnplarantnnana nvaygnsnhsnshvfssvhyerefpeetetpatrgralgqpcrvlgphs kpcvemlkglltqramprgqappapcqcprvessmpedrksstpgslhe etphsrstrentsrcsapatalliqkalvrgglgtlaadanfimatgqa ladacqmepeeveimatellkgreapegmasslgclnlgsslgsldqhq gsgetlipprl | 8 |
| Mouse CaV1.4 | CACNA1F | msesevgkdttpepspangtgpgpewglcpgpptvgtdtsgasglgtpr rrtqhnkhktvavasaqrspralfcltltnpirrscisivewkpfdili lltifancvalgvyipfpeddsntanhnleqveyvflviftvetvlkiv ayglvlhpsayirngwnlldfiivvvglfsvlleqgpgrpgdaphtggk pggfdvkalrafrvlrplrlvsgvpslhivlnsimkalvpllhiallvl fviiiyaiiglelflgrmhktcyflgsdmeaeedpspcassgsgrsctl nhtecrgrwpgpnggitnfdnfffamltvfqcitmegwtdvlywmqdam gyelpwvyfvslvifgsffvlnlvlgvlsgefskerekakargdfqklr ekqqmeedlrgyldwitqaeeldlhdpsvdgnlaslaeegraghrpqls eltnrrrgrlrwfshstrsthstsshaslpasdtgsmtdtpgdedeeeg tmasctrclnkimktricrhfrranrglrarcrravksnacywavlllv flntltiasehhgqplwltqtqeyankvllclftvemllklyglgpsvy | 9 |

TABLE 1-continued

L-Type Voltage Gated Calcium Channels (CaV1)Alpha Subunits

| Name | Gene Symbol | Amino Acid Sequence | SEQ ID NO: |
|---|---|---|---|
| | | vasffnrfdcfvvcggilettlvevgamqplgisvlrcvrllrifkvtr<br>hwaslsnlvasllnsmksiaslllllflfiiifsllgmqlfggkfnfdq<br>thtkrstfdtfpqalltvfqiltgedwnvvmydgimayggpffpgmlvc<br>vyfiilficgnyillnvflaiavdnlasgdagtakdkgrekssegnppk<br>enkvlvpggenedakgarsegaapgmeeeeeeeeeeeeeeengaghv<br>ellqevvpkekvvpipegsaffclsqtnplrkachtlihhhiftslilv<br>fiilssvslaaedpirahsfrnhilgyfdyaftsiftveilllkmtvfga<br>flhrgsfcrswfnlldllvvsyslisfgihssaisvvkilrvlrvlrpl<br>rainrakglkhvvqcvfvairtignimivttllqfmfacigvqlfkgkf<br>ysctdeakhtlkeckgsfliypdgdvsrplvrerlwvnsdfnfdnvlsa<br>mmalftvstfegwpallykaidanaedegpiynyhveisvffivyiiii<br>affmmnifvgfviitfraqgeqeyqnceldknqrqcveyalkaqplrry<br>ipknphqyrvwatvnsaafeylmfllillntvalamqhyeqtapfnyam<br>dilnmvftglftiemvlkiiafkpkhyfadawntfdalivvgsvvdiav<br>tevnngghlgessedssrisitffrlfrvmrlvkllskgegirtllwtf<br>iksfqalpyvalliamiffiyavigmqmfgkvalqdgtqinrnnnfqtf<br>pqavlllfrcatgeawqeimlaslpgnrcdpesdfgpgeeftcgssfai<br>vyfisffmlcafliinlfvavimdnfdyltrdwsilgphhldefkriws<br>eydpgakgrikhldvvallrriqpplgfgklcphrvackrlvamnvpln<br>sdgtvtfnatlfalvrtslkiktegnldqanqelrmvikkiwkrikqkl<br>ldevipppdeeevtvgkfyatfliqdyfrkfrrrkekgllgreaptsts<br>salqaglrslqdlgpeirqaltydteeeeeeeeavggeaeeeeaennpe<br>pykdsidsqpqsrwnsrisvslpvkeklpdslstgpsdddglapnsrqp<br>sviqagsqphrrssgvfmftipeegsiqlkgtqgqdnqneeqevpdwtp<br>dldeqagtpsnpvllpphwsqqhvnghhvprrrllpptpagrkpsftiq<br>clqrqgscedlpipgtyhrgrtsgpsraqgswaappqkgrllyaplllv<br>eestvgegylgklggplrtftclqvpgahpnpshrkrgsadslveavli<br>seglglfaqdprfvalakqeiadachltldemdsaasdllaqrttslys<br>deesilsrfdeedlgdemacvhal | |
| Mouse CaV1.3 | CACNL1A2 | mnlptfssdliliksvlsqetdarykgrvvsavestedfsqafaeanya<br>rgtrlpisgegptsqpnsskqtvlswqaaidaarqakaaqtmstsappp<br>vgslsqrkrqqyakskkqgnssnsrparalfclslnnpirracisivew<br>kpfdifillaifancvalaiyipfpeddsnstnhnlekveyafliiftv<br>etflkiiayglllhpnayvrngwnlldfvivivglfsvileqltketeg<br>gnhssgksggfdvkalrafrvlrplrlvsgvpslqvvlnsiikamvpll<br>hiallvlfviiiyaiiglelfigkmhktcffadsdivaeedpapcafsg<br>ngrqctangtecrsgwvgpnggitnfdnfafamltvfqcitmegwtdvl<br>ywvndaigwewpwvyfvsliilgsffvlnlvlgvlsgefskerekakar<br>gdfqklrekqqleedlkgyldwitqaedidpeneeeggeegkrntsmpt<br>setesvntenvsgegetqgccgtlcqaisksklsrrwrrwnrfnrrrcr<br>aavksvtfywlvivlvflntltissehynqpdwltqiqdiankvllalf<br>tcemlvkmyslglqayfvslfnrfdcfvvcggitetilvelelmsplgv<br>svfrcvrllrifkvtrhwtslsnlvasllnsmksiasllllllflfiiif<br>sllgmqlfggkfnfdetqtkrstfdnfpqalltvfqiltgedwnavmyd<br>gimayggpsssgmivciyfiilficgnyillnvflaiavdnladaesln<br>taqkeeaaeekerkkiarkeslenkknnkpevnqiansdnkvtiddyqed<br>aedkdpyppcdvpvgeeeeeeeedepevpagrprrriselnmkekiapi<br>pegsaffilsktnpirvgchklinhhiftnlilvfimlssaalaaedpi<br>rshsfrntilgyfdyaftaiftveilllkmttfgaflhkgafcrnyfnll<br>dmlvvgvslvsfgiqssaisvvkilrvlrvlrplrainrakglkhvvqc<br>vfvairtignimivttllqfmfacigvqlfkgkfyrctdeaksnpeecr<br>glfilykdgdvdspvvreriwqnsdfnfdnvlsammalftvstfegwpa<br>llykaidsngenvgpvynyrveisiffiiyiiivaffmmnifvgfvivt<br>fqeqgekeykneceldknqrqcveyalkarplrryipknpyqykfwyvvn<br>sspfeymmfvlimlntlclamqhyeqskmfndamdilnmvftgvftvem<br>vlkviafkpkgyfsdawntfdslivigsiidvalseadnseesnrisit<br>ffrlfrvmrlvkllsrgegirtlllwtfiksfqalpyvalliamlffiya<br>vigmqmfgkvamrdnnqinrnnnfqtfpqavlllfrcatgeawqeimla<br>clpgklcdpdsdynpgeeytcgsnfaivyfisfymlcafliinlfvavi<br>mdnfdyltrdwsilgphhldefkriwseydpeakgrikhldvvtllrri<br>qpplgfgklcphrvackrlvamnmplnsdgtvmfnatlfalvrtalkik<br>tegnleqaneelravikkiwkktsmklldqvvppagddevtvgkfyatf<br>liqdyfrkfkkrkeqglvgkypaknttialqaglrtlhdigpeirrais<br>cdlqddepedskpeeedvfkrngallgnhvnhvnsdrrdslqqtntthr<br>plhvqrpsmppasdtekplfppagnsgchnhhnhnsigkqaptstnanl<br>nnanmskaahgkppsignlehvsenghysckhdrelqrrssikrtryye<br>tyirsesgdeqfpticredpeihgyfrdprclgeqeyfsseecceddss<br>ptwsrqnynyynrypgssmdferprgyhhpqgfledddsptgydsrrsp<br>rrrllpptppshrrssfnfeclrrqssqddvlpspalphraalplhlmq<br>qqimavagldsskaqyspshstrswatppatppyrdwspcytpliqvd<br>rsesmdqvngslpslhrsswytdepdisyrtftpasltvpssfrnknsd<br>kqrsadslveavliseglgryardpkfvsatkheiadacdltidemesa<br>astllngsvcprangdmgpishrqdyelqdfgpgysdeepdpgreeedl<br>ademicittl | 10 |

TABLE 1-continued

L-Type Voltage Gated Calcium Channels (CaV1)Alpha Subunits

| Name | Gene Symbol | Amino Acid Sequence | SEQ ID NO: |
|---|---|---|---|
| Mouse CaV1.2 | CACNL1A1 | mvnentrmyvpeenhqgsnygsprpahanmnanaaaglapehiptpgaa lswqaaidaarqaklmgsagnatistvsstqrkrqqygkpkkqggttat rpprallcltlknpirracisivewkpfeiiilltifancvalaiyipf peddsnatnsnlerveylfliiftveaflkviaygllfhpnaylrngwn lldfiivvvglfsaileqatkadganalggkgagfdvkalrafrvlrpl rlvsgvpslqvvlnsiikamvpllhiallvlfviiiyaiiglelfmgkm hktcynqegiidvpaeedpspcaletghgrqcqngtvckpgwdgpkhgi tnfdnfafamltvfqcitmegwtdvlywmqdamgyelpwvyfvslvifg sffvlnlvlgvlsgefskerekakargdfqklrekqqleedlkgyldwi tqaedidpenedegmdedkprnmsmptsetesvntenvaggdiegencg arlahriskskfsrywrrwnrfcrrkcraavksnvfywlviflvflntl tiasehynqphwltevqdtankallalftaemllkmyslglqayfvslf nrfdcfivcggiletilvetkimsplgisvlrcvrllrifkitrywnsl snlvasllnsvrsiaslllllflfiiifsllgmqlfggkfnfdemqtrr stfdnfpqsflltvfqiltgedwnsvmydgimayggpsfpgmlvciyfii lficgnyillnvflaiavdnladaeesltsaqkeeeeekerkklartasp ekkqevmekpaveeskeekielksitadgesppttkinmddlqpsened ksphsnpdtageedeeepempvgprprplselhlkekavpmpeasaffi fspnnrfrlqchrivndtiftnlillffillssislaaedpvqhtsfrnh ilgnadyvftsiftleiiikmtaygaflhkgsfcrnyfnildllvvsvs lisfgiqssainvvkilrvlrvlrplrainrakglkhvvqcvfvairti gniviyttllqfmfacigvqlfkgklytcsdsskqteaeckgnyitykd gevdhpiiqprswenskfdfdnvlaammalftvstfegwpellyrsids htedkgpiynyrveisiffiiyiiiiaffmmnifvgfvivtfqeqgeqe ykncceldknqrqcveyalkarplrryipknqhqykvwyvvnstyfeylm fvlillnticlamqhyggsclfkiamnilnmlftglftvemilkliafk pkgyfsdpwnvfdflivigsiidvilsetnpaehtqcspsmsaeensri sitffrlfrvmrlvkllsrgegirtllwtfiksfqalpyvallivmlff iyavigmqvfgkiaindtteinrnnnfqtfpqavllfrcatgeawqdi mlacmpgkkcapesepsnstegetpcgssfavfyfisfymlcafliinl fvavimdnfdyltrdwsilgphhidefkriwaeydpeakgrikhldvvt llrriqpplgfgklcphrvackrlvsmnmplnsdgtvmfnatlfalvrt alriktegnleqaneelraiikkiwkrtsmklldqvvppagddevtvgk fyatfliqeyfrkfkkrkeqglvgkpsqrnalslqaglrtlhdigpeir raisgdltaeeeldkamkeavsaaseddifrragglfgnhvtyyqsdsr gnfpqtfatqrplhinktgnnqadtespsheklvdstftpssysstgsn aninnanntalgrfphpagyssvtstveghgpplspavrvqeaawklss krchsresqgatvnqeifpdetrsvrmseeaeycsepslstdmfsyqe dehrqltcpeedkreiqpspkrsflrsaslgrrasfhleclkrqkdqgg disqktalplhlvhhqalavaglspllqrshspttfprpcptppvtpgs rgrplrpiptlrlegaesseklnssfpsihcsswseettacsgsssmar rarpvsltvpsqagapgrqfhgsasslveavliseglgqfaqdpkfiev ttqeladacdmtieemenaadnilsggaqqspngtllpfvncrdpgqdr avapedescayalgrgrseealadsrsyvsnl | 11 |
| Mouse CaV1.1 | CACNL1A3 | meppspqdeglrkkqpkkpvpeilprppralfcltlqnplrkacisive wkpfetiilltifancvalavylpmpeddnntlnlglekleyfflivfs ieaamkiiaygflfhqdaylrsgwnvldfiivflgvftvileqvniiqt ntapmsskgagldvkalrafrvlrplrlvsgvpslqvvlnsifkamlpl fhiallvlfmviiyaiiglelfkgkmhktcyfigtdivatvenekpspc artgsgrpctingsecrggwpgpnhgithfdnfgfsmltvyqcismegw tdvlywvndaignewpwiyfvtlillgsffilnlvlgvlsgeftkerek aksrgtfqklrekqqleedlrgymswitqgevmdvddlregklsldegg sdteslyeieglnkiiqfirhwrqwnrvfrwkchdlvkskvfywlvili valntlsiasehhnqplwlthlqdvanrvlltlftiemlmkmyglglrq yfmsifnrfdcfvvcsgileilllvesgamsplgisvlrcirllrlfkit kywtlslsnlvasllnsirsiasllllllflfiiifallgmqlfggrydfe dtevrrsnfdnfpqalisvfqvltgedwnsvmyngimayggptypgvlv ciyfiilfvcgnyillnvflaiavdnlaeaesltsaqkakaeeerkrkm skglpdkseeeratvtkkleqkskgegipttaklkidefesnvnevkdp ypsadfpgddeedepeipvsprprplaelqlkekavpipeassffifsp tnkirvlchrivnatwftnfillfillssaalaaedpiradsmrnqile yfdyvftavftveivlkmttygaflhkgsfcrnyfnildllvvavslis mglessaisvvkilrvlrvlrplrainrakglkhvvqcvfvairtigni vlvttllqfmfacigvqlfkgkfyscndlskmteeeecrgyyyiykdgdp tqielrprqwihndfhfdnvlsammslftvstfegwpqllykaidsnee dtgpvynnrvemaiffiiyiiliaffmmnifvgfvivtfqeqgeteykn celdknqrqcvqyalkarplrcyipknpyqvwyvvtssyfeylmfal imlnticlgmqhynqseqmnhisdilnvaftiiftlemvlkliafkpra yfgdpwnvfdflivigsiidvilseidtflassgglyclgggcgnvdpd esarissaffrlfrvmrlvkllnraegvrtllwtfiksfqalpyvalli vmlffiyavigmqmfgkiamvdgtqinrnnnfqtfpqavllfrcatge awqeillacsygklcdpesdyapgeehtcgtnfayyyfisfymlcafli inlfvavimdnfdyltrdwsilgphhldefkaiwaeydpeakgrikhld | 12 |

TABLE 1-continued

L-Type Voltage Gated Calcium Channels (CaV1)Alpha Subunits

| Name | Gene Symbol | Amino Acid Sequence | SEQ ID NO: |
|---|---|---|---|
| | | vvtllrriqpplgfgkfcphrvackrlvgmnmplnsdgtvtfnatlfal vrtalkiktegnfeqaneelraiikkiwkrtsmklldqvippigddevt vgkfyatfliqehfrkfmkrqeeyygyrpkkdtvgiqaglrtieeeaap eihraisgdptaeeeleramveaameegifrrtgglfgqvdnflertns lppvmanqrplqfaeiemeelespvfledfpqnpgthplarantnnana nvaygnsshrnnpvfssicyereflgeadmpvtregplsqpcsgsgphs rshydklkrpmtqrgmpegqvppspcqlsqaehpvqkegkgptsrflet pnsrnfeehvprnsahrctapatamliqealvrggldslaadanfvmat gqaladacqmepeevevaatellkqespeagpclgalslrsspgppesd dwgsqttlitprceayte | |

Hence, the antibodies described herein specifically bind to a polypeptide of SEQ ID NOs: 5-12, or a fragment or epitope thereof. In certain embodiments, such antibodies specifically bind to a contiguous fragment of about or at least about 5, 6, 7, 8, 9, 10, 11, 12, 13, 14, 15, 16, 17, 18, 19, 20, 21, 22, 23, 24, 25, 26, 27, 28, 29, 30, 40, or 50 or more amino acids of SEQ ID NOs: 5-12. In particular embodiments, the antibodies or antigen-binding fragments thereof specifically bind to one or more sequences in Table E1 (see Example 1; and SEQ ID NOs:1-4).

In certain embodiments, antibodies and antigen-binding fragments thereof as described herein include a heavy chain and a light chain CDR set, respectively interposed between a heavy chain and a light chain framework region (FR) set which provide support to the CDRs and define the spatial relationship of the CDRs relative to each other. As used herein, the term "CDR set" refers to the three hypervariable regions of a heavy or light chain V region. Proceeding from the N-terminus of a heavy or light chain, these regions are denoted as "CDR1," "CDR2," and "CDR3" respectively. An antigen-binding site, therefore, includes six CDRs, comprising the CDR set from each of a heavy and a light chain V region. A polypeptide comprising a single CDR, (e.g., a CDR1, CDR2 or CDR3) is referred to herein as a "molecular recognition unit." Crystallographic analysis of a number of antigen-antibody complexes has demonstrated that the amino acid residues of CDRs form extensive contact with bound antigen, wherein the most extensive antigen contact is with the heavy chain CDR3. Thus, the molecular recognition units are primarily responsible for the specificity of an antigen-binding site.

Exemplary antibody sequences are provided in Table 2 below.

TABLE 2

Exemplary Polypeptide Sequences

| Description | Sequence | SEQ ID NO: |
|---|---|---|
| Heavy chain variable region ($V_H$) Clone 1C10 | SQXXSITCTVSGFSLTSYGVHWVRQSPGKGLEWLGVIWRGGNTDYSAAFM SRLIITKDNSKSQVFFKMNSLQADDTAIYYCVKKAYYYGSNYYTMDYWGQ GTSVTVSS | 13 |
| $V_H$CDR1 Clone 1C10 | GFSLTSYG | 14 |
| $V_H$CDR2 Clone 1C10 | IWRGGNT | 15 |
| $V_H$CDR3 1C10 | VKKAYYYGSNYYTMDY | 16 |
| Light chain variable region ($V_L$) Clone 1C10 | DVLMTQTPLSLPVSLGDQASISCRSSQSIVHSNGNTYLEWYLQKPGQSPK LLIYKVSNRFSGVPDRFSGSGSGTDFTLKISRVEAEDLGVYYCFQGSHVP FTFGSGTKLEIK | 17 |
| $V_H$CDR1 Clone 1C10 | QSIVHSNGNTY | 18 |
| $V_H$CDR2 Clone 1C10 | KVS | 19 |
| $V_H$CDR3 Clone 1C10 | FQGSHVPFT | 20 |
| Heavy chain variable region ($V_H$) Clone 1E7 | KXSGYTFTEYTMHWVKQSHGKSLEWIGGINRNNGGTYYNQKVRGKATLTV DKSSSTAYMELRSLTSEDSAVYYCAHRFAYWGQGTLVTVSA | 21 |

TABLE 2-continued

Exemplary Polypeptide Sequences

| Description | Sequence | SEQ ID NO: |
|---|---|---|
| $V_H$CDR1 Clone 1E7 | GYTFTEYT | 22 |
| $V_H$CDR2 Clone 1E7 | INRNNGGT | 23 |
| $V_H$CDR3 Clone 1E7 | AHRFAY | 24 |
| Light chain variable region ($V_L$) Clone 1E7 | DIVLTQSPASLAVSLGQRATISCRASESVDSYGNSFMHWYQQKPGQPPKLLIYRASNLESGIPARFSGSGSGTDFTLTINPVEADDVATYYCQQSNEDPFTFGSGTKLEIK | 25 |
| $V_H$CDR1 Clone 1E7 | ESVDSYGNSF | 26 |
| $V_H$CDR2 Clone 1E7 | RAS | 27 |
| $V_H$CDR3 Clone 1E7 | QQSNEDPFT | 28 |
| Heavy chain variable region ($V_H$) Clone 1F4 | GGLVQPGGSRKLSCAASGFTFSSFGMHWVRQAPEKGLEWVAYISSGSSTIYYADTVKGRFTISRDNPKNTLFLQMTSLRSEDTAMYYCARRGVRRPGEAMDYWGQGTSVTVSS | 29 |
| $V_H$CDR1 Clone 1F4 | GFTFSSFG | 30 |
| $V_H$CDR2 Clone 1F4 | ISSGSSTI | 31 |
| $V_H$CDR3 Clone 1F4 | ARRGVRRPGEAMDY | 32 |
| Light chain variable region ($V_L$) Clone 1F4 | DIVLTQSPASLAVSLGQRATISCRASKSVSTSGYSYMHWYQQKPGQPPKLLIYLASNLESGVPARFSGSGSGTDFTLNIHPVEEEDAATYYCQHSRELTXSEGGPSWI*N | 33 |
| $V_H$CDR1 Clone 1F4 | KSVSTSGYSY | 34 |
| $V_H$CDR2 Clone 1F4 | LAS | 35 |
| $V_H$CDR3 Clone 1F4 | QHSRELH | 36 |
| Heavy chain variable region ($V_H$) Clone 2D5 | PGASVKISCKTSGYTFTEYTMHWVKQSHGKSLEWIGGINRNNGGTYYNQKVRGKATLTVDKSSSTAYMELRSLTS*GFCSL | 37 |
| $V_H$CDR1 Clone 2D5 | GYTFTEYT | 38 |
| $V_H$CDR2 Clone 2D5 | INRNNGGT | 39 |
| $V_H$CDR3 | ----- | 40 |
| Light chain variable region ($V_L$) Clone 2D5 | DIVLTQSPASLAVSLGQRATISCRASKSVSTSGYSYMHWYQQKPGQPPKLLIYLASNLESGVPARFSGSGSGTDFTLNIHPVEEEDAATYYCQHIRELTRSEGGPSWK*N | 41 |
| $V_H$CDR1 Clone 2D5 | KSVSTSGYSY | 42 |
| $V_H$CDR2 Clone 2D5 | LAS | 43 |

TABLE 2-continued

Exemplary Polypeptide Sequences

| Description | Sequence | SEQ ID NO: |
|---|---|---|
| V$_H$CDR3 Clone 2D5 | QHIRELT | 44 |
| Heavy chain variable region (V$_H$) Clone 5F4 | LVQPGXXLKLSCKSNEYEFPSHDMSWVRTTPEKRLELVAAINSDGGNTYY PDTMERRFIISRDNTKKTLYLQMSSLRSEDTALYYCARHSMVTPDLLTGA KGLWSLSLQ | 45 |
| V$_H$CDR1 Clone 5F4 | EYEFPSHD | 46 |
| V$_H$CDR2 Clone 5F4 | INSDGGNT | 47 |
| V$_H$CDR3 Clone 5F4 | ARHSMVTPDLL | 48 |
| Light chain variable region (V$_L$) Clone 5F4 | DIVLTQSPASLAVSLGQRATISCRASKSVSTSGYSYMHWYQQKPGQPPKL LIYLASNLESGVPARFSGSGSGTDFTLNIHPVEEEDAATYYCQHIRELTR SEGGPSWK*N | 49 |
| V$_H$CDR1 Clone 5F4 | KSVSTSGYSY | 50 |
| V$_H$CDR2 Clone 5F4 | LAS | 51 |
| V$_H$CDR3 Clone 5F4 | QHIRELTR | 52 |
| Heavy chain variable region (V$_H$) Clone 6C6 | PGASVKISCKGSGYTFTDYTMHWVKQSHAKSLEWIGVISSYSGNTNYNQK FEGKATMTVDKSSSTAYMELARLTSEDSAIYYCARH | 53 |
| V$_H$CDR1 Clone 6C6 | GYTFTDYT | 54 |
| V$_H$CDR2 Clone 6C6 | ISSYSGNT | 55 |
| V$_H$CDR3 Clone 6C6 | ----- | 56 |
| Light chain variable region (V$_L$) Clone 6C6 | DVVMTQTPLTLSVTIGQPASISCKSSQSLLDSDGKTYLNWLLQRPGQSPK RLIYLVSKLDSGVPDRFTGSGSGTDFTLKISRVEAEDLGVYYCWQGTHFP FTFGSGTKLEIK | 57 |
| V$_H$CDR1 Clone 6C6 | QSLLDSDGKTY | 58 |
| V$_H$CDR2 Clone 6C6 | LVS | 59 |
| V$_H$CDR3 Clone 6C6 | WQGTHFPFT | 60 |
| Heavy chain variable region (V$_H$) Clone 6E1 | LVKPGGSLKLSCAASGFTFSSYAMSWVRQTPEKRLEWVASISSGGSTYYP DSVKGRFTISRDNARNILYLQMSSLRSEDTAMYYCARLGDGYYPFAYWGQ GTLVTVSA | 61 |
| V$_H$CDR1 Clone 6E1 | GFTFSSYA | 62 |
| V$_H$CDR2 Clone 6E1 | ISSGGST | 63 |
| V$_H$CDR3 Clone 6E1 | ARLGDGYYPFAY | 64 |

TABLE 2-continued

Exemplary Polypeptide Sequences

| Description | Sequence | SEQ ID NO: |
|---|---|---|
| Light chain variable region ($V_L$) Clone 6E1 | ----- | 65 |
| $V_H$CDR1 Clone 6E1 | ----- | 66 |
| $V_H$CDR2 Clone 6E1 | ----- | 67 |
| $V_H$CDR3 Clone 6E1 | ----- | 68 |
| Heavy chain variable region ($V_H$) Clone 6H7 | KGXGYTFTDYTMHWVKQSHAKSLEWIGVISSYSGNTNYNQKFEGKATMTVDKSSSTAYMELARLTSEDSAIYYCARHYGYDVTFWGQGTLVTVSA | 69 |
| $V_H$CDR1 Clone 6H7 | GYTFTDYT | 70 |
| $V_H$CDR2 Clone 6H7 | ISSYSGNT | 71 |
| $V_H$CDR3 Clone 6H7 | ARHYGYDVTF | 72 |
| Light chain variable region ($V_L$) Clone 6H7 | DIVLTQSPASLAVSLGQRATISCRASKSVSTSGYSYMHWYQQKPGQPPKLLIYLASNLESGVPARFSGSGSGTDFTLNIHPVEEEXAATYYCQHIRXAYTFGGGTKL | 73 |
| $V_H$CDR1 Clone 6H7 | KSVSTSGYSY | 74 |
| $V_H$CDR2 Clone 6H7 | LAS | 75 |
| $V_H$CDR3 Clone 6H7 | QHIRELTR | 76 |
| Heavy chain variable region ($V_H$) Clone 8G1 | LVQPGGSRKLSCAASGFTFSNFGMHWVRQAPEKGLEWVAYISSGSNTIYYADTVKGRFTISRDNGKNTLFLQMTSLRSEDTAIYYCASYGNYAAYWGQGTLVTVSA | 77 |
| $V_H$CDR1 Clone 8G1 | GFTFSNFG | 78 |
| $V_H$CDR2 Clone 8G1 | ISSGSNTI | 79 |
| $V_H$CDR3 Clone 8G1 | ASYGNYAAY | 80 |
| Light chain variable region ($V_L$) Clone 8G1 | DIVLTQSPASLAVSLGQRATISCRASKSVSTSGYSYMHWYQQKPGQPPKLLIYLASNLESGVPARFSGSGSGTDFTLNIHPVEEEXAATYYCQHIRXAYTFGGGTKL | 81 |
| $V_H$CDR1 Clone 8G1 | KSVSTSGYSY | 82 |
| $V_H$CDR2 Clone 8G1 | LAS | 83 |
| $V_H$CDR3 Clone 8G1 | QHIRXAYT | 84 |

TABLE 2-continued

Exemplary Polypeptide Sequences

| Description | Sequence | SEQ ID NO: |
|---|---|---|
| Heavy chain variable region (V$_H$)Clone 9C3 | LSITCTVSGFSLTDYGVSWIRQSPGKGLEWLGIIWGGGSTYYNSVLKSRL SINKDNXKSQVFLKMNSLQTDDTAMYYCAKHRGDWGQGTLVTVSA | 85 |
| V$_H$CDR1 Clone 9C3 | GFSLTDYG | 86 |
| V$_H$CDR2 Clone 9C3 | IWGGGST | 87 |
| V$_H$CDR3 Clone 9C3 | AKHRGD | 88 |
| Light chain variable region (V$_L$) Clone 9C3 | DIVLTQSPASLAVSLGQRATISCRASKSVSTSGYSYMHWYQQKPGQPPKL LIYLASNLESGVPARFSGSGSGTDFTLNIHPVEEEXAAXYYCQHIRELTR SEGGPSWK | 89 |
| V$_H$CDR1 Clone 9C3 | KSVSTSGYSY | 90 |
| V$_H$CDR2 Clone 9C3 | LAS | 91 |
| V$_H$CDR3 Clone 9C3 | STLGSLH | 92 |
| Heavy chain variable region (V$_H$)Clone 1D2 | ----- | 93 |
| V$_H$CDR1 Clone 1D2 | ----- | 94 |
| V$_H$CDR2 Clone 1D2 | ----- | 95 |
| V$_H$CDR3 Clone 1D2 | ----- | 96 |
| Light chain variable region (V$_L$) Clone 1D2 | DIVLTQSPASLAVSLGQRATISCRASKSVSTSGYSYMHWYQQKPGQPPKL LIYLASNLESGVPARFSGSGSGTDFTLNIHPVEEEXAATYYCQHIRELTR SEGGPSWK*N | 97 |
| V$_H$CDR1 Clone 1D2 | KSVSTSGYSY | 98 |
| V$_H$CDR2 Clone 1D2 | LAS | 99 |
| V$_H$CDR3 Clone 1D2 | QHIRELT | 100 |
| Heavy chain variable region (V$_H$)Clone 5G10 | ----- | 101 |
| V$_H$CDR1 Clone 5G10 | ----- | 102 |
| V$_H$CDR2 Clone 5G10 | ----- | 103 |
| V$_H$CDR3 Clone 5G10 | ----- | 104 |

TABLE 2-continued

Exemplary Polypeptide Sequences

| Description | Sequence | SEQ ID NO: |
|---|---|---|
| Light chain variable region (V$_L$) Clone 5G10 | DIVLTQSPASLAVSLGQRATISCRASKSVSTSGYSYMHWYQQKPGQPPKL LIYLASNLESGVPARFSGSGSGTDFTLNIHPVEEEDAATYYCQHIRELTR SEGGPSWK | 105 |
| V$_H$CDR1 Clone 5G10 | KSVSTSGYSY | 106 |
| V$_H$CDR2 Clone 5G10 | LAS | 107 |
| V$_H$CDR3 Clone 5G10 | CQHIRELTR | 108 |

Hence, in certain embodiments, an antibody, or antigen-binding fragment thereof, comprises one or more of the sequences in Table 2 (e.g., SEQ ID NOs:13-108), including combinations and variants thereof. For instance, in particular embodiments, the antibody, or antigen-binding fragment thereof, comprises the V$_H$ sequence set forth SEQ ID NO:13, and/or the V$_L$ sequence set forth in SEQ ID NO:17. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 13 (e.g., SEQ ID NOS:14-16 respectively), and/or a light chain variable region (V$_L$) that comprises complementary determining region V$_L$CDR1, V$_L$CDR2, and/or V$_L$CDR3 sequence contained in SEQ ID NO:17 (e.g., SEQ ID NOS:18-20, respectively).

In some embodiments, the antibody, or antigen-binding fragment thereof, comprises the V$_H$ sequence set forth SEQ ID NO:21, and/or the V$_L$ sequence set forth in SEQ ID NO:25. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 21 (e.g., SEQ ID NOS:22-24 respectively), and/or a light chain variable region (V$_L$) that comprises complementary determining region V$_L$CDR1, V$_L$CDR2, and/or V$_L$CDR3 sequence contained in SEQ ID NO:25 (e.g., SEQ ID NOS:26-28, respectively).

In some embodiments, the antibody, or antigen-binding fragment thereof, comprises the V$_H$ sequence set forth SEQ ID NO:29, and/or the V$_L$ sequence set forth in SEQ ID NO:33. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 29 (e.g., SEQ ID NOS:30-32 respectively), and/or a light chain variable region (V$_L$) that comprises complementary determining region V$_L$CDR1, V$_L$CDR2, and/or V$_L$CDR3 sequence contained in SEQ ID NO:33 (e.g., SEQ ID NOS:34-36, respectively).

In some embodiments, the antibody, or antigen-binding fragment thereof, comprises the V$_H$ sequence set forth SEQ ID NO:37, and/or the V$_L$ sequence set forth in SEQ ID NO:41. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 37 (e.g., SEQ ID NOS:38-40 respectively), and/or a light chain variable region (V$_L$) that comprises complementary determining region V$_L$CDR1, V$_L$CDR2, and/or V$_L$CDR3 sequence contained in SEQ ID NO:41 (e.g., SEQ ID NOS:42-44, respectively).

In some embodiments, the antibody, or antigen-binding fragment thereof, comprises the V$_H$ sequence set forth SEQ ID NO:45, and/or the V$_L$ sequence set forth in SEQ ID NO:49. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 45 (e.g., SEQ ID NOS:46-48 respectively), and/or a light chain variable region (V$_L$) that comprises complementary determining region V$_L$CDR1, V$_L$CDR2, and/or V$_L$CDR3 sequence contained in SEQ ID NO:49 (e.g., SEQ ID NOS:50-52, respectively).

In some embodiments, the antibody, or antigen-binding fragment thereof, comprises the V$_H$ sequence set forth SEQ ID NO:53, and/or the V$_L$ sequence set forth in SEQ ID NO:57. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 53 (e.g., SEQ ID NOS:54-56 respectively), and/or a light chain variable region (V$_L$) that comprises complementary determining region V$_L$CDR1, V$_L$CDR2, and/or V$_L$CDR3 sequence contained in SEQ ID NO:57 (e.g., SEQ ID NOS:58-60, respectively).

In some embodiments, the antibody, or antigen-binding fragment thereof, comprises the V$_H$ sequence set forth SEQ ID NO:61, and/or the V$_L$ sequence set forth in SEQ ID NO:65. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 61 (e.g., SEQ ID NOS:62-64 respectively), and/or a light chain variable region (V$_L$) that comprises complementary determining region V$_L$CDR1, V$_L$CDR2, and/or V$_L$CDR3 sequence contained in SEQ ID NO:65 (e.g., SEQ ID NOS:66-68, respectively).

In some embodiments, the antibody, or antigen-binding fragment thereof, comprises the V$_H$ sequence set forth SEQ ID NO:69, and/or the V$_L$ sequence set forth in SEQ ID NO:73. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 69 (e.g., SEQ ID NOS:70-72 respectively), and/or a light chain variable region (V$_L$) that comprises complementary determining region V$_L$CDR1, V$_L$CDR2, and/or V$_L$CDR3 sequence contained in SEQ ID NO:73 (e.g., SEQ ID NOS:74-76, respectively).

In some embodiments, the antibody, or antigen-binding fragment thereof, comprises the V$_H$ sequence set forth SEQ ID NO:77, and/or the V$_L$ sequence set forth in SEQ ID NO:81. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 77 (e.g., SEQ ID NOS:78-80 respectively), and/or a light chain variable region (V$_L$) that comprises complementary determining region V$_L$CDR1, V$_L$CDR2, and/or V$_L$CDR3 sequence contained in SEQ ID NO:81 (e.g., SEQ ID NOS:82-84, respectively).

In some embodiments, the antibody, or antigen-binding fragment thereof, comprises the V$_H$ sequence set forth SEQ ID NO:85, and/or the V$_L$ sequence set forth in SEQ ID NO:89. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 85 (e.g., SEQ ID NOS:86-88 respectively), and/or a light chain variable region (V$_L$) that comprises complementary determining region V$_L$CDR1, V$_L$CDR2, and/or V$_L$CDR3 sequence contained in SEQ ID NO:89 (e.g., SEQ ID NOS:90-92, respectively).

In some embodiments, the antibody, or antigen-binding fragment thereof, comprises the V$_H$ sequence set forth SEQ ID NO:93, and/or the V$_L$ sequence set forth in SEQ ID NO:97. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 93 (e.g., SEQ ID NOS:94-96 respectively), and/or a light chain variable region (V$_L$) that comprises complementary determining region V$_L$CDR1, V$_L$CDR2, and/or V$_L$CDR3 sequence contained in SEQ ID NO:97 (e.g., SEQ ID NOS:98-100, respectively).

In some embodiments, the antibody, or antigen-binding fragment thereof, comprises the V$_H$ sequence set forth SEQ ID NO:101, and/or the V$_L$ sequence set forth in SEQ ID NO:105. In some embodiments, the antibody, or antigen-binding fragment thereof, comprises a heavy chain variable region (V$_H$) that comprises complementary determining region V$_H$CDR1, V$_H$CDR2, and/or V$_H$CDR3 sequences contained in SEQ ID NO: 101 (e.g., SEQ ID NOS:102-104 respectively), and/or a light chain variable region (V$_L$) that comprises complementary determining region V$_L$CDR1, V$_L$CDR2, and/or V$_L$CDR3 sequence contained in SEQ ID NO:105 (e.g., SEQ ID NOS:106-108, respectively).

In some embodiments, the CDR sequences are defined according to the rules of Kabat, Clothia, or combinations thereof (see also IMGT®, the international ImMunoGeneTics information) System®.

As used herein, the term "FR set" refers to the four flanking amino acid sequences which frame the CDRs of a CDR set of a heavy or light chain V region. Some FR residues may contact bound antigen; however, FRs are primarily responsible for folding the V region into the antigen-binding site, particularly the FR residues directly adjacent to the CDRs. Within FRs, certain amino residues and certain structural features are very highly conserved. In this regard, all V region sequences contain an internal disulfide loop of around 90 amino acid residues. When the V regions fold into a binding-site, the CDRs are displayed as projecting loop motifs which form an antigen-binding surface. It is generally recognized that there are conserved structural regions of FRs which influence the folded shape of the CDR loops into certain "canonical" structures—regardless of the precise CDR amino acid sequence. Further, certain FR residues are known to participate in non-covalent interdomain contacts which stabilize the interaction of the antibody heavy and light chains.

The structures and locations of immunoglobulin variable domains may be determined by reference to Kabat, E. A. et al., Sequences of Proteins of Immunological Interest. 4th Edition. US Department of Health and Human Services. 1987, and updates thereof.

In some embodiments, the antibody is a "monoclonal antibody," which refers to a homogeneous antibody population wherein the monoclonal antibody is comprised of amino acids (naturally occurring and non-naturally occurring) that are involved in the selective binding of an epitope. Monoclonal antibodies are highly specific, being directed against a single epitope. The term "monoclonal antibody" encompasses not only intact monoclonal antibodies and full-length monoclonal antibodies, but also fragments thereof (such as Fab, Fab', F(ab')$_2$, Fv), single chain (ScFv), variants thereof, fusion proteins comprising an antigen-binding portion, humanized monoclonal antibodies, chimeric monoclonal antibodies, and any other modified configuration of the immunoglobulin molecule that comprises an antigen-binding fragment (epitope recognition site) of the required specificity and the ability to bind to an epitope. It is not intended to be limited as regards the source of the antibody or the manner in which it is made (e.g., by hybridoma, phage selection, recombinant expression, transgenic animals). The term includes whole immunoglobulins as well as the fragments, etc. described herein under the definition of "antibody."

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')$_2$ fragment which comprises both antigen-binding sites. An Fv fragment for use according to certain embodiments can be produced by preferential proteolytic cleavage of an IgM, and on rare occasions of an IgG or IgA immunoglobulin molecule. Fv fragments are, however, more commonly derived using recombinant techniques known in the art. The Fv fragment includes a non-covalent V$_H$::V$_L$ heterodimer including an antigen-binding site which retains much of the antigen recognition and binding capabilities of the native antibody molecule. See Inbar et al., *PNAS USA.* 69:2659-2662, 1972; Hochman et al., *Biochem.* 15:2706-2710, 1976; and Ehrlich et al., *Biochem.* 19:4091-4096, 1980.

In certain embodiments, single chain Fv or scFV antibodies are contemplated. For example, Kappa bodies (III et al., Prot. Eng. 10:949-57, 1997); minibodies (Martin et al., *EMBO J* 13:5305-9, 1994); diabodies (Holliger et al., *PNAS* 90: 6444-8, 1993); or Janusins (Traunecker et al., *EMBO J* 10: 3655-59, 1991; and Traunecker et al., *Int. J. Cancer Suppl.* 7:51-52, 1992), may be prepared using standard molecular biology techniques following the teachings of the present application with regard to selecting antibodies having the desired specificity.

A single chain Fv (sFv) polypeptide is a covalently linked V$_H$::V$_L$ heterodimer which is expressed from a gene fusion including $V_H$- and $V_L$-encoding genes linked by a peptide-encoding linker. Huston et al. (*PNAS USA.* 85(16):5879-5883, 1988). A number of methods have been described to discern chemical structures for converting the naturally aggregated—but chemically separated—light and heavy polypeptide chains from an antibody V region into an sFv molecule which will fold into a three dimensional structure substantially similar to the structure of an antigen-binding site. See, e.g., U.S. Pat. Nos. 5,091,513 and 5,132,405, to Huston et al.; and U.S. Pat. No. 4,946,778, to Ladner et al.

In certain embodiments, the antibodies or antigen-binding fragments thereof are humanized. These embodiments refer to a chimeric molecule, generally prepared using recombinant techniques, having an antigen-binding site derived from an immunoglobulin from a non-human species and the remaining immunoglobulin structure of the molecule based upon the structure and/or sequence of a human immunoglobulin. The antigen-binding site may comprise either complete variable domains fused onto constant domains or only the CDRs grafted onto appropriate framework regions in the variable domains. Epitope binding sites may be wild-type or modified by one or more amino acid substitutions. This eliminates the constant region as an immunogen in human individuals, but the possibility of an immune response to the foreign variable region remains (LoBuglio et al., *PNAS USA* 86:4220-4224, 1989; Queen et al., *PNAS USA.* 86:10029-10033, 1988; Riechmann et al., *Nature.* 332:323-327, 1988). Illustrative methods for humanization of antibodies include the methods described in U.S. Pat. No. 7,462,697.

Another approach focuses not only on providing human-derived constant regions, but modifying the variable regions as well so as to reshape them as closely as possible to human form. It is known that the variable regions of both heavy and light chains contain three complementarity-determining regions (CDRs) which vary in response to the epitopes in question and determine binding capability, flanked by four framework regions (FRs) which are relatively conserved in a given species and which putatively provide a scaffolding for the CDRs. When nonhuman antibodies are prepared with respect to a particular epitope, the variable regions can be "reshaped" or "humanized" by grafting CDRs derived from nonhuman antibody on the FRs present in the human antibody to be modified. Application of this approach to various antibodies has been reported by Sato et al., *Cancer Res.* 53:851-856, 1993; Riechmann et al., *Nature* 332:323-327, 1988; Verhoeyen et al., *Science* 239:1534-1536, 1988; Kettleborough et al., *Protein Engineering.* 4:773-3783, 1991; Maeda et al., *Human Antibodies Hybridoma* 2:124-134, 1991; Gorman et al., *PNAS USA.* 88:4181-4185, 1991; Tempest et al., *Bio/Technology* 9:266-271, 1991; Co et al., *PNAS USA.* 88:2869-2873, 1991; Carter et al., *PNAS USA.* 89:4285-4289, 1992; and Co et al., *J Immunol.* 148:1149-1154, 1992. In some embodiments, humanized antibodies preserve all CDR sequences (for example, a humanized mouse antibody which contains all six CDRs from the mouse antibodies). In other embodiments, humanized antibodies have one or more CDRs (one, two, three, four, five, six) which are altered with respect to the original antibody, which are also termed one or more CDRs "derived from" one or more CDRs from the original antibody.

The antibodies, and antigen-binding fragments thereof, described herein can comprise the light chain constant regions or heavy chain constant regions (e.g., Fc regions) of any variety of immunoglobulin subtypes (e.g., IgA, IgD, IgE, IgG, IgM, including subclasses and combinations thereof, e.g., IgG1, IgG2, IgG2, IgG3, IgG4), from any variety of mammals such as mouse, human, rabbit, or goat. The "Fc region" sequence is usually derived from the heavy chain of an immunoglobulin (Ig) molecule. A typical Ig molecule is composed of two heavy chains and two light chains. The heavy chains can be divided into at least three functional regions: the Fd region, the Fc region (fragment crystallizable region), and the hinge region, the latter being found only in IgG, IgA, and IgD immunoglobulins. The Fd region comprises the variable (VH) and constant (CH1) domains of the heavy chains, and together with the variable (VL) and constant (CL) domains of the light chains forms the antigen-binding fragment or Fab region.

The Fc region of IgG, IgA, and IgD immunoglobulins comprises the heavy chain constant domains 2 and 3, designated respectively as CH2 and CH3 regions; and the Fc region of IgE and IgM immunoglobulins comprises the heavy chain constant domains 2, 3, and 4, designated respectively as CH2, CH3, and CH4 regions. The Fc region is mainly responsible for the immunoglobulin effector functions, which include, for example, complement fixation and binding to cognate Fc receptors of effector cells.

The hinge region (found in IgG, IgA, and IgD) acts as a flexible spacer that allows the Fab portion to move freely in space relative to the Fc region. In contrast to the constant regions, the hinge regions are structurally diverse, varying in both sequence and length among immunoglobulin classes and subclasses (see supra). The hinge region may also contain one or more glycosylation site(s), which include a number of structurally distinct types of sites for carbohydrate attachment. For example, IgA1 contains five glycosylation sites within a 17 amino acid segment of the hinge region, conferring significant resistance of the hinge region polypeptide to intestinal proteases. Residues in the hinge proximal region of the CH2 domain can also influence the specificity of the interaction between an immunoglobulin and its respective Fc receptor(s) (see, e.g., Shin et al., *Intern. Rev. Immunol.* 10:177-186, 1993).

The term "Fc region" or "Fc fragment" or "Fc" as used herein, thus refers to a portion of an antibody, or antigen-binding fragment thereof, which contains one or more of a CH2 region, a CH3 region, and/or a CH4 region from one or more selected immunoglobulin(s), including fragments and variants and combinations thereof. An "Fc region" may also include one or more hinge region(s) of the heavy chain constant region of an immunoglobulin. In certain embodiments, the Fc region does not contain one or more of the CH1, CL, VL, and/or VH regions of an immunoglobulin.

The Fc region can comprise the CH2 region, CH3 region, CH4 region, and/or hinge region(s) of any one or more immunoglobulin classes, including but not limited to IgA, IgD, IgE, IgG, IgM, including subclasses and combinations thereof. In some embodiments, the Fc region is from an IgA immunoglobulin (e.g., mouse, human, rabbit, goat), including subclasses IgA1 and/or IgA2. In certain embodiments, the Fc region is from an IgD immunoglobulin (e.g., mouse, human, rabbit, goat). In particular embodiments, the Fc region is from an IgE immunoglobulin (e.g., mouse, human, rabbit, goat). In some embodiments, the Fc region is from an IgG immunoglobulin (e.g., mouse, human, rabbit, goat), including subclasses IgG1, IgG2, IgG2, IgG3, and/or IgG4. In certain embodiments, the Fc region is from an IgM immunoglobulin (e.g., mouse, human, rabbit, goat).

Also included are antibodies, or antigen-binding fragments thereof, which comprise "variants" of the sequences described herein (e.g., Table 2, SEQ ID NOS: 13-108). A "variant" sequence, as the term is used herein, refers to a polypeptide or polynucleotide sequence that differs from a reference sequence disclosed herein (e.g., Table 2, SEQ ID NOS: 13-108, by 1, 2, 3, 4, 5, 6, 7, 8, 9, 10, 11, 12, 13, 14, 15, 16, 17, 18, 19, 29 or more substitutions, deletions (e.g., truncations), additions, and/or insertions. Certain variants thus include fragments of a reference sequence described herein. Variant polypeptides are biologically active, that is, they continue to possess the binding activity of a reference polypeptide. Such variants may result from, for example, genetic polymorphism and/or from human manipulation.

In many instances, a biologically active variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides described herein and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence according to Table A below.

TABLE A

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their utility.

In making such changes, the hydropathic index of amino acids may be considered. The importance of the hydropathic amino acid index in conferring interactive biologic function on a protein is generally understood in the art (Kyte & Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte & Doolittle, 1982). These values are: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred.

It is also understood in the art that the substitution of like amino acids can be made effectively on the basis of hydrophilicity. U.S. Pat. No. 4,554,101 (specifically incorporated herein by reference in its entirety), states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his.

A variant may also, or alternatively, contain non-conservative changes. In a certain embodiment, variant polypeptides differ from a native or reference sequence by substitution, deletion or addition of about or fewer than about 10, 9, 8, 7, 6, 5, 4, 3, 2 amino acids, or even 1 amino acid. Variants may also (or alternatively) be modified by, for example, the deletion or addition of amino acids that have minimal influence on the immunogenicity, secondary structure, enzymatic activity, and/or hydropathic nature of the polypeptide.

In general, variants will display at least about 30%, 40%, 50%, 55%, 60%, 65%, 70%, 75%, 80%, 85%, 90%, 91%, 92%, 93%, 94%, 95%, 96%, 97%, 98%, 99% similarity or sequence identity or sequence homology to a reference polypeptide sequence (e.g., Table 2, SEQ ID NOs: 13-108). Moreover, sequences differing from the reference sequences by the addition (e.g., C-terminal addition, N-terminal addition, both), deletion, truncation, insertion, or substitution (e.g., conservative substitution) of about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100 amino acids (including all integers and ranges in between) but which retain the properties or activities of a parent or reference polypeptide sequence are contemplated.

In some embodiments, variant polypeptides differ from reference sequence by at least one but by less than 50, 40, 30, 20, 15, 10, 9, 8, 7, 6, 5, 4, 3 or 2 amino acid residue(s). In other embodiments, variant polypeptides differ from a reference sequence by at least 1% but less than 20%, 15%, 10% or 5% of the residues. (If this comparison requires alignment, the sequences should be aligned for maximum similarity. In some instances, "looped" out sequences from deletions or insertions, or mismatches, are considered differences.

Calculations of sequence similarity or sequence identity between sequences (the terms are used interchangeably herein) are performed as follows. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In certain embodiments, the length of a reference sequence aligned for comparison purposes is at least 30%, preferably at least 40%, more preferably at least 50%, 60%, and even more preferably at least 70%, 80%, 90%, 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position.

The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a certain embodiment, the percent identity between two amino acid sequences is determined using the Needleman and Wunsch, (J. Mol. Biol. 48: 444-453, 1970) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6. In certain embodiments, the percent identity between two nucleotide sequences is determined using the GAP program in the GCG software package, using a NWSgapdna.CMP matrix and a gap weight of 40, 50, 60, 70, or 80 and a length weight of 1, 2, 3, 4, 5, or 6. A preferred set of parameters includes a Blossum 62 scoring matrix with a gap penalty of 12, a gap extend penalty of 4, and a frameshift gap penalty of 5.

The percent identity between two amino acid or nucleotide sequences can be determined using the algorithm of E. Meyers and W. Miller (*Cabios.* 4:11-17, 1989) which has been incorporated into the ALIGN program (version 2.0), using a PAM120 weight residue table, a gap length penalty of 12 and a gap penalty of 4.

The nucleic acid and protein sequences described herein can be used as a "query sequence" to perform a search against public databases to, for example, identify other family members or related sequences. Such searches can be performed using the NBLAST and XBLAST programs (version 2.0) of Altschul, et al., (1990, *J. Mol. Biol,* 215: 403-10). BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (Nucleic Acids Res. 25: 3389-3402, 1997). When utilizing BLAST and Gapped BLAST programs, the default parameters of the respective programs (e.g., XBLAST and NBLAST) can be used.

In one embodiment, as noted above, polynucleotides and/or polypeptides can be evaluated using a BLAST alignment tool. A local alignment consists simply of a pair of sequence segments, one from each of the sequences being compared. A modification of Smith-Waterman or Sellers algorithms will find all segment pairs whose scores cannot be improved by extension or trimming, called high-scoring segment pairs (HSPs). The results of the BLAST alignments include statistical measures to indicate the likelihood that the BLAST score can be expected from chance alone.

The raw score, S, is calculated from the number of gaps and substitutions associated with each aligned sequence wherein higher similarity scores indicate a more significant alignment. Substitution scores are given by a look-up table (see PAM, BLOSUM).

Gap scores are typically calculated as the sum of G, the gap opening penalty and L, the gap extension penalty. For a gap of length n, the gap cost would be G+Ln. The choice of gap costs, G and L is empirical, but it is customary to choose a high value for G (10-15), e.g., 11, and a low value for L (1-2) e.g., 1.

The bit score, 5', is derived from the raw alignment score S in which the statistical properties of the scoring system used have been taken into account. Bit scores are normalized with respect to the scoring system, therefore they can be used to compare alignment scores from different searches. The terms "bit score" and "similarity score" are used interchangeably. The bit score gives an indication of how good the alignment is; the higher the score, the better the alignment.

The E-Value, or expected value, describes the likelihood that a sequence with a similar score will occur in the database by chance. It is a prediction of the number of different alignments with scores equivalent to or better than S that are expected to occur in a database search by chance. The smaller the E-Value, the more significant the alignment. For example, an alignment having an E value of $e^{-117}$ means that a sequence with a similar score is very unlikely to occur simply by chance. Additionally, the expected score for aligning a random pair of amino acids is required to be negative, otherwise long alignments would tend to have high score independently of whether the segments aligned were related. Additionally, the BLAST algorithm uses an appropriate substitution matrix, nucleotide or amino acid and for gapped alignments uses gap creation and extension penalties. For example, BLAST alignment and comparison of polypeptide sequences are typically done using the BLOSUM62 matrix, a gap existence penalty of 11 and a gap extension penalty of 1.

In one embodiment, sequence similarity scores are reported from BLAST analyses done using the BLOSUM62 matrix, a gap existence penalty of 11 and a gap extension penalty of 1.

In a particular embodiment, sequence identity/similarity scores provided herein refer to the value obtained using GAP Version 10 (GCG, Accelrys, San Diego, Calif.) using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix (Henikoff and Henikoff, *PNAS USA.* 89:10915-10919, 1992). GAP uses the algorithm of Needleman and Wunsch (*J Mol Biol.* 48:443-453, 1970) to find the alignment of two complete sequences that maximizes the number of matches and minimizes the number of gaps.

In one particular embodiment, the variant polypeptide comprises an amino acid sequence that can be optimally aligned with a reference polypeptide sequence (see, e.g., the Tables, the Sequence Listing; SEQ ID NOs:1-108) to generate a BLAST bit scores or sequence similarity scores of at least about 50, 60, 70, 80, 90, 100, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, or more, including all integers and ranges in between, wherein the BLAST alignment used the BLOSUM62 matrix, a gap existence penalty of 11, and a gap extension penalty of 1.

As noted above, a reference polypeptide may be altered in various ways including amino acid substitutions, deletions, truncations, additions, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (*PNAS USA.* 82: 488-492, 1985); Kunkel et al., (*Methods in Enzymol.* 154: 367-382, 1987), U.S. Pat. No. 4,873,192, Watson, J. D. et al., ("Molecular Biology of the Gene," Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) Atlas of Protein Sequence and Structure (Natl. Biomed. Res. Found., Washington, D.C.).

Methods for screening gene products of combinatorial libraries made by such modifications, and for screening cDNA libraries for gene products having a selected property are known in the art. Such methods are adaptable for rapid screening of the gene libraries generated by combinatorial mutagenesis of reference polypeptides. As one example, recursive ensemble mutagenesis (REM), a technique which enhances the frequency of functional mutants in the libraries, can be used in combination with the screening assays to identify polypeptide variants (Arkin and Yourvan, *PNAS USA* 89: 7811-7815, 1992; Delgrave et al., *Protein Engineering.* 6: 327-331, 1993).

Also included are antibodies, or antigen-binding fragments thereof, which "competitively inhibit" the binding of the antibodies described herein (see, e.g., Example 1) to a human or mouse L-type voltage-gated calcium channel alpha 1 subunit polypeptide. Methods for determining mAb specificity and affinity by competitive inhibition can be found, for example, in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993); Muller, Meth. Enzymol. 92:589-601, 1983; and Jia, X-C. et al., J. Immunol. Methods 288:91-98, 2004, each of which is incorporated reference.

Particular embodiments include antibodies, or antigen-binding fragments thereof, which competitively inhibit the binding of an antibody to an amino acid sequence on a human or mouse L-type voltage-gated calcium channel (SEQ ID NOs: 1-4). In specific embodiments, the antibody (which is competitively inhibited) is a monoclonal antibody, for example, a whole monoclonal antibody such as an IgG antibody, as described herein. In particular embodiments, the antibody (which is competitively inhibited) is an IgG1 or IgG2a immunoglobulin subtype.

In certain embodiments, the antibody, or antigen-binding fragment thereof, is conjugated or covalently attached to a detectable entity, for example, to facilitate detection. Exemplary detectable entities include, without limitation, iodine-based labels, radioisotopes, fluorophores/fluorescent dyes, and nanoparticles.

Exemplary iodine-based labels include diatrizoic acid (Hypaque®, GE Healthcare) and its anionic form, diatrizoate. Diatrizoic acid is a radio-contrast agent used in advanced X-ray techniques such as CT scanning. Also included are iodine radioisotopes, described below.

Exemplary radioisotopes that can be used as detectable entities include $^{32}P$, $^{33}P$, $^{35}S$, $^{3}H$, $^{18}F$, 11C, $^{13}N$, $^{15}O$, $^{111}In$, $^{169}Yb$, $^{99}mTC$, $^{55}Fe$, and isotopes of iodine such as $^{123}I$, $^{124}I$, $^{125}I$, and $^{131}I$. These radioisotopes have different half-lives, types of decay, and levels of energy which can be tailored to match the needs of a particular protocol.

Examples of fluorophores or fluorochromes that can be used as directly detectable entities include fluorescein, tetramethylrhodamine, Texas Red, Oregon Green®, and a number of others (e.g., Haugland, Handbook of Fluorescent Probes—9th Ed., 2002, Molec. Probes, Inc., Eugene Oreg.; Haugland, The Handbook: A Guide to Fluorescent Probes and Labeling Technologies-10th Ed., 2005, Invitrogen, Carlsbad, Calif.). Also included are light-emitting or otherwise detectable dyes. The light emitted by the dyes can be visible light or invisible light, such as ultraviolet or infrared light. In exemplary embodiments, the dye may be a fluorescence resonance energy transfer (FRET) dye; a xanthene dye, such as fluorescein and rhodamine; a dye that has an amino group in the alpha or beta position (such as a naphthylamine dye, 1-dimethylaminonaphthyl-5-sulfonate, 1-anilino-8-naphthalende sulfonate and 2-p-touidinyl-6-naphthalene sulfonate); a dye that has 3-phenyl-7-isocyanatocoumarin; an acridine, such as 9-isothiocyanatoacridine and acridine orange; a pyrene, a bensoxadiazole and a stilbene; a dye that has 3-(ε-carboxypentyl)-3'-ethyl-5,5'-dimethyloxacarbocyanine (CYA); 6-carboxy fluorescein (FAM); 5&6-carboxyrhodamine-110 (R110); 6-carboxyrhodamine-6G (R6G); N,N,N',N'-tetramethyl-6-carboxyrhodamine (TAMRA); 6-carboxy-X-rhodamine (ROX); 6-carboxy-4',5'-dichloro-2',7'-dimethoxyfluorescein (JOE); ALEXA FLUOR™; Cy2; Texas Red and Rhoda mine Red; 6-carboxy-2',4,7,7'-tetrachlorofluorescein (TET); 6-carboxy-2',4,4',5',7,7'-hexachlorofluorescein (HEX); 5-carboxy-2',4',5',7'-tetrachlorofluorescein (ZOE); NAN; NED; Cy3; Cy3.5; Cy5; Cy5.5; Cy7; and Cy7.5; IR800CW, ICG, Alexa Fluor 350; Alexa Fluor 488; Alexa Fluor 532; Alexa Fluor 546; Alexa Fluor 568; Alexa Fluor 594; Alexa Fluor 647; Alexa Fluor 680, or Alexa Fluor 750.

Nanoparticles usually range from about 1-1000 nm in size and include diverse chemical structures such as gold and silver particles and quantum dots. When irradiated with angled incident white light, silver or gold nanoparticles ranging from about 40-120 nm will scatter monochromatic light with high intensity. The wavelength of the scattered light is dependent on the size of the particle. Four to five different particles in close proximity will each scatter monochromatic light, which when superimposed will give a specific, unique color. Derivatized nanoparticles such as silver or gold particles can be attached to a broad array of molecules including, proteins, antibodies, small molecules, receptor ligands, and nucleic acids. Specific examples of nanoparticles include metallic nanoparticles and metallic nanoshells such as gold particles, silver particles, copper particles, platinum particles, cadmium particles, composite particles, gold hollow spheres, gold-coated silica nanoshells, and silica-coated gold shells. Also included are silica, latex, polystyrene, polycarbonate, polyacrylate, PVDF nanoparticles, and colored particles of any of these materials.

Quantum dots are fluorescing crystals about 1-5 nm in diameter that are excitable by light over a large range of wavelengths. Upon excitation by light having an appropriate wavelength, these crystals emit light, such as monochromatic light, with a wavelength dependent on their chemical composition and size. Quantum dots such as CdSe, ZnSe, InP, or InAs possess unique optical properties; these and similar quantum dots are available from a number of commercial sources (e.g., NN-Labs, Fayetteville, Ark.; Ocean Nanotech, Fayetteville, Ark.; Nanoco Technologies, Manchester, UK; Sigma-Aldrich, St. Louis, Mo.).

Antibodies may be prepared by any of a variety of techniques known to those of ordinary skill in the art. See, e.g., Harlow and Lane, Antibodies: A Laboratory Manual, Cold Spring Harbor Laboratory, 1988. Monoclonal antibodies specific for a polypeptide of interest may be prepared, for example, using the technique of Kohler and Milstein, Eur. J. Immunol. 6:511-519, 1976, and improvements thereto. Also included are methods that utilize transgenic animals such as mice to express human antibodies. See, e.g., Neuberger et al., Nature Biotechnology 14:826, 1996; Lonberg et al., Handbook of Experimental Pharmacology 113:49-101, 1994; and Lonberg et al., Internal Review of Immunology 13:65-93, 1995. Particular examples include the VELOCIMMUNE® platform by REGERNEREX® (see, e.g., U.S. Pat. No. 6,596,541). Antibodies can also be prepared by recombinant techniques, described herein and known in the art.

The antibodies described herein can be used in any of the therapeutic methods and compositions described herein.

Polynucleotides, Host Cells, and Methods of Production

Certain embodiments relate to polynucleotides that encode the antibodies, and antigen-binding fragments thereof, and vectors that comprise such polynucleotides, for example, where the polynucleotides are operably linked to one or more regulatory elements. Also included are recombinant host cells that comprise such polynucleotides, vectors, antibodies, and antigen-binding fragments thereof, in addition to methods of recombinant production of the foregoing.

Antibodies and antigen-binding fragments thereof may be prepared using standard techniques. In particular embodiments, an antibody, or antigen-binding fragment thereof, is expressed as a recombinant protein in an expression system, as described herein and known in the art.

Polynucleotides can contain one or multiple copies of a nucleic acid encoding an antibody, or antigen-binding fragment thereof.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g., phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example, in preparation of nucleic acid constructs, mutagenesis, sequencing, introduction of DNA into cells and gene expression, and analysis of proteins, are described in detail in Current Protocols in Molecular Biology, Second Edition, Ausubel et al. eds., John Wiley & Sons, 1992, or subsequent updates thereto.

As will be understood by those of skill in the art, it may be advantageous in some instances to produce polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence. Such polynucleotides are commonly referred to as "codon-optimized." Any of the polynucleotides described herein may be utilized in a codon-optimized form. In certain embodiments, a polynucleotide can be codon optimized for use in specific bacteria such as *E. coli* or yeast such as *S. cerevisiae* (see, e.g., Burgess-Brown et al., *Protein Expr Purif.* 59:94-102, 2008).

In some embodiments, nucleic acids or vectors encoding an antibody, or an antigen-binding fragment thereof, are introduced directly into a host cell, and the cell is incubated under conditions sufficient to induce expression of the encoded polypeptide(s). Therefore, according to certain related embodiments, there is provided a recombinant host cell which comprises a polynucleotide that encodes one or more antibodies, or antigen-binding fragments thereof, described herein, optionally in combination with other components of an antibody (e.g., Fc regions), and which optionally comprise additional exogenous polynucleotides.

Expression of antibodies, or antigen-binding fragments thereof, in the host cell may be achieved by culturing the recombinant host cells (containing the polynucleotide(s)) under appropriate conditions. Following production by expression, the antibodies, or antigen-binding fragments thereof, may be isolated and/or purified using any suitable technique, and then used as desired. The term "host cell" is used to refer to a cell into which has been introduced, or which is capable of having introduced into it, a nucleic acid sequence encoding one or more of the antibodies, or antigen-binding fragments thereof, described herein. The term includes the progeny of the parent cell, whether or not the progeny are identical in morphology or in genetic make-up to the original parent, so long as the selected gene is present. Host cells may be chosen for certain characteristics, for instance, the expression of aminoacyl tRNA synthetase(s) that can incorporate unnatural amino acids into the antibody, or antigen-binding fragment thereof.

Systems for cloning and expression of a heterologous or recombinant protein in a variety of different host cells are well known. Suitable host cells include mammalian cells, bacteria, yeast, and baculovirus systems. Mammalian cell lines available in the art for expression of a proteins include Chinese hamster ovary (CHO) cells, HeLa cells, baby hamster kidney cells, HEK-293 cells, NSO mouse melanoma cells and many others. Additional examples of useful mammalian host cell lines include monkey kidney CV1 line transformed by SV40 (COS-7, ATCC CRL 1651); human embryonic kidney line (293 or 293 cells sub-cloned for growth in suspension culture, Graham et al., *J. Gen Virol.* 36:59 (1977)); baby hamster kidney cells (BHK, ATCC CCL 10); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2). Other useful mammalian host cell lines include Chinese hamster ovary (CHO) cells, including DHFR-CHO cells (Urlaub et al., PNAS USA 77:4216 (1980)); and myeloma cell lines such as NSO and Sp2/0. For a review of certain mammalian host cell lines suitable for antibody production, see, e.g., Yazaki and Wu, *Methods in Molecular Biology*, Vol. 248 (B. K. C Lo, ed., Humana Press, Totowa, N.J., 2003), pp. 255-268. Certain preferred mammalian cell expression systems include CHO and HEK293-cell based expression systems including 293F cells. Mammalian expression systems can utilize attached cell lines, for example, in T-flasks, roller bottles, or cell factories, or suspension cultures, for example, in 1 L and 5 L spinners, 5 L, 14 L, 40 L, 100 L and 200 L stir tank bioreactors, or 20/50 L and 100/200 L WAVE bioreactors, among others known in the art.

A common, preferred bacterial host is *E. coli*. The expression of proteins in prokaryotic cells such as *E. coli* is well established in the art. For a review, see for example, Pluckthun, A. *Bio/Technology.* 9:545-551 (1991). Expression in eukaryotic cells in culture is also available to those skilled in the art as an option for recombinant production of polypeptides (see Ref, *Curr. Opinion Biotech.* 4:573-576, 1993; and Trill et al., *Curr. Opinion Biotech.* 6:553-560, 1995). In specific embodiments, protein expression may be controlled by a T7 RNA polymerase (e.g., pET vector series). These and related embodiments may utilize the expression host strain BL21(DE3), a λDE3 lysogen of BL21 that supports T7-mediated expression and is deficient in Ion and ompT proteases for improved target protein stability. Also included are expression host strains carrying plasmids encoding tRNAs rarely used in *E. coli*, such as Rosetta™ (DE3) and Rosetta 2 (DE3) strains. Cell lysis and sample handling may also be improved using reagents such as Benzonase® nuclease and BugBuster® Protein Extraction Reagent. For cell culture, auto-inducing media can improve the efficiency of many expression systems, including high-throughput expression systems. Media of this type (e.g., Overnight Express™ Autoinduction System) gradually elicit protein expression through metabolic shift without the addition of artificial inducing agents such as IPTG. Particular embodiments employ hexahistidine tags (such as His.Tag® fusions), followed by immobilized metal affinity chromatography (IMAC) purification, or related techniques. In certain aspects, however, clinical grade proteins can be isolated from *E. coli* inclusion bodies, without or without the use of affinity tags (see, e.g., Shimp et al., *Protein Expr Purif.* 50:58-67, 2006). As a further example, certain embodiments may employ a cold-shock induced *E. coli* high-yield production system, because over-expression of proteins in *Escherichia coli* at low temperature improves their solubility and stability (see, e.g., Qing et al., *Nature Biotechnology.* 22:877-882, 2004).

In addition, a host cell strain may be chosen for its ability to modulate the expression of the inserted sequences or to process the expressed protein in the desired fashion. Such modifications of the polypeptide include, but are not limited to, post-translational modifications such as acetylation, carboxylation, glycosylation, phosphorylation, lipidation, and acylation. Post-translational processing, which cleaves a "prepro" form of the protein may also be used to facilitate correct insertion, folding and/or function. Different host cells such as yeast, CHO, HeLa, MDCK, HEK293, and W138, in addition to bacterial cells, which have or even lack specific cellular machinery and characteristic mechanisms for such post-translational activities, may be chosen to ensure the correct modification and processing of the protein (e.g., antibody) of interest.

For long-term, high-yield production of recombinant proteins, stable expression is generally preferred. For example, cell lines that stably express a polynucleotide of interest may be transformed using expression vectors which may contain viral origins of replication and/or endogenous expression elements and a selectable marker gene on the same or on a separate vector. Following the introduction of the vector, cells may be allowed to grow for about 1-2 days in an enriched media before they are switched to selective media. The purpose of the selectable marker is to confer resistance to selection, and its presence allows growth and recovery of cells which, successfully express the introduced sequences. Resistant clones of stably transformed cells may be proliferated using tissue culture techniques appropriate to the cell type. Transient production, such as by transient transfection or infection, can also be employed. Exemplary mammalian expression systems that are suitable for transient production include HEK293 (e.g., 293F cells) and CHO-based systems.

Host cells transformed with a polynucleotide sequence of interest may be cultured under conditions suitable for the expression and recovery of the protein from cell culture. Certain specific embodiments utilize serum free cell expression systems. Examples include HEK293 cells and CHO cells that can grow on serum free medium (see, e.g., Rosser et al., *Protein Expr. Purif.* 40:237-43, 2005; and U.S. Pat. No. 6,210,922).

The protein(s) produced by a recombinant cell can be purified and characterized according to a variety of techniques known in the art. Exemplary systems for performing protein purification and analyzing protein purity include fast protein liquid chromatography (FPLC) (e.g., AKTA and Bio-Rad FPLC systems), high-performance liquid chromatography (HPLC) (e.g., Beckman and Waters HPLC). Exemplary chemistries for purification include ion exchange chromatography (e.g., Q, S), size exclusion chromatography, salt gradients, affinity purification (e.g., Ni, Co, FLAG, maltose, glutathione, protein A/G), gel filtration, reverse-phase, ceramic HyperD® ion exchange chromatography, and hydrophobic interaction columns (HIC), among others known in the art. Also included are analytical methods such as SDS-PAGE (e.g., coomassie, silver stain), immunoblot, Bradford, and ELISA, which may be utilized during any step of the production or purification process, typically to measure the purity of the protein composition.

Also included are methods of concentrating recombinantly produced proteins, e.g., antibodies. Examples include lyophilization, which is typically employed when the solution contains few soluble components other than the protein of interest. Lyophilization is often performed after HPLC run, and can remove most or all volatile components from the mixture. Also included are ultrafiltration techniques, which typically employ one or more selective permeable membranes to concentrate a protein solution. The membrane allows water and small molecules to pass through and retains the protein; the solution can be forced against the membrane by mechanical pump, gas pressure, or centrifugation, among other techniques.

In certain embodiments, the antibodies, or antigen-binding fragments thereof, have a purity of at least about 90%, as measured according to routine techniques in the art. In certain embodiments, such as diagnostic compositions or certain therapeutic compositions, the antibodies, or antigen-binding fragments thereof, have a purity of at least about 95%. In specific embodiments, such as therapeutic or pharmaceutical compositions, the antibodies, or antigen-binding fragments thereof, have a purity of at least about 97% or 98% or 99%. In other embodiments, such as when being used as reference or research reagents, the antibodies, or antigen-binding fragments thereof, can be of lesser purity, and may have a purity of at least about 50%, 60%, 70%, or 80%. Purity can be measured overall or in relation to selected components, such as other proteins, e.g., purity on a protein basis.

In certain embodiments, the compositions described here are about substantially endotoxin free, including, for example, about 95% endotoxin free, preferably about 99% endotoxin free, and more preferably about 99.99% endotoxin free. The presence of endotoxins can be detected according to routine techniques in the art, as described herein. In specific embodiments, the antibodies, or antigen-binding fragments thereof, are made from a eukaryotic cell such as a mammalian or human cell in substantially serum free media.

Methods of Use

Embodiments include methods relating to the use of the antibodies and antigen-binding fragments thereof described herein. In particular embodiments, such methods comprise contacting a cell expressing an L-type voltage-gated calcium channel with an antibody or antigen-binding fragment thereof described herein, thereby modulating the activity of the L-type voltage gated calcium channel. In some aspects, the antibody or antigen-binding fragment specifically binds to the channel. In some embodiments, the antibody or antigen-binding fragment specifically binds to an extracellular pore loop of an alpha 1 subunit of the L-type voltage gated calcium channel. In specific embodiments, the antibody or antigen-binding fragment thereof specifically binds to the extracellular pore loop between transmembrane segments S5 an S6 of domain 1 of the alpha one subunit. The alpha 1 subunit can belong to a Cav1.1, Cav1.2, Cav1.3, or Cav1.4 calcium channel, or any isoform or variant thereof. In certain embodiments, the cell is an immune cell, such as a hematopoietic cell.

Certain embodiments provide methods for modulating the activity of a cell comprising contacting the cell with an antibody or antigen binding fragment thereof as described herein. In some embodiments, the cell expresses an L-type voltage gated calcium channel. In some embodiments, the antibody or antigen-binding fragment thereof increases the cellular activity of the cell. In some embodiments, the antibody or antigen-binding fragment thereof decreases the cellular activity of the cell.

Particular embodiments relate to methods of modulating an immune response in a subject comprising administering to the subject an effective amount of an antibody or antigen-binding fragment thereof described herein. In some embodiments, the antibody or antigen-binding fragment thereof contacts an immune cell expressing an L-type voltage-gated calcium channel and modulates an activity of the immune cell. In certain embodiments, administering an antibody or antigen-binding fragment described herein increases an immune response in the subject. In some embodiments, administering an antibody or antigen-binding fragment described herein decreases an immune response in the subject.

Certain embodiments relate to methods of treating a disease in a subject comprising administering to the subject an effective amount of an antibody or antigen-binding fragment thereof as described herein. In some embodiments, the disease is an inflammatory disease. In some embodiments, the disease is a cancer.

Particular embodiments relate to modulating activity of an L-type voltage-gated calcium channel. Modulating activity refers to increasing activity, decreasing activity, or a combination of both. In some aspects, activity of the channel refers to the calcium conductance of the channel. Methods of altering channel activity can include altering calcium conductance by changing the probabilities the channel is found in an open or closed conformation, altering the voltage thresholds that trigger conversion into an open conformation, changing the duration of time the channel is open following activation of the channel, or altering the calcium conductance of the channel when it is in an open or closed conformation.

In some embodiments, an antibody or antigen binding fragment thereof as described herein contacts an L-type voltage-gated calcium channel and thereby modulates the activity of the channel. In some embodiments, the antibody or antigen-binding fragment thereof inhibits activity of the L-type voltage gated channel. In particular embodiments, inhibiting activity of an L-type voltage-gated calcium channel reduces activity by a statistically significant amount. In particular embodiments, inhibiting activity of an L-type voltage-gated calcium channel results in a decrease in channel activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between).

In some embodiments, the antibody or antigen-binding fragment increases activity of the L-type voltage gated channel. In particular embodiments, increasing activity of an L-type voltage-gated calcium channel increases the activity by a statistically significant amount. In particular embodiments, increasing activity of an L-type voltage-gated calcium channel results in an increase in channel activity of a 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In certain embodiments, increasing in channel activity results in a 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 10,000-fold, or greater than 10,000-fold increase (including all integers and ranges in between) of channel activity.

In certain embodiments, modulation of activity of an L-type voltage-gated calcium channel is quantified by standard techniques known in the art. In some embodiments, modulation of activity of an L-type voltage-gated calcium channel is measured by contacting the channel with an antibody or antigen-binding fragment described herein, measuring the activity of the channel, and comparing the measurement to a measurement of a control channel. In particular embodiments, activity of the channel is assessed by measuring calcium conductance of the channel. Standard techniques for measuring calcium conductance of an L-type voltage-gated calcium channel are known in the art and include, but are not limited to electrophysiological techniques such as patch clamp recording, single channel recording, and whole cell recording; calcium imaging techniques utilizing chemical indicators such as fura-2, indo-1, fluo-3, fluo-4, Calcium Green-1, or genetically encoded indicators such as Pericams, Cameleons, and GCaMP, and measurement of events correlated to L-type voltage-gated channel activity such as expression, phosphorylation, or translocation of a protein.

In some embodiments, contacting a cell expressing an L-type voltage-gated channel with an antibody or antigen binding fragment thereof of the current invention modulates activity of the cell. Modulating the activity of a cell refers to modulating at least one cellular process. Examples of a cellular process include, but are not limited to, cell survival, apoptosis, necrosis, programed cell death, transcription, translation, lipid synthesis, maturation, differentiation, catabolism, digestion, absorption, secretion, division, cell growth, migration, remodeling, repair, and storage. In some embodiments, the antibody or antigen-binding fragment thereof decreases activity of the cell. In some embodiments, the antibody or antigen-binding fragment thereof increases activity of the cell. In some embodiments, the antibody or antigen-binding fragment thereof both increases and decreases activity of the cell. Activity of a cell can be modulated, for example, by modulating the degree to which a cell performs the activity, or by increasing or decreasing the number of cells that perform the activity. Cellular activity can be both increased and decreased, for example, by an antibody that initially increases the activity of the then produces a sustained decrease in the cell, or for example, by increasing the activity in one population of cells and decreasing the activity in a different population of cells.

Some embodiments contemplate a model whereby L-type voltage-gated calcium channels regulate cellular activities and processes by regulating the intracellular concentration of calcium. Calcium ions are signaling molecules as the cytosolic concentration of calcium ions regulates a multitude of enzymes and proteins. Movement of calcium ions into the cytosol can influence cellular processes or activities by regulating the voltage gradient across membrane, for example, by contributing to the action potential of a cardiac cell, or by acting as a secondary messenger. Secondary messengers are molecules that relay and amplify signals, for example, from the cell surface, to target molecules in the cell, such as in the cytosol and/or nucleus. Calcium ions are usually maintained at a low concentration in the cytoplasm through active extracellular transport of calcium ions, or transport of calcium ions into intracellular stores such as the endoplasmic reticulum. A transient rise in the cytoplasmic calcium concentration allows calcium ions to bind to a large number of calcium-binding proteins that serve as molecular targets, for example, calmodulin, a Ca2+-binding protein abundant in the cytosol of all cells. Calcium ions bind to and activate calmodulin, which then initiates its effects by binding to still other downstream targets, such as protein kinases. Calcium signaling can activate other secondary messenger systems, such as the phospholipase C/protein kinase C signaling cascade. This signaling in turn can coordinate and trigger cellular processes or activity, for example, transcription, translation, secretion or maturation.

Thus, some embodiments contemplate, but are not bound by, a model whereby L-type voltage-gated calcium channels regulate a cellular process or activity by regulating cytosolic calcium concentrations. In some embodiments, modulating the activity of an L-type calcium channel modulates an activity of the cell expressing the channel by regulating intracellular calcium signaling. Thus, in some embodiments, where an activity of the cell is positively regulated by calcium, enhancing, agonizing, activating, or increasing activity of an L-type calcium channel increases the activity of the cell by increasing the cytosolic concentration of calcium ions in the cell, and conversely, decreasing or inhibiting calcium channel activity decreases, or prevents an increase of, intracellular calcium concentrations and inhibits or decreases the activity of the cell. Conversely, if a cellular activity is negatively coupled to calcium signaling in a cell expressing an L-type voltage gated calcium channel, increasing channel activity will inhibit the cellular activity, and inhibiting the channel activity will increase the cellular activity. In some embodiments, modulating an L-type voltage-gated calcium channel of a cell modulates one or more cellular activities regulated by calcium in the cell, while not modulating one or more different cellular activities regulated by calcium in the cell.

In some embodiments, an antibody or antigen binding fragment thereof as described herein contacts a cell expressing an L-type voltage-gated calcium channel and thereby modulates an activity of the cell. In some embodiments, the antibody or antigen-binding fragment thereof inhibits the activity of the cell. In particular embodiments, inhibiting the activity of the cell reduces activity of the cell by a statistically significant amount. In particular embodiments, inhibiting the activity of the cell results in a decrease of cellular activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between).

In some embodiments, the antibody or antigen-binding fragment increases the activity of the cell. In particular embodiments, increasing the activity of the cell increases the activity by a statistically significant amount. In particular embodiments, increasing the activity of a cell results in an increase of cellular activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In certain embodiments, increasing in activity of a cell results in a 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 10,000-fold, or greater than 10,000-fold increase (including all integers and ranges in between) of channel activity.

In certain embodiments, modulation of an activity in a cell is quantified by standard techniques known in the art. In some embodiments, modulation of activity of an L-type voltage-gated calcium channel is measured by contacting the cell with an antibody or antigen-binding fragment thereof, measuring the activity of the cell, and comparing the measurement to a measurement of a control cell. In some embodiments, cell activity is measured in cultured cells, animal models, or samples or biopsy taken from a subject. Techniques to examine cellular activity are well known in the art, and include assays to examine cell survival, transcription, translation, lipid synthesis, differentiation, absorption, secretion, division, growth, migration, and remodeling. Appropriate functional assays can be readily determined by one skilled in the art taking into consideration the cell type involved and the activity to be measured.

In certain embodiments, antibodies and antigen-binding fragments thereof as described herein contact voltage-gated calcium channels that are expressed in immune cells, such as hematopoietic cells. Hematopoietic cells include cells from the myeloid lineage (including monocytes, macrophages, neutrophils, basophils, eosinophils, erythrocytes, megakaryocytes, platelets, mast cells and dendritic cells) and cells from the lymphoid lineage (including T cells, B cells, and natural killer (NK) cells). In some embodiments, the antibodies and antigen-binding fragments thereof decrease immune cell activity. In some embodiments, antibodies and antigen-binding fragments thereof increase immune cell activity. In some embodiments, antibodies and antigen-binding fragments thereof increase and decrease immune cell activity, for example, by initially increasing immune cell function and then decreasing immune cell function, or by increasing the activity of one population of immune cells and decreasing the activity of another population of immune cells.

Examples of immune cell activity include, but are not limited to, a cellular process of an immune cell, as well as cellular processes or activities that contribute to an innate or adaptive immune response. Activities contributing to adaptive immune response include activities performed by cells of lymphoid lineage, such as T cells and B cells. In T cells, these activities include, but are not limited to, inducing maturation of B cells in plasma cells and memory B cells, activation of cytotoxic T cells and macrophages, cytokine production and secretion by helper ($CD4^+$) T cells; lysing cells (such as virally infected cells or tumor cells) by cytotoxic ($CD8^+$) T cells; suppression of T cell mediated immunity by regulatory (suppressor) T cells; expansion by cell division in memory T cells. T cell activities also include T cell receptor binding to antigens and T cell maturation. In B cells, activities include antibody production and secretion by plasma cells, antigen binding to the B cell receptor, and B cell receptor activation. B cell activities also include maturation and survival. Examples of immune cell activity that contributes to innate immunity include release of histamine-containing granules and chemokines by mast cells, engulfment of cells, pathogens, or particles by phagocytes and macrophages; release of oxidizing agents, free oxygen radicals, and hypochlorite by neutrophils; release of histamine, toxic proteins, and free radicals by basophils and eosinophils; and destruction of infected cells by Natural Killer (NK) cells. Certain embodiments contemplate, but are not bound by, a model whereby these examples of immune cell function are considered positively coupled to calcium signaling.

Maturation generally refers to a process whereby a less specialized cell develops into a more specialized cell type. Maturation involves signal-regulated adjustments in cells, immune cells, and/or thymocytic cells that lead to cellular specialization. Examples of maturation in the immune system include, but are not limited to, monocyte maturation to macrophage; B thymocyte maturation to B lymphocyte, and further maturing to a plasma cell or memory B cell; and T thymocyte maturation to T lymphocyte, and further maturation to cytotoxic T lymphocyte, cytokine induced killer T cell, helper T cell, regulatory T cell, or a natural killer T cell.

In some embodiments, an antibody or antigen binding fragment thereof as described herein contacts an immune cell expressing an L-type voltage gated calcium channel and thereby modulates an activity of the immune cell. In some embodiments, the antibody or antigen-binding fragment inhibits the activity of the immune cell. In particular embodiments, inhibiting the activity of the immune cell reduce activity by a statistically significant amount. In particular embodiments, inhibiting the activity of the cell results in a decrease of cellular activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between).

In some embodiments, the antibody or antigen-binding fragment increases the activity of the immune cell. In particular embodiments, increasing the activity of the immune cell increase the activity by a statistically significant amount. In particular embodiments, increasing the immune cell activity results in an increase of immune cell activity of 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% (including all integers and ranges in between). In certain embodiments, increasing the activity of an immune cell results in a 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 200-fold, 300-fold, 400-fold, 500-fold, 1,000-fold, 10,000-fold, or greater than 10,000-fold increase (including all integers and ranges in between) of channel activity.

Appropriate functional assays can be readily determined by one skilled in the art taking into consideration the cell type involved. For example, cell survival, cell proliferation, cell differentiation and/or cell activation of an immune cell could be assessed by standard techniques. For example, changes in gene expression associated with particular processes can be measured with known techniques in the art, for example, fluorescence in situ hybridization, immunohistochemistry, qPCR, and western blot analysis. Alternatively, measurements of processes such cytokine secretion or cytolytic ability can be directly assessed using techniques known in the art. Suitable assays to assess immune function of various hematopoietic cells are known in the art.

Some embodiments relate to methods of contacting immune cells with antibodies or antigen-binding fragments described herein to modify activity of an immune cell for the purposes of treating a subject in need thereof. In some aspects, the subject is in need of treatment for a disease. In particular embodiments, immune cells are contacted in vitro for the purposes of treating a subject, for example, through adoptive cell transfer. Adoptive cell transfer, as used herein, refers to the transfer immune-derived cells, back into the same patient or into a new recipient host with the goal of transferring the immunologic functionality and characteristics into the new host. If possible, use of autologous cells helps the recipient by minimizing graft versus host disease issues. In certain embodiments, an antibody or antigen-binding fragment thereof described herein is administered to the subject.

As used herein, the term "immune response" includes T cell mediated and/or B cell mediated immune responses. Exemplary immune responses include T cell responses, e.g., cytokine production and cellular cytotoxicity. In addition, the term immune response includes immune responses that are indirectly affected by T cell activation, e.g., antibody production (humoral responses) and activation of cytokine responsive cells, e.g., macrophages. Immune cells involved in the immune response include lymphocytes, such as B cells and T cells (CD4+, CD8+, Th1 and Th2 cells); antigen presenting cells (e.g., professional antigen presenting cells such as dendritic cells, macrophages, B lymphocytes, Langerhans cells, and nonprofessional antigen presenting cells such as keratinocytes, endothelial cells, astrocytes, fibroblasts, oligodendrocytes); natural killer cells; myeloid cells, such as macrophages, eosinophils, mast cells, basophils, and granulocytes. In some embodiments, the antibodies or antigen-binding fragments described herein are effective to reduce inflammatory cell trafficking to the site of inflammation. In some embodiments, the term "immune response" encompasses activation of pattern recognition receptors (PRRs) and release of inflammatory mediators on macrophages, dendritic cells, histiocytes, Kupffer cells and/or mastocytes. Examples of inflammatory mediators include lysosome granules, histamine, IFN-gamma, IL-8, Leukotriene B4, nitric oxide, prostaglandins, and TNF-alpha.

In particular embodiments, antibodies and antigen-binding fragments described herein that decrease L-type voltage channel activity are used as immunosuppressants, which find application, for example, in the treatment of autoimmune diseases, in reducing the risk of transplant rejection, and/or in the treatment of other disorders requiring suppression of the immune system, such as treatment of allergy. In some embodiments, antibodies or antigen-binding fragments thereof that inhibit L-type voltage-gated calcium channels expressed in T cells or B cells are useful, for example, as immunosuppressants. In another example, antibodies or antigen-binding fragments thereof that inhibit L-type voltage-gated calcium channels in mast cells are useful, for example, to reduce mast cell activity and treat allergy.

Examples of autoimmune diseases that may be treated in accordance with certain embodiments of the invention include, but are not limited to, X-linked agammaglobulinemia, systemic lupus erythematosus, inflammatory (rheumatoid) arthritis, Hashimoto's thyroiditis, pernicious anemia, inflammatory bowel disease (Crohn's disease and ulcerative colitis), psoriasis, renal fibroses, pulmonary fibroses, hepatic fibroses, Addison's disease, Type I diabetes, systemic lupus erythematosus (SLE), dermatomyositis, Sjogren's syndrome, multiple sclerosis, myasthenia gravis, Reiter's syndrome, and Grave's disease. Clinical indicators of response can be measured for each of these diseases. For example, a reduction in pain, reduction in inflammation of tissues (for example, joints), improved tissue (for example, kidney) function, or improved ability to digest food can serve as indicators of successful immunosuppression.

Certain embodiments contemplate the administration of a therapeutic agent targeted to a voltage-gated calcium channel expressed in hematopoietic cells in conjunction with an anti-inflammatory agent or immunosuppressive agent. Certain embodiments contemplate the administration of an antibody or antigen-binding fragment described herein in conjunction with a known anti-inflammatory agent or immunosuppressive agent. Certain embodiments contemplate the administration of an antibody or antigen-binding fragment described herein in conjunction with an anti-inflammatory agent or immunosuppressive agent. Examples of immunosuppressive agents include non-steroidal anti-inflammatory agents (such as diclofenac, diflunisal, etodolac, flurbiprofen, ibuprofen, indomethacin, ketoprofen, ketorolac, nabumetone, naproxen, oxaprozin, piroxicam, sulindac, tolmetin, celecoxib, or rofecoxib), steroids (such as cortisone, dexamethasone, hydrocortisone, methylprednisolone, prednisolone, prednisone, or triamcinolone) and immunosuppressive agents (such as cyclosporin, tacrolimus, mycophenolic acid, or sirolimus). Other examples include biological response modifiers (such as Kineret® (anakinra), Enbrel® (etanercept), or Remicade® (infliximab)), disease-modifying anti-rheumatic drugs (DMARD) (such as Arava® (leflunomide)), Hyalgan® (hyaluronan) and Synvisc® (hylan G-F20).

In particular embodiments, antibodies and antigen-binding fragments described herein that increase activity of an L-type voltage-gated calcium channel that is expressed on an immune cell. These antibodies are used, for example, to increase or generate an immune response. Such agents and methods may be useful in the treatment of cancer and/or treatment of immune suppression.

Certain embodiments therefore relate to the treatment of cancer in a subject in need thereof, comprising administering to the subject an antibody or antigen-binding fragment thereof, as described herein. In some embodiments, the subject is not significantly immunosuppressed or immunodeficient. Examples of cancers include breast cancer, cervical cancer, prostate cancer, gastrointestinal cancer, lung cancer, ovarian cancer, testicular cancer, head and neck cancer, bladder cancer, kidney cancer (e.g., renal cell carcinoma), soft tissue sarcoma, squamous cell carcinoma, CNS or brain cancer, melanoma, non-melanoma cancer, thyroid cancer, endometrial cancer, an epithelial tumor, bone cancer, and hematopoietic cancer. In certain embodiments, the lung cancer is osteosarcoma, chondrosarcoma, or a Ewing Sarcoma Family of Tumors (ESFTs). In certain embodiments, the gastrointestinal cancer is esophageal cancer, stomach (gastric) cancer, pancreatic cancer, liver cancer, gallbladder (biliary) cancer, small intestinal cancer, colorectal cancer, anal or rectal cancer, or gastrointestinal carcinoid or stromal tumor. In certain embodiments, the melanoma is lentigo maligna, lentigo maligna melanoma, superficial spreading melanoma, acral lentiginous melanoma, mucosal melanoma, nodular melanoma, polypoid melanoma, desmoplastic melanoma, amelanotic melanoma, soft-tissue melanoma, or uveal melanoma. In certain embodiments, the hematopoietic cancer is a lymphoma, leukemia, or multiple myeloma. In certain embodiments, the lymphoma is a T-cell lymphoma, B-cell lymphoma, small lymphocytic lymphoma, mangle cell lymphoma, anaplastic large cell lymphoma (ALCL), follicular lymphoma, Hodgkin's lymphoma, or non-Hodgkin's lymphoma. In certain embodiments, the leukemia is chronic lymphocytic leukemia (CLL), hairy cell leukemia, acute lymphoblastic leukemia, myelocytic leukemia, acute myeloid or myelogenous leukemia, or chronic myelogenous leukemia. In certain embodiments, the brain cancer is a glioma, meningioma, pituitary adenoma, vestibular schwannoma, primary CNS lymphoma, neuroblastoma, primitive neuroectodermal tumor (medulloblastoma), or glioblastoma multiforme.

Certain methods include the treatment of cancers that express (e.g., over-express) one or more Cav1 channels. For instance, in certain embodiments, the cancer expresses (e.g., over-expresses), Cav1.1, Cav1.2, Cav1.3, Cav1.4, or any combination thereof. In some embodiments, the cancer expresses (e.g., over-expresses) Cav1.1 and the therapeutic antibody or antigen-binding fragment thereof binds (e.g., selectively binds) to Cav1.1. In some embodiments, the cancer expresses (e.g., over-expresses) Cav1.2 and the therapeutic antibody or antigen-binding fragment thereof binds (e.g., selectively binds) to Cav1.2. In some embodiments, the cancer expresses (e.g., over-expresses) Cav1.3 and the therapeutic antibody or antigen-binding fragment thereof binds (e.g., selectively binds) to Cav1.3. In some embodiments, the cancer expresses (e.g., over-expresses) Cav1.4 and the therapeutic antibody or antigen-binding fragment thereof binds (e.g., selectively binds) to Cav1.4.

FIG. 10 illustrates the association between Cav channel expression and certain cancer types. Thus, certain embodiments relate to the treatment of any one or more of the cancers in FIG. 10, which optionally express (e.g., over-express) one or more Cav1 channels. In some embodiments, the antibody or antigen-binding fragment thereof binds to Cav1.1 and is used in the treatment of a skeletal muscle cancer, larynx cancer, thyroid cancer, prostate cancer, leukemia, solid tumor, Burkett lymphoma, meduloblastoma, endometrial cancer, or lung carcinoma that expresses (e.g., over-expresses) Cav1.1 (see, e.g., FIG. 10). In some embodiments, the antibody or antigen-binding fragment thereof binds to Cav1.2 and is used in the treatment of a cancer of the spleen, cancer of the thymus, uterine cancer, brain cancer, colon cancer, chondrosarcoma, lymphoma, leukemia, neuroblastoma, or Hodgkin's lymphoma that expresses (e.g., over-expresses) Cav1.2 (see, e.g., FIG. 10). In some embodiments, the antibody or antigen-binding fragment thereof binds to Cav1.3 and is used in the treatment of a cancer of the bone, brain, lung, intestine, pituitary gland, pancreas, adrenal gland, kidney, testis, bronchial epithelium, or breast (e.g., breast carcinoma) that expresses (e.g., over-expresses) Cav1.3 (see, e.g., FIG. 10). In some embodiments, the antibody or antigen-binding fragment thereof binds to Cav1.4 and is used in the treatment of a cancer of the lung, muscle, thymus, pineal gland, small intestine, spleen that expresses (e.g., over-expresses) Cav1.4, or in the treatment of leukemia, lymphoma, or meningioma that expresses (e.g., over-expresses) Cav1.4 (see, e.g., FIG. 10).

Some methods include administering an antibody in combination with an additional cancer therapy. In certain embodiments, the additional cancer therapy selected from one or more of an anti-cancer agent, radiotherapy, surgery, transplantation, photodynamic therapy, symptomatic care, and antibiotic therapy. In certain embodiments, the additional anti-cancer agent is selected from a small molecule and an antibody. In certain embodiments, the small molecule is a cytotoxic, chemotherapeutic, or anti-angiogenic agent. In certain embodiments, the small molecule cytotoxic, chemotherapeutic, or anti-angiogenic agent is selected from one or more of alkylating agents, anti-metabolites, anthracyclines, anti-tumor antibiotics, platinums, type I topoisomerase inhibitors, type II topoisomerase inhibitors, vinca alkaloids, and taxanes.

In certain embodiments, the additional small molecule is selected from one or more of chlorambucil, cyclophosphamide, cilengitide, lomustine (CCNU), melphalan, procarbazine, thiotepa, carmustine (BCNU), enzastaurin, busulfan, daunorubicin, doxorubicin, gefitinib, erlotinib idarubicin, temozolomide, epirubicin, mitoxantrone, bleomycin, cisplatin, carboplatin, oxaliplatin, camptothecins, irinotecan, topotecan, amsacrine, etoposide, etoposide phosphate, teniposide, temsirolimus, everolimus, vincristine, vinblastine, vinorelbine, vindesine, CT52923, paclitaxel, imatinib, dasatinib, sorafenib, pazopanib, sunitnib, vatalanib, geftinib, erlotinib, AEE-788, dichoroacetate, tamoxifen, fasudil, SB-681323, semaxanib, donepizil, galantamine, memantine, rivastigmine, tacrine, rasigiline, naltrexone, lubiprostone, safinamide, istradefylline, pimavanserin, pitolisant, isradipine, pridopidine (ACR16), tetrabenazine, bexarotene, glatirimer acetate, fingolimod, and mitoxantrone, including pharmaceutically acceptable salts and acids thereof.

In certain embodiments, the additional antibody is selected from one or more of 3F8, 8H9, abagovomab, adecatumumab, afutuzumab, alacizumab (pegol), alemtuzumab, altumomab pentetate, amatuximab, anatumomab mafenotox, apolizumab, arcitumomab, bavituximab, bectumomab, belimumab, bevacizumab, bivatuzumab (mertansine), brentuximab vedotin, cantuzumab (mertansine), cantuzumab (ravtansine), capromab (pendetide), carlumab, catumaxomab, cetuximab, citatuzumab (bogatox), cixutumumab, clivatuzumab (tetraxetan), conatumumab, dacetuzumab, daclizumab, dalotuzumab, detumomab, drozitumab, ecromeximab, edrecolomab, elotuzumab, enavatuzumab, ensituximab, epratuzumab, ertumaxomab, etaracizumab, farletuzumab, FBTA05, figitumumab, flanvotumab, galiximab, gemtuzumab, ganitumab, gemtuzumab (ozogamicin), girentuximab, glembatumumab (vedotin), ibritumomab tiuxetan, icrucumab, igovomab, indatuximab ravtansine, intetumumab, inotuzumab ozogamicin, ipilimumab (MDX-101), iratumumab, labetuzumab, lexatumumab, lintuzumab, lorvotuzumab (mertansine), lucatumumab, lumiliximab, mapatumumab, matuzumab, milatuzumab, mitumomab, mogamulizumab, moxetumomab (pasudotox), nacolomab (tafenatox), naptumomab (estafenatox), narnatumab, necitumumab, nimotuzumab, nivolumab, Neuradiab® (with or without radioactive iodine), NR-LU-10, ofatumumab, olaratumab, onartuzumab, oportuzumab (monatox), oregovomab, panitumumab, patritumab, pemtumomab, pertuzumab, pritumumab, racotumomab, radretumab, ramucirumab, rilotumumab, rituximab, robatumumab, samalizumab, sibrotuzumab, siltuximab, tabalumab, tanezumab, taplitumomab (paptox), tenatumomab, teprotumumab, TGN1412, ticilimumab, trastuzumab, tremelimumab, tigatuzumab, TNX-650, tositumomab, TRBS07, tucotuzumab (celmoleukin), ublituximab, urelumab, veltuzumab, volociximab, votumumab, and zalutumumab, including antigen-binding fragments thereof.

Also included are compositions for use in treating cancer, comprising a pharmaceutically acceptable carrier and an antibody or antigen-binding fragment thereof, as described herein. Some embodiments include compositions (e.g., pharmaceutical compositions), comprising a pharmaceutically acceptable carrier, an anti-cancer agent, and an antibody or antigen-binding fragment thereof, as described herein.

Certain embodiments of the invention provide for the use of the antibodies and antigen-binding fragments thereof described herein to increase an immune response in an immunocompromised subject, for example, to treat or prevent an opportunistic infection in an immunocompromised subject. Immunocompromised subjects are more susceptible to opportunistic infections, for example, viral, fungal, protozoan, or bacterial infections, prion diseases, and certain neoplasms. Those who can be considered to be immunocompromised include, but are not limited to, subjects with AIDS (or HIV positive), subjects with severe combined immune deficiency (SCID), diabetics, subjects who have had transplants and who are taking immunosuppressive agents/therapies, and those who are receiving chemotherapy for cancer. Immunocompromised individuals also include subjects with most forms of cancer (other than skin cancer), sickle cell anemia, cystic fibrosis, those who do not have a spleen, subjects with end stage kidney disease (dialysis), and those who have been taking corticosteroids on a frequent basis by pill or injection within the last year. Subjects with severe liver, lung, or heart disease also can be immunocompromised.

Formulations and Administration

The antibodies and antigen-binding fragments thereof as described herein may be administered in any manner which is medically acceptable. This may include injections, by parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the invention, by such means as depot injections or erodible implants. Localized delivery is particularly contemplated, by such means as delivery via a catheter to one or more arteries, such as the renal artery or a vessel supplying a localized tumor.

The subject antibodies may be formulated with a pharmaceutically acceptable carrier. The term "pharmaceutically acceptable carrier" means one or more organic or inorganic ingredients, natural or synthetic, with which the antibody is combined to facilitate its application. A suitable carrier includes sterile saline although other aqueous and non-aqueous isotonic sterile solutions and sterile suspensions known to be pharmaceutically acceptable are known to those of ordinary skill in the art.

Solutions or suspensions may include, for example, a sterile diluent (such as water), saline solution (e.g., phosphate buffered saline (PBS), physiological saline, Ringer's solution, isotonic sodium chloride), fixed oil, polyethylene glycol, glycerin, propylene glycol or other synthetic solvent; antimicrobial agents (such as benzyl alcohol and methyl parabens); antioxidants (such as ascorbic acid and sodium bisulfite), chelating agents (such as ethylenediaminetetraacetic acid (EDTA)); and/or buffers (such as acetates, citrates, phosphates, and other organic acids), including combinations of the foregoing. Also included as suitable carriers are solutions containing thickening and solubilizing agents, such as glucose, polyethylene glycol, polypropylene glycol and mixtures thereof. A surfactant may be added to facilitate the formation of a homogeneous solution or suspension. Surfactants are compounds that non-covalently interact with the antibody, or antigen-binding fragment thereof, so as to facilitate dissolution or homogeneous suspension of the conjugate in the aqueous system.

Additional examples of carriers include low molecular weight (e.g., less than about 10 residues) polypeptides or peptides; proteins such as serum albumin, gelatin, or immunoglobulins; hydrophilic polymers such as polyvinylpyrrolidone; amino acids such as glycine, glutamine, asparagine, arginine, or lysine; monosaccharides, disaccharides, and other carbohydrates including glucose, mannose, or dextrins; sugar alcohols such as mannitol or sorbitol; salt-forming counterions such as sodium; and/or nonionic surfactants such as polysorbate 20 (TWEEN™) polyethylene glycol (PEG), and poloxamers (PLURONICS™), and the like.

In some embodiments, the antibody, or antigen-binding fragment thereof, is entrapped in microcapsules prepared, for example, by coacervation techniques or by interfacial polymerization (for example, hydroxymethylcellulose or gelatin-microcapsules and poly-(methylmethacylate)microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical Sciences, 16th edition, Oslo, A., Ed., (1980). The particle(s) or liposomes may further comprise other diagnostic agents, such as detectable entities.

In particular embodiments, the antibody, or antigen-binding fragment thereof, is a freeze-dried or lyophilized, cryo-desiccated. These terms refer to a dehydration process of freezing the antibody composition and then reducing the surrounding pressure to allow the frozen water in the composition to sublimate directly from the solid phase to the gas phase. Also included are solid compositions such as powders, granules, compressed tablets, pills, capsules, and the like. In some embodiments, solid composition contain one or more inert diluents or edible carriers. In certain embodiments, one or more of the following may be present: binders such as carboxymethylcellulose, ethyl cellulose, microcrystalline cellulose, gum tragacanth or gelatin; and excipients such as starch, lactose or dextrins, disintegrating agents such as alginic acid, sodium alginate, Primogel, corn starch and the like.

Certain embodiments include kits, comprising one or more of the antibodies, or antigen-binding fragments thereof, as described herein, optionally in one or more containers. The kits can include written instructions on how to use and/or prepare the antibodies for use, for example, as a medicament. In some embodiments, the written instructions describe how to use the antibodies, or antigen-binding fragments thereof, to administer antibodies or antigen-binding fragments thereof to a subject in need thereof.

An "effective amount" refers to that amount which is capable of ameliorating or delaying progression of the diseased, degenerative or damaged condition. An effective amount can be determined on an individual basis and will be based, in part, on consideration of the symptoms to be treated and results sought. An effective amount can be determined by one of ordinary skill in the art employing such factors and using no more than routine experimentation.

The kits herein may also include a one or more additional therapeutic agents or other components suitable or desired for the indication being treated, or for the desired diagnostic application. An additional therapeutic agent may be contained in a second container, if desired.

The following Examples are offered by way of illustration and not by way of limitation.

EXAMPLES

Example 1

Design and Generation of Antibodies Directed Against L-Type Voltage Gated Calcium Channels Antibodies were designed to the target L-type voltage-gated calcium channel subtypes Cav1.1, Cav1.2, Cav1.3, or Cav1.4. For each channel, an amino acid sequence was selected to use as targets for use as an antigen for generating mouse monoclonal antibodies. Amino acid sequences were selected to meet several criteria. First, the amino acid sequences had to be unique to their respective channels. Second, the amino acid sequences had to reside on an exposed portion of the channel positioned outside of the cell. Third, the amino acid sequence had to be found in both the mouse and human channel. Fourth, the sequence needed to be in a region of the channel that would affect the channel's activity when bound by an antibody.

For each of the L-type voltage-gated calcium channel subtype, an amino acid sequence located in the extracellular domain of the pore loop between transmembrane segments S5 and S6 of motif I of the alpha 1 subunit was selected (see FIG. 1). The amino acid sequences are displayed in table E1. Each sequence that was selected is unique to the channel subtype, positioned in an extracellular region of the channel, and conserved in mouse and human. Further, the extracellular domain of the pore loop between transmembrane segments S5 and S6 contributes to channel selectivity.

TABLE E1

Target Amino Acid Sequences

| Description | Sequence | SEQ ID NO: |
|---|---|---|
| Cav1.4 | GPGRPGDAPHTG | 1 |
| Cav1.3 | LTKETEGGNHSSGKSG | 2 |
| Cav1.2 | ATKADGANALGGKGA | 3 |
| Cav1.1 | PMQIELRHREWVH | 4 |

Monoclonal antibodies were generated using standard methods known in the art. Briefly, each peptide from table E1 was used to immunize 2 mice. After an immune response was detected, spleens of immunized mice were harvested, and lymphocytes were then isolated and fused with myeloma cells to generate hybridomas. Hybridomas were subcultured and cryopreserved (FIG. 2).

Example 2

Figure 9:
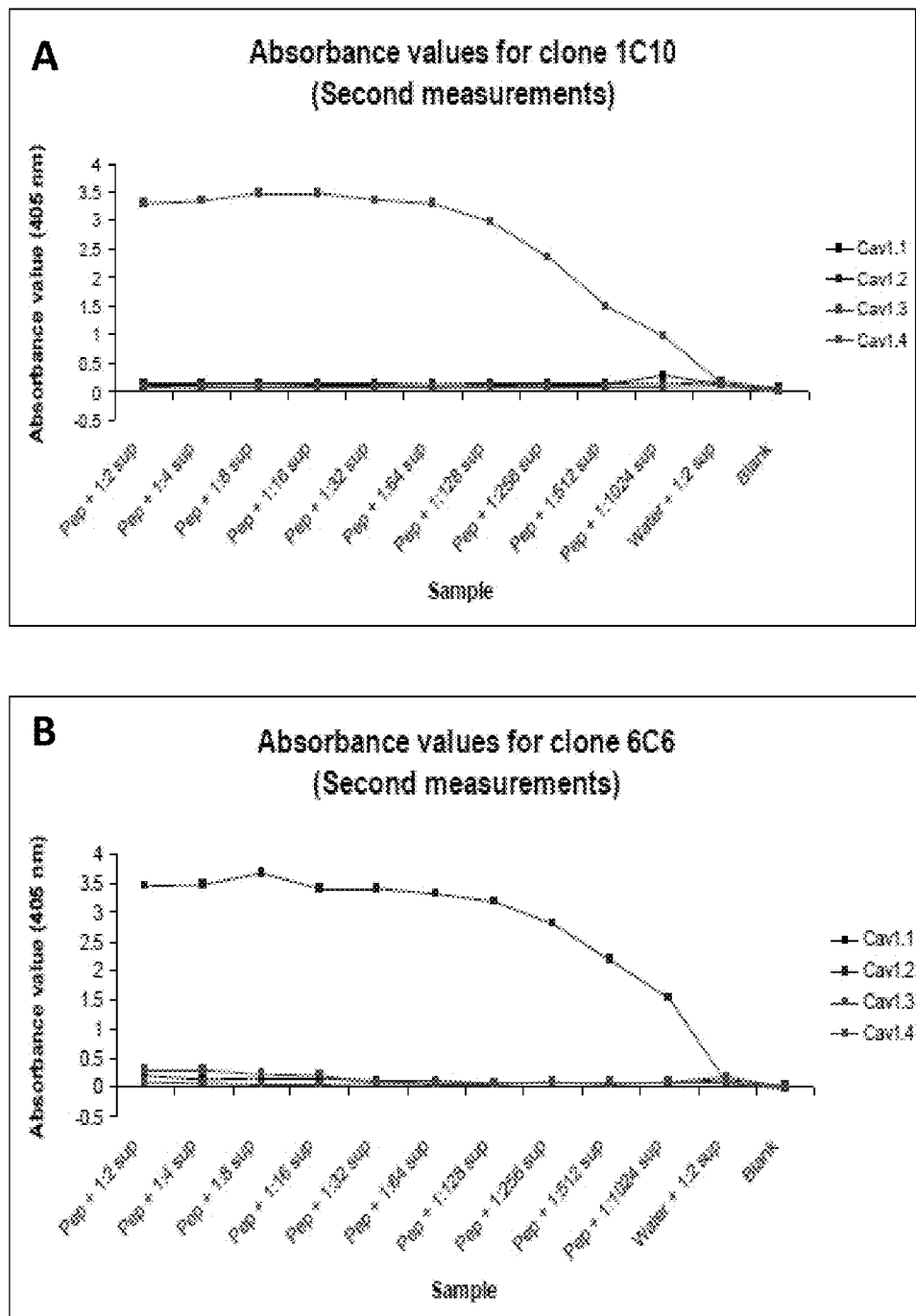
FIG. 9 shows representative results of selective binding data for hybridomas. Clone 1C10 (9A) selectively binds to Cav1.4, and clone 6C6 (9B) selectively binds to Cav1.2. Also shown are the binding data for clone 1C8 (9C), clone 6A3 (9D) which selectively binds to Cav1.2, clone 1D2 (9F) which selectively binds to Cav1.2, clone 1E7 (9F) which selectively binds to Cav1.2, clone 1F4 (9G) which selectively binds to Cav1.1, clone 2D5 (9H) which selectively binds to Cav1.4, clone 5F4 (9I), clone 5G10 (9J), clone 6E1 (9K), clone 6H7 (9L), clone 8G1 (9M), clone 9C3 (9N), and clone 10E11 (9O).
Figure 9:
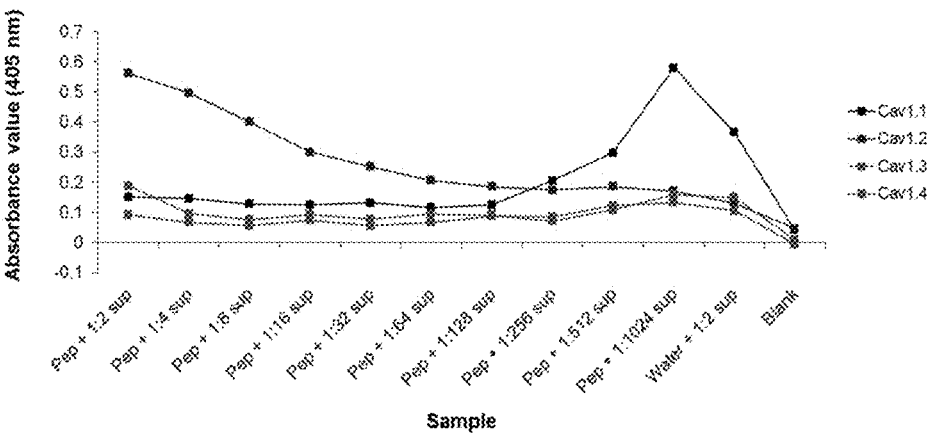
Figure 9:
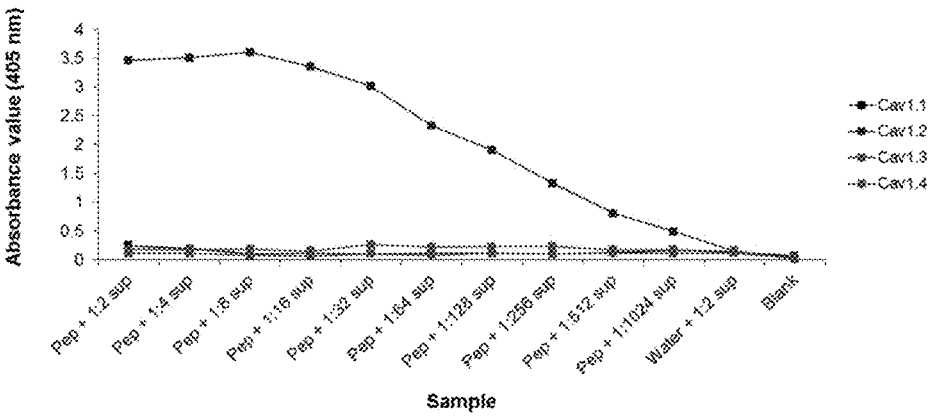
Figure 9:
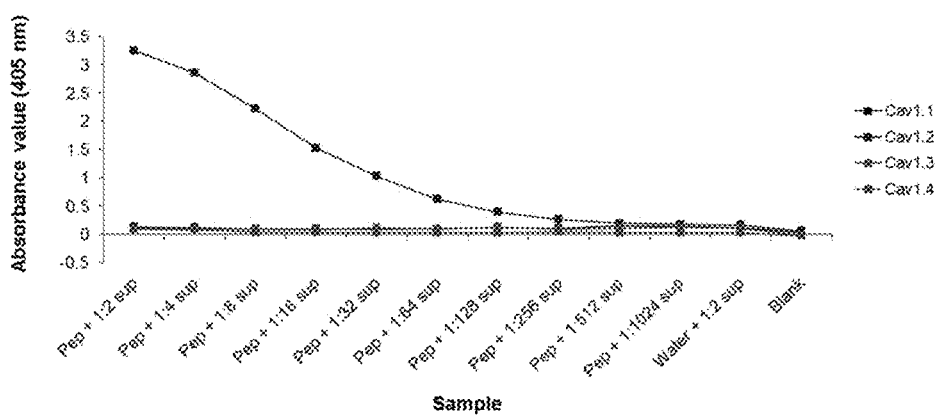
Figure 9:
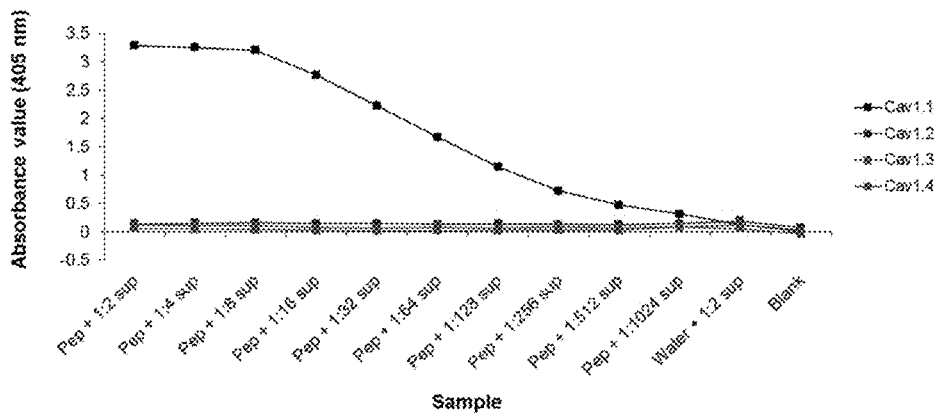
Figure 9:
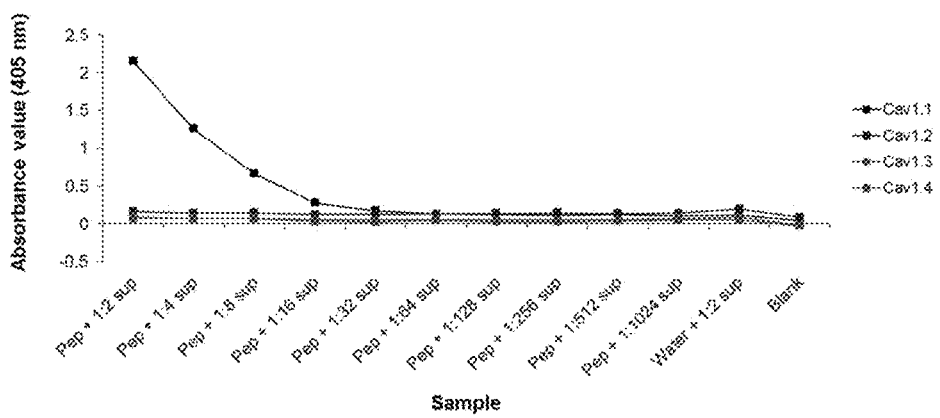
Figure 9:
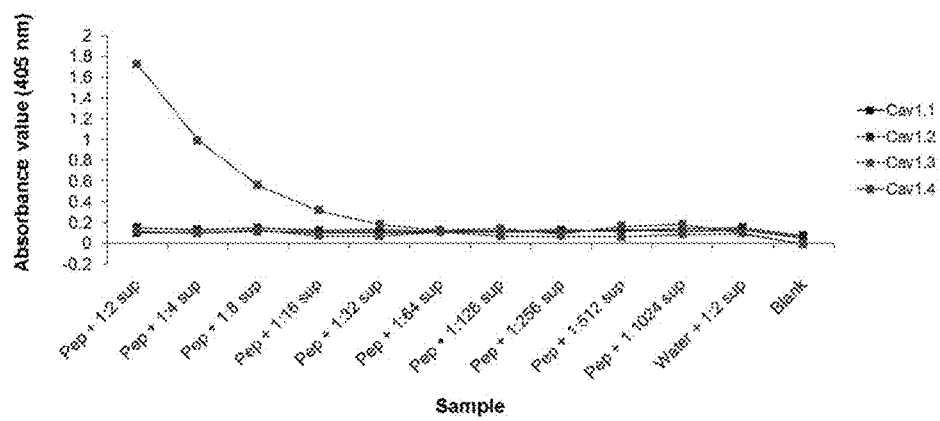
Figure 9:
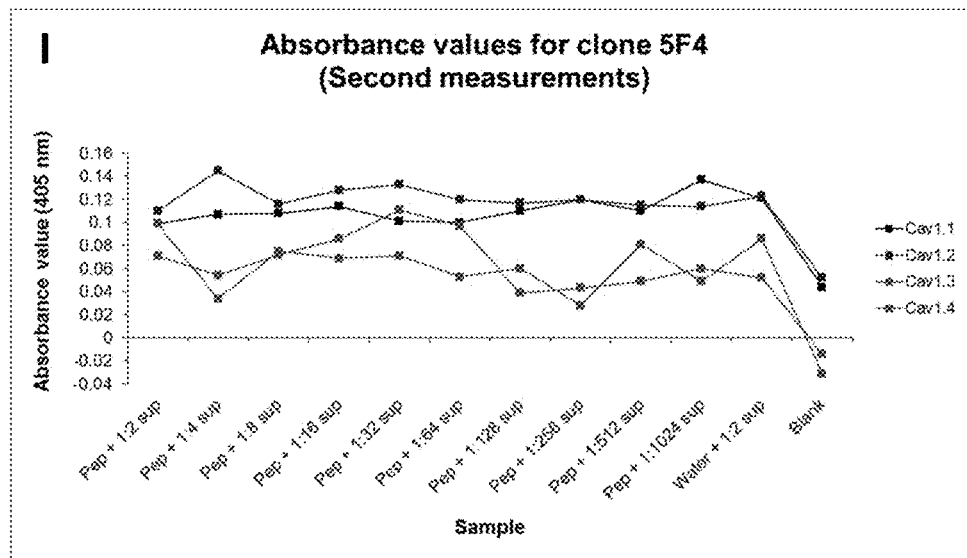
Figure 9:
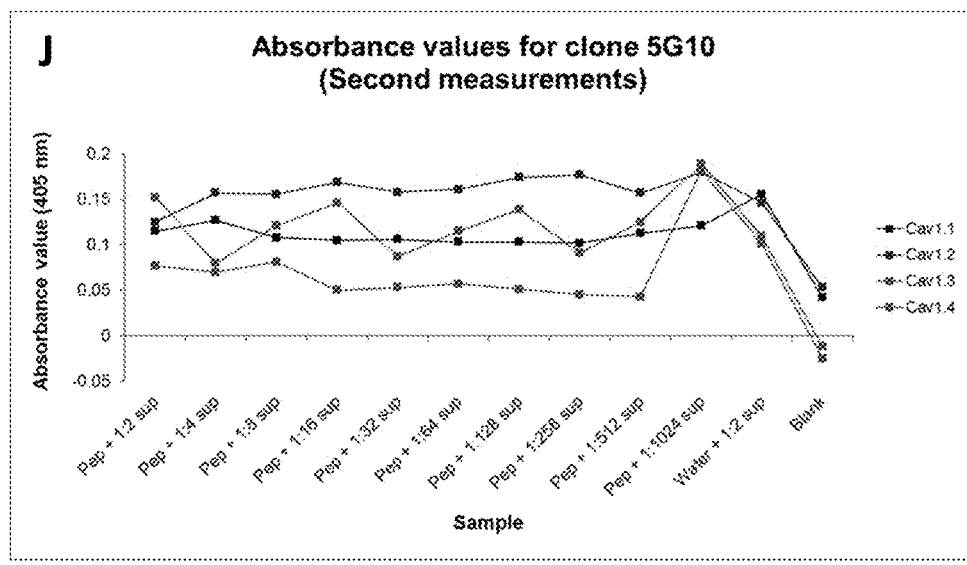
Figure 9:
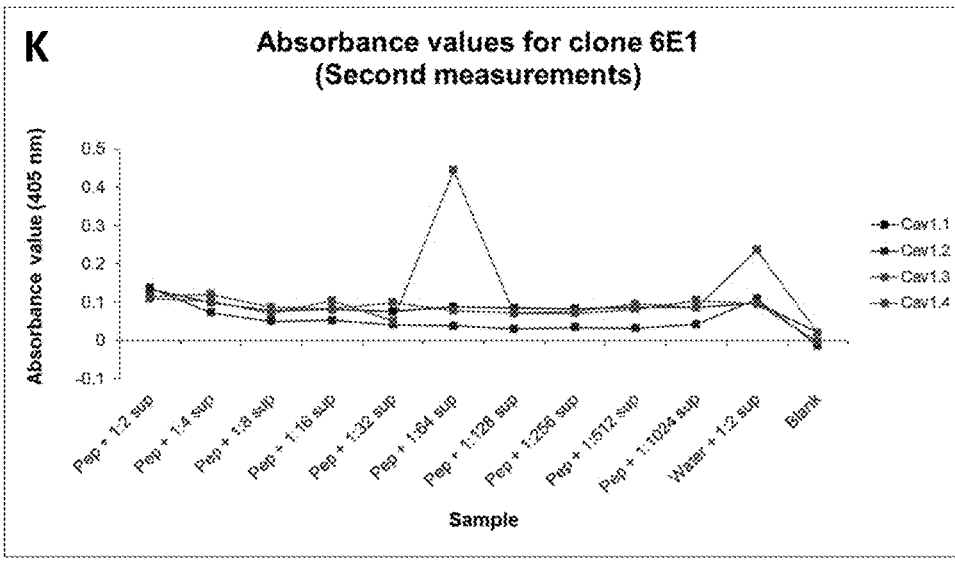
Figure 9:
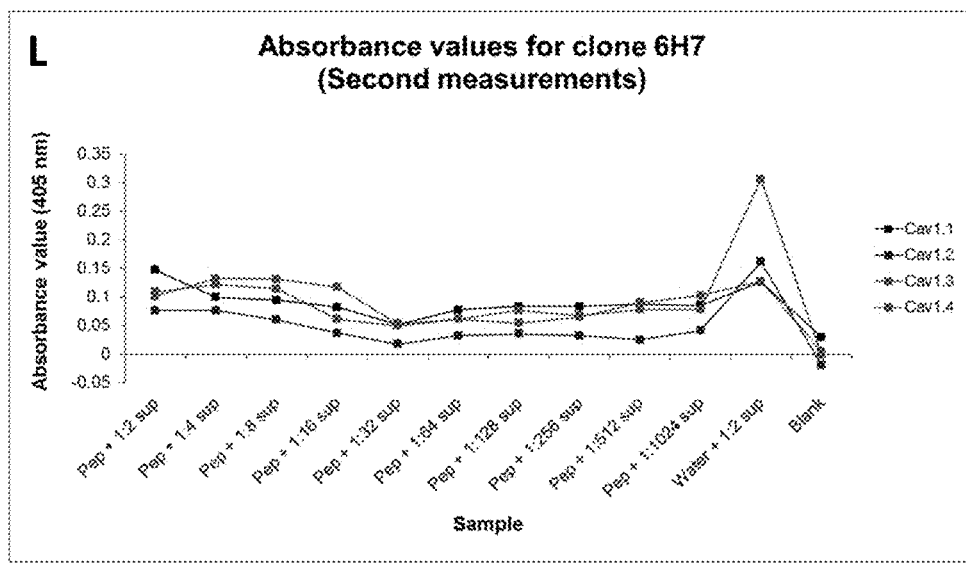
Figure 9:
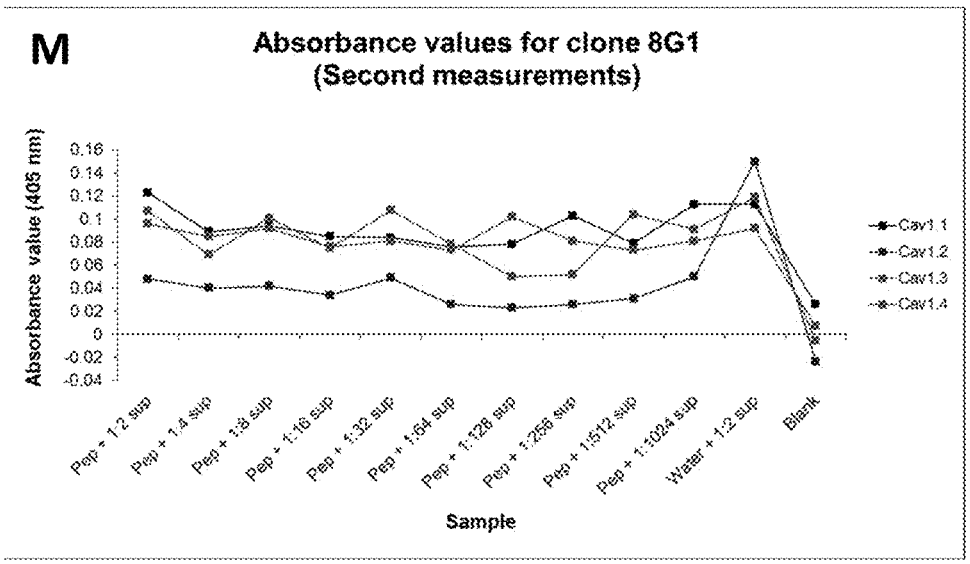
Figure 9:
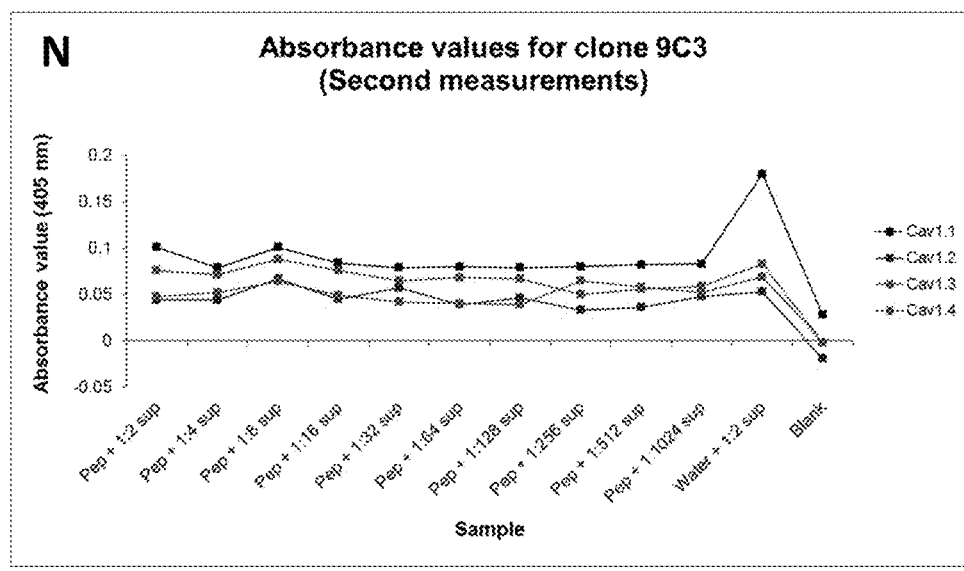
Figure 9:
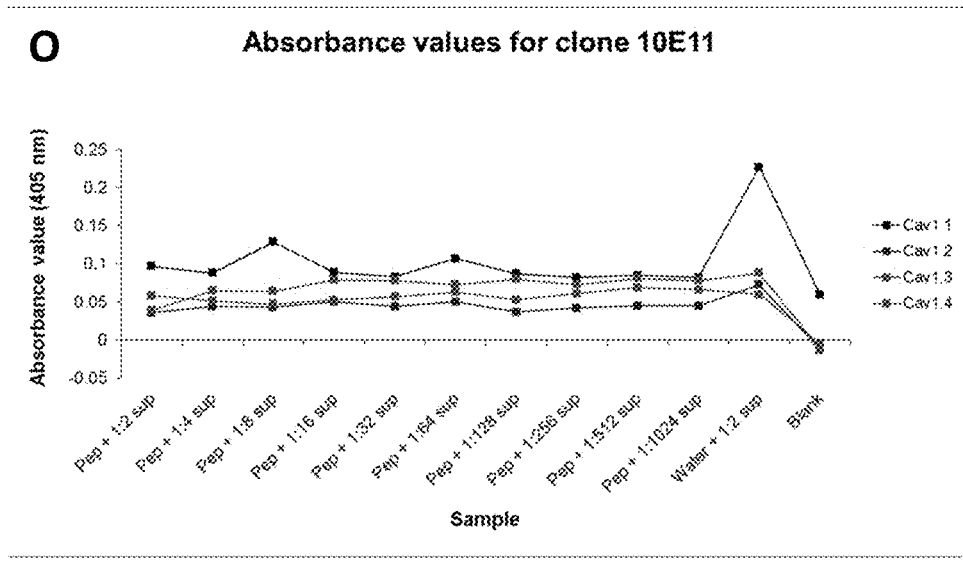

Characterization of Hybridoma Antibody Directed Against L-Type Voltage Gated Calcium Channels ELISA experiments were preformed to characterize monoclonal antibodies generated to target the extracellular pore domain of the L-type voltage-gated calcium channels. Sixty-three antibodies of interest were tested for their abilities to bind to the peptides with amino acid sequences from Table E1 that were used to generate the antibodies. Antibody binding was tested in wells coated with BSA and all the peptides with from each L-type voltage gated calcium channel, BSA and the Cav1.1 peptide, BSA and the Cav1.2 peptide, BSA and the Cav1.3 peptide, and BSA and the Cava.4 peptide. Binding was detected with a mixture of IgG and IgM secondary antibodies, and signal was compared to negative controls. Representative results of these experiments are presented (FIG. 3). The results indicated that the antibodies could specifically bind to the target peptides. Clones were observed that bound only to Cav1.1 (for example, see clones 1E7 and 1F4; FIG. 3), only to Cav1.2 (clones 1F7 and 6C6; FIGS. 3 and 9), only to Cav1.3 (clones 11310, 1611, and 2D4; FIG. 3), and only to Cav1.4 (clones 1C10 and 263, FIG. 3). In addition, some antibodies were observed that could bind to two Cav1 channels (for example, clones 1A3, 169, and 1C8) or three Cav1 channels (1D2). These results demonstrate that monoclonal antibodies that recognize extracellular pore loops of L-type voltage gated-calcium channels were successfully generated.

To determine if the antibodies could bind to L-type voltage gated calcium channels expressed on immune cells, flow cytometry experiments were performed to test the binding of the monoclonal antibodies to immune cells. Splenocytes and thymocytes were isolated from spleens and thymi that were harvested from wild-type C571316 mice. Cells were prepared for flow cytometry. Supernatants containing antibody were collected from hybridoma cultures to test the ability of the monoclonal antibodies to bind to the cells. FITC conjugated Goat anti-mouse IgG andante mouse IgM was used for secondary antibody to detect monoclonal binding.

Figure 4:
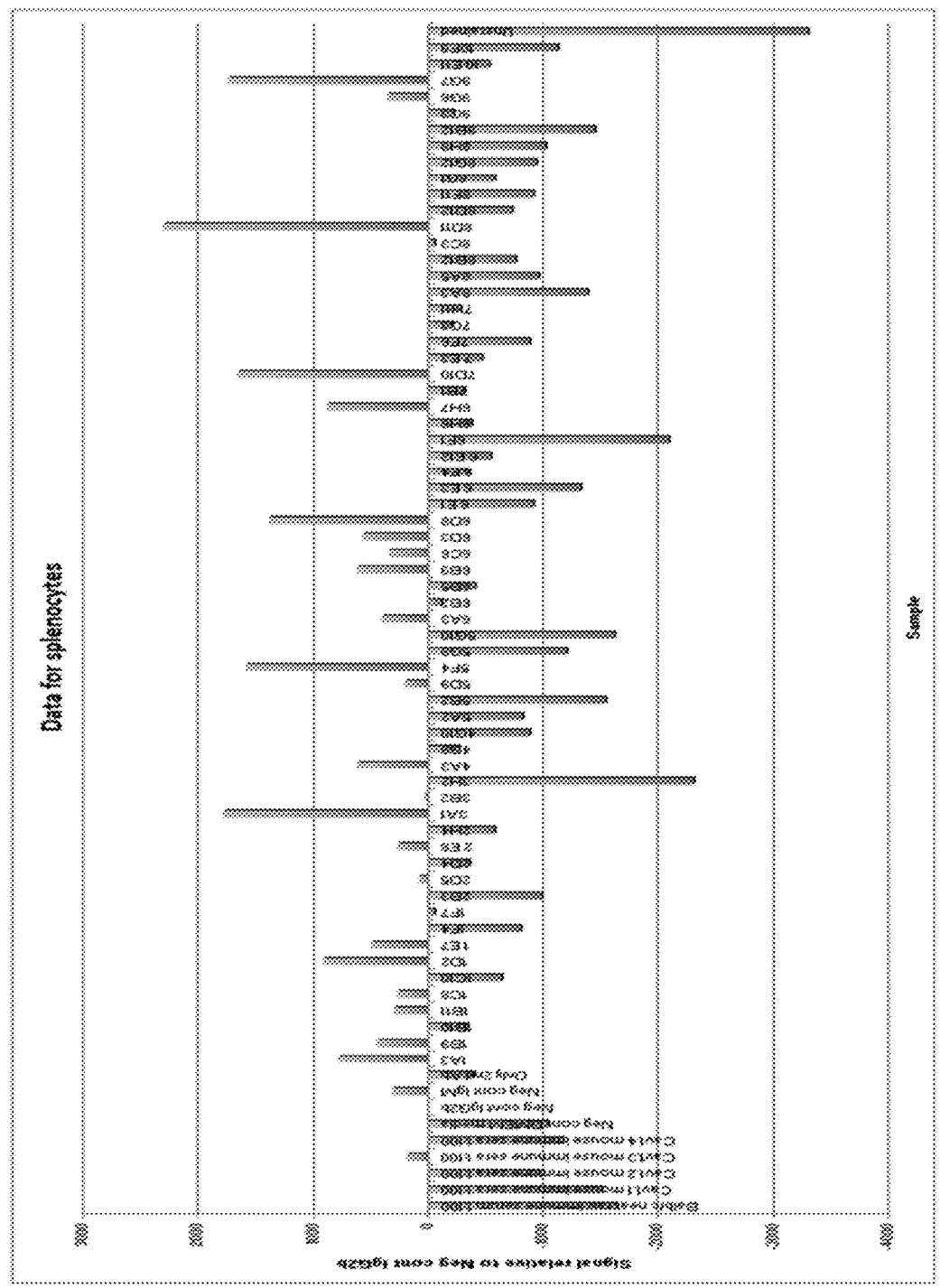
FIG. 4 shows representative results of flow cytometry experiments performed on antibodies produced by hybridoma clones. Supernatants containing monoclonal antibodies produced by hybridomas were tested to determine binding to wild-type mouse splenocytes. The binding signals of the monoclonal antibodies relative to IgG2b control antibody are displayed.
Figure 5:
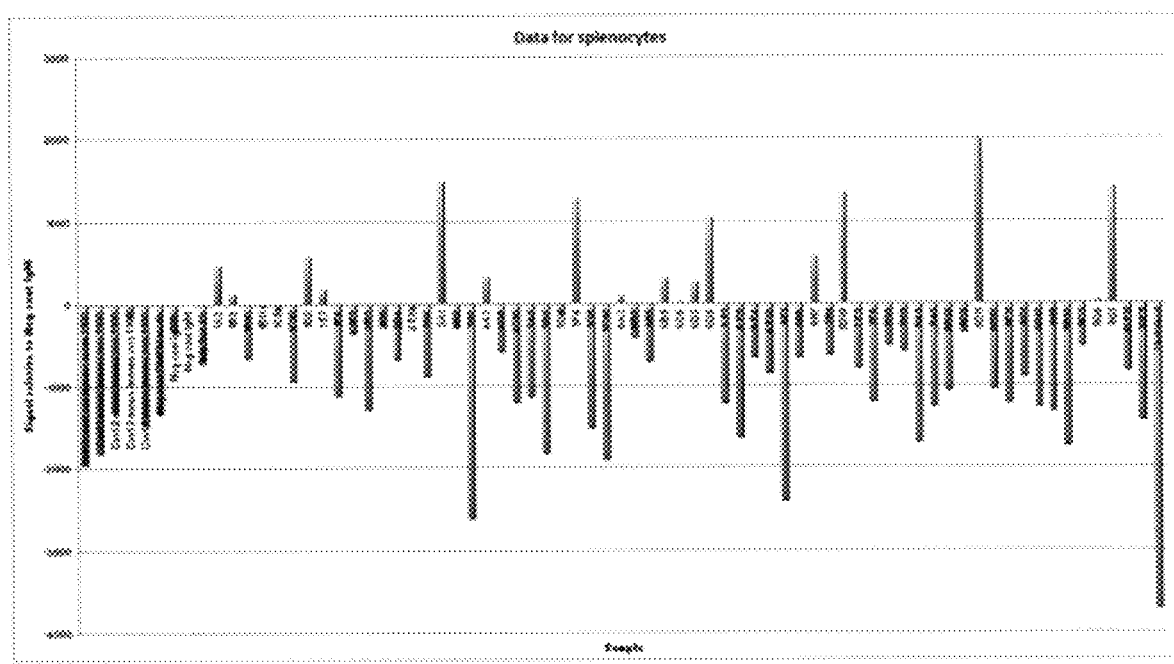
FIG. 5 shows representative results of flow cytometry experiments performed on antibodies produced by hybridoma clones. Supernatants containing monoclonal antibodies produced by hybridomas were tested to determine binding to wild-type mouse splenocytes. The binding signals of the monoclonal antibodies relative to IgM control antibody are displayed.

Antibodies collected from hybridoma clones were tested for their ability to bind to wild-type mouse splenocytes. Splenocytes consist of a variety of cell populations such as T and B lymphocytes, dendritic cells and macrophages. Negative controls included unstained (no antibody or media), negative control DMEM media, negative control IgG2b antibody, and negative IgM antibody. Binding was quantified as a ratio of test antibody signal to negative control igG2b antibody (FIG. 4) or negative control IgM antibody (FIG. 5). Representative results (FIGS. 4 and 5) demonstrate that monoclonal antibodies that bind to splenocytes were identified, for example, clones 3A1, 5F4, and 7D10.

Figure 6:
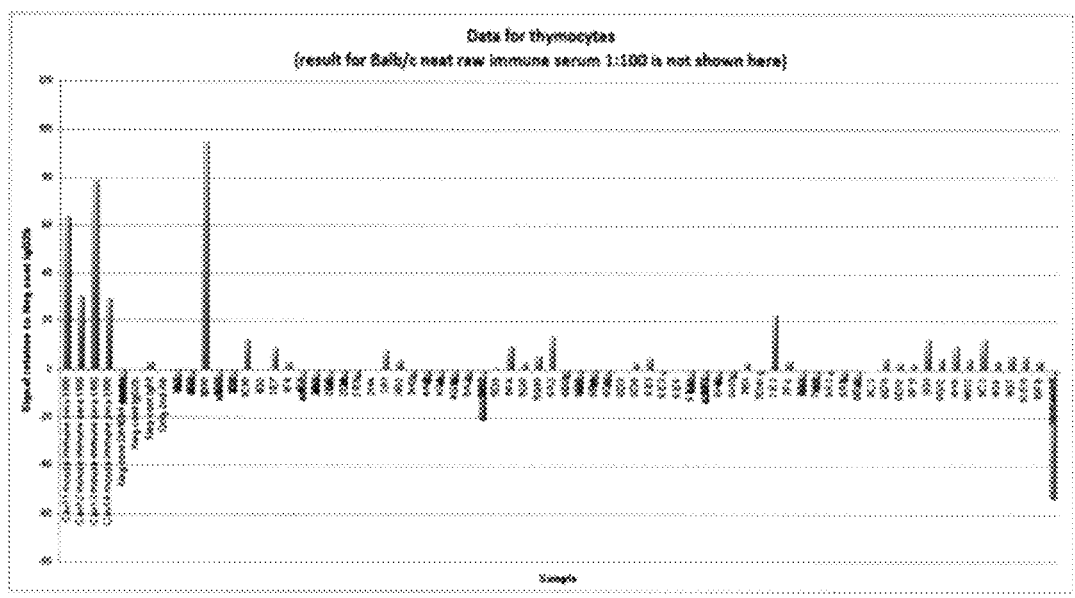
FIG. 6 shows representative results of flow cytometry experiments performed on antibodies produced by hybridoma clones. Supernatants containing monoclonal antibodies produced by hybridomas were tested to determine binding to wild-type mouse thymocytes. The binding signals of the monoclonal antibodies relative to IgG2b control antibody are displayed.
Figure 7:
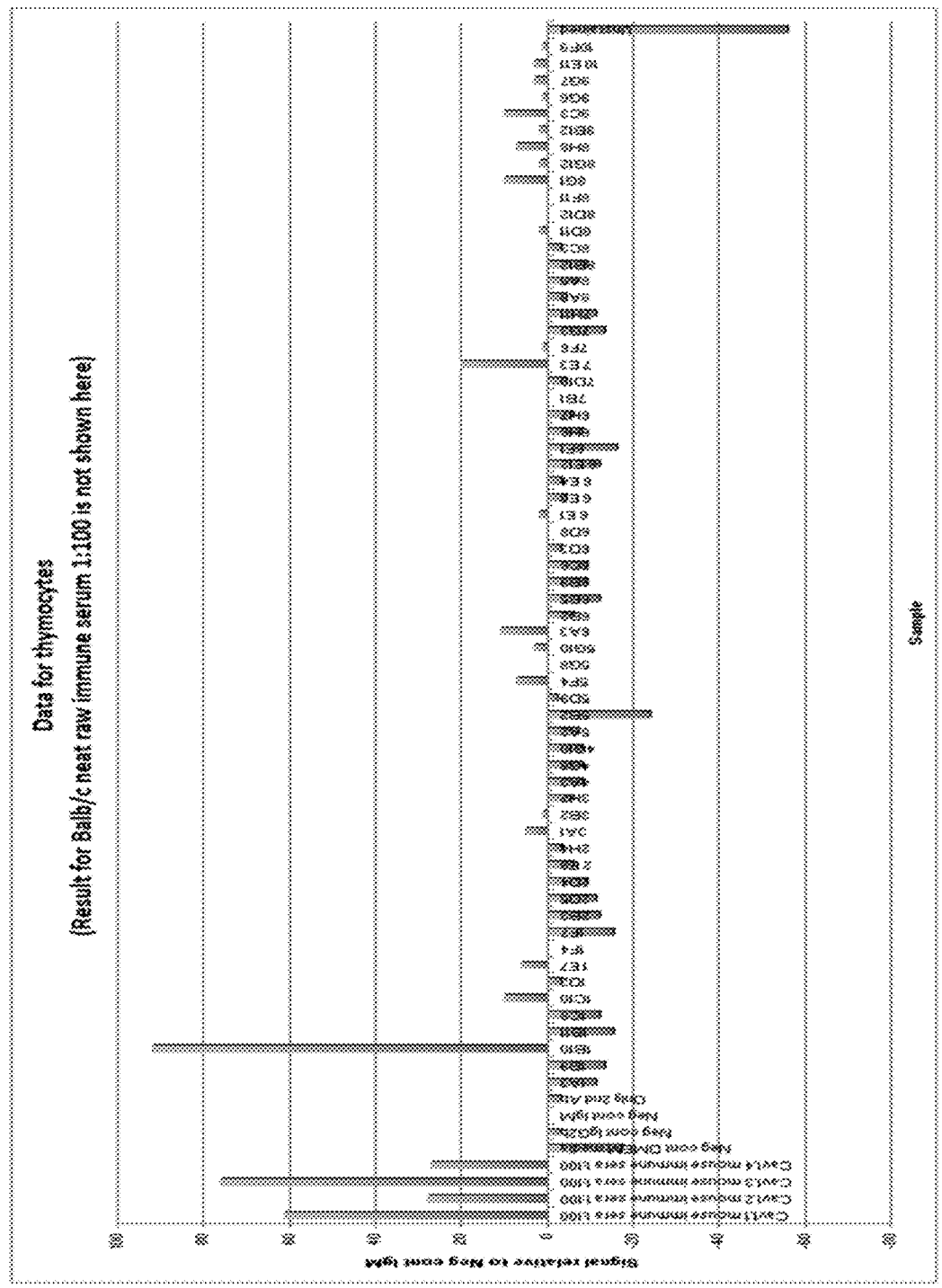
FIG. 7 shows representative results of flow cytometry experiments performed on antibodies produced by hybridoma clones. Supernatants containing monoclonal antibodies produced by hybridomas were tested to determine binding to wild-type mouse thymocytes. The binding signals of the monoclonal antibodies relative to IgM control antibody are displayed.

A similar experiment tested antibodies collected from hybridoma clones for their ability to bind to wild-type mouse thymocytes. Thymocytes are hematopoietic progenitor cells present in the thymus that differentiate into mature T lymphocytes. Immunosera from mice immunized with Cav1.1, Cav1.2, Cav1.3, and Cav1.4 were used as positive controls. Negative controls included unstained (no antibody or media), negative control DMEM media, negative control IgG2b antibody, and negative IgM antibody. Binding was quantified as a ratio of test antibody signal to negative control igG2b antibody (FIG. 6) or negative control IgM antibody (FIG. 7). Representative results (FIGS. 5 and 6) demonstrate that monoclonal antibodies that bind to thymocytes were identified, for example, clones 1E10 and 7E3.

Taken together, these results demonstrate that monoclonal antibodies were generated that can recognize extracellular pore loops of L-type voltage-gated calcium channel alpha 1 subunits and that can bind to targets on immune cells. Following this series of experiments, 31 clones on interest were identified (Summarized in FIG. 8) based on their ability to bind to an L-type voltage-gated calcium channel subtype and to bind to a target on a splenocyte or thymocyte. Twenty-eight hybridomas were identified that produce antibodies selective for one subtype (Cav1.4, Cav1.3, Cav1.2, or Cav1.1), three hybridomas were identified that produce antibodies selective for two subtypes (Cav1.4 and Cav1.2; or Cav1.3 and Cav1.2), and one hybridoma was identified that produces antibody selective for three subtypes (Cav1.4, Cav1.3, and Cav1.2).

Example 3

Hybridoma Antibodies Bind to and Inhibit Growth of Jurkat T-Cells

The hybridoma clones were additionally evaluated in a flow cytometry-based binding assay using the human Jurkat leukemia cell line (Jurkat). Cell binding and growth inhibition assays were performed using standard techniques. The results are shown in Table E2 below.

TABLE E2

Jurkat Binding and Growth Assays

| Clone ID | Binding Specificity | | | | Iso-type | Cell binding | Growth Inhibition |
| --- | --- | --- | --- | --- | --- | --- | --- |
| | Cav1.1 | Cav1.2 | Cav1.3 | Cav1.4 | | | Jurkat |
| 1C8 | | Yes | | | IgG | Yes | Yes |
| 1C10 | | | | Yes | IgG | Yes | Yes |

TABLE E2-continued

Jurkat Binding and Growth Assays

| Clone ID | Binding Specificity | | | | Iso-type | Cell binding | Growth Inhibition |
| --- | --- | --- | --- | --- | --- | --- | --- |
| | Cav1.1 | Cav1.2 | Cav1.3 | Cav1.4 | | | Jurkat |
| 1D2 | | Yes | Yes | Yes | IgM | Yes | Yes |
| 1E7 | Yes | | | | IgM | Yes | Yes |
| 1F4 | Yes | | | | IgG | Yes | Yes |
| 2D5 | | Yes | | | IgG | Yes | Yes |
| 5F4 | | Yes | | | IgG | Yes | Yes |
| 5G10 | | Yes | | | IgG | NS | Yes |
| 6A3 | | Yes | Yes | | IgG | Yes | Yes |
| 6C6 | | Yes | | | IgG | Yes | NS |
| 6E1 | | Yes | | | IgG | Yes | Yes |
| 6H7 | | Yes | | | IgG | Yes | Yes |
| 8G1 | | Yes | | | IgG | Yes | Yes |
| 9C3 | | Yes | | | IgG | Yes | Yes |
| 10E11 | | Yes | | | IgG | Yes | Yes |

NS—Non-specific at time of assay.

These results show that supernatants from the hybridoma clones in Table E2 were able to bind to and inhibit the growth of human Jurkat T-cells, evidencing the therapeutic potential of these antibodies in the treatment of various cancers, including hematopoietic cancers.

The invention claimed is:

1. An isolated antibody, or antigen-binding fragment thereof, which binds to an alpha 1 subunit of an L-type voltage-gated calcium channel, wherein the antibody or antigen-binding fragment thereof, specifically binds to an amino acid sequence of an extracellular domain selected from SEQ ID NO:1 and which comprises a heavy chain variable region ($V_H$) having the $V_H$ sequence of SEQ ID NO: 13; and a light chain variable region ($V_L$) having the $V_L$ sequence of SEQ ID NO: 17, wherein (i) $V_H$ comprises $V_H$CDR1, $V_H$CDR2 and $V_H$CDR3 amino acid sequences of SEQ ID NOS:14-16; and (ii) $V_L$ comprises $V_L$CDR1, $V_L$CDR2 and $V_L$CDR3 amino acid sequences of SEQ ID NOS:18-20; wherein the antibody, or antigen-binding fragment thereof has binding specificity for Cav1.4 (SEQ ID NOS:5 and 9) and does not significantly bind to Cav1.1, Cav1.2 or Cav1.3.

* * * * *

SEQUENCE LISTING

```
<160> NUMBER OF SEQ ID NOS: 108

<210> SEQ ID NO 1
<211> LENGTH: 12
<212> TYPE: PRT
<213> ORGANISM: Unknown
<220> FEATURE:
<223> OTHER INFORMATION: Conserved mammalian extracellular domain of
      Cav1.4

<400> SEQUENCE: 1

Gly Pro Gly Arg Pro Gly Asp Ala Pro His Thr Gly
1               5                   10

<210> SEQ ID NO 2
<211> LENGTH: 16
<212> TYPE: PRT
<213> ORGANISM: Unknown
<220> FEATURE:
<223> OTHER INFORMATION: Conserved mammalian extracellular domain of
      Cav1.3

<400> SEQUENCE: 2

Leu Thr Lys Glu Thr Glu Gly Gly Asn His Ser Ser Gly Lys Ser Gly
1               5                   10                  15

<210> SEQ ID NO 3
<211> LENGTH: 15
<212> TYPE: PRT
<213> ORGANISM: Unknown
<220> FEATURE:
<223> OTHER INFORMATION: Conserved mammalian extracellular domain of
      Cav1.2
```

-continued

```
<400> SEQUENCE: 3

Ala Thr Lys Ala Asp Gly Ala Asn Ala Leu Gly Gly Lys Gly Ala
1               5                   10                  15

<210> SEQ ID NO 4
<211> LENGTH: 13
<212> TYPE: PRT
<213> ORGANISM: Unknown
<220> FEATURE:
<223> OTHER INFORMATION: Conserved mammalian extracellular domain of
      Cav1.1

<400> SEQUENCE: 4

Pro Met Gln Ile Glu Leu Arg His Arg Glu Trp Val His
1               5                   10

<210> SEQ ID NO 5
<211> LENGTH: 1977
<212> TYPE: PRT
<213> ORGANISM: Homo sapiens

<400> SEQUENCE: 5

Met Ser Glu Ser Glu Gly Gly Lys Asp Thr Thr Pro Glu Pro Ser Pro
1               5                   10                  15

Ala Asn Gly Ala Gly Pro Gly Pro Glu Trp Gly Leu Cys Pro Gly Pro
                20                  25                  30

Pro Ala Val Glu Gly Glu Ser Ser Gly Ala Ser Gly Leu Gly Thr Pro
            35                  40                  45

Lys Arg Arg Asn Gln His Ser Lys His Lys Thr Val Ala Val Ala Ser
    50                  55                  60

Ala Gln Arg Ser Pro Arg Ala Leu Phe Cys Leu Thr Leu Ala Asn Pro
65                  70                  75                  80

Leu Arg Arg Ser Cys Ile Ser Ile Val Glu Trp Lys Pro Phe Asp Ile
                85                  90                  95

Leu Ile Leu Leu Thr Ile Phe Ala Asn Cys Val Ala Leu Gly Val Tyr
                100                 105                 110

Ile Pro Phe Pro Glu Asp Asp Ser Asn Thr Ala Asn His Asn Leu Glu
            115                 120                 125

Gln Val Glu Tyr Val Phe Leu Val Ile Phe Thr Val Glu Thr Val Leu
    130                 135                 140

Lys Ile Val Ala Tyr Gly Leu Val Leu His Pro Ser Ala Tyr Ile Arg
145                 150                 155                 160

Asn Gly Trp Asn Leu Leu Asp Phe Ile Ile Val Val Val Gly Leu Phe
                165                 170                 175

Ser Val Leu Leu Glu Gln Gly Pro Gly Arg Pro Gly Asp Ala Pro His
                180                 185                 190

Thr Gly Gly Lys Pro Gly Gly Phe Asp Val Lys Ala Leu Arg Ala Phe
            195                 200                 205

Arg Val Leu Arg Pro Leu Arg Leu Val Ser Gly Val Pro Ser Leu His
    210                 215                 220

Ile Val Leu Asn Ser Ile Met Lys Ala Leu Val Pro Leu Leu His Ile
225                 230                 235                 240

Ala Leu Leu Val Leu Phe Val Ile Ile Tyr Ala Ile Ile Gly Leu
                245                 250                 255

Glu Leu Phe Leu Gly Arg Met His Lys Thr Cys Tyr Phe Leu Gly Ser
                260                 265                 270
```

-continued

Asp Met Glu Ala Glu Asp Pro Ser Pro Cys Ala Ser Ser Gly Ser
         275                 280                 285

Gly Arg Ala Cys Thr Leu Asn Gln Thr Glu Cys Arg Gly Arg Trp Pro
290                 295                 300

Gly Pro Asn Gly Gly Ile Thr Asn Phe Asp Asn Phe Phe Ala Met
305             310                 315                 320

Leu Thr Val Phe Gln Cys Val Thr Met Glu Gly Trp Thr Asp Val Leu
                325                 330                 335

Tyr Trp Met Gln Asp Ala Met Gly Tyr Glu Leu Pro Trp Val Tyr Phe
             340                 345                 350

Val Ser Leu Val Ile Phe Gly Ser Phe Phe Val Leu Asn Leu Val Leu
         355                 360                 365

Gly Val Leu Ser Gly Glu Phe Ser Lys Glu Arg Glu Lys Ala Lys Ala
     370                 375                 380

Arg Gly Asp Phe Gln Lys Gln Arg Glu Lys Gln Gln Met Glu Glu Asp
385                 390                 395                 400

Leu Arg Gly Tyr Leu Asp Trp Ile Thr Gln Ala Glu Glu Leu Asp Met
             405                 410                 415

Glu Asp Pro Ser Ala Asp Asp Asn Leu Gly Ser Met Ala Glu Glu Gly
         420                 425                 430

Arg Ala Gly His Arg Pro Gln Leu Ala Glu Leu Thr Asn Arg Arg Arg
435                 440                 445

Gly Arg Leu Arg Trp Phe Ser His Ser Thr Arg Ser Thr His Ser Thr
     450                 455                 460

Ser Ser His Ala Ser Leu Pro Ala Ser Asp Thr Gly Ser Met Thr Glu
465                 470                 475                 480

Thr Gln Gly Asp Glu Asp Glu Glu Glu Gly Ala Leu Ala Ser Cys Thr
                485                 490                 495

Arg Cys Leu Asn Lys Ile Met Lys Thr Arg Val Cys Arg Arg Leu Arg
             500                 505                 510

Arg Ala Asn Arg Val Leu Arg Ala Arg Cys Arg Arg Ala Val Lys Ser
         515                 520                 525

Asn Ala Cys Tyr Trp Ala Val Leu Leu Val Phe Leu Asn Thr Leu
     530                 535                 540

Thr Ile Ala Ser Glu His His Gly Gln Pro Val Trp Leu Thr Gln Ile
545                 550                 555                 560

Gln Glu Tyr Ala Asn Lys Val Leu Leu Cys Leu Phe Thr Val Glu Met
             565                 570                 575

Leu Leu Lys Leu Tyr Gly Leu Gly Pro Ser Ala Tyr Val Ser Ser Phe
         580                 585                 590

Phe Asn Arg Phe Asp Cys Phe Val Cys Gly Ile Leu Glu Thr
     595                 600                 605

Thr Leu Val Glu Val Gly Ala Met Gln Pro Leu Gly Ile Ser Val Leu
     610                 615                 620

Arg Cys Val Arg Leu Leu Arg Ile Phe Lys Val Thr Arg His Trp Ala
625                 630                 635                 640

Ser Leu Ser Asn Leu Val Ala Ser Leu Leu Asn Ser Met Lys Ser Ile
             645                 650                 655

Ala Ser Leu Leu Leu Leu Leu Phe Leu Phe Ile Ile Ile Phe Ser Leu
         660                 665                 670

Leu Gly Met Gln Leu Phe Gly Gly Lys Phe Asn Phe Asp Gln Thr His
     675                 680                 685

```
Thr Lys Arg Ser Thr Phe Asp Thr Phe Pro Gln Ala Leu Thr Val
    690             695             700

Phe Gln Ile Leu Thr Gly Glu Asp Trp Asn Val Val Met Tyr Asp Gly
705             710              715             720

Ile Met Ala Tyr Gly Gly Pro Phe Phe Pro Gly Met Leu Val Cys Ile
            725             730             735

Tyr Phe Ile Ile Leu Phe Ile Cys Gly Asn Tyr Ile Leu Leu Asn Val
            740             745             750

Phe Leu Ala Ile Ala Val Asp Asn Leu Ala Ser Gly Asp Ala Gly Thr
            755             760             765

Ala Lys Asp Lys Gly Gly Glu Lys Ser Asn Glu Lys Asp Leu Pro Gln
770             775             780

Glu Asn Glu Gly Leu Val Pro Gly Val Glu Lys Glu Glu Glu Gly
785             790             795             800

Ala Arg Arg Glu Gly Ala Asp Met Glu Glu Glu Glu Glu Glu Glu
            805             810             815

Glu Glu Glu Glu Glu Glu Glu Glu Gly Ala Gly Val Glu Leu
            820             825             830

Leu Gln Glu Val Val Pro Lys Glu Lys Val Val Pro Ile Pro Glu Gly
    835             840             845

Ser Ala Phe Phe Cys Leu Ser Gln Thr Asn Pro Leu Arg Lys Gly Cys
850             855             860

His Thr Leu Ile His His Val Phe Thr Asn Leu Ile Leu Val Phe
865             870             875             880

Ile Ile Leu Ser Ser Val Ser Leu Ala Ala Glu Asp Pro Ile Arg Ala
            885             890             895

His Ser Phe Arg Asn His Ile Leu Gly Tyr Phe Asp Tyr Ala Phe Thr
            900             905             910

Ser Ile Phe Thr Val Glu Ile Leu Leu Lys Met Thr Val Phe Gly Ala
    915             920             925

Phe Leu His Arg Gly Ser Phe Cys Arg Ser Trp Phe Asn Met Leu Asp
    930             935             940

Leu Leu Val Val Ser Val Ser Leu Ile Ser Phe Gly Ile His Ser Ser
945             950             955             960

Ala Ile Ser Val Val Lys Ile Leu Arg Val Leu Arg Val Leu Arg Pro
            965             970             975

Leu Arg Ala Ile Asn Arg Ala Lys Gly Leu Lys His Val Val Gln Cys
    980             985             990

Val Phe Val Ala Ile Arg Thr Ile Gly Asn Ile Met Ile Val Thr Thr
        995             1000            1005

Leu Leu Gln Phe Met Phe Ala Cys Ile Gly Val Gln Leu Phe Lys
    1010            1015            1020

Gly Lys Phe Tyr Thr Cys Thr Asp Glu Ala Lys His Thr Pro Gln
    1025            1030            1035

Glu Cys Lys Gly Ser Phe Leu Val Tyr Pro Asp Gly Asp Val Ser
    1040            1045            1050

Arg Pro Leu Val Arg Glu Arg Leu Trp Val Asn Ser Asp Phe Asn
    1055            1060            1065

Phe Asp Asn Val Leu Ser Ala Met Met Ala Leu Phe Thr Val Ser
    1070            1075            1080

Thr Phe Glu Gly Trp Pro Ala Leu Leu Tyr Lys Ala Ile Asp Ala
    1085            1090            1095
```

```
Tyr Ala Glu Asp His Gly Pro Ile Tyr Asn Tyr Arg Val Glu Ile
1100                1105                1110

Ser Val Phe Phe Ile Val Tyr Ile Ile Ile Ile Ala Phe Phe Met
1115                1120                1125

Met Asn Ile Phe Val Gly Phe Val Ile Ile Thr Phe Arg Ala Gln
1130                1135                1140

Gly Glu Gln Glu Tyr Gln Asn Cys Glu Leu Asp Lys Asn Gln Arg
1145                1150                1155

Gln Cys Val Glu Tyr Ala Leu Lys Ala Gln Pro Leu Arg Arg Tyr
1160                1165                1170

Ile Pro Lys Asn Pro His Gln Tyr Arg Val Trp Ala Thr Val Asn
1175                1180                1185

Ser Ala Ala Phe Glu Tyr Leu Met Phe Leu Leu Ile Leu Leu Asn
1190                1195                1200

Thr Val Ala Leu Ala Met Gln His Tyr Glu Gln Thr Ala Pro Phe
1205                1210                1215

Asn Tyr Ala Met Asp Ile Leu Asn Met Val Phe Thr Gly Leu Phe
1220                1225                1230

Thr Ile Glu Met Val Leu Lys Ile Ile Ala Phe Lys Pro Lys His
1235                1240                1245

Tyr Phe Thr Asp Ala Trp Asn Thr Phe Asp Ala Leu Ile Val Val
1250                1255                1260

Gly Ser Ile Val Asp Ile Ala Val Thr Glu Val Asn Asn Gly Gly
1265                1270                1275

His Leu Gly Glu Ser Ser Glu Asp Ser Ser Arg Ile Ser Ile Thr
1280                1285                1290

Phe Phe Arg Leu Phe Arg Val Met Arg Leu Val Lys Leu Leu Ser
1295                1300                1305

Lys Gly Glu Gly Ile Arg Thr Leu Leu Trp Thr Phe Ile Lys Ser
1310                1315                1320

Phe Gln Ala Leu Pro Tyr Val Ala Leu Leu Ile Ala Met Ile Phe
1325                1330                1335

Phe Ile Tyr Ala Val Ile Gly Met Gln Met Phe Gly Lys Val Ala
1340                1345                1350

Leu Gln Asp Gly Thr Gln Ile Asn Arg Asn Asn Asn Phe Gln Thr
1355                1360                1365

Phe Pro Gln Ala Val Leu Leu Leu Phe Arg Cys Ala Thr Gly Glu
1370                1375                1380

Ala Trp Gln Glu Ile Met Leu Ala Ser Leu Pro Gly Asn Arg Cys
1385                1390                1395

Asp Pro Glu Ser Asp Phe Gly Pro Gly Glu Glu Phe Thr Cys Gly
1400                1405                1410

Ser Asn Phe Ala Ile Ala Tyr Phe Ile Ser Phe Phe Met Leu Cys
1415                1420                1425

Ala Phe Leu Ile Ile Asn Leu Phe Val Ala Val Ile Met Asp Asn
1430                1435                1440

Phe Asp Tyr Leu Thr Arg Asp Trp Ser Ile Leu Gly Pro His His
1445                1450                1455

Leu Asp Glu Phe Lys Arg Ile Trp Ser Glu Tyr Asp Pro Gly Ala
1460                1465                1470

Lys Gly Arg Ile Lys His Leu Asp Val Val Ala Leu Leu Arg Arg
1475                1480                1485
```

```
Ile Gln Pro Pro Leu Gly Phe Gly Lys Leu Cys Pro His Arg Val
    1490                1495                1500

Ala Cys Lys Arg Leu Val Ala Met Asn Met Pro Leu Asn Ser Asp
    1505                1510                1515

Gly Thr Val Thr Phe Asn Ala Thr Leu Phe Ala Leu Val Arg Thr
    1520                1525                1530

Ser Leu Lys Ile Lys Thr Glu Gly Asn Leu Glu Gln Ala Asn Gln
    1535                1540                1545

Glu Leu Arg Ile Val Ile Lys Lys Ile Trp Lys Arg Met Lys Gln
    1550                1555                1560

Lys Leu Leu Asp Glu Val Ile Pro Pro Asp Glu Glu Val
    1565                1570                1575

Thr Val Gly Lys Phe Tyr Ala Thr Phe Leu Ile Gln Asp Tyr Phe
    1580                1585                1590

Arg Lys Phe Arg Arg Lys Glu Lys Gly Leu Leu Gly Asn Asp
    1595                1600                1605

Ala Ala Pro Ser Thr Ser Ser Ala Leu Gln Ala Gly Leu Arg Ser
    1610                1615                1620

Leu Gln Asp Leu Gly Pro Glu Met Arg Gln Ala Leu Thr Cys Asp
    1625                1630                1635

Thr Glu Glu Glu Glu Glu Gly Gln Glu Gly Val Glu Glu Glu
    1640                1645                1650

Asp Glu Lys Asp Leu Glu Thr Asn Lys Ala Thr Met Val Ser Gln
    1655                1660                1665

Pro Ser Ala Arg Arg Gly Ser Gly Ile Ser Val Ser Leu Pro Val
    1670                1675                1680

Gly Asp Arg Leu Pro Asp Ser Leu Ser Phe Gly Pro Ser Asp Asp
    1685                1690                1695

Asp Arg Gly Thr Pro Thr Ser Ser Gln Pro Ser Val Pro Gln Ala
    1700                1705                1710

Gly Ser Asn Thr His Arg Arg Gly Ser Gly Ala Leu Ile Phe Thr
    1715                1720                1725

Ile Pro Glu Glu Gly Asn Ser Gln Pro Lys Gly Thr Lys Gly Gln
    1730                1735                1740

Asn Lys Gln Asp Glu Asp Glu Glu Val Pro Asp Arg Leu Ser Tyr
    1745                1750                1755

Leu Asp Glu Gln Ala Gly Thr Pro Pro Cys Ser Val Leu Leu Pro
    1760                1765                1770

Pro His Arg Ala Gln Arg Tyr Met Asp Gly His Leu Val Pro Arg
    1775                1780                1785

Arg Arg Leu Leu Pro Pro Thr Pro Ala Gly Arg Lys Pro Ser Phe
    1790                1795                1800

Thr Ile Gln Cys Leu Gln Arg Gln Gly Ser Cys Glu Asp Leu Pro
    1805                1810                1815

Ile Pro Gly Thr Tyr His Arg Gly Arg Asn Ser Gly Pro Asn Arg
    1820                1825                1830

Ala Gln Gly Ser Trp Ala Thr Pro Pro Gln Arg Gly Arg Leu Leu
    1835                1840                1845

Tyr Ala Pro Leu Leu Leu Val Glu Glu Gly Ala Ala Gly Glu Gly
    1850                1855                1860

Tyr Leu Gly Arg Ser Ser Gly Pro Leu Arg Thr Phe Thr Cys Leu
    1865                1870                1875
```

-continued

```
His Val Pro Gly Thr His Ser Asp Pro Ser His Gly Lys Arg Gly
    1880                1885                1890

Ser Ala Asp Ser Leu Val Glu Ala Val Leu Ile Ser Glu Gly Leu
    1895                1900                1905

Gly Leu Phe Ala Arg Asp Pro Arg Phe Val Ala Leu Ala Lys Gln
    1910                1915                1920

Glu Ile Ala Asp Ala Cys Arg Leu Thr Leu Asp Glu Met Asp Asn
    1925                1930                1935

Ala Ala Ser Asp Leu Leu Ala Gln Gly Thr Ser Ser Leu Tyr Ser
    1940                1945                1950

Asp Glu Glu Ser Ile Leu Ser Arg Phe Asp Glu Glu Asp Leu Gly
    1955                1960                1965

Asp Glu Met Ala Cys Val His Ala Leu
    1970                1975

<210> SEQ ID NO 6
<211> LENGTH: 2161
<212> TYPE: PRT
<213> ORGANISM: Homo sapiens

<400> SEQUENCE: 6

Met Met Met Met Met Met Met Lys Lys Met Gln His Gln Arg Gln Gln
1               5                   10                  15

Gln Ala Asp His Ala Asn Glu Ala Asn Tyr Ala Arg Gly Thr Arg Leu
            20                  25                  30

Pro Leu Ser Gly Glu Gly Pro Thr Ser Gln Pro Asn Ser Ser Lys Gln
        35                  40                  45

Thr Val Leu Ser Trp Gln Ala Ile Asp Ala Ala Arg Gln Ala Lys
    50                  55                  60

Ala Ala Gln Thr Met Ser Thr Ser Ala Pro Pro Val Gly Ser Leu
65                  70                  75                  80

Ser Gln Arg Lys Arg Gln Gln Tyr Ala Lys Ser Lys Lys Gln Gly Asn
                85                  90                  95

Ser Ser Asn Ser Arg Pro Ala Arg Ala Leu Phe Cys Leu Ser Leu Asn
            100                 105                 110

Asn Pro Ile Arg Arg Ala Cys Ile Ser Ile Val Glu Trp Lys Pro Phe
        115                 120                 125

Asp Ile Phe Ile Leu Leu Ala Ile Phe Ala Asn Cys Val Ala Leu Ala
    130                 135                 140

Ile Tyr Ile Pro Phe Pro Glu Asp Asp Ser Asn Ser Thr Asn His Asn
145                 150                 155                 160

Leu Glu Lys Val Glu Tyr Ala Phe Leu Ile Ile Phe Thr Val Glu Thr
                165                 170                 175

Phe Leu Lys Ile Ile Ala Tyr Gly Leu Leu Leu His Pro Asn Ala Tyr
            180                 185                 190

Val Arg Asn Gly Trp Asn Leu Leu Asp Phe Val Ile Val Ile Val Gly
        195                 200                 205

Leu Phe Ser Val Ile Leu Glu Gln Leu Thr Lys Glu Thr Glu Gly Gly
    210                 215                 220

Asn His Ser Ser Gly Lys Ser Gly Gly Phe Asp Val Lys Ala Leu Arg
225                 230                 235                 240

Ala Phe Arg Val Leu Arg Pro Leu Arg Leu Val Ser Gly Val Pro Ser
                245                 250                 255

Leu Gln Val Val Leu Asn Ser Ile Ile Lys Ala Met Val Pro Leu Leu
            260                 265                 270
```

```
His Ile Ala Leu Leu Val Leu Phe Val Ile Ile Tyr Ala Ile Ile
            275                 280                 285

Gly Leu Glu Leu Phe Ile Gly Lys Met His Lys Thr Cys Phe Ala
        290                 295                 300

Asp Ser Asp Ile Val Ala Glu Asp Pro Ala Pro Cys Ala Phe Ser
305                 310                 315                 320

Gly Asn Gly Arg Gln Cys Thr Ala Asn Gly Thr Glu Cys Arg Ser Gly
                325                 330                 335

Trp Val Gly Pro Asn Gly Gly Ile Thr Asn Phe Asp Asn Phe Ala Phe
            340                 345                 350

Ala Met Leu Thr Val Phe Gln Cys Ile Thr Met Glu Gly Trp Thr Asp
            355                 360                 365

Val Leu Tyr Trp Met Asn Asp Ala Met Gly Phe Glu Leu Pro Trp Val
            370                 375                 380

Tyr Phe Val Ser Leu Val Ile Phe Gly Ser Phe Phe Val Leu Asn Leu
385                 390                 395                 400

Val Leu Gly Val Leu Ser Gly Glu Phe Ser Lys Glu Arg Glu Lys Ala
                405                 410                 415

Lys Ala Arg Gly Asp Phe Gln Lys Leu Arg Glu Lys Gln Gln Leu Glu
            420                 425                 430

Glu Asp Leu Lys Gly Tyr Leu Asp Trp Ile Thr Gln Ala Glu Asp Ile
            435                 440                 445

Asp Pro Glu Asn Glu Glu Gly Glu Glu Gly Lys Arg Asn Thr
450                 455                 460

Ser Met Pro Thr Ser Glu Thr Glu Ser Val Asn Thr Glu Asn Val Ser
465                 470                 475                 480

Gly Glu Gly Glu Asn Arg Gly Cys Cys Gly Ser Leu Cys Gln Ala Ile
                485                 490                 495

Ser Lys Ser Lys Leu Ser Arg Arg Trp Arg Arg Trp Asn Arg Phe Asn
            500                 505                 510

Arg Arg Arg Cys Arg Ala Ala Val Lys Ser Val Thr Phe Tyr Trp Leu
            515                 520                 525

Val Ile Val Leu Val Phe Leu Asn Thr Leu Thr Ile Ser Ser Glu His
            530                 535                 540

Tyr Asn Gln Pro Asp Trp Leu Thr Gln Ile Gln Asp Ile Ala Asn Lys
545                 550                 555                 560

Val Leu Leu Ala Leu Phe Thr Cys Glu Met Leu Val Lys Met Tyr Ser
                565                 570                 575

Leu Gly Leu Gln Ala Tyr Phe Val Ser Leu Phe Asn Arg Phe Asp Cys
            580                 585                 590

Phe Val Val Cys Gly Gly Ile Thr Glu Thr Ile Leu Val Glu Leu Glu
            595                 600                 605

Ile Met Ser Pro Leu Gly Ile Ser Val Phe Arg Cys Val Arg Leu Leu
610                 615                 620

Arg Ile Phe Lys Val Thr Arg His Trp Thr Ser Leu Ser Asn Leu Val
625                 630                 635                 640

Ala Ser Leu Leu Asn Ser Met Lys Ser Ile Ala Ser Leu Leu Leu Leu
                645                 650                 655

Leu Phe Leu Phe Ile Ile Ile Phe Ser Leu Leu Gly Met Gln Leu Phe
            660                 665                 670

Gly Gly Lys Phe Asn Phe Asp Glu Thr Gln Thr Lys Arg Ser Thr Phe
            675                 680                 685
```

-continued

```
Asp Asn Phe Pro Gln Ala Leu Leu Thr Val Phe Gln Ile Leu Thr Gly
    690                 695                 700

Glu Asp Trp Asn Ala Val Met Tyr Asp Gly Ile Met Ala Tyr Gly Gly
705                 710                 715                 720

Pro Ser Ser Ser Gly Met Ile Val Cys Ile Tyr Phe Ile Ile Leu Phe
                725                 730                 735

Ile Cys Gly Asn Tyr Ile Leu Leu Asn Val Phe Leu Ala Ile Ala Val
            740                 745                 750

Asp Asn Leu Ala Asp Ala Glu Ser Leu Asn Thr Ala Gln Lys Glu Glu
        755                 760                 765

Ala Glu Glu Lys Glu Arg Lys Lys Ile Ala Arg Lys Glu Ser Leu Glu
770                 775                 780

Asn Lys Lys Asn Asn Lys Pro Glu Val Asn Gln Ile Ala Asn Ser Asp
785                 790                 795                 800

Asn Lys Val Thr Ile Asp Asp Tyr Arg Glu Glu Asp Glu Asp Lys Asp
                805                 810                 815

Pro Tyr Pro Pro Cys Asp Val Pro Val Gly Glu Glu Glu Glu Glu Glu
            820                 825                 830

Glu Glu Asp Glu Pro Glu Val Pro Ala Gly Pro Arg Pro Arg Arg Ile
        835                 840                 845

Ser Glu Leu Asn Met Lys Glu Lys Ile Ala Pro Ile Pro Glu Gly Ser
850                 855                 860

Ala Phe Phe Ile Leu Ser Lys Thr Asn Pro Ile Arg Val Gly Cys His
865                 870                 875                 880

Lys Leu Ile Asn His His Ile Phe Thr Asn Leu Ile Leu Val Phe Ile
                885                 890                 895

Met Leu Ser Ser Ala Ala Leu Ala Ala Glu Asp Pro Ile Arg Ser His
            900                 905                 910

Ser Phe Arg Asn Thr Ile Leu Gly Tyr Phe Asp Tyr Ala Phe Thr Ala
        915                 920                 925

Ile Phe Thr Val Glu Ile Leu Leu Lys Met Thr Thr Phe Gly Ala Phe
930                 935                 940

Leu His Lys Gly Ala Phe Cys Arg Asn Tyr Phe Asn Leu Leu Asp Met
945                 950                 955                 960

Leu Val Val Gly Val Ser Leu Val Ser Phe Gly Ile Gln Ser Ser Ala
                965                 970                 975

Ile Ser Val Val Lys Ile Leu Arg Val Leu Arg Val Leu Arg Pro Leu
            980                 985                 990

Arg Ala Ile Asn Arg Ala Lys Gly Leu Lys His Val Val Gln Cys Val
        995                 1000                1005

Phe Val Ala Ile Arg Thr Ile Gly Asn Ile Met Ile Val Thr Thr
    1010                1015                1020

Leu Leu Gln Phe Met Phe Ala Cys Ile Gly Val Gln Leu Phe Lys
    1025                1030                1035

Gly Lys Phe Tyr Arg Cys Thr Asp Glu Ala Lys Ser Asn Pro Glu
    1040                1045                1050

Glu Cys Arg Gly Leu Phe Ile Leu Tyr Lys Asp Gly Asp Val Asp
    1055                1060                1065

Ser Pro Val Val Arg Glu Arg Ile Trp Gln Asn Ser Asp Phe Asn
    1070                1075                1080

Phe Asp Asn Val Leu Ser Ala Met Met Ala Leu Phe Thr Val Ser
    1085                1090                1095
```

```
Thr Phe Glu Gly Trp Pro Ala Leu Leu Tyr Lys Ala Ile Asp Ser
    1100            1105                1110

Asn Gly Glu Asn Ile Gly Pro Ile Tyr Asn His Arg Val Glu Ile
    1115            1120                1125

Ser Ile Phe Phe Ile Ile Tyr Ile Ile Val Ala Phe Phe Met
    1130            1135                1140

Met Asn Ile Phe Val Gly Phe Val Ile Val Thr Phe Gln Glu Gln
    1145            1150                1155

Gly Glu Lys Glu Tyr Lys Asn Cys Glu Leu Asp Lys Asn Gln Arg
    1160            1165                1170

Gln Cys Val Glu Tyr Ala Leu Lys Ala Arg Pro Leu Arg Arg Tyr
    1175            1180                1185

Ile Pro Lys Asn Pro Tyr Gln Tyr Lys Phe Trp Tyr Val Val Asn
    1190            1195                1200

Ser Ser Pro Phe Glu Tyr Met Met Phe Val Leu Ile Met Leu Asn
    1205            1210                1215

Thr Leu Cys Leu Ala Met Gln His Tyr Glu Gln Ser Lys Met Phe
    1220            1225                1230

Asn Asp Ala Met Asp Ile Leu Asn Met Val Phe Thr Gly Val Phe
    1235            1240                1245

Thr Val Glu Met Val Leu Lys Val Ile Ala Phe Lys Pro Lys Gly
    1250            1255                1260

Tyr Phe Ser Asp Ala Trp Asn Thr Phe Asp Ser Leu Ile Val Ile
    1265            1270                1275

Gly Ser Ile Ile Asp Val Ala Leu Ser Glu Ala Asp Pro Thr Glu
    1280            1285                1290

Ser Glu Asn Val Pro Val Pro Thr Ala Thr Pro Gly Asn Ser Glu
    1295            1300                1305

Glu Ser Asn Arg Ile Ser Ile Thr Phe Phe Arg Leu Phe Arg Val
    1310            1315                1320

Met Arg Leu Val Lys Leu Leu Ser Arg Gly Glu Gly Ile Arg Thr
    1325            1330                1335

Leu Leu Trp Thr Phe Ile Lys Ser Phe Gln Ala Leu Pro Tyr Val
    1340            1345                1350

Ala Leu Leu Ile Ala Met Leu Phe Phe Ile Tyr Ala Val Ile Gly
    1355            1360                1365

Met Gln Met Phe Gly Lys Val Ala Met Arg Asp Asn Asn Gln Ile
    1370            1375                1380

Asn Arg Asn Asn Asn Phe Gln Thr Phe Pro Gln Ala Val Leu Leu
    1385            1390                1395

Leu Phe Arg Cys Ala Thr Gly Glu Ala Trp Gln Glu Ile Met Leu
    1400            1405                1410

Ala Cys Leu Pro Gly Lys Leu Cys Asp Pro Glu Ser Asp Tyr Asn
    1415            1420                1425

Pro Gly Glu Glu Tyr Thr Cys Gly Ser Asn Phe Ala Ile Val Tyr
    1430            1435                1440

Phe Ile Ser Phe Tyr Met Leu Cys Ala Phe Leu Ile Ile Asn Leu
    1445            1450                1455

Phe Val Ala Val Ile Met Asp Asn Phe Asp Tyr Leu Thr Arg Asp
    1460            1465                1470

Trp Ser Ile Leu Gly Pro His His Leu Asp Glu Phe Lys Arg Ile
    1475            1480                1485
```

```
Trp Ser Glu Tyr Asp Pro Glu Ala Lys Gly Arg Ile Lys His Leu
    1490            1495                1500

Asp Val Val Thr Leu Leu Arg Arg Ile Gln Pro Pro Leu Gly Phe
    1505            1510                1515

Gly Lys Leu Cys Pro His Arg Val Ala Cys Lys Arg Leu Val Ala
    1520            1525                1530

Met Asn Met Pro Leu Asn Ser Asp Gly Thr Val Met Phe Asn Ala
    1535            1540                1545

Thr Leu Phe Ala Leu Val Arg Thr Ala Leu Lys Ile Lys Thr Glu
    1550            1555                1560

Gly Asn Leu Glu Gln Ala Asn Glu Glu Leu Arg Ala Val Ile Lys
    1565            1570                1575

Lys Ile Trp Lys Lys Thr Ser Met Lys Leu Leu Asp Gln Val Val
    1580            1585                1590

Pro Pro Ala Gly Asp Asp Glu Val Thr Val Gly Lys Phe Tyr Ala
    1595            1600                1605

Thr Phe Leu Ile Gln Asp Tyr Phe Arg Lys Phe Lys Lys Arg Lys
    1610            1615                1620

Glu Gln Gly Leu Val Gly Lys Tyr Pro Ala Lys Asn Thr Thr Ile
    1625            1630                1635

Ala Leu Gln Ala Gly Leu Arg Thr Leu His Asp Ile Gly Pro Glu
    1640            1645                1650

Ile Arg Arg Ala Ile Ser Cys Asp Leu Gln Asp Glu Pro Glu
    1655            1660                1665

Glu Thr Lys Arg Glu Glu Asp Asp Val Phe Lys Arg Asn Gly
    1670            1675                1680

Ala Leu Leu Gly Asn His Val Asn His Val Asn Ser Asp Arg Arg
    1685            1690                1695

Asp Ser Leu Gln Gln Thr Asn Thr Thr His Arg Pro Leu His Val
    1700            1705                1710

Gln Arg Pro Ser Ile Pro Pro Ala Ser Asp Thr Glu Lys Pro Leu
    1715            1720                1725

Phe Pro Pro Ala Gly Asn Ser Val Cys His Asn His Asn His
    1730            1735                1740

Asn Ser Ile Gly Lys Gln Val Pro Thr Ser Thr Asn Ala Asn Leu
    1745            1750                1755

Asn Asn Ala Asn Met Ser Lys Ala Ala His Gly Lys Arg Pro Ser
    1760            1765                1770

Ile Gly Asn Leu Glu His Val Ser Glu Asn Gly His His Ser Ser
    1775            1780                1785

His Lys His Asp Arg Glu Pro Gln Arg Arg Ser Ser Val Lys Arg
    1790            1795                1800

Thr Arg Tyr Tyr Glu Thr Tyr Ile Arg Ser Asp Ser Gly Asp Glu
    1805            1810                1815

Gln Leu Pro Thr Ile Cys Arg Glu Asp Pro Glu Ile His Gly Tyr
    1820            1825                1830

Phe Arg Asp Pro His Cys Leu Gly Glu Gln Glu Tyr Phe Ser Ser
    1835            1840                1845

Glu Glu Cys Tyr Glu Asp Asp Ser Ser Pro Thr Trp Ser Arg Gln
    1850            1855                1860

Asn Tyr Gly Tyr Tyr Ser Arg Tyr Pro Gly Arg Asn Ile Asp Ser
    1865            1870                1875
```

```
Glu Arg Pro Arg Gly Tyr His His Pro Gln Gly Phe Leu Glu Asp
    1880                1885                1890

Asp Asp Ser Pro Val Cys Tyr Asp Ser Arg Arg Ser Pro Arg Arg
    1895                1900                1905

Arg Leu Leu Pro Pro Thr Pro Ala Ser His Arg Arg Ser Ser Phe
    1910                1915                1920

Asn Phe Glu Cys Leu Arg Arg Gln Ser Ser Gln Glu Glu Val Pro
    1925                1930                1935

Ser Ser Pro Ile Phe Pro His Arg Thr Ala Leu Pro Leu His Leu
    1940                1945                1950

Met Gln Gln Gln Ile Met Ala Val Ala Gly Leu Asp Ser Ser Lys
    1955                1960                1965

Ala Gln Lys Tyr Ser Pro Ser His Ser Thr Arg Ser Trp Ala Thr
    1970                1975                1980

Pro Pro Ala Thr Pro Pro Tyr Arg Asp Trp Thr Pro Cys Tyr Thr
    1985                1990                1995

Pro Leu Ile Gln Val Glu Gln Ser Glu Ala Leu Asp Gln Val Asn
    2000                2005                2010

Gly Ser Leu Pro Ser Leu His Arg Ser Ser Trp Tyr Thr Asp Glu
    2015                2020                2025

Pro Asp Ile Ser Tyr Arg Thr Phe Thr Pro Ala Ser Leu Thr Val
    2030                2035                2040

Pro Ser Ser Phe Arg Asn Lys Asn Ser Asp Lys Gln Arg Ser Ala
    2045                2050                2055

Asp Ser Leu Val Glu Ala Val Leu Ile Ser Glu Gly Leu Gly Arg
    2060                2065                2070

Tyr Ala Arg Asp Pro Lys Phe Val Ser Ala Thr Lys His Glu Ile
    2075                2080                2085

Ala Asp Ala Cys Asp Leu Thr Ile Asp Glu Met Glu Ser Ala Ala
    2090                2095                2100

Ser Thr Leu Leu Asn Gly Asn Val Arg Pro Arg Ala Asn Gly Asp
    2105                2110                2115

Val Gly Pro Leu Ser His Arg Gln Asp Tyr Glu Leu Gln Asp Phe
    2120                2125                2130

Gly Pro Gly Tyr Ser Asp Glu Glu Pro Asp Pro Gly Arg Asp Glu
    2135                2140                2145

Glu Asp Leu Ala Asp Glu Met Ile Cys Ile Thr Thr Leu
    2150                2155                2160

<210> SEQ ID NO 7
<211> LENGTH: 2221
<212> TYPE: PRT
<213> ORGANISM: Homo sapiens

<400> SEQUENCE: 7

Met Val Asn Glu Asn Thr Arg Met Tyr Ile Pro Glu Glu Asn His Gln
1               5                   10                  15

Gly Ser Asn Tyr Gly Ser Pro Arg Pro Ala His Ala Asn Met Asn Ala
                20                  25                  30

Asn Ala Ala Ala Gly Leu Ala Pro Glu His Ile Pro Thr Pro Gly Ala
            35                  40                  45

Ala Leu Ser Trp Gln Ala Ala Ile Asp Ala Ala Arg Gln Ala Lys Leu
        50                  55                  60
```

```
Met Gly Ser Ala Gly Asn Ala Thr Ile Ser Thr Val Ser Ser Thr Gln
 65                  70                  75                  80

Arg Lys Arg Gln Gln Tyr Gly Lys Pro Lys Gln Gly Ser Thr Thr
             85                  90                  95

Ala Thr Arg Pro Pro Arg Ala Leu Leu Cys Leu Thr Leu Lys Asn Pro
             100                 105                 110

Ile Arg Arg Ala Cys Ile Ser Ile Val Glu Trp Lys Pro Phe Glu Ile
             115                 120                 125

Ile Ile Leu Leu Thr Ile Phe Ala Asn Cys Val Ala Leu Ala Ile Tyr
             130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
             165                 170                 175

Lys Val Ile Ala Tyr Gly Leu Leu Phe His Pro Asn Ala Tyr Leu Arg
             180                 185                 190

Asn Gly Trp Asn Leu Leu Asp Phe Ile Ile Val Val Gly Leu Phe
             195                 200                 205

Ser Ala Ile Leu Glu Gln Ala Thr Lys Ala Asp Gly Ala Asn Ala Leu
210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
             245                 250                 255

Val Leu Asn Ser Ile Ile Lys Ala Met Val Pro Leu Leu His Ile Ala
             260                 265                 270

Leu Leu Val Leu Phe Val Ile Ile Tyr Ala Ile Ile Gly Leu Glu
             275                 280                 285

Leu Phe Met Gly Lys Met His Lys Thr Cys Tyr Asn Gln Glu Gly Ile
290                 295                 300

Ala Asp Val Pro Ala Glu Asp Pro Ser Pro Cys Ala Leu Glu Thr
305                 310                 315                 320

Gly His Gly Arg Gln Cys Gln Asn Gly Thr Val Cys Lys Pro Gly Trp
             325                 330                 335

Asp Gly Pro Lys His Gly Ile Thr Asn Phe Asp Asn Phe Ala Phe Ala
             340                 345                 350

Met Leu Thr Val Phe Gln Cys Ile Thr Met Glu Gly Trp Thr Asp Val
             355                 360                 365

Leu Tyr Trp Val Asn Asp Ala Val Gly Arg Asp Trp Pro Trp Ile Tyr
             370                 375                 380

Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
             405                 410                 415

Ala Arg Gly Asp Phe Gln Lys Leu Arg Glu Lys Gln Gln Leu Glu Glu
             420                 425                 430

Asp Leu Lys Gly Tyr Leu Asp Trp Ile Thr Gln Ala Glu Asp Ile Asp
             435                 440                 445

Pro Glu Asn Glu Asp Glu Gly Met Asp Glu Lys Pro Arg Asn Met
             450                 455                 460

Ser Met Pro Thr Ser Glu Thr Glu Ser Val Asn Thr Glu Asn Val Ala
465                 470                 475                 480
```

-continued

```
Gly Gly Asp Ile Glu Gly Glu Asn Cys Gly Ala Arg Leu Ala His Arg
                485                 490                 495
Ile Ser Lys Ser Lys Phe Ser Arg Tyr Trp Arg Trp Asn Arg Phe
        500                 505                 510
Cys Arg Arg Lys Cys Arg Ala Ala Val Lys Ser Asn Val Phe Tyr Trp
            515                 520                 525
Leu Val Ile Phe Leu Val Phe Leu Asn Thr Leu Thr Ile Ala Ser Glu
        530                 535                 540
His Tyr Asn Gln Pro Asn Trp Leu Thr Glu Val Gln Asp Thr Ala Asn
545                 550                 555                 560
Lys Ala Leu Leu Ala Leu Phe Thr Ala Glu Met Leu Leu Lys Met Tyr
                565                 570                 575
Ser Leu Gly Leu Gln Ala Tyr Phe Val Ser Leu Phe Asn Arg Phe Asp
            580                 585                 590
Cys Phe Val Val Cys Gly Gly Ile Leu Glu Thr Ile Leu Val Glu Thr
        595                 600                 605
Lys Ile Met Ser Pro Leu Gly Ile Ser Val Leu Arg Cys Val Arg Leu
    610                 615                 620
Leu Arg Ile Phe Lys Ile Thr Arg Tyr Trp Asn Ser Leu Ser Asn Leu
625                 630                 635                 640
Val Ala Ser Leu Leu Asn Ser Val Arg Ser Ile Ala Ser Leu Leu Leu
                645                 650                 655
Leu Leu Phe Leu Phe Ile Ile Phe Ser Leu Leu Gly Met Gln Leu
            660                 665                 670
Phe Gly Gly Lys Phe Asn Phe Asp Glu Met Gln Thr Arg Arg Ser Thr
        675                 680                 685
Phe Asp Asn Phe Pro Gln Ser Leu Leu Thr Val Phe Gln Ile Leu Thr
    690                 695                 700
Gly Glu Asp Trp Asn Ser Val Met Tyr Asp Gly Ile Met Ala Tyr Gly
705                 710                 715                 720
Gly Pro Ser Phe Pro Gly Met Leu Val Cys Ile Tyr Phe Ile Ile Leu
                725                 730                 735
Phe Ile Cys Gly Asn Tyr Ile Leu Leu Asn Val Phe Leu Ala Ile Ala
            740                 745                 750
Val Asp Asn Leu Ala Asp Ala Glu Ser Leu Thr Ser Ala Gln Lys Glu
        755                 760                 765
Glu Glu Glu Glu Lys Glu Arg Lys Lys Leu Ala Arg Thr Ala Ser Pro
    770                 775                 780
Glu Lys Lys Gln Glu Leu Val Glu Lys Pro Ala Val Gly Glu Ser Lys
785                 790                 795                 800
Glu Glu Lys Ile Glu Leu Lys Ser Ile Thr Ala Asp Gly Glu Ser Pro
                805                 810                 815
Pro Ala Thr Lys Ile Asn Met Asp Asp Leu Gln Pro Asn Glu Asn Glu
            820                 825                 830
Asp Lys Ser Pro Tyr Pro Asn Pro Glu Thr Thr Gly Glu Glu Asp Glu
        835                 840                 845
Glu Glu Pro Glu Met Pro Val Gly Pro Arg Pro Arg Pro Leu Ser Glu
    850                 855                 860
Leu His Leu Lys Glu Lys Ala Val Pro Met Pro Glu Ala Ser Ala Phe
865                 870                 875                 880
Phe Ile Phe Ser Ser Asn Asn Arg Phe Arg Leu Gln Cys His Arg Ile
                885                 890                 895
```

-continued

```
Val Asn Asp Thr Ile Phe Thr Asn Leu Ile Leu Phe Ile Leu Leu
            900                 905                 910

Ser Ser Ile Ser Leu Ala Ala Glu Asp Pro Val Gln His Thr Ser Phe
        915                 920                 925

Arg Asn His Ile Leu Phe Tyr Phe Asp Ile Val Phe Thr Thr Ile Phe
    930                 935                 940

Thr Ile Glu Ile Ala Leu Lys Ile Leu Gly Asn Ala Asp Tyr Val Phe
945                 950                 955                 960

Thr Ser Ile Phe Thr Leu Glu Ile Ile Leu Lys Met Thr Ala Tyr Gly
                965                 970                 975

Ala Phe Leu His Lys Gly Ser Phe Cys Arg Asn Tyr Phe Asn Ile Leu
            980                 985                 990

Asp Leu Leu Val Val Ser Val Ser Leu Ile Ser Phe Gly Ile Gln Ser
        995                 1000                1005

Ser Ala Ile Asn Val Val Lys Ile Leu Arg Val Leu Arg Val Leu
   1010                 1015                1020

Arg Pro Leu Arg Ala Ile Asn Arg Ala Lys Gly Leu Lys His Val
   1025                 1030                1035

Val Gln Cys Val Phe Val Ala Ile Arg Thr Ile Gly Asn Ile Val
   1040                 1045                1050

Ile Val Thr Thr Leu Leu Gln Phe Met Phe Ala Cys Ile Gly Val
   1055                 1060                1065

Gln Leu Phe Lys Gly Lys Leu Tyr Thr Cys Ser Asp Ser Ser Lys
   1070                 1075                1080

Gln Thr Glu Ala Glu Cys Lys Gly Asn Tyr Ile Thr Tyr Lys Asp
   1085                 1090                1095

Gly Glu Val Asp His Pro Ile Ile Gln Pro Arg Ser Trp Glu Asn
   1100                 1105                1110

Ser Lys Phe Asp Phe Asp Asn Val Leu Ala Ala Met Met Ala Leu
   1115                 1120                1125

Phe Thr Val Ser Thr Phe Glu Gly Trp Pro Glu Leu Leu Tyr Arg
   1130                 1135                1140

Ser Ile Asp Ser His Thr Glu Asp Lys Gly Pro Ile Tyr Asn Tyr
   1145                 1150                1155

Arg Val Glu Ile Ser Ile Phe Phe Ile Ile Tyr Ile Ile Ile Ile
   1160                 1165                1170

Ala Phe Phe Met Met Asn Ile Phe Val Gly Phe Val Ile Val Thr
   1175                 1180                1185

Phe Gln Glu Gln Gly Glu Gln Glu Tyr Lys Asn Cys Glu Leu Asp
   1190                 1195                1200

Lys Asn Gln Arg Gln Cys Val Glu Tyr Ala Leu Lys Ala Arg Pro
   1205                 1210                1215

Leu Arg Arg Tyr Ile Pro Lys Asn Gln His Gln Tyr Lys Val Trp
   1220                 1225                1230

Tyr Val Val Asn Ser Thr Tyr Phe Glu Tyr Leu Met Phe Val Leu
   1235                 1240                1245

Ile Leu Leu Asn Thr Ile Cys Leu Ala Met Gln His Tyr Gly Gln
   1250                 1255                1260

Ser Cys Leu Phe Lys Ile Ala Met Asn Ile Leu Asn Met Leu Phe
   1265                 1270                1275

Thr Gly Leu Phe Thr Val Glu Met Ile Leu Lys Leu Ile Ala Phe
   1280                 1285                1290
```

```
Lys Pro Lys Gly Tyr Phe Ser Asp Pro Trp Asn Val Phe Asp Phe
    1295                1300                1305

Leu Ile Val Ile Gly Ser Ile Ile Asp Val Ile Leu Ser Glu Thr
    1310                1315                1320

Asn His Tyr Phe Cys Asp Ala Trp Asn Thr Phe Asp Ala Leu Ile
    1325                1330                1335

Val Val Gly Ser Ile Val Asp Ile Ala Ile Thr Glu Val Asn Pro
    1340                1345                1350

Ala Glu His Thr Gln Cys Ser Pro Ser Met Asn Ala Glu Glu Asn
    1355                1360                1365

Ser Arg Ile Ser Ile Thr Phe Phe Arg Leu Phe Arg Val Met Arg
    1370                1375                1380

Leu Val Lys Leu Leu Ser Arg Gly Glu Gly Ile Arg Thr Leu Leu
    1385                1390                1395

Trp Thr Phe Ile Lys Ser Phe Gln Ala Leu Pro Tyr Val Ala Leu
    1400                1405                1410

Leu Ile Val Met Leu Phe Phe Ile Tyr Ala Val Ile Gly Met Gln
    1415                1420                1425

Val Phe Gly Lys Ile Ala Leu Asn Asp Thr Thr Glu Ile Asn Arg
    1430                1435                1440

Asn Asn Asn Phe Gln Thr Phe Pro Gln Ala Val Leu Leu Leu Phe
    1445                1450                1455

Arg Cys Ala Thr Gly Glu Ala Trp Gln Asp Ile Met Leu Ala Cys
    1460                1465                1470

Met Pro Gly Lys Lys Cys Ala Pro Glu Ser Glu Pro Ser Asn Ser
    1475                1480                1485

Thr Glu Gly Glu Thr Pro Cys Gly Ser Ser Phe Ala Val Phe Tyr
    1490                1495                1500

Phe Ile Ser Phe Tyr Met Leu Cys Ala Phe Leu Ile Ile Asn Leu
    1505                1510                1515

Phe Val Ala Val Ile Met Asp Asn Phe Asp Tyr Leu Thr Arg Asp
    1520                1525                1530

Trp Ser Ile Leu Gly Pro His His Leu Asp Glu Phe Lys Arg Ile
    1535                1540                1545

Trp Ala Glu Tyr Asp Pro Glu Ala Lys Gly Arg Ile Lys His Leu
    1550                1555                1560

Asp Val Val Thr Leu Leu Arg Arg Ile Gln Pro Pro Leu Gly Phe
    1565                1570                1575

Gly Lys Leu Cys Pro His Arg Val Ala Cys Lys Arg Leu Val Ser
    1580                1585                1590

Met Asn Met Pro Leu Asn Ser Asp Gly Thr Val Met Phe Asn Ala
    1595                1600                1605

Thr Leu Phe Ala Leu Val Arg Thr Ala Leu Arg Ile Lys Thr Glu
    1610                1615                1620

Gly Asn Leu Glu Gln Ala Asn Glu Glu Leu Arg Ala Ile Ile Lys
    1625                1630                1635

Lys Ile Trp Lys Arg Thr Ser Met Lys Leu Leu Asp Gln Val Val
    1640                1645                1650

Pro Pro Ala Gly Asp Asp Glu Val Thr Val Gly Lys Phe Tyr Ala
    1655                1660                1665

Thr Phe Leu Ile Gln Glu Tyr Phe Arg Lys Phe Lys Lys Arg Lys
    1670                1675                1680
```

-continued

Glu Gln Gly Leu Val Gly Lys Pro Ser Gln Arg Asn Ala Leu Ser
1685                1690                1695

Leu Gln Ala Gly Leu Arg Thr Leu His Asp Ile Gly Pro Glu Ile
1700                1705                1710

Arg Arg Ala Ile Ser Gly Asp Leu Thr Ala Glu Glu Leu Asp
1715                1720                1725

Lys Ala Met Lys Glu Ala Val Ser Ala Ala Ser Glu Asp Asp Ile
1730                1735                1740

Phe Arg Arg Ala Gly Gly Leu Phe Gly Asn His Val Ser Tyr Tyr
1745                1750                1755

Gln Ser Asp Gly Arg Ser Ala Phe Pro Gln Thr Phe Thr Thr Gln
1760                1765                1770

Arg Pro Leu His Ile Asn Lys Ala Gly Ser Ser Gln Gly Asp Thr
1775                1780                1785

Glu Ser Pro Ser His Glu Lys Leu Val Asp Ser Thr Phe Thr Pro
1790                1795                1800

Ser Ser Tyr Ser Ser Thr Gly Ser Asn Ala Asn Ile Asn Asn Ala
1805                1810                1815

Asn Asn Thr Ala Leu Gly Arg Leu Pro Arg Pro Ala Gly Tyr Pro
1820                1825                1830

Ser Thr Val Ser Thr Val Glu Gly His Gly Pro Pro Leu Ser Pro
1835                1840                1845

Ala Ile Arg Val Gln Glu Val Ala Trp Lys Leu Ser Ser Asn Arg
1850                1855                1860

Glu Arg His Val Pro Met Cys Glu Asp Leu Glu Leu Arg Arg Asp
1865                1870                1875

Ser Gly Ser Ala Gly Thr Gln Ala His Cys Leu Leu Leu Arg Arg
1880                1885                1890

Ala Asn Pro Ser Arg Cys His Ser Arg Glu Ser Gln Ala Ala Met
1895                1900                1905

Ala Gly Gln Glu Glu Thr Ser Gln Asp Glu Thr Tyr Glu Val Lys
1910                1915                1920

Met Asn His Asp Thr Glu Ala Cys Ser Glu Pro Ser Leu Leu Ser
1925                1930                1935

Thr Glu Met Leu Ser Tyr Gln Asp Asp Glu Asn Arg Gln Leu Thr
1940                1945                1950

Leu Pro Glu Glu Asp Lys Arg Asp Ile Arg Gln Ser Pro Lys Arg
1955                1960                1965

Gly Phe Leu Arg Ser Ala Ser Leu Gly Arg Arg Ala Ser Phe His
1970                1975                1980

Leu Glu Cys Leu Lys Arg Gln Lys Asp Arg Gly Gly Asp Ile Ser
1985                1990                1995

Gln Lys Thr Val Leu Pro Leu His Leu Val His Gln Ala Leu
2000                2005                2010

Ala Val Ala Gly Leu Ser Pro Leu Leu Gln Arg Ser His Ser Pro
2015                2020                2025

Ala Ser Phe Pro Arg Pro Phe Ala Thr Pro Pro Ala Thr Pro Gly
2030                2035                2040

Ser Arg Gly Trp Pro Pro Gln Pro Val Pro Thr Leu Arg Leu Glu
2045                2050                2055

Gly Val Glu Ser Ser Glu Lys Leu Asn Ser Ser Phe Pro Ser Ile
2060                2065                2070

```
His Cys Gly Ser Trp Ala Glu Thr Thr Pro Gly Gly Gly Gly Ser
    2075                2080                2085

Ser Ala Ala Arg Arg Val Arg Pro Val Ser Leu Met Val Pro Ser
    2090                2095                2100

Gln Ala Gly Ala Pro Gly Arg Gln Phe His Gly Ser Ala Ser Ser
    2105                2110                2115

Leu Val Glu Ala Val Leu Ile Ser Glu Gly Leu Gly Gln Phe Ala
    2120                2125                2130

Gln Asp Pro Lys Phe Ile Glu Val Thr Thr Gln Glu Leu Ala Asp
    2135                2140                2145

Ala Cys Asp Met Thr Ile Glu Met Glu Ser Ala Ala Asp Asn
    2150                2155                2160

Ile Leu Ser Gly Gly Ala Pro Gln Ser Pro Asn Gly Ala Leu Leu
    2165                2170                2175

Pro Phe Val Asn Cys Arg Asp Ala Gly Gln Asp Arg Ala Gly Gly
    2180                2185                2190

Glu Glu Asp Ala Gly Cys Val Arg Ala Arg Gly Arg Pro Ser Glu
    2195                2200                2205

Glu Glu Leu Gln Asp Ser Arg Val Tyr Val Ser Ser Leu
    2210                2215                2220

<210> SEQ ID NO 8
<211> LENGTH: 1873
<212> TYPE: PRT
<213> ORGANISM: Homo sapiens

<400> SEQUENCE: 8

Met Glu Pro Ser Ser Pro Gln Asp Glu Gly Leu Arg Lys Lys Gln Pro
1               5                   10                  15

Lys Lys Pro Val Pro Glu Ile Leu Pro Arg Pro Arg Ala Leu Phe
                20                  25                  30

Cys Leu Thr Leu Glu Asn Pro Leu Arg Lys Ala Cys Ile Ser Ile Val
            35                  40                  45

Glu Trp Lys Pro Phe Glu Thr Ile Ile Leu Leu Thr Ile Phe Ala Asn
    50                  55                  60

Cys Val Ala Leu Ala Val Tyr Leu Pro Met Pro Glu Asp Asp Asn Asn
65                  70                  75                  80

Ser Leu Asn Leu Gly Leu Glu Lys Leu Glu Tyr Phe Phe Leu Ile Val
                85                  90                  95

Phe Ser Ile Glu Ala Ala Met Lys Ile Ile Ala Tyr Gly Phe Leu Phe
                100                 105                 110

His Gln Asp Ala Tyr Leu Arg Ser Gly Trp Asn Val Leu Asp Phe Thr
            115                 120                 125

Ile Val Phe Leu Gly Val Phe Thr Val Ile Leu Glu Gln Val Asn Val
    130                 135                 140

Ile Gln Ser His Thr Ala Pro Met Ser Ser Lys Gly Ala Gly Leu Asp
145                 150                 155                 160

Val Lys Ala Leu Arg Ala Phe Arg Val Leu Arg Pro Leu Arg Leu Val
                165                 170                 175

Ser Gly Val Pro Ser Leu Gln Val Leu Asn Ser Ile Phe Lys Ala
                180                 185                 190

Met Leu Pro Leu Phe His Ile Ala Leu Leu Val Leu Phe Met Val Ile
            195                 200                 205

Ile Tyr Ala Ile Ile Gly Leu Glu Leu Phe Lys Gly Lys Met His Lys
    210                 215                 220
```

```
Thr Cys Tyr Phe Ile Gly Thr Asp Ile Val Ala Thr Val Glu Asn Glu
225                 230                 235                 240

Glu Pro Ser Pro Cys Ala Arg Thr Gly Ser Gly Arg Arg Cys Thr Ile
                245                 250                 255

Asn Gly Ser Glu Cys Arg Gly Gly Trp Pro Gly Pro Asn His Gly Ile
            260                 265                 270

Thr His Phe Asp Asn Phe Gly Phe Ser Met Leu Thr Val Tyr Gln Cys
        275                 280                 285

Ile Thr Met Glu Gly Trp Thr Asp Val Leu Tyr Trp Val Asn Asp Ala
290                 295                 300

Ile Gly Asn Glu Trp Pro Trp Ile Tyr Phe Val Thr Leu Ile Leu Leu
305                 310                 315                 320

Gly Ser Phe Phe Ile Leu Asn Leu Val Leu Gly Val Leu Ser Gly Glu
                325                 330                 335

Phe Thr Lys Glu Arg Glu Lys Ala Lys Ser Arg Gly Thr Phe Gln Lys
            340                 345                 350

Leu Arg Glu Lys Gln Gln Leu Asp Glu Asp Leu Arg Gly Tyr Met Ser
        355                 360                 365

Trp Ile Thr Gln Gly Glu Val Met Asp Val Glu Asp Phe Arg Glu Gly
370                 375                 380

Lys Leu Ser Leu Asp Glu Gly Gly Ser Asp Thr Glu Ser Leu Tyr Glu
385                 390                 395                 400

Ile Ala Gly Leu Asn Lys Ile Ile Gln Phe Ile Arg His Trp Arg Gln
                405                 410                 415

Trp Asn Arg Ile Phe Arg Trp Lys Cys His Asp Ile Val Lys Ser Lys
            420                 425                 430

Val Phe Tyr Trp Leu Val Ile Leu Ile Val Ala Leu Asn Thr Leu Ser
        435                 440                 445

Ile Ala Ser Glu His His Asn Gln Pro Leu Trp Leu Thr Arg Leu Gln
450                 455                 460

Asp Ile Ala Asn Arg Val Leu Leu Ser Leu Phe Thr Thr Glu Met Leu
465                 470                 475                 480

Met Lys Met Tyr Gly Leu Gly Leu Arg Gln Tyr Phe Met Ser Ile Phe
                485                 490                 495

Asn Arg Phe Asp Cys Phe Val Val Cys Ser Gly Ile Leu Glu Ile Leu
            500                 505                 510

Leu Val Glu Ser Gly Ala Met Thr Pro Leu Gly Ile Ser Val Leu Arg
        515                 520                 525

Cys Ile Arg Leu Leu Arg Ile Phe Lys Ile Thr Lys Tyr Trp Thr Ser
530                 535                 540

Leu Ser Asn Leu Val Ala Ser Leu Leu Asn Ser Ile Arg Ser Ile Ala
545                 550                 555                 560

Ser Leu Leu Leu Leu Leu Phe Leu Phe Ile Val Ile Phe Ala Leu Leu
                565                 570                 575

Gly Met Gln Leu Phe Gly Gly Arg Tyr Asp Phe Glu Asp Thr Glu Val
            580                 585                 590

Arg Arg Ser Asn Phe Asp Asn Phe Pro Gln Ala Leu Ile Ser Val Phe
        595                 600                 605

Gln Val Leu Thr Gly Glu Asp Trp Thr Ser Met Met Tyr Asn Gly Ile
610                 615                 620

Met Ala Tyr Gly Gly Pro Ser Tyr Pro Gly Met Leu Val Cys Ile Tyr
625                 630                 635                 640
```

```
Phe Ile Ile Leu Phe Val Cys Gly Asn Tyr Ile Leu Leu Asn Val Phe
                645                 650                 655

Leu Ala Ile Ala Val Asp Asn Leu Ala Glu Ala Glu Ser Leu Thr Ser
        660                 665                 670

Ala Gln Lys Ala Lys Ala Glu Glu Lys Lys Arg Arg Lys Met Ser Lys
        675                 680                 685

Gly Leu Pro Asp Lys Ser Glu Glu Lys Ser Thr Met Ala Lys Lys
    690                 695                 700

Leu Glu Gln Lys Pro Lys Gly Glu Gly Ile Pro Thr Thr Ala Lys Leu
705                 710                 715                 720

Lys Ile Asp Glu Phe Glu Ser Asn Val Asn Glu Val Lys Asp Pro Tyr
                725                 730                 735

Pro Ser Ala Asp Phe Pro Gly Asp Asp Glu Glu Asp Glu Pro Glu Ile
                740                 745                 750

Pro Leu Ser Pro Arg Pro Arg Pro Leu Ala Glu Leu Gln Leu Lys Glu
                755                 760                 765

Lys Ala Val Pro Ile Pro Glu Ala Ser Ser Phe Phe Ile Phe Ser Pro
        770                 775                 780

Thr Asn Lys Ile Arg Val Leu Cys His Arg Ile Val Asn Ala Thr Trp
785                 790                 795                 800

Phe Thr Asn Phe Ile Leu Leu Phe Ile Leu Leu Ser Ser Ala Ala Leu
                805                 810                 815

Ala Ala Glu Asp Pro Ile Arg Ala Asp Ser Met Arg Asn Gln Ile Leu
                820                 825                 830

Lys His Phe Asp Ile Gly Phe Thr Ser Val Phe Thr Val Glu Ile Val
        835                 840                 845

Leu Lys Met Thr Thr Tyr Gly Ala Phe Leu His Lys Gly Ser Phe Cys
        850                 855                 860

Arg Asn Tyr Phe Asn Met Leu Asp Leu Leu Val Val Ala Val Ser Leu
865                 870                 875                 880

Ile Ser Met Gly Leu Glu Ser Ser Ala Ile Ser Val Val Lys Ile Leu
                885                 890                 895

Arg Val Leu Arg Val Leu Arg Pro Leu Arg Ala Ile Asn Arg Ala Lys
                900                 905                 910

Gly Leu Lys His Val Val Gln Cys Met Phe Val Ala Ile Ser Thr Ile
        915                 920                 925

Gly Asn Ile Val Leu Val Thr Thr Leu Leu Gln Phe Met Phe Ala Cys
        930                 935                 940

Ile Gly Val Gln Leu Phe Lys Gly Lys Phe Phe Arg Cys Thr Asp Leu
945                 950                 955                 960

Ser Lys Met Thr Glu Glu Cys Arg Gly Tyr Tyr Val Tyr Lys
                965                 970                 975

Asp Gly Asp Pro Met Gln Ile Glu Leu Arg His Arg Glu Trp Val His
                980                 985                 990

Ser Asp Phe His Phe Asp Asn Val Leu Ser Ala Met Met Ser Leu Phe
        995                 1000                1005

Thr Val Ser Thr Phe Glu Gly Trp Pro Gln Leu Leu Tyr Lys Ala
    1010                1015                1020

Ile Asp Ser Asn Ala Glu Asp Val Gly Pro Ile Tyr Asn Asn Arg
    1025                1030                1035

Val Glu Met Ala Ile Phe Phe Ile Ile Tyr Ile Ile Leu Ile Ala
    1040                1045                1050
```

-continued

```
Phe Phe Met Met Asn Ile Phe Val Gly Phe Val Ile Val Thr Phe
    1055                1060                1065

Gln Glu Gln Gly Glu Thr Glu Tyr Lys Asn Cys Glu Leu Asp Lys
    1070                1075                1080

Asn Gln Arg Gln Cys Val Gln Tyr Ala Leu Lys Ala Arg Pro Leu
    1085                1090                1095

Arg Cys Tyr Ile Pro Lys Asn Pro Tyr Gln Tyr Gln Val Trp Tyr
    1100                1105                1110

Ile Val Thr Ser Ser Tyr Phe Glu Tyr Leu Met Phe Ala Leu Ile
    1115                1120                1125

Met Leu Asn Thr Ile Cys Leu Gly Met Gln His Tyr Asn Gln Ser
    1130                1135                1140

Glu Gln Met Asn His Ile Ser Asp Ile Leu Asn Val Ala Phe Thr
    1145                1150                1155

Ile Ile Phe Thr Leu Glu Met Ile Leu Lys Leu Met Ala Phe Lys
    1160                1165                1170

Ala Arg Gly Tyr Phe Gly Asp Pro Trp Asn Val Phe Asp Phe Leu
    1175                1180                1185

Ile Val Ile Gly Ser Ile Ile Asp Val Ile Leu Ser Glu Ile Asp
    1190                1195                1200

Thr Phe Leu Ala Ser Ser Gly Gly Leu Tyr Cys Leu Gly Gly Gly
    1205                1210                1215

Cys Gly Asn Val Asp Pro Asp Glu Ser Ala Arg Ile Ser Ser Ala
    1220                1225                1230

Phe Phe Arg Leu Phe Arg Val Met Arg Leu Ile Lys Leu Leu Ser
    1235                1240                1245

Arg Ala Glu Gly Val Arg Thr Leu Leu Trp Thr Phe Ile Lys Ser
    1250                1255                1260

Phe Gln Ala Leu Pro Tyr Val Ala Leu Leu Ile Val Met Leu Phe
    1265                1270                1275

Phe Ile Tyr Ala Val Ile Gly Met Gln Met Phe Gly Lys Ile Ala
    1280                1285                1290

Leu Val Asp Gly Thr Gln Ile Asn Arg Asn Asn Asn Phe Gln Thr
    1295                1300                1305

Phe Pro Gln Ala Val Leu Leu Leu Phe Arg Cys Ala Thr Gly Glu
    1310                1315                1320

Ala Trp Gln Glu Ile Leu Leu Ala Cys Ser Tyr Gly Lys Leu Cys
    1325                1330                1335

Asp Pro Glu Ser Asp Tyr Ala Pro Gly Glu Glu Tyr Thr Cys Gly
    1340                1345                1350

Thr Asn Phe Ala Tyr Tyr Tyr Phe Ile Ser Phe Tyr Met Leu Cys
    1355                1360                1365

Ala Phe Leu Val Ile Asn Leu Phe Val Ala Val Ile Met Asp Asn
    1370                1375                1380

Phe Asp Tyr Leu Thr Arg Asp Trp Ser Ile Leu Gly Pro His His
    1385                1390                1395

Leu Asp Glu Phe Lys Ala Ile Trp Ala Glu Tyr Asp Pro Glu Ala
    1400                1405                1410

Lys Gly Arg Ile Lys His Leu Asp Val Val Thr Leu Leu Arg Arg
    1415                1420                1425

Ile Gln Pro Pro Leu Gly Phe Gly Lys Phe Cys Pro His Arg Val
    1430                1435                1440
```

```
Ala Cys Lys Arg Leu Val Gly Met Asn Met Pro Leu Asn Ser Asp
1445                1450                1455

Gly Thr Val Thr Phe Asn Ala Thr Leu Phe Ala Leu Val Arg Thr
1460                1465                1470

Ala Leu Lys Ile Lys Thr Glu Gly Asn Phe Glu Gln Ala Asn Glu
1475                1480                1485

Glu Leu Arg Ala Ile Ile Lys Lys Ile Trp Lys Arg Thr Ser Met
1490                1495                1500

Lys Leu Leu Asp Gln Val Ile Pro Pro Ile Gly Asp Asp Glu Val
1505                1510                1515

Thr Val Gly Lys Phe Tyr Ala Thr Phe Leu Ile Gln Glu His Phe
1520                1525                1530

Arg Lys Phe Met Lys Arg Gln Glu Glu Tyr Tyr Gly Tyr Arg Pro
1535                1540                1545

Lys Lys Asp Ile Val Gln Ile Gln Ala Gly Leu Arg Thr Ile Glu
1550                1555                1560

Glu Glu Ala Ala Pro Glu Ile Cys Arg Thr Val Ser Gly Asp Leu
1565                1570                1575

Ala Ala Glu Glu Glu Leu Glu Arg Ala Met Val Glu Ala Ala Met
1580                1585                1590

Glu Glu Gly Ile Phe Arg Arg Thr Gly Gly Leu Phe Gly Gln Val
1595                1600                1605

Asp Asn Phe Leu Glu Arg Thr Asn Ser Leu Pro Pro Val Met Ala
1610                1615                1620

Asn Gln Arg Pro Leu Gln Phe Ala Glu Ile Glu Met Glu Glu Met
1625                1630                1635

Glu Ser Pro Val Phe Leu Glu Asp Phe Pro Gln Asp Pro Arg Thr
1640                1645                1650

Asn Pro Leu Ala Arg Ala Asn Thr Asn Asn Ala Asn Ala Asn Val
1655                1660                1665

Ala Tyr Gly Asn Ser Asn His Ser Asn Ser His Val Phe Ser Ser
1670                1675                1680

Val His Tyr Glu Arg Glu Phe Pro Glu Glu Thr Glu Thr Pro Ala
1685                1690                1695

Thr Arg Gly Arg Ala Leu Gly Gln Pro Cys Arg Val Leu Gly Pro
1700                1705                1710

His Ser Lys Pro Cys Val Glu Met Leu Lys Gly Leu Leu Thr Gln
1715                1720                1725

Arg Ala Met Pro Arg Gly Gln Ala Pro Pro Ala Pro Cys Gln Cys
1730                1735                1740

Pro Arg Val Glu Ser Ser Met Pro Glu Asp Arg Lys Ser Ser Thr
1745                1750                1755

Pro Gly Ser Leu His Glu Glu Thr Pro His Ser Arg Ser Thr Arg
1760                1765                1770

Glu Asn Thr Ser Arg Cys Ser Ala Pro Ala Thr Ala Leu Leu Ile
1775                1780                1785

Gln Lys Ala Leu Val Arg Gly Gly Leu Gly Thr Leu Ala Ala Asp
1790                1795                1800

Ala Asn Phe Ile Met Ala Thr Gly Gln Ala Leu Ala Asp Ala Cys
1805                1810                1815

Gln Met Glu Pro Glu Glu Val Glu Ile Met Ala Thr Glu Leu Leu
1820                1825                1830
```

-continued

```
Lys Gly Arg Glu Ala Pro Glu Gly Met Ala Ser Ser Leu Gly Cys
1835                1840                1845

Leu Asn Leu Gly Ser Ser Leu Gly Ser Leu Asp Gln His Gln Gly
    1850                1855                1860

Ser Gln Glu Thr Leu Ile Pro Pro Arg Leu
    1865                1870

<210> SEQ ID NO 9
<211> LENGTH: 1984
<212> TYPE: PRT
<213> ORGANISM: Mus musculus

<400> SEQUENCE: 9

Met Ser Glu Ser Glu Val Gly Lys Asp Thr Thr Pro Glu Pro Ser Pro
1               5                   10                  15

Ala Asn Gly Thr Gly Pro Gly Pro Glu Trp Gly Leu Cys Pro Gly Pro
                20                  25                  30

Pro Thr Val Gly Thr Asp Thr Ser Gly Ala Ser Gly Leu Gly Thr Pro
            35                  40                  45

Arg Arg Arg Thr Gln His Asn Lys His Lys Thr Val Ala Val Ala Ser
        50                  55                  60

Ala Gln Arg Ser Pro Arg Ala Leu Phe Cys Leu Thr Leu Thr Asn Pro
65                  70                  75                  80

Ile Arg Arg Ser Cys Ile Ser Ile Val Glu Trp Lys Pro Phe Asp Ile
                85                  90                  95

Leu Ile Leu Leu Thr Ile Phe Ala Asn Cys Val Ala Leu Gly Val Tyr
            100                 105                 110

Ile Pro Phe Pro Glu Asp Asp Ser Asn Thr Ala Asn His Asn Leu Glu
        115                 120                 125

Gln Val Glu Tyr Val Phe Leu Val Ile Phe Thr Val Glu Thr Val Leu
    130                 135                 140

Lys Ile Val Ala Tyr Gly Leu Val Leu His Pro Ser Ala Tyr Ile Arg
145                 150                 155                 160

Asn Gly Trp Asn Leu Leu Asp Phe Ile Ile Val Val Gly Leu Phe
                165                 170                 175

Ser Val Leu Leu Glu Gln Gly Pro Gly Arg Pro Gly Asp Ala Pro His
            180                 185                 190

Thr Gly Gly Lys Pro Gly Gly Phe Asp Val Lys Ala Leu Arg Ala Phe
        195                 200                 205

Arg Val Leu Arg Pro Leu Arg Leu Val Ser Gly Val Pro Ser Leu His
    210                 215                 220

Ile Val Leu Asn Ser Ile Met Lys Ala Leu Val Pro Leu Leu His Ile
225                 230                 235                 240

Ala Leu Leu Val Leu Phe Val Ile Ile Tyr Ala Ile Ile Gly Leu
                245                 250                 255

Glu Leu Phe Leu Gly Arg Met His Lys Thr Cys Tyr Phe Leu Gly Ser
            260                 265                 270

Asp Met Glu Ala Glu Asp Pro Ser Pro Cys Ala Ser Ser Gly Ser
        275                 280                 285

Gly Arg Ser Cys Thr Leu Asn His Thr Glu Cys Arg Gly Arg Trp Pro
    290                 295                 300

Gly Pro Asn Gly Gly Ile Thr Asn Phe Asp Asn Phe Phe Ala Met
305                 310                 315                 320
```

```
Leu Thr Val Phe Gln Cys Ile Thr Met Glu Gly Trp Thr Asp Val Leu
            325                 330                 335

Tyr Trp Met Gln Asp Ala Met Gly Tyr Glu Leu Pro Trp Val Tyr Phe
            340                 345                 350

Val Ser Leu Val Ile Phe Gly Ser Phe Phe Val Leu Asn Leu Val Leu
            355                 360                 365

Gly Val Leu Ser Gly Glu Phe Ser Lys Glu Arg Glu Lys Ala Lys Ala
            370                 375                 380

Arg Gly Asp Phe Gln Lys Leu Arg Glu Lys Gln Gln Met Glu Glu Asp
385                 390                 395                 400

Leu Arg Gly Tyr Leu Asp Trp Ile Thr Gln Ala Glu Glu Leu Asp Leu
                405                 410                 415

His Asp Pro Ser Val Asp Gly Asn Leu Ala Ser Leu Ala Glu Glu Gly
            420                 425                 430

Arg Ala Gly His Arg Pro Gln Leu Ser Glu Leu Thr Asn Arg Arg Arg
            435                 440                 445

Gly Arg Leu Arg Trp Phe Ser His Ser Thr Arg Ser Thr His Ser Thr
            450                 455                 460

Ser Ser His Ala Ser Leu Pro Ala Ser Asp Thr Gly Ser Met Thr Asp
465                 470                 475                 480

Thr Pro Gly Asp Glu Asp Glu Glu Gly Thr Met Ala Ser Cys Thr
                485                 490                 495

Arg Cys Leu Asn Lys Ile Met Lys Thr Arg Ile Cys Arg His Phe Arg
            500                 505                 510

Arg Ala Asn Arg Gly Leu Arg Ala Arg Cys Arg Arg Ala Val Lys Ser
            515                 520                 525

Asn Ala Cys Tyr Trp Ala Val Leu Leu Leu Val Phe Leu Asn Thr Leu
            530                 535                 540

Thr Ile Ala Ser Glu His His Gly Gln Pro Leu Trp Leu Thr Gln Thr
545                 550                 555                 560

Gln Glu Tyr Ala Asn Lys Val Leu Leu Cys Leu Phe Thr Val Glu Met
                565                 570                 575

Leu Leu Lys Leu Tyr Gly Leu Gly Pro Ser Val Tyr Val Ala Ser Phe
            580                 585                 590

Phe Asn Arg Phe Asp Cys Phe Val Val Cys Gly Gly Ile Leu Glu Thr
            595                 600                 605

Thr Leu Val Glu Val Gly Ala Met Gln Pro Leu Gly Ile Ser Val Leu
            610                 615                 620

Arg Cys Val Arg Leu Leu Arg Ile Phe Lys Val Thr Arg His Trp Ala
625                 630                 635                 640

Ser Leu Ser Asn Leu Val Ala Ser Leu Leu Asn Ser Met Lys Ser Ile
                645                 650                 655

Ala Ser Leu Leu Leu Leu Leu Phe Leu Phe Ile Ile Ile Phe Ser Leu
            660                 665                 670

Leu Gly Met Gln Leu Phe Gly Gly Lys Phe Asn Phe Asp Gln Thr His
            675                 680                 685

Thr Lys Arg Ser Thr Phe Asp Thr Phe Pro Gln Ala Leu Leu Thr Val
            690                 695                 700

Phe Gln Ile Leu Thr Gly Glu Asp Trp Asn Val Val Met Tyr Asp Gly
705                 710                 715                 720

Ile Met Ala Tyr Gly Gly Pro Phe Phe Pro Gly Met Leu Val Cys Val
                725                 730                 735
```

```
Tyr Phe Ile Ile Leu Phe Ile Cys Gly Asn Tyr Ile Leu Leu Asn Val
            740                 745                 750

Phe Leu Ala Ile Ala Val Asp Asn Leu Ala Ser Gly Asp Ala Gly Thr
            755                 760                 765

Ala Lys Asp Lys Gly Arg Glu Lys Ser Ser Glu Gly Asn Pro Pro Lys
    770                 775                 780

Glu Asn Lys Val Leu Val Pro Gly Gly Glu Asn Glu Asp Ala Lys Gly
785                 790                 795                 800

Ala Arg Ser Glu Gly Ala Ala Pro Gly Met Glu Glu Glu Glu Glu Glu
                805                 810                 815

Glu Glu Glu Glu Glu Glu Glu Glu Glu Glu Asn Gly Ala Gly His
        820                 825                 830

Val Glu Leu Leu Gln Glu Val Val Pro Lys Glu Lys Val Val Pro Ile
            835                 840                 845

Pro Glu Gly Ser Ala Phe Phe Cys Leu Ser Gln Thr Asn Pro Leu Arg
    850                 855                 860

Lys Ala Cys His Thr Leu Ile His His Ile Phe Thr Ser Leu Ile
865                 870                 875                 880

Leu Val Phe Ile Ile Leu Ser Ser Val Ser Leu Ala Ala Glu Asp Pro
                885                 890                 895

Ile Arg Ala His Ser Phe Arg Asn His Ile Leu Gly Tyr Phe Asp Tyr
            900                 905                 910

Ala Phe Thr Ser Ile Phe Thr Val Glu Ile Leu Leu Lys Met Thr Val
            915                 920                 925

Phe Gly Ala Phe Leu His Arg Gly Ser Phe Cys Arg Ser Trp Phe Asn
    930                 935                 940

Leu Leu Asp Leu Leu Val Ser Val Ser Leu Ile Ser Phe Gly Ile
945                 950                 955                 960

His Ser Ser Ala Ile Ser Val Val Lys Ile Leu Arg Val Leu Arg Val
                965                 970                 975

Leu Arg Pro Leu Arg Ala Ile Asn Arg Ala Lys Gly Leu Lys His Val
            980                 985                 990

Val Gln Cys Val Phe Val Ala Ile Arg Thr Ile Gly Asn Ile Met Ile
    995                 1000                1005

Val Thr Thr Leu Leu Gln Phe Met Phe Ala Cys Ile Gly Val Gln
    1010                1015                1020

Leu Phe Lys Gly Lys Phe Tyr Ser Cys Thr Asp Glu Ala Lys His
    1025                1030                1035

Thr Leu Lys Glu Cys Lys Gly Ser Phe Leu Ile Tyr Pro Asp Gly
    1040                1045                1050

Asp Val Ser Arg Pro Leu Val Arg Glu Arg Leu Trp Val Asn Ser
    1055                1060                1065

Asp Phe Asn Phe Asp Asn Val Leu Ser Ala Met Met Ala Leu Phe
    1070                1075                1080

Thr Val Ser Thr Phe Glu Gly Trp Pro Ala Leu Leu Tyr Lys Ala
    1085                1090                1095

Ile Asp Ala Asn Ala Glu Asp Glu Gly Pro Ile Tyr Asn Tyr His
    1100                1105                1110

Val Glu Ile Ser Val Phe Phe Ile Val Tyr Ile Ile Ile Ile Ala
    1115                1120                1125

Phe Phe Met Met Asn Ile Phe Val Gly Phe Val Ile Ile Thr Phe
    1130                1135                1140
```

-continued

Arg Ala Gln Gly Glu Gln Glu Tyr Gln Asn Cys Glu Leu Asp Lys
1145                1150                1155

Asn Gln Arg Gln Cys Val Glu Tyr Ala Leu Lys Ala Gln Pro Leu
1160                1165                1170

Arg Arg Tyr Ile Pro Lys Asn Pro His Gln Tyr Arg Val Trp Ala
1175                1180                1185

Thr Val Asn Ser Ala Ala Phe Glu Tyr Leu Met Phe Leu Leu Ile
1190                1195                1200

Leu Leu Asn Thr Val Ala Leu Ala Met Gln His Tyr Glu Gln Thr
1205                1210                1215

Ala Pro Phe Asn Tyr Ala Met Asp Ile Leu Asn Met Val Phe Thr
1220                1225                1230

Gly Leu Phe Thr Ile Glu Met Val Leu Lys Ile Ile Ala Phe Lys
1235                1240                1245

Pro Lys His Tyr Phe Ala Asp Ala Trp Asn Thr Phe Asp Ala Leu
1250                1255                1260

Ile Val Val Gly Ser Val Val Asp Ile Ala Val Thr Glu Val Asn
1265                1270                1275

Asn Gly Gly His Leu Gly Glu Ser Ser Glu Asp Ser Ser Arg Ile
1280                1285                1290

Ser Ile Thr Phe Phe Arg Leu Phe Arg Val Met Arg Leu Val Lys
1295                1300                1305

Leu Leu Ser Lys Gly Glu Gly Ile Arg Thr Leu Leu Trp Thr Phe
1310                1315                1320

Ile Lys Ser Phe Gln Ala Leu Pro Tyr Val Ala Leu Leu Ile Ala
1325                1330                1335

Met Ile Phe Phe Ile Tyr Ala Val Ile Gly Met Gln Met Phe Gly
1340                1345                1350

Lys Val Ala Leu Gln Asp Gly Thr Gln Ile Asn Arg Asn Asn Asn
1355                1360                1365

Phe Gln Thr Phe Pro Gln Ala Val Leu Leu Leu Phe Arg Cys Ala
1370                1375                1380

Thr Gly Glu Ala Trp Gln Glu Ile Met Leu Ala Ser Leu Pro Gly
1385                1390                1395

Asn Arg Cys Asp Pro Glu Ser Asp Phe Gly Pro Gly Glu Glu Phe
1400                1405                1410

Thr Cys Gly Ser Ser Phe Ala Ile Val Tyr Phe Ile Ser Phe Phe
1415                1420                1425

Met Leu Cys Ala Phe Leu Ile Ile Asn Leu Phe Val Ala Val Ile
1430                1435                1440

Met Asp Asn Phe Asp Tyr Leu Thr Arg Asp Trp Ser Ile Leu Gly
1445                1450                1455

Pro His His Leu Asp Glu Phe Lys Arg Ile Trp Ser Glu Tyr Asp
1460                1465                1470

Pro Gly Ala Lys Gly Arg Ile Lys His Leu Asp Val Val Ala Leu
1475                1480                1485

Leu Arg Arg Ile Gln Pro Pro Leu Gly Phe Gly Lys Leu Cys Pro
1490                1495                1500

His Arg Val Ala Cys Lys Arg Leu Val Ala Met Asn Val Pro Leu
1505                1510                1515

Asn Ser Asp Gly Thr Val Thr Phe Asn Ala Thr Leu Phe Ala Leu
1520                1525                1530

```
Val Arg Thr Ser Leu Lys Ile Lys Thr Glu Gly Asn Leu Asp Gln
    1535                1540                1545

Ala Asn Gln Glu Leu Arg Met Val Ile Lys Lys Ile Trp Lys Arg
    1550                1555                1560

Ile Lys Gln Lys Leu Leu Asp Glu Val Ile Pro Pro Pro Asp Glu
    1565                1570                1575

Glu Glu Val Thr Val Gly Lys Phe Tyr Ala Thr Phe Leu Ile Gln
    1580                1585                1590

Asp Tyr Phe Arg Lys Phe Arg Arg Lys Glu Lys Gly Leu Leu
    1595                1600                1605

Gly Arg Glu Ala Pro Thr Ser Thr Ser Ser Ala Leu Gln Ala Gly
    1610                1615                1620

Leu Arg Ser Leu Gln Asp Leu Gly Pro Glu Ile Arg Gln Ala Leu
    1625                1630                1635

Thr Tyr Asp Thr Glu Glu Glu Glu Glu Glu Glu Ala Val Gly
    1640                1645                1650

Gln Glu Ala Glu Glu Glu Ala Glu Asn Asn Pro Glu Pro Tyr
    1655                1660                1665

Lys Asp Ser Ile Asp Ser Gln Pro Gln Ser Arg Trp Asn Ser Arg
    1670                1675                1680

Ile Ser Val Ser Leu Pro Val Lys Glu Lys Leu Pro Asp Ser Leu
    1685                1690                1695

Ser Thr Gly Pro Ser Asp Asp Asp Gly Leu Ala Pro Asn Ser Arg
    1700                1705                1710

Gln Pro Ser Val Ile Gln Ala Gly Ser Gln Pro His Arg Arg Ser
    1715                1720                1725

Ser Gly Val Phe Met Phe Thr Ile Pro Glu Glu Gly Ser Ile Gln
    1730                1735                1740

Leu Lys Gly Thr Gln Gly Gln Asp Asn Gln Asn Glu Glu Gln Glu
    1745                1750                1755

Val Pro Asp Trp Thr Pro Asp Leu Asp Glu Gln Ala Gly Thr Pro
    1760                1765                1770

Ser Asn Pro Val Leu Leu Pro Pro His Trp Ser Gln Gln His Val
    1775                1780                1785

Asn Gly His His Val Pro Arg Arg Arg Leu Leu Pro Pro Thr Pro
    1790                1795                1800

Ala Gly Arg Lys Pro Ser Phe Thr Ile Gln Cys Leu Gln Arg Gln
    1805                1810                1815

Gly Ser Cys Glu Asp Leu Pro Ile Pro Gly Thr Tyr His Arg Gly
    1820                1825                1830

Arg Thr Ser Gly Pro Ser Arg Ala Gln Gly Ser Trp Ala Ala Pro
    1835                1840                1845

Pro Gln Lys Gly Arg Leu Leu Tyr Ala Pro Leu Leu Leu Val Glu
    1850                1855                1860

Glu Ser Thr Val Gly Glu Gly Tyr Leu Gly Lys Leu Gly Gly Pro
    1865                1870                1875

Leu Arg Thr Phe Thr Cys Leu Gln Val Pro Gly Ala His Pro Asn
    1880                1885                1890

Pro Ser His Arg Lys Arg Gly Ser Ala Asp Ser Leu Val Glu Ala
    1895                1900                1905

Val Leu Ile Ser Glu Gly Leu Gly Leu Phe Ala Gln Asp Pro Arg
    1910                1915                1920
```

```
Phe Val Ala Leu Ala Lys Gln Glu Ile Ala Asp Ala Cys His Leu
    1925                1930                1935

Thr Leu Asp Glu Met Asp Ser Ala Ala Ser Asp Leu Leu Ala Gln
    1940                1945                1950

Arg Thr Thr Ser Leu Tyr Ser Asp Glu Glu Ser Ile Leu Ser Arg
    1955                1960                1965

Phe Asp Glu Glu Asp Leu Gly Asp Glu Met Ala Cys Val His Ala
    1970                1975                1980

Leu

<210> SEQ ID NO 10
<211> LENGTH: 2166
<212> TYPE: PRT
<213> ORGANISM: Mus musculus

<400> SEQUENCE: 10

Met Asn Leu Pro Thr Phe Ser Ser Asp Leu Ile Leu Ile Lys Ser Val
1               5                   10                  15

Leu Ser Gln Glu Thr Asp Ala Arg Tyr Lys Gly Arg Val Val Ser Ala
                20                  25                  30

Val Glu Ser Thr Glu Asp Phe Ser Gln Ala Phe Ala Glu Ala Asn Tyr
            35                  40                  45

Ala Arg Gly Thr Arg Leu Pro Ile Ser Gly Gly Pro Thr Ser Gln
        50                  55                  60

Pro Asn Ser Ser Lys Gln Thr Val Leu Ser Trp Gln Ala Ala Ile Asp
65                  70                  75                  80

Ala Ala Arg Gln Ala Lys Ala Ala Gln Thr Met Ser Thr Ser Ala Pro
                85                  90                  95

Pro Pro Val Gly Ser Leu Ser Gln Arg Lys Arg Gln Gln Tyr Ala Lys
            100                 105                 110

Ser Lys Lys Gln Gly Asn Ser Ser Asn Ser Arg Pro Ala Arg Ala Leu
        115                 120                 125

Phe Cys Leu Ser Leu Asn Asn Pro Ile Arg Arg Ala Cys Ile Ser Ile
    130                 135                 140

Val Glu Trp Lys Pro Phe Asp Ile Phe Ile Leu Leu Ala Ile Phe Ala
145                 150                 155                 160

Asn Cys Val Ala Leu Ala Ile Tyr Ile Pro Phe Pro Glu Asp Asp Ser
                165                 170                 175

Asn Ser Thr Asn His Asn Leu Glu Lys Val Glu Tyr Ala Phe Leu Ile
            180                 185                 190

Ile Phe Thr Val Glu Thr Phe Leu Lys Ile Ile Ala Tyr Gly Leu Leu
        195                 200                 205

Leu His Pro Asn Ala Tyr Val Arg Asn Gly Trp Asn Leu Leu Asp Phe
    210                 215                 220

Val Ile Val Ile Val Gly Leu Phe Ser Val Ile Leu Glu Gln Leu Thr
225                 230                 235                 240

Lys Glu Thr Glu Gly Gly Asn His Ser Ser Gly Lys Ser Gly Gly Phe
                245                 250                 255

Asp Val Lys Ala Leu Arg Ala Phe Arg Val Leu Arg Pro Leu Arg Leu
            260                 265                 270

Val Ser Gly Val Pro Ser Leu Gln Val Val Leu Asn Ser Ile Ile Lys
        275                 280                 285

Ala Met Val Pro Leu Leu His Ile Ala Leu Leu Val Leu Phe Val Ile
    290                 295                 300
```

```
Ile Ile Tyr Ala Ile Ile Gly Leu Glu Leu Phe Ile Gly Lys Met His
305                 310                 315                 320

Lys Thr Cys Phe Phe Ala Asp Ser Asp Ile Val Ala Glu Glu Asp Pro
            325                 330                 335

Ala Pro Cys Ala Phe Ser Gly Asn Gly Arg Gln Cys Thr Ala Asn Gly
            340                 345                 350

Thr Glu Cys Arg Ser Gly Trp Val Gly Pro Asn Gly Ile Thr Asn
            355                 360                 365

Phe Asp Asn Phe Ala Phe Ala Met Leu Thr Val Phe Gln Cys Ile Thr
            370                 375                 380

Met Glu Gly Trp Thr Asp Val Leu Tyr Trp Val Asn Asp Ala Ile Gly
385                 390                 395                 400

Trp Glu Trp Pro Trp Val Tyr Phe Val Ser Leu Ile Ile Leu Gly Ser
            405                 410                 415

Phe Phe Val Leu Asn Leu Val Leu Gly Val Leu Ser Gly Glu Phe Ser
            420                 425                 430

Lys Glu Arg Glu Lys Ala Lys Ala Arg Gly Asp Phe Gln Lys Leu Arg
            435                 440                 445

Glu Lys Gln Gln Leu Glu Glu Asp Leu Lys Gly Tyr Leu Asp Trp Ile
450                 455                 460

Thr Gln Ala Glu Asp Ile Asp Pro Glu Asn Glu Glu Glu Gly Gly Glu
465                 470                 475                 480

Glu Gly Lys Arg Asn Thr Ser Met Pro Thr Ser Glu Thr Glu Ser Val
            485                 490                 495

Asn Thr Glu Asn Val Ser Gly Glu Gly Glu Thr Gln Gly Cys Cys Gly
            500                 505                 510

Thr Leu Cys Gln Ala Ile Ser Lys Ser Lys Leu Ser Arg Arg Trp Arg
            515                 520                 525

Arg Trp Asn Arg Phe Asn Arg Arg Cys Arg Ala Ala Val Lys Ser
            530                 535                 540

Val Thr Phe Tyr Trp Leu Val Ile Val Leu Val Phe Leu Asn Thr Leu
545                 550                 555                 560

Thr Ile Ser Ser Glu His Tyr Asn Gln Pro Asp Trp Leu Thr Gln Ile
            565                 570                 575

Gln Asp Ile Ala Asn Lys Val Leu Leu Ala Leu Phe Thr Cys Glu Met
            580                 585                 590

Leu Val Lys Met Tyr Ser Leu Gly Leu Gln Ala Tyr Phe Val Ser Leu
            595                 600                 605

Phe Asn Arg Phe Asp Cys Phe Val Val Cys Gly Gly Ile Thr Glu Thr
            610                 615                 620

Ile Leu Val Glu Leu Glu Leu Met Ser Pro Leu Gly Val Ser Val Phe
625                 630                 635                 640

Arg Cys Val Arg Leu Leu Arg Ile Phe Lys Val Thr Arg His Trp Thr
            645                 650                 655

Ser Leu Ser Asn Leu Val Ala Ser Leu Leu Asn Ser Met Lys Ser Ile
            660                 665                 670

Ala Ser Leu Leu Leu Leu Leu Phe Leu Phe Ile Ile Ile Phe Ser Leu
            675                 680                 685

Leu Gly Met Gln Leu Phe Gly Gly Lys Phe Asn Phe Asp Glu Thr Gln
            690                 695                 700

Thr Lys Arg Ser Thr Phe Asp Asn Phe Pro Gln Ala Leu Leu Thr Val
705                 710                 715                 720
```

```
Phe Gln Ile Leu Thr Gly Glu Asp Trp Asn Ala Val Met Tyr Asp Gly
                725                 730                 735

Ile Met Ala Tyr Gly Gly Pro Ser Ser Ser Gly Met Ile Val Cys Ile
            740                 745                 750

Tyr Phe Ile Ile Leu Phe Ile Cys Gly Asn Tyr Ile Leu Leu Asn Val
        755                 760                 765

Phe Leu Ala Ile Ala Val Asp Asn Leu Ala Asp Ala Glu Ser Leu Asn
    770                 775                 780

Thr Ala Gln Lys Glu Glu Ala Glu Glu Lys Glu Arg Lys Lys Ile Ala
785                 790                 795                 800

Arg Lys Glu Ser Leu Glu Asn Lys Lys Asn Asn Lys Pro Glu Val Asn
                805                 810                 815

Gln Ile Ala Asn Ser Asp Asn Lys Val Thr Ile Asp Asp Tyr Gln Glu
            820                 825                 830

Asp Ala Glu Asp Lys Asp Pro Tyr Pro Pro Cys Asp Val Pro Val Gly
        835                 840                 845

Glu Glu Glu Glu Glu Glu Glu Asp Glu Pro Glu Val Pro Ala Gly
    850                 855                 860

Pro Arg Pro Arg Arg Ile Ser Glu Leu Asn Met Lys Glu Lys Ile Ala
865                 870                 875                 880

Pro Ile Pro Glu Gly Ser Ala Phe Phe Ile Leu Ser Lys Thr Asn Pro
                885                 890                 895

Ile Arg Val Gly Cys His Lys Leu Ile Asn His His Ile Phe Thr Asn
            900                 905                 910

Leu Ile Leu Val Phe Ile Met Leu Ser Ser Ala Ala Leu Ala Ala Glu
        915                 920                 925

Asp Pro Ile Arg Ser His Ser Phe Arg Asn Thr Ile Leu Gly Tyr Phe
    930                 935                 940

Asp Tyr Ala Phe Thr Ala Ile Phe Thr Val Glu Ile Leu Leu Lys Met
945                 950                 955                 960

Thr Thr Phe Gly Ala Phe Leu His Lys Gly Ala Phe Cys Arg Asn Tyr
                965                 970                 975

Phe Asn Leu Leu Asp Met Leu Val Val Gly Val Ser Leu Val Ser Phe
            980                 985                 990

Gly Ile Gln Ser Ser Ala Ile Ser Val Val Lys Ile Leu Arg Val Leu
        995                 1000                1005

Arg Val  Leu Arg Pro Leu Arg  Ala Ile Asn Arg Ala  Lys Gly Leu
    1010                1015                1020

Lys His  Val Val Gln Cys Val  Phe Val Ala Ile Arg  Thr Ile Gly
    1025                1030                1035

Asn Ile  Met Ile Val Thr Thr  Leu Leu Gln Phe Met  Phe Ala Cys
    1040                1045                1050

Ile Gly  Val Gln Leu Phe Lys  Gly Lys Phe Tyr Arg  Cys Thr Asp
    1055                1060                1065

Glu Ala  Lys Ser Asn Pro Glu  Glu Cys Arg Gly Leu  Phe Ile Leu
    1070                1075                1080

Tyr Lys  Asp Gly Asp Val Asp  Ser Pro Val Val Arg  Glu Arg Ile
    1085                1090                1095

Trp Gln  Asn Ser Asp Phe Asn  Phe Asp Asn Val Leu  Ser Ala Met
    1100                1105                1110

Met Ala  Leu Phe Thr Val Ser  Thr Phe Glu Gly Trp  Pro Ala Leu
    1115                1120                1125
```

```
Leu Tyr Lys Ala Ile Asp Ser Asn Gly Glu Asn Val Gly Pro Val
    1130            1135            1140

Tyr Asn Tyr Arg Val Glu Ile Ser Ile Phe Phe Ile Ile Tyr Ile
    1145            1150            1155

Ile Ile Val Ala Phe Phe Met Met Asn Ile Phe Val Gly Phe Val
    1160            1165            1170

Ile Val Thr Phe Gln Glu Gln Gly Glu Lys Glu Tyr Lys Asn Cys
    1175            1180            1185

Glu Leu Asp Lys Asn Gln Arg Gln Cys Val Glu Tyr Ala Leu Lys
    1190            1195            1200

Ala Arg Pro Leu Arg Arg Tyr Ile Pro Lys Asn Pro Tyr Gln Tyr
    1205            1210            1215

Lys Phe Trp Tyr Val Val Asn Ser Ser Pro Phe Glu Tyr Met Met
    1220            1225            1230

Phe Val Leu Ile Met Leu Asn Thr Leu Cys Leu Ala Met Gln His
    1235            1240            1245

Tyr Glu Gln Ser Lys Met Phe Asn Asp Ala Met Asp Ile Leu Asn
    1250            1255            1260

Met Val Phe Thr Gly Val Phe Thr Val Glu Met Val Leu Lys Val
    1265            1270            1275

Ile Ala Phe Lys Pro Lys Gly Tyr Phe Ser Asp Ala Trp Asn Thr
    1280            1285            1290

Phe Asp Ser Leu Ile Val Ile Gly Ser Ile Ile Asp Val Ala Leu
    1295            1300            1305

Ser Glu Ala Asp Asn Ser Glu Glu Ser Asn Arg Ile Ser Ile Thr
    1310            1315            1320

Phe Phe Arg Leu Phe Arg Val Met Arg Leu Val Lys Leu Leu Ser
    1325            1330            1335

Arg Gly Glu Gly Ile Arg Thr Leu Leu Trp Thr Phe Ile Lys Ser
    1340            1345            1350

Phe Gln Ala Leu Pro Tyr Val Ala Leu Leu Ile Ala Met Leu Phe
    1355            1360            1365

Phe Ile Tyr Ala Val Ile Gly Met Gln Met Phe Gly Lys Val Ala
    1370            1375            1380

Met Arg Asp Asn Asn Gln Ile Asn Arg Asn Asn Asn Phe Gln Thr
    1385            1390            1395

Phe Pro Gln Ala Val Leu Leu Leu Phe Arg Cys Ala Thr Gly Glu
    1400            1405            1410

Ala Trp Gln Glu Ile Met Leu Ala Cys Leu Pro Gly Lys Leu Cys
    1415            1420            1425

Asp Pro Asp Ser Asp Tyr Asn Pro Gly Glu Glu Tyr Thr Cys Gly
    1430            1435            1440

Ser Asn Phe Ala Ile Val Tyr Phe Ile Ser Phe Tyr Met Leu Cys
    1445            1450            1455

Ala Phe Leu Ile Ile Asn Leu Phe Val Ala Val Ile Met Asp Asn
    1460            1465            1470

Phe Asp Tyr Leu Thr Arg Asp Trp Ser Ile Leu Gly Pro His His
    1475            1480            1485

Leu Asp Glu Phe Lys Arg Ile Trp Ser Glu Tyr Asp Pro Glu Ala
    1490            1495            1500

Lys Gly Arg Ile Lys His Leu Asp Val Val Thr Leu Leu Arg Arg
    1505            1510            1515
```

```
Ile Gln Pro Pro Leu Gly Phe Gly Lys Leu Cys Pro His Arg Val
1520                1525                1530

Ala Cys Lys Arg Leu Val Ala Met Asn Met Pro Leu Asn Ser Asp
1535                1540                1545

Gly Thr Val Met Phe Asn Ala Thr Leu Phe Ala Leu Val Arg Thr
1550                1555                1560

Ala Leu Lys Ile Lys Thr Glu Gly Asn Leu Glu Gln Ala Asn Glu
1565                1570                1575

Glu Leu Arg Ala Val Ile Lys Lys Ile Trp Lys Lys Thr Ser Met
1580                1585                1590

Lys Leu Leu Asp Gln Val Val Pro Pro Ala Gly Asp Asp Glu Val
1595                1600                1605

Thr Val Gly Lys Phe Tyr Ala Thr Phe Leu Ile Gln Asp Tyr Phe
1610                1615                1620

Arg Lys Phe Lys Lys Arg Lys Glu Gln Gly Leu Val Gly Lys Tyr
1625                1630                1635

Pro Ala Lys Asn Thr Thr Ile Ala Leu Gln Ala Gly Leu Arg Thr
1640                1645                1650

Leu His Asp Ile Gly Pro Glu Ile Arg Arg Ala Ile Ser Cys Asp
1655                1660                1665

Leu Gln Asp Asp Glu Pro Glu Asp Ser Lys Pro Glu Glu Glu Asp
1670                1675                1680

Val Phe Lys Arg Asn Gly Ala Leu Leu Gly Asn His Val Asn His
1685                1690                1695

Val Asn Ser Asp Arg Arg Asp Ser Leu Gln Gln Thr Asn Thr Thr
1700                1705                1710

His Arg Pro Leu His Val Gln Arg Pro Ser Met Pro Pro Ala Ser
1715                1720                1725

Asp Thr Glu Lys Pro Leu Phe Pro Pro Ala Gly Asn Ser Gly Cys
1730                1735                1740

His Asn His His Asn His Asn Ser Ile Gly Lys Gln Ala Pro Thr
1745                1750                1755

Ser Thr Asn Ala Asn Leu Asn Asn Ala Asn Met Ser Lys Ala Ala
1760                1765                1770

His Gly Lys Pro Pro Ser Ile Gly Asn Leu Glu His Val Ser Glu
1775                1780                1785

Asn Gly His Tyr Ser Cys Lys His Asp Arg Glu Leu Gln Arg Arg
1790                1795                1800

Ser Ser Ile Lys Arg Thr Arg Tyr Tyr Glu Thr Tyr Ile Arg Ser
1805                1810                1815

Glu Ser Gly Asp Glu Gln Phe Pro Thr Ile Cys Arg Glu Asp Pro
1820                1825                1830

Glu Ile His Gly Tyr Phe Arg Asp Pro Arg Cys Leu Gly Glu Gln
1835                1840                1845

Glu Tyr Phe Ser Ser Glu Glu Cys Cys Glu Asp Asp Ser Ser Pro
1850                1855                1860

Thr Trp Ser Arg Gln Asn Tyr Asn Tyr Tyr Asn Arg Tyr Pro Gly
1865                1870                1875

Ser Ser Met Asp Phe Glu Arg Pro Arg Gly Tyr His His Pro Gln
1880                1885                1890

Gly Phe Leu Glu Asp Asp Asp Ser Pro Thr Gly Tyr Asp Ser Arg
1895                1900                1905
```

Arg Ser Pro Arg Arg Leu Leu Pro Pro Thr Pro Pro Ser His
    1910            1915                1920

Arg Arg Ser Ser Phe Asn Phe Glu Cys Leu Arg Arg Gln Ser Ser
    1925            1930                1935

Gln Asp Asp Val Leu Pro Ser Pro Ala Leu Pro His Arg Ala Ala
    1940            1945                1950

Leu Pro Leu His Leu Met Gln Gln Gln Ile Met Ala Val Ala Gly
    1955            1960                1965

Leu Asp Ser Ser Lys Ala Gln Lys Tyr Ser Pro Ser His Ser Thr
    1970            1975                1980

Arg Ser Trp Ala Thr Pro Pro Ala Thr Pro Pro Tyr Arg Asp Trp
    1985            1990                1995

Ser Pro Cys Tyr Thr Pro Leu Ile Gln Val Asp Arg Ser Glu Ser
    2000            2005                2010

Met Asp Gln Val Asn Gly Ser Leu Pro Ser Leu His Arg Ser Ser
    2015            2020                2025

Trp Tyr Thr Asp Glu Pro Asp Ile Ser Tyr Arg Thr Phe Thr Pro
    2030            2035                2040

Ala Ser Leu Thr Val Pro Ser Ser Phe Arg Asn Lys Asn Ser Asp
    2045            2050                2055

Lys Gln Arg Ser Ala Asp Ser Leu Val Glu Ala Val Leu Ile Ser
    2060            2065                2070

Glu Gly Leu Gly Arg Tyr Ala Arg Asp Pro Lys Phe Val Ser Ala
    2075            2080                2085

Thr Lys His Glu Ile Ala Asp Ala Cys Asp Leu Thr Ile Asp Glu
    2090            2095                2100

Met Glu Ser Ala Ala Ser Thr Leu Leu Asn Gly Ser Val Cys Pro
    2105            2110                2115

Arg Ala Asn Gly Asp Met Gly Pro Ile Ser His Arg Gln Asp Tyr
    2120            2125                2130

Glu Leu Gln Asp Phe Gly Pro Gly Tyr Ser Asp Glu Glu Pro Asp
    2135            2140                2145

Pro Gly Arg Glu Glu Glu Asp Leu Ala Asp Glu Met Ile Cys Ile
    2150            2155                2160

Thr Thr Leu
    2165

<210> SEQ ID NO 11
<211> LENGTH: 2139
<212> TYPE: PRT
<213> ORGANISM: Mus musculus

<400> SEQUENCE: 11

Met Val Asn Glu Asn Thr Arg Met Tyr Val Pro Glu Glu Asn His Gln
1               5                   10                  15

Gly Ser Asn Tyr Gly Ser Pro Arg Pro Ala His Ala Asn Met Asn Ala
            20                  25                  30

Asn Ala Ala Ala Gly Leu Ala Pro Glu His Ile Pro Thr Pro Gly Ala
        35                  40                  45

Ala Leu Ser Trp Gln Ala Ala Ile Asp Ala Ala Arg Gln Ala Lys Leu
    50                  55                  60

Met Gly Ser Ala Gly Asn Ala Thr Ile Ser Thr Val Ser Ser Thr Gln
65                  70                  75                  80

-continued

```
Arg Lys Arg Gln Gln Tyr Gly Lys Pro Lys Gln Gly Thr Thr
                85                  90                  95

Ala Thr Arg Pro Pro Arg Ala Leu Leu Cys Leu Thr Leu Lys Asn Pro
            100                 105                 110

Ile Arg Arg Ala Cys Ile Ser Ile Val Glu Trp Lys Pro Phe Glu Ile
            115                 120                 125

Ile Ile Leu Leu Thr Ile Phe Ala Asn Cys Val Ala Leu Ala Ile Tyr
            130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
            165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Gly Leu Phe
            195                 200                 205

Ser Ala Ile Leu Glu Gln Ala Thr Lys Ala Asp Gly Ala Asn Ala Leu
            210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
            245                 250                 255

Val Leu Asn Ser Ile Ile Lys Ala Met Val Pro Leu Leu His Ile Ala
            260                 265                 270

Leu Leu Val Leu Phe Val Ile Ile Tyr Ala Ile Ile Gly Leu Glu
            275                 280                 285

Leu Phe Met Gly Lys Met His Lys Thr Cys Tyr Asn Gln Glu Gly Ile
            290                 295                 300

Ile Asp Val Pro Ala Glu Glu Asp Pro Ser Pro Cys Ala Leu Glu Thr
305                 310                 315                 320

Gly His Gly Arg Gln Cys Gln Asn Gly Thr Val Cys Lys Pro Gly Trp
            325                 330                 335

Asp Gly Pro Lys His Gly Ile Thr Asn Phe Asp Asn Phe Ala Phe Ala
            340                 345                 350

Met Leu Thr Val Phe Gln Cys Ile Thr Met Glu Gly Trp Thr Asp Val
            355                 360                 365

Leu Tyr Trp Met Gln Asp Ala Met Gly Tyr Glu Leu Pro Trp Val Tyr
            370                 375                 380

Phe Val Ser Leu Val Ile Phe Gly Ser Phe Phe Val Leu Asn Leu Val
385                 390                 395                 400

Leu Gly Val Leu Ser Gly Glu Phe Ser Lys Glu Arg Glu Lys Ala Lys
            405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Asp
            435                 440                 445

Pro Glu Asn Glu Asp Glu Gly Met Asp Glu Asp Lys Pro Arg Asn Met
450                 455                 460

Ser Met Pro Thr Ser Glu Thr Glu Ser Val Asn Thr Glu Asn Val Ala
465                 470                 475                 480

Gly Gly Asp Ile Glu Gly Glu Asn Cys Gly Ala Arg Leu Ala His Arg
            485                 490                 495
```

```
Ile Ser Lys Ser Lys Phe Ser Arg Tyr Trp Arg Trp Asn Arg Phe
            500                 505                 510
Cys Arg Arg Lys Cys Arg Ala Ala Val Lys Ser Asn Val Phe Tyr Trp
    515                 520                 525
Leu Val Ile Phe Leu Val Phe Leu Asn Thr Leu Thr Ile Ala Ser Glu
        530                 535                 540
His Tyr Asn Gln Pro His Trp Leu Thr Glu Val Gln Asp Thr Ala Asn
545                 550                 555                 560
Lys Ala Leu Leu Ala Leu Phe Thr Ala Glu Met Leu Leu Lys Met Tyr
                565                 570                 575
Ser Leu Gly Leu Gln Ala Tyr Phe Val Ser Leu Phe Asn Arg Phe Asp
            580                 585                 590
Cys Phe Ile Val Cys Gly Gly Ile Leu Glu Thr Ile Leu Val Glu Thr
        595                 600                 605
Lys Ile Met Ser Pro Leu Gly Ile Ser Val Leu Arg Cys Val Arg Leu
610                 615                 620
Leu Arg Ile Phe Lys Ile Thr Arg Tyr Trp Asn Ser Leu Ser Asn Leu
625                 630                 635                 640
Val Ala Ser Leu Leu Asn Ser Val Arg Ser Ile Ala Ser Leu Leu Leu
                645                 650                 655
Leu Leu Phe Leu Phe Ile Ile Ile Phe Ser Leu Leu Gly Met Gln Leu
            660                 665                 670
Phe Gly Gly Lys Phe Asn Phe Asp Glu Met Gln Thr Arg Arg Ser Thr
            675                 680                 685
Phe Asp Asn Phe Pro Gln Ser Leu Leu Thr Val Phe Gln Ile Leu Thr
690                 695                 700
Gly Glu Asp Trp Asn Ser Val Met Tyr Asp Gly Ile Met Ala Tyr Gly
705                 710                 715                 720
Gly Pro Ser Phe Pro Gly Met Leu Val Cys Ile Tyr Phe Ile Ile Leu
            725                 730                 735
Phe Ile Cys Gly Asn Tyr Ile Leu Leu Asn Val Phe Leu Ala Ile Ala
            740                 745                 750
Val Asp Asn Leu Ala Asp Ala Glu Ser Leu Thr Ser Ala Gln Lys Glu
        755                 760                 765
Glu Glu Glu Glu Lys Glu Arg Lys Lys Leu Ala Arg Thr Ala Ser Pro
    770                 775                 780
Glu Lys Lys Gln Glu Val Met Glu Lys Pro Ala Val Glu Glu Ser Lys
785                 790                 795                 800
Glu Glu Lys Ile Glu Leu Lys Ser Ile Thr Ala Asp Gly Glu Ser Pro
                805                 810                 815
Pro Thr Thr Lys Ile Asn Met Asp Asp Leu Gln Pro Ser Glu Asn Glu
            820                 825                 830
Asp Lys Ser Pro His Ser Asn Pro Asp Thr Ala Gly Glu Glu Asp Glu
            835                 840                 845
Glu Glu Pro Glu Met Pro Val Gly Pro Arg Pro Arg Pro Leu Ser Glu
850                 855                 860
Leu His Leu Lys Glu Lys Ala Val Pro Met Pro Glu Ala Ser Ala Phe
865                 870                 875                 880
Phe Ile Phe Ser Pro Asn Asn Arg Phe Arg Leu Gln Cys His Arg Ile
                885                 890                 895
Val Asn Asp Thr Ile Phe Thr Asn Leu Ile Leu Phe Phe Ile Leu Leu
            900                 905                 910
```

-continued

Ser Ser Ile Ser Leu Ala Ala Glu Asp Pro Val Gln His Thr Ser Phe
    915                 920                 925

Arg Asn His Ile Leu Gly Asn Ala Asp Tyr Val Phe Thr Ser Ile Phe
    930                 935                 940

Thr Leu Glu Ile Ile Leu Lys Met Thr Ala Tyr Gly Ala Phe Leu His
945                 950                 955                 960

Lys Gly Ser Phe Cys Arg Asn Tyr Phe Asn Ile Leu Asp Leu Leu Val
            965                 970                 975

Val Ser Val Ser Leu Ile Ser Phe Gly Ile Gln Ser Ser Ala Ile Asn
            980                 985                 990

Val Val Lys Ile Leu Arg Val Leu Arg Val Leu Arg Pro Leu Arg Ala
            995                 1000                1005

Ile Asn Arg Ala Lys Gly Leu Lys His Val Val Gln Cys Val Phe
    1010                1015                1020

Val Ala Ile Arg Thr Ile Gly Asn Ile Val Ile Val Thr Thr Leu
    1025                1030                1035

Leu Gln Phe Met Phe Ala Cys Ile Gly Val Gln Leu Phe Lys Gly
    1040                1045                1050

Lys Leu Tyr Thr Cys Ser Asp Ser Ser Lys Gln Thr Glu Ala Glu
    1055                1060                1065

Cys Lys Gly Asn Tyr Ile Thr Tyr Lys Asp Gly Glu Val Asp His
    1070                1075                1080

Pro Ile Ile Gln Pro Arg Ser Trp Glu Asn Ser Lys Phe Asp Phe
    1085                1090                1095

Asp Asn Val Leu Ala Ala Met Met Ala Leu Phe Thr Val Ser Thr
    1100                1105                1110

Phe Glu Gly Trp Pro Glu Leu Leu Tyr Arg Ser Ile Asp Ser His
    1115                1120                1125

Thr Glu Asp Lys Gly Pro Ile Tyr Asn Tyr Arg Val Glu Ile Ser
    1130                1135                1140

Ile Phe Phe Ile Ile Tyr Ile Ile Ile Ala Phe Phe Met Met
    1145                1150                1155

Asn Ile Phe Val Gly Phe Val Ile Val Thr Phe Gln Glu Gln Gly
    1160                1165                1170

Glu Gln Glu Tyr Lys Asn Cys Glu Leu Asp Lys Asn Gln Arg Gln
    1175                1180                1185

Cys Val Glu Tyr Ala Leu Lys Ala Arg Pro Leu Arg Arg Tyr Ile
    1190                1195                1200

Pro Lys Asn Gln His Gln Tyr Lys Val Trp Tyr Val Val Asn Ser
    1205                1210                1215

Thr Tyr Phe Glu Tyr Leu Met Phe Val Leu Ile Leu Leu Asn Thr
    1220                1225                1230

Ile Cys Leu Ala Met Gln His Tyr Gly Gln Ser Cys Leu Phe Lys
    1235                1240                1245

Ile Ala Met Asn Ile Leu Asn Met Leu Phe Thr Gly Leu Phe Thr
    1250                1255                1260

Val Glu Met Ile Leu Lys Leu Ile Ala Phe Lys Pro Lys Gly Tyr
    1265                1270                1275

Phe Ser Asp Pro Trp Asn Val Phe Asp Phe Leu Ile Val Ile Gly
    1280                1285                1290

Ser Ile Ile Asp Val Ile Leu Ser Glu Thr Asn Pro Ala Glu His
    1295                1300                1305

```
Thr Gln Cys Ser Pro Ser Met Ser Ala Glu Glu Asn Ser Arg Ile
    1310            1315                1320

Ser Ile Thr Phe Phe Arg Leu Phe Arg Val Met Arg Leu Val Lys
    1325            1330                1335

Leu Leu Ser Arg Gly Glu Gly Ile Arg Thr Leu Leu Trp Thr Phe
    1340            1345                1350

Ile Lys Ser Phe Gln Ala Leu Pro Tyr Val Ala Leu Leu Ile Val
    1355            1360                1365

Met Leu Phe Phe Ile Tyr Ala Val Ile Gly Met Gln Val Phe Gly
    1370            1375                1380

Lys Ile Ala Leu Asn Asp Thr Thr Glu Ile Asn Arg Asn Asn Asn
    1385            1390                1395

Phe Gln Thr Phe Pro Gln Ala Val Leu Leu Leu Phe Arg Cys Ala
    1400            1405                1410

Thr Gly Glu Ala Trp Gln Asp Ile Met Leu Ala Cys Met Pro Gly
    1415            1420                1425

Lys Lys Cys Ala Pro Glu Ser Glu Pro Ser Asn Ser Thr Glu Gly
    1430            1435                1440

Glu Thr Pro Cys Gly Ser Ser Phe Ala Val Phe Tyr Phe Ile Ser
    1445            1450                1455

Phe Tyr Met Leu Cys Ala Phe Leu Ile Ile Asn Leu Phe Val Ala
    1460            1465                1470

Val Ile Met Asp Asn Phe Asp Tyr Leu Thr Arg Asp Trp Ser Ile
    1475            1480                1485

Leu Gly Pro His His Leu Asp Glu Phe Lys Arg Ile Trp Ala Glu
    1490            1495                1500

Tyr Asp Pro Glu Ala Lys Gly Arg Ile Lys His Leu Asp Val Val
    1505            1510                1515

Thr Leu Leu Arg Arg Ile Gln Pro Pro Leu Gly Phe Gly Lys Leu
    1520            1525                1530

Cys Pro His Arg Val Ala Cys Lys Arg Leu Val Ser Met Asn Met
    1535            1540                1545

Pro Leu Asn Ser Asp Gly Thr Val Met Phe Asn Ala Thr Leu Phe
    1550            1555                1560

Ala Leu Val Arg Thr Ala Leu Arg Ile Lys Thr Glu Gly Asn Leu
    1565            1570                1575

Glu Gln Ala Asn Glu Glu Leu Arg Ala Ile Ile Lys Lys Ile Trp
    1580            1585                1590

Lys Arg Thr Ser Met Lys Leu Leu Asp Gln Val Val Pro Pro Ala
    1595            1600                1605

Gly Asp Asp Glu Val Thr Val Gly Lys Phe Tyr Ala Thr Phe Leu
    1610            1615                1620

Ile Gln Glu Tyr Phe Arg Lys Phe Lys Lys Arg Lys Glu Gln Gly
    1625            1630                1635

Leu Val Gly Lys Pro Ser Gln Arg Asn Ala Leu Ser Leu Gln Ala
    1640            1645                1650

Gly Leu Arg Thr Leu His Asp Ile Gly Pro Glu Ile Arg Arg Ala
    1655            1660                1665

Ile Ser Gly Asp Leu Thr Ala Glu Glu Glu Leu Asp Lys Ala Met
    1670            1675                1680

Lys Glu Ala Val Ser Ala Ala Ser Glu Asp Asp Ile Phe Arg Arg
    1685            1690                1695
```

```
Ala Gly Gly Leu Phe Gly Asn His Val Thr Tyr Tyr Gln Ser Asp
    1700            1705                1710

Ser Arg Gly Asn Phe Pro Gln Thr Phe Ala Thr Gln Arg Pro Leu
    1715            1720                1725

His Ile Asn Lys Thr Gly Asn Asn Gln Ala Asp Thr Glu Ser Pro
    1730            1735                1740

Ser His Glu Lys Leu Val Asp Ser Thr Phe Thr Pro Ser Ser Tyr
    1745            1750                1755

Ser Ser Thr Gly Ser Asn Ala Asn Ile Asn Asn Ala Asn Asn Thr
    1760            1765                1770

Ala Leu Gly Arg Phe Pro His Pro Ala Gly Tyr Ser Ser Thr Val
    1775            1780                1785

Ser Thr Val Glu Gly His Gly Pro Pro Leu Ser Pro Ala Val Arg
    1790            1795                1800

Val Gln Glu Ala Ala Trp Lys Leu Ser Ser Lys Arg Cys His Ser
    1805            1810                1815

Arg Glu Ser Gln Gly Ala Thr Val Asn Gln Glu Ile Phe Pro Asp
    1820            1825                1830

Glu Thr Arg Ser Val Arg Met Ser Glu Glu Ala Glu Tyr Cys Ser
    1835            1840                1845

Glu Pro Ser Leu Leu Ser Thr Asp Met Phe Ser Tyr Gln Glu Asp
    1850            1855                1860

Glu His Arg Gln Leu Thr Cys Pro Glu Glu Asp Lys Arg Glu Ile
    1865            1870                1875

Gln Pro Ser Pro Lys Arg Ser Phe Leu Arg Ser Ala Ser Leu Gly
    1880            1885                1890

Arg Arg Ala Ser Phe His Leu Glu Cys Leu Lys Arg Gln Lys Asp
    1895            1900                1905

Gln Gly Gly Asp Ile Ser Gln Lys Thr Ala Leu Pro Leu His Leu
    1910            1915                1920

Val His His Gln Ala Leu Ala Val Ala Gly Leu Ser Pro Leu Leu
    1925            1930                1935

Gln Arg Ser His Ser Pro Thr Thr Phe Pro Arg Pro Cys Pro Thr
    1940            1945                1950

Pro Pro Val Thr Pro Gly Ser Arg Gly Arg Pro Leu Arg Pro Ile
    1955            1960                1965

Pro Thr Leu Arg Leu Glu Gly Ala Glu Ser Ser Glu Lys Leu Asn
    1970            1975                1980

Ser Ser Phe Pro Ser Ile His Cys Ser Ser Trp Ser Glu Glu Thr
    1985            1990                1995

Thr Ala Cys Ser Gly Ser Ser Ser Met Ala Arg Arg Ala Arg Pro
    2000            2005                2010

Val Ser Leu Thr Val Pro Ser Gln Ala Gly Ala Pro Gly Arg Gln
    2015            2020                2025

Phe His Gly Ser Ala Ser Ser Leu Val Glu Ala Val Leu Ile Ser
    2030            2035                2040

Glu Gly Leu Gly Gln Phe Ala Gln Asp Pro Lys Phe Ile Glu Val
    2045            2050                2055

Thr Thr Gln Glu Leu Ala Asp Ala Cys Asp Met Thr Ile Glu Glu
    2060            2065                2070

Met Glu Asn Ala Ala Asp Asn Ile Leu Ser Gly Gly Ala Gln Gln
    2075            2080                2085
```

```
Ser Pro Asn Gly Thr Leu Leu Pro Phe Val Asn Cys Arg Asp Pro
    2090                2095                2100

Gly Gln Asp Arg Ala Val Ala Pro Glu Asp Glu Ser Cys Ala Tyr
    2105                2110                2115

Ala Leu Gly Arg Gly Arg Ser Glu Glu Ala Leu Ala Asp Ser Arg
    2120                2125                2130

Ser Tyr Val Ser Asn Leu
    2135

<210> SEQ ID NO 12
<211> LENGTH: 1880
<212> TYPE: PRT
<213> ORGANISM: Mus musculus

<400> SEQUENCE: 12

Met Glu Pro Pro Ser Pro Gln Asp Glu Gly Leu Arg Lys Lys Gln Pro
1               5                   10                  15

Lys Lys Pro Val Pro Glu Ile Leu Pro Arg Pro Pro Arg Ala Leu Phe
            20                  25                  30

Cys Leu Thr Leu Gln Asn Pro Leu Arg Lys Ala Cys Ile Ser Ile Val
        35                  40                  45

Glu Trp Lys Pro Phe Glu Thr Ile Ile Leu Leu Thr Ile Phe Ala Asn
    50                  55                  60

Cys Val Ala Leu Ala Val Tyr Leu Pro Met Pro Glu Asp Asp Asn Asn
65                  70                  75                  80

Thr Leu Asn Leu Gly Leu Glu Lys Leu Glu Tyr Phe Phe Leu Ile Val
                85                  90                  95

Phe Ser Ile Glu Ala Ala Met Lys Ile Ile Ala Tyr Gly Phe Leu Phe
            100                 105                 110

His Gln Asp Ala Tyr Leu Arg Ser Gly Trp Asn Val Leu Asp Phe Ile
        115                 120                 125

Ile Val Phe Leu Gly Val Phe Thr Val Ile Leu Glu Gln Val Asn Ile
    130                 135                 140

Ile Gln Thr Asn Thr Ala Pro Met Ser Ser Lys Gly Ala Gly Leu Asp
145                 150                 155                 160

Val Lys Ala Leu Arg Ala Phe Arg Val Leu Arg Pro Leu Arg Leu Val
                165                 170                 175

Ser Gly Val Pro Ser Leu Gln Val Leu Asn Ser Ile Phe Lys Ala
            180                 185                 190

Met Leu Pro Leu Phe His Ile Ala Leu Leu Val Leu Phe Met Val Ile
        195                 200                 205

Ile Tyr Ala Ile Ile Gly Leu Glu Leu Phe Lys Gly Lys Met His Lys
    210                 215                 220

Thr Cys Tyr Phe Ile Gly Thr Asp Ile Val Ala Thr Val Glu Asn Glu
225                 230                 235                 240

Lys Pro Ser Pro Cys Ala Arg Thr Gly Ser Gly Arg Pro Cys Thr Ile
                245                 250                 255

Asn Gly Ser Glu Cys Arg Gly Gly Trp Pro Gly Pro Asn His Gly Ile
            260                 265                 270

Thr His Phe Asp Asn Phe Gly Phe Ser Met Leu Thr Val Tyr Gln Cys
        275                 280                 285

Ile Ser Met Glu Gly Trp Thr Asp Val Leu Tyr Trp Val Asn Asp Ala
    290                 295                 300

Ile Gly Asn Glu Trp Pro Trp Ile Tyr Phe Val Thr Leu Ile Leu Leu
305                 310                 315                 320
```

```
Gly Ser Phe Phe Ile Leu Asn Leu Val Leu Gly Val Leu Ser Gly Glu
                325                 330                 335

Phe Thr Lys Glu Arg Glu Lys Ala Lys Ser Arg Gly Thr Phe Gln Lys
            340                 345                 350

Leu Arg Glu Lys Gln Gln Leu Glu Glu Asp Leu Arg Gly Tyr Met Ser
        355                 360                 365

Trp Ile Thr Gln Gly Glu Val Met Asp Val Asp Leu Arg Glu Gly
    370                 375                 380

Lys Leu Ser Leu Asp Glu Gly Gly Ser Asp Thr Glu Ser Leu Tyr Glu
385                 390                 395                 400

Ile Glu Gly Leu Asn Lys Ile Ile Gln Phe Ile Arg His Trp Arg Gln
            405                 410                 415

Trp Asn Arg Val Phe Arg Trp Lys Cys His Asp Leu Val Lys Ser Lys
            420                 425                 430

Val Phe Tyr Trp Leu Val Ile Leu Ile Val Ala Leu Asn Thr Leu Ser
            435                 440                 445

Ile Ala Ser Glu His His Asn Gln Pro Leu Trp Leu Thr His Leu Gln
    450                 455                 460

Asp Val Ala Asn Arg Val Leu Leu Thr Leu Phe Thr Ile Glu Met Leu
465                 470                 475                 480

Met Lys Met Tyr Gly Leu Gly Leu Arg Gln Tyr Phe Met Ser Ile Phe
            485                 490                 495

Asn Arg Phe Asp Cys Phe Val Val Cys Ser Gly Ile Leu Glu Ile Leu
            500                 505                 510

Leu Val Glu Ser Gly Ala Met Ser Pro Leu Gly Ile Ser Val Leu Arg
        515                 520                 525

Cys Ile Arg Leu Leu Arg Leu Phe Lys Ile Thr Lys Tyr Trp Thr Ser
    530                 535                 540

Leu Ser Asn Leu Val Ala Ser Leu Leu Asn Ser Ile Arg Ser Ile Ala
545                 550                 555                 560

Ser Leu Leu Leu Leu Leu Phe Leu Phe Ile Ile Ile Phe Ala Leu Leu
            565                 570                 575

Gly Met Gln Leu Phe Gly Gly Arg Tyr Asp Phe Glu Asp Thr Glu Val
            580                 585                 590

Arg Arg Ser Asn Phe Asp Asn Phe Pro Gln Ala Leu Ile Ser Val Phe
        595                 600                 605

Gln Val Leu Thr Gly Glu Asp Trp Asn Ser Val Met Tyr Asn Gly Ile
    610                 615                 620

Met Ala Tyr Gly Gly Pro Thr Tyr Pro Gly Val Leu Val Cys Ile Tyr
625                 630                 635                 640

Phe Ile Ile Leu Phe Val Cys Gly Asn Tyr Ile Leu Leu Asn Val Phe
            645                 650                 655

Leu Ala Ile Ala Val Asp Asn Leu Ala Glu Ala Glu Ser Leu Thr Ser
            660                 665                 670

Ala Gln Lys Ala Lys Ala Glu Glu Arg Lys Arg Arg Lys Met Ser Lys
        675                 680                 685

Gly Leu Pro Asp Lys Ser Glu Glu Arg Ala Thr Val Thr Lys Lys
    690                 695                 700

Leu Glu Gln Lys Ser Lys Gly Glu Gly Ile Pro Thr Thr Ala Lys Leu
705                 710                 715                 720

Lys Ile Asp Glu Phe Glu Ser Asn Val Asn Glu Val Lys Asp Pro Tyr
            725                 730                 735
```

```
Pro Ser Ala Asp Phe Pro Gly Asp Glu Glu Asp Glu Pro Glu Ile
                740                 745                 750

Pro Val Ser Pro Arg Pro Arg Pro Leu Ala Glu Leu Gln Leu Lys Glu
        755                 760                 765

Lys Ala Val Pro Ile Pro Glu Ala Ser Ser Phe Phe Ile Phe Ser Pro
770                 775                 780

Thr Asn Lys Ile Arg Val Leu Cys His Arg Ile Val Asn Ala Thr Trp
785                 790                 795                 800

Phe Thr Asn Phe Ile Leu Leu Phe Ile Leu Leu Ser Ser Ala Ala Leu
                805                 810                 815

Ala Ala Glu Asp Pro Ile Arg Ala Asp Ser Met Arg Asn Gln Ile Leu
            820                 825                 830

Glu Tyr Phe Asp Tyr Val Phe Thr Ala Val Phe Thr Val Glu Ile Val
                835                 840                 845

Leu Lys Met Thr Thr Tyr Gly Ala Phe Leu His Lys Gly Ser Phe Cys
        850                 855                 860

Arg Asn Tyr Phe Asn Ile Leu Asp Leu Leu Val Val Ala Val Ser Leu
865                 870                 875                 880

Ile Ser Met Gly Leu Glu Ser Ser Ala Ile Ser Val Val Lys Ile Leu
                885                 890                 895

Arg Val Leu Arg Val Leu Arg Pro Leu Arg Ala Ile Asn Arg Ala Lys
            900                 905                 910

Gly Leu Lys His Val Val Gln Cys Val Phe Val Ala Ile Arg Thr Ile
                915                 920                 925

Gly Asn Ile Val Leu Val Thr Thr Leu Leu Gln Phe Met Phe Ala Cys
        930                 935                 940

Ile Gly Val Gln Leu Phe Lys Gly Lys Phe Tyr Ser Cys Asn Asp Leu
945                 950                 955                 960

Ser Lys Met Thr Glu Glu Cys Arg Gly Tyr Tyr Tyr Ile Tyr Lys
                965                 970                 975

Asp Gly Asp Pro Thr Gln Ile Glu Leu Arg Pro Arg Gln Trp Ile His
            980                 985                 990

Asn Asp Phe His Phe Asp Asn Val Leu Ser Ala Met Met Ser Leu Phe
        995                 1000                1005

Thr Val Ser Thr Phe Glu Gly Trp Pro Gln Leu Leu Tyr Lys Ala
    1010                1015                1020

Ile Asp Ser Asn Glu Glu Asp Thr Gly Pro Val Tyr Asn Asn Arg
    1025                1030                1035

Val Glu Met Ala Ile Phe Ile Ile Tyr Ile Ile Leu Ile Ala
    1040                1045                1050

Phe Phe Met Met Asn Ile Phe Val Gly Phe Val Ile Val Thr Phe
    1055                1060                1065

Gln Glu Gln Gly Glu Thr Glu Tyr Lys Asn Cys Glu Leu Asp Lys
    1070                1075                1080

Asn Gln Arg Gln Cys Val Gln Tyr Ala Leu Lys Ala Arg Pro Leu
    1085                1090                1095

Arg Cys Tyr Ile Pro Lys Asn Pro Tyr Gln Tyr Gln Val Trp Tyr
    1100                1105                1110

Val Val Thr Ser Ser Tyr Phe Glu Tyr Leu Met Phe Ala Leu Ile
    1115                1120                1125

Met Leu Asn Thr Ile Cys Leu Gly Met Gln His Tyr Asn Gln Ser
    1130                1135                1140
```

-continued

```
Glu Gln Met Asn His Ile Ser Asp Ile Leu Asn Val Ala Phe Thr
    1145            1150                1155
Ile Ile Phe Thr Leu Glu Met Val Leu Lys Leu Ile Ala Phe Lys
    1160            1165                1170
Pro Arg Ala Tyr Phe Gly Asp Pro Trp Asn Val Phe Asp Phe Leu
    1175            1180                1185
Ile Val Ile Gly Ser Ile Ile Asp Val Ile Leu Ser Glu Ile Asp
    1190            1195                1200
Thr Phe Leu Ala Ser Ser Gly Gly Leu Tyr Cys Leu Gly Gly Gly
    1205            1210                1215
Cys Gly Asn Val Asp Pro Asp Glu Ser Ala Arg Ile Ser Ser Ala
    1220            1225                1230
Phe Phe Arg Leu Phe Arg Val Met Arg Leu Val Lys Leu Leu Asn
    1235            1240                1245
Arg Ala Glu Gly Val Arg Thr Leu Leu Trp Thr Phe Ile Lys Ser
    1250            1255                1260
Phe Gln Ala Leu Pro Tyr Val Ala Leu Leu Ile Val Met Leu Phe
    1265            1270                1275
Phe Ile Tyr Ala Val Ile Gly Met Gln Met Phe Gly Lys Ile Ala
    1280            1285                1290
Met Val Asp Gly Thr Gln Ile Asn Arg Asn Asn Asn Phe Gln Thr
    1295            1300                1305
Phe Pro Gln Ala Val Leu Leu Leu Phe Arg Cys Ala Thr Gly Glu
    1310            1315                1320
Ala Trp Gln Glu Ile Leu Leu Ala Cys Ser Tyr Gly Lys Leu Cys
    1325            1330                1335
Asp Pro Glu Ser Asp Tyr Ala Pro Gly Glu Glu His Thr Cys Gly
    1340            1345                1350
Thr Asn Phe Ala Tyr Tyr Tyr Phe Ile Ser Phe Tyr Met Leu Cys
    1355            1360                1365
Ala Phe Leu Ile Ile Asn Leu Phe Val Ala Val Ile Met Asp Asn
    1370            1375                1380
Phe Asp Tyr Leu Thr Arg Asp Trp Ser Ile Leu Gly Pro His His
    1385            1390                1395
Leu Asp Glu Phe Lys Ala Ile Trp Ala Glu Tyr Asp Pro Glu Ala
    1400            1405                1410
Lys Gly Arg Ile Lys His Leu Asp Val Val Thr Leu Leu Arg Arg
    1415            1420                1425
Ile Gln Pro Pro Leu Gly Phe Gly Lys Phe Cys Pro His Arg Val
    1430            1435                1440
Ala Cys Lys Arg Leu Val Gly Met Asn Met Pro Leu Asn Ser Asp
    1445            1450                1455
Gly Thr Val Thr Phe Asn Ala Thr Leu Phe Ala Leu Val Arg Thr
    1460            1465                1470
Ala Leu Lys Ile Lys Thr Glu Gly Asn Phe Glu Gln Ala Asn Glu
    1475            1480                1485
Glu Leu Arg Ala Ile Ile Lys Lys Ile Trp Lys Arg Thr Ser Met
    1490            1495                1500
Lys Leu Leu Asp Gln Val Ile Pro Pro Ile Gly Asp Asp Glu Val
    1505            1510                1515
Thr Val Gly Lys Phe Tyr Ala Thr Phe Leu Ile Gln Glu His Phe
    1520            1525                1530
```

Arg Lys Phe Met Lys Arg Gln Glu Tyr Tyr Gly Tyr Arg Pro
1535                1540                1545

Lys Lys Asp Thr Val Gln Ile Gln Ala Gly Leu Arg Thr Ile Glu
    1550                1555                1560

Glu Glu Ala Ala Pro Glu Ile His Arg Ala Ile Ser Gly Asp Pro
    1565                1570                1575

Thr Ala Glu Glu Glu Leu Glu Arg Ala Met Val Glu Ala Ala Met
    1580                1585                1590

Glu Glu Gly Ile Phe Arg Arg Thr Gly Gly Leu Phe Gly Gln Val
    1595                1600                1605

Asp Asn Phe Leu Glu Arg Thr Asn Ser Leu Pro Val Met Ala
    1610                1615                1620

Asn Gln Arg Pro Leu Gln Phe Ala Glu Ile Glu Met Glu Glu Leu
    1625                1630                1635

Glu Ser Pro Val Phe Leu Glu Asp Phe Pro Gln Asn Pro Gly Thr
    1640                1645                1650

His Pro Leu Ala Arg Ala Asn Thr Asn Asn Ala Asn Ala Asn Val
    1655                1660                1665

Ala Tyr Gly Asn Ser Ser His Arg Asn Asn Pro Val Phe Ser Ser
    1670                1675                1680

Ile Cys Tyr Glu Arg Glu Phe Leu Gly Glu Ala Asp Met Pro Val
    1685                1690                1695

Thr Arg Glu Gly Pro Leu Ser Gln Pro Cys Ser Gly Ser Gly Pro
    1700                1705                1710

His Ser Arg Ser His Val Asp Lys Leu Lys Arg Pro Met Thr Gln
    1715                1720                1725

Arg Gly Met Pro Glu Gly Gln Val Pro Pro Ser Pro Cys Gln Leu
    1730                1735                1740

Ser Gln Ala Glu His Pro Val Gln Lys Glu Gly Lys Gly Pro Thr
    1745                1750                1755

Ser Arg Phe Leu Glu Thr Pro Asn Ser Arg Asn Phe Glu Glu His
    1760                1765                1770

Val Pro Arg Asn Ser Ala His Arg Cys Thr Ala Pro Ala Thr Ala
    1775                1780                1785

Met Leu Ile Gln Glu Ala Leu Val Arg Gly Gly Leu Asp Ser Leu
    1790                1795                1800

Ala Ala Asp Ala Asn Phe Val Met Ala Thr Gly Gln Ala Leu Ala
    1805                1810                1815

Asp Ala Cys Gln Met Glu Pro Glu Glu Val Glu Val Ala Ala Thr
    1820                1825                1830

Glu Leu Leu Lys Gln Glu Ser Pro Glu Ala Gly Pro Cys Leu Gly
    1835                1840                1845

Ala Leu Ser Leu Arg Ser Ser Pro Gly Pro Pro Glu Ser Asp Asp
    1850                1855                1860

Trp Gly Ser Gln Thr Thr Leu Ile Thr Pro Arg Cys Glu Ala Tyr
    1865                1870                1875

Thr Glu
    1880

<210> SEQ ID NO 13
<211> LENGTH: 108
<212> TYPE: PRT
<213> ORGANISM: Artificial Sequence
<220> FEATURE:
<223> OTHER INFORMATION: Produced from hybridoma cells

```
<220> FEATURE:
<221> NAME/KEY: misc_feature
<222> LOCATION: (3)..(4)
<223> OTHER INFORMATION: Xaa can be any naturally occurring amino acid

<400> SEQUENCE: 13

Ser Gln Xaa Xaa Ser Ile Thr Cys Thr Val Ser Gly Phe Ser Leu Thr
1               5                   10                  15

Ser Tyr Gly Val His Trp Val Arg Gln Ser Pro Gly Lys Gly Leu Glu
            20                  25                  30

Trp Leu Gly Val Ile Trp Arg Gly Gly Asn Thr Asp Tyr Ser Ala Ala
        35                  40                  45

Phe Met Ser Arg Leu Ile Ile Thr Lys Asp Asn Ser Lys Ser Gln Val
    50                  55                  60

Phe Phe Lys Met Asn Ser Leu Gln Ala Asp Asp Thr Ala Ile Tyr Tyr
65                  70                  75                  80

Cys Val Lys Lys Ala Tyr Tyr Tyr Gly Ser Asn Tyr Tyr Thr Met Asp
                85                  90                  95

Tyr Trp Gly Gln Gly Thr Ser Val Thr Val Ser Ser
            100                 105

<210> SEQ ID NO 14
<211> LENGTH: 8
<212> TYPE: PRT
<213> ORGANISM: Artificial Sequence
<220> FEATURE:
<223> OTHER INFORMATION: Produced from hybridoma cells

<400> SEQUENCE: 14

Gly Phe Ser Leu Thr Ser Tyr Gly
1               5

<210> SEQ ID NO 15
<211> LENGTH: 7
<212> TYPE: PRT
<213> ORGANISM: Artificial Sequence
<220> FEATURE:
<223> OTHER INFORMATION: Produced from hybridoma cells

<400> SEQUENCE: 15

Ile Trp Arg Gly Gly Asn Thr
1               5

<210> SEQ ID NO 16
<211> LENGTH: 16
<212> TYPE: PRT
<213> ORGANISM: Artificial Sequence
<220> FEATURE:
<223> OTHER INFORMATION: Produced from hybridoma cell line

<400> SEQUENCE: 16

Val Lys Lys Ala Tyr Tyr Tyr Gly Ser Asn Tyr Tyr Thr Met Asp Tyr
1               5                   10                  15

<210> SEQ ID NO 17
<211> LENGTH: 112
<212> TYPE: PRT
<213> ORGANISM: Artificial Sequence
<220> FEATURE:
<223> OTHER INFORMATION: Produced from hybridoma cell line

<400> SEQUENCE: 17

Asp Val Leu Met Thr Gln Thr Pro Leu Ser Leu Pro Val Ser Leu Gly
1               5                   10                  15
```

```
Asp Gln Ala Ser Ile Ser Cys Arg Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                85                  90                  95

Ser His Val Pro Phe Thr Phe Gly Ser Gly Thr Lys Leu Glu Ile Lys
                100                 105                 110

<210> SEQ ID NO 18
<211> LENGTH: 11
<212> TYPE: PRT
<213> ORGANISM: Artificial Sequence
<220> FEATURE:
<223> OTHER INFORMATION: Produced from hybridoma cell line

<400> SEQUENCE: 18

Gln Ser Ile Val His Ser Asn Gly Asn Thr Tyr
1               5                   10

<210> SEQ ID NO 19
<211> LENGTH: 3
<212> TYPE: PRT
<213> ORGANISM: Artificial Sequence
<220> FEATURE:
<223> OTHER INFORMATION: Produced from hybridoma cell line

<400> SEQUENCE: 19

Lys Val Ser
1

<210> SEQ ID NO 20
<211> LENGTH: 9
<212> TYPE: PRT
<213> ORGANISM: Artificial Sequence
<220> FEATURE:
<223> OTHER INFORMATION: Produced from hybridoma cell line

<400> SEQUENCE: 20

Phe Gln Gly Ser His Val Pro Phe Thr
1               5

<210> SEQ ID NO 21
<211> LENGTH: 91
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (2)..(2)
<223> OTHER INFORMATION: Xaa can be any naturally occurring amino acid

<400> SEQUENCE: 21

Lys Xaa Ser Gly Tyr Thr Phe Thr Glu Tyr Thr Met His Trp Val Lys
1               5                   10                  15

Gln Ser His Gly Lys Ser Leu Glu Trp Ile Gly Gly Ile Asn Arg Asn
                20                  25                  30
```

```
Asn Gly Gly Thr Tyr Tyr Asn Gln Lys Val Arg Gly Lys Ala Thr Leu
         35                  40                  45

Thr Val Asp Lys Ser Ser Ser Thr Ala Tyr Met Glu Leu Arg Ser Leu
 50                  55                  60

Thr Ser Glu Asp Ser Ala Val Tyr Tyr Cys Ala His Arg Phe Ala Tyr
 65                  70                  75                  80

Trp Gly Gln Gly Thr Leu Val Thr Val Ser Ala
             85                  90

<210> SEQ ID NO 22
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 22

Gly Tyr Thr Phe Thr Glu Tyr Thr
 1               5

<210> SEQ ID NO 23
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 23

Ile Asn Arg Asn Asn Gly Gly Thr
 1               5

<210> SEQ ID NO 24
<211> LENGTH: 6
<212> TYPE: PRT
<213> ORGANISM: Artificial Sequence
<220> FEATURE:
<223> OTHER INFORMATION: Produced from hybridoma cell line

<400> SEQUENCE: 24

Ala His Arg Phe Ala Tyr
 1               5

<210> SEQ ID NO 25
<211> LENGTH: 111
<212> TYPE: PRT
<213> ORGANISM: Artificial Sequence
<220> FEATURE:
<223> OTHER INFORMATION: Produced from hybridoma cell line

<400> SEQUENCE: 25

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
             20                  25                  30

Gly Asn Ser Phe Met His Trp Tyr Gln Gln Lys Pro Gly Gln Pro Pro
         35                  40                  45

Lys Leu Leu Ile Tyr Arg Ala Ser Asn Leu Glu Ser Gly Ile Pro Ala
 50                  55                  60

Arg Phe Ser Gly Ser Gly Ser Gly Thr Asp Phe Thr Leu Thr Ile Asn
 65                  70                  75                  80

Pro Val Glu Ala Asp Asp Val Ala Thr Tyr Tyr Cys Gln Gln Ser Asn
                 85                  90                  95
```

Glu Asp Pro Phe Thr Phe Gly Ser Gly Thr Lys Leu Glu Ile Lys
            100                 105                 110

<210> SEQ ID NO 26
<211> LENGTH: 10
<212> TYPE: PRT
<213> ORGANISM: Artificial Sequence
<220> FEATURE:
<223> OTHER INFORMATION: Produced from hybridoma cell line

<400> SEQUENCE: 26

Glu Ser Val Asp Ser Tyr Gly Asn Ser Phe
1               5                   10

<210> SEQ ID NO 27
<211> LENGTH: 3
<212> TYPE: PRT
<213> ORGANISM: Artificial Sequence
<220> FEATURE:
<223> OTHER INFORMATION: Produced from hybridoma cell line

<400> SEQUENCE: 27

Arg Ala Ser
1

<210> SEQ ID NO 28
<211> LENGTH: 9
<212> TYPE: PRT
<213> ORGANISM: Artificial Sequence
<220> FEATURE:
<223> OTHER INFORMATION: Produced from hybridoma cell line

<400> SEQUENCE: 28

Gln Gln Ser Asn Glu Asp Pro Phe Thr
1               5

<210> SEQ ID NO 29
<211> LENGTH: 113
<212> TYPE: PRT
<213> ORGANISM: Artificial Sequence
<220> FEATURE:
<223> OTHER INFORMATION: Produced from hybridoma cell line

<400> SEQUENCE: 29

Gly Gly Leu Val Gln Pro Gly Gly Ser Arg Lys Leu Ser Cys Ala Ala
1               5                   10                  15

Ser Gly Phe Thr Phe Ser Ser Phe Gly Met His Trp Val Arg Gln Ala
            20                  25                  30

Pro Glu Lys Gly Leu Glu Trp Val Ala Tyr Ile Ser Ser Gly Ser Ser
        35                  40                  45

Thr Ile Tyr Tyr Ala Asp Thr Val Lys Gly Arg Phe Thr Ile Ser Arg
    50                  55                  60

Asp Asn Pro Lys Asn Thr Leu Phe Leu Gln Met Thr Ser Leu Arg Ser
65                  70                  75                  80

Glu Asp Thr Ala Met Tyr Tyr Cys Ala Arg Arg Gly Val Arg Arg Pro
                85                  90                  95

Gly Glu Ala Met Asp Tyr Trp Gly Gln Gly Thr Ser Val Thr Val Ser
            100                 105                 110

Ser

<210> SEQ ID NO 30
<211> LENGTH: 8

```
<212> TYPE: PRT
<213> ORGANISM: Artificial Sequence
<220> FEATURE:
<223> OTHER INFORMATION: Produced from hybridoma cell line

<400> SEQUENCE: 30

Gly Phe Thr Phe Ser Ser Phe Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 31

Ile Ser Ser Gly Ser Ser Thr Ile
1               5

<210> SEQ ID NO 32
<211> LENGTH: 14
<212> TYPE: PRT
<213> ORGANISM: Artificial Sequence
<220> FEATURE:
<223> OTHER INFORMATION: Produced from hybridoma cell line

<400> SEQUENCE: 32

Ala Arg Arg Gly Val Arg Arg Pro Gly Glu Ala Met Asp Tyr
1               5                   10

<210> SEQ ID NO 33
<211> LENGTH: 110
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (100)..(100)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid

<400> SEQUENCE: 33

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
                20                  25                  30

Gly Tyr Ser Tyr Met His Trp Tyr Gln Gln Lys Pro Gly Gln Pro Pro
            35                  40                  45

Lys Leu Leu Ile Tyr Leu Ala Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Leu Thr Xaa Ser Glu Gly Gly Pro Ser Trp Ile Xaa Asn
            100                 105                 110

<210> SEQ ID NO 34
<211> LENGTH: 10
<212> TYPE: PRT
```

```
<213> ORGANISM: Artificial Sequence
<220> FEATURE:
<223> OTHER INFORMATION: Produced from hybridoma cell line

<400> SEQUENCE: 34

Lys Ser Val Ser Thr Ser Gly Tyr Ser Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Produced from hybridoma cell line

<400> SEQUENCE: 35

Leu Ala Ser
1

<210> SEQ ID NO 36
<211> LENGTH: 7
<212> TYPE: PRT
<213> ORGANISM: Artificial Sequence
<220> FEATURE:
<223> OTHER INFORMATION: Produced from hybridoma cell line

<400> SEQUENCE: 36

Gln His Ser Arg Glu Leu His
1               5

<210> SEQ ID NO 37
<211> LENGTH: 81
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (76)..(76)
<223> OTHER INFORMATION: Xaa can be any naturally occurring amino acid

<400> SEQUENCE: 37

Pro Gly Ala Ser Val Lys Ile Ser Cys Lys Thr Ser Gly Tyr Thr Phe
1               5                   10                  15

Thr Glu Tyr Thr Met His Trp Val Lys Gln Ser His Gly Lys Ser Leu
            20                  25                  30

Glu Trp Ile Gly Gly Ile Asn Arg Asn Asn Gly Gly Thr Tyr Tyr Asn
        35                  40                  45

Gln Lys Val Arg Gly Lys Ala Thr Leu Thr Val Asp Lys Ser Ser Ser
    50                  55                  60

Thr Ala Tyr Met Glu Leu Arg Ser Leu Thr Ser Xaa Gly Phe Cys Ser
65                  70                  75                  80

Leu

<210> SEQ ID NO 38
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 38

Gly Tyr Thr Phe Thr Glu Tyr Thr
1               5
```

```
<210> SEQ ID NO 39
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 39

Ile Asn Arg Asn Asn Gly Gly Thr
1               5

<210> SEQ ID NO 40

<400> SEQUENCE: 40

000

<210> SEQ ID NO 41
<211> LENGTH: 110
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (109)..(109)
<223> OTHER INFORMATION: Xaa can be any naturally occurring amino acid

<400> SEQUENCE: 41

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Xaa Asn
            100                 105                 110

<210> SEQ ID NO 42
<211> LENGTH: 10
<212> TYPE: PRT
<213> ORGANISM: Artificial Sequence
<220> FEATURE:
<223> OTHER INFORMATION: Produced from hybridoma cell line

<400> SEQUENCE: 42

Lys Ser Val Ser Thr Ser Gly Tyr Ser Tyr
1               5                   10

<210> SEQ ID NO 43
<211> LENGTH: 3
<212> TYPE: PRT
<213> ORGANISM: Artificial Sequence
<220> FEATURE:
<223> OTHER INFORMATION: Produced from hybridoma cell line
```

```
<400> SEQUENCE: 43

Leu Ala Ser
1

<210> SEQ ID NO 44
<211> LENGTH: 7
<212> TYPE: PRT
<213> ORGANISM: Artificial Sequence
<220> FEATURE:
<223> OTHER INFORMATION: Produced from hybridoma cell line

<400> SEQUENCE: 44

Gln His Ile Arg Glu Leu Thr
1               5

<210> SEQ ID NO 45
<211> LENGTH: 109
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (6)..(7)
<223> OTHER INFORMATION: Xaa can be any naturally occurring amino acid

<400> SEQUENCE: 45

Leu Val Gln Pro Gly Xaa Xaa Leu Lys Leu Ser Cys Lys Ser Asn Glu
1               5                   10                  15

Tyr Glu Phe Pro Ser His Asp Met Ser Trp Val Arg Thr Thr Pro Glu
            20                  25                  30

Lys Arg Leu Glu Leu Val Ala Ala Ile Asn Ser Asp Gly Gly Asn Thr
        35                  40                  45

Tyr Tyr Pro Asp Thr Met Glu Arg Arg Phe Ile Ile Ser Arg Asp Asn
    50                  55                  60

Thr Lys Lys Thr Leu Tyr Leu Gln Met Ser Ser Leu Arg Ser Glu Asp
65                  70                  75                  80

Thr Ala Leu Tyr Tyr Cys Ala Arg His Ser Met Val Thr Pro Asp Leu
                85                  90                  95

Leu Thr Gly Ala Lys Gly Leu Trp Ser Leu Ser Leu Gln
            100                 105

<210> SEQ ID NO 46
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 46

Glu Tyr Glu Phe Pro Ser His Asp
1               5

<210> SEQ ID NO 47
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 47

Ile Asn Ser Asp Gly Gly Asn Thr
1               5
```

```
<210> SEQ ID NO 48
<211> LENGTH: 11
<212> TYPE: PRT
<213> ORGANISM: Artificial Sequence
<220> FEATURE:
<223> OTHER INFORMATION: Produced from hybridoma cell line

<400> SEQUENCE: 48

Ala Arg His Ser Met Val Thr Pro Asp Leu Leu
1               5                   10

<210> SEQ ID NO 49
<211> LENGTH: 110
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (109)..(109)
<223> OTHER INFORMATION: Xaa can be any naturally occurring amino acid

<400> SEQUENCE: 49

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys Xaa Asn
            100                 105                 110

<210> SEQ ID NO 50
<211> LENGTH: 10
<212> TYPE: PRT
<213> ORGANISM: Artificial Sequence
<220> FEATURE:
<223> OTHER INFORMATION: Produced from hybridoma cell line

<400> SEQUENCE: 50

Lys Ser Val Ser Thr Ser Gly Tyr Ser Tyr
1               5                   10

<210> SEQ ID NO 51
<211> LENGTH: 3
<212> TYPE: PRT
<213> ORGANISM: Artificial Sequence
<220> FEATURE:
<223> OTHER INFORMATION: Produced from hybridoma cell line

<400> SEQUENCE: 51

Leu Ala Ser
1

<210> SEQ ID NO 52
<211> LENGTH: 8
<212> TYPE: PRT
```

<213> ORGANISM: Artificial Sequence
<220> FEATURE:
<223> OTHER INFORMATION: Produced from hybridoma cell line

<400> SEQUENCE: 52

Gln His Ile Arg Glu Leu Thr Arg
1               5

<210> SEQ ID NO 53
<211> LENGTH: 86
<212> TYPE: PRT
<213> ORGANISM: Artificial Sequence
<220> FEATURE:
<223> OTHER INFORMATION: Produced from hybridoma cell line

<400> SEQUENCE: 53

Pro Gly Ala Ser Val Lys Ile Ser Cys Lys Gly Ser Gly Tyr Thr Phe
1               5                   10                  15

Thr Asp Tyr Thr Met His Trp Val Lys Gln Ser His Ala Lys Ser Leu
                20                  25                  30

Glu Trp Ile Gly Val Ile Ser Ser Tyr Ser Gly Asn Thr Asn Tyr Asn
            35                  40                  45

Gln Lys Phe Glu Gly Lys Ala Thr Met Thr Val Asp Lys Ser Ser Ser
        50                  55                  60

Thr Ala Tyr Met Glu Leu Ala Arg Leu Thr Ser Glu Asp Ser Ala Ile
65                  70                  75                  80

Tyr Tyr Cys Ala Arg His
                85

<210> SEQ ID NO 54
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 54

Gly Tyr Thr Phe Thr Asp Tyr Thr
1               5

<210> SEQ ID NO 55
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 55

Ile Ser Ser Tyr Ser Gly Asn Thr
1               5

<210> SEQ ID NO 56

<400> SEQUENCE: 56

000

<210> SEQ ID NO 57
<211> LENGTH: 112
<212> TYPE: PRT
<213> ORGANISM: Artificial Sequence
<220> FEATURE:
<223> OTHER INFORMATION: Produced from hybridoma cell line

<400> SEQUENCE: 57

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Phe Thr Phe Gly Ser Gly Thr Lys Leu Glu Ile Lys
            100                 105                 110

<210> SEQ ID NO 58
<211> LENGTH: 11
<212> TYPE: PRT
<213> ORGANISM: Artificial Sequence
<220> FEATURE:
<223> OTHER INFORMATION: Produced from hybridoma cell line

<400> SEQUENCE: 58

Gln Ser Leu Leu Asp Ser Asp Gly Lys Thr Tyr
1               5                   10

<210> SEQ ID NO 59
<211> LENGTH: 3
<212> TYPE: PRT
<213> ORGANISM: Artificial Sequence
<220> FEATURE:
<223> OTHER INFORMATION: Produced from hybridoma cell line

<400> SEQUENCE: 59

Leu Val Ser
1

<210> SEQ ID NO 60
<211> LENGTH: 9
<212> TYPE: PRT
<213> ORGANISM: Artificial Sequence
<220> FEATURE:
<223> OTHER INFORMATION: Produced from hybridoma cell line

<400> SEQUENCE: 60

Trp Gln Gly Thr His Phe Pro Phe Thr
1               5

<210> SEQ ID NO 61
<211> LENGTH: 108
<212> TYPE: PRT
<213> ORGANISM: Artificial Sequence
<220> FEATURE:
<223> OTHER INFORMATION: Produced from hybridoma cell line

<400> SEQUENCE: 61

Leu Val Lys Pro Gly Gly Ser Leu Lys Leu Ser Cys Ala Ala Ser Gly
1               5                   10                  15

Phe Thr Phe Ser Ser Tyr Ala Met Ser Trp Val Arg Gln Thr Pro Glu
            20                  25                  30

```
Lys Arg Leu Glu Trp Val Ala Ser Ile Ser Ser Gly Gly Ser Thr Tyr
             35                  40                  45

Tyr Pro Asp Ser Val Lys Gly Arg Phe Thr Ile Ser Arg Asp Asn Ala
 50                  55                  60

Arg Asn Ile Leu Tyr Leu Gln Met Ser Ser Leu Arg Ser Glu Asp Thr
 65                  70                  75                  80

Ala Met Tyr Tyr Cys Ala Arg Leu Gly Asp Gly Tyr Tyr Pro Phe Ala
                 85                  90                  95

Tyr Trp Gly Gln Gly Thr Leu Val Thr Val Ser Ala
            100                 105
```

```
<210> SEQ ID NO 62
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 62

Gly Phe Thr Phe Ser Ser Tyr Ala
1               5
```

```
<210> SEQ ID NO 63
<211> LENGTH: 7
<212> TYPE: PRT
<213> ORGANISM: Artificial Sequence
<220> FEATURE:
<223> OTHER INFORMATION: Produced from hybridoma cell line

<400> SEQUENCE: 63

Ile Ser Ser Gly Gly Ser Thr
1               5
```

```
<210> SEQ ID NO 64
<211> LENGTH: 12
<212> TYPE: PRT
<213> ORGANISM: Artificial Sequence
<220> FEATURE:
<223> OTHER INFORMATION: Produced from hybridoma cell line

<400> SEQUENCE: 64

Ala Arg Leu Gly Asp Gly Tyr Tyr Pro Phe Ala Tyr
1               5                   10
```

```
<210> SEQ ID NO 65

<400> SEQUENCE: 65

000
```

```
<210> SEQ ID NO 66

<400> SEQUENCE: 66

000
```

```
<210> SEQ ID NO 67
<211> LENGTH: 6
<212> TYPE: PRT
<213> ORGANISM: Homo sapiens

<400> SEQUENCE: 67

Ala Ala Ala Ala Ala Ala
1               5
```

```
<210> SEQ ID NO 68
<211> LENGTH: 8
<212> TYPE: PRT
<213> ORGANISM: Homo sapiens

<400> SEQUENCE: 68

Ala Ala Ala Ala Ala Ala Ala Ala
1               5

<210> SEQ ID NO 69
<211> LENGTH: 95
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (3)..(3)
<223> OTHER INFORMATION: Xaa can be any naturally occurring amino acid

<400> SEQUENCE: 69

Lys Gly Xaa Gly Tyr Thr Phe Thr Asp Tyr Thr Met His Trp Val Lys
1               5                   10                  15

Gln Ser His Ala Lys Ser Leu Glu Trp Ile Gly Val Ile Ser Ser Tyr
            20                  25                  30

Ser Gly Asn Thr Asn Tyr Asn Gln Lys Phe Glu Gly Lys Ala Thr Met
        35                  40                  45

Thr Val Asp Lys Ser Ser Ser Thr Ala Tyr Met Glu Leu Ala Arg Leu
    50                  55                  60

Thr Ser Glu Asp Ser Ala Ile Tyr Tyr Cys Ala Arg His Tyr Gly Tyr
65                  70                  75                  80

Asp Val Thr Phe Trp Gly Gln Gly Thr Leu Val Thr Val Ser Ala
                85                  90                  95

<210> SEQ ID NO 70
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 70

Gly Tyr Thr Phe Thr Asp Tyr Thr
1               5

<210> SEQ ID NO 71
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 71

Ile Ser Ser Tyr Ser Gly Asn Thr
1               5

<210> SEQ ID NO 72
<211> LENGTH: 10
<212> TYPE: PRT
<213> ORGANISM: Artificial Sequence
<220> FEATURE:
<223> OTHER INFORMATION: Produced from hybridoma cell line
```

<400> SEQUENCE: 72

Ala Arg His Tyr Gly Tyr Asp Val Thr Phe
1               5                   10

<210> SEQ ID NO 73
<211> LENGTH: 107
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid

<400> SEQUENCE: 73

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Xaa Ala Ala Thr Tyr Tyr Cys Gln His Ile Arg
                85                  90                  95

Xaa Ala Tyr Thr Phe Gly Gly Gly Thr Lys Leu
            100                 105

<210> SEQ ID NO 74
<211> LENGTH: 10
<212> TYPE: PRT
<213> ORGANISM: Artificial Sequence
<220> FEATURE:
<223> OTHER INFORMATION: Produced from hybridoma cell line

<400> SEQUENCE: 74

Lys Ser Val Ser Thr Ser Gly Tyr Ser Tyr
1               5                   10

<210> SEQ ID NO 75
<211> LENGTH: 3
<212> TYPE: PRT
<213> ORGANISM: Artificial Sequence
<220> FEATURE:
<223> OTHER INFORMATION: Produced from hybridoma cell line

<400> SEQUENCE: 75

Leu Ala Ser
1

<210> SEQ ID NO 76
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 76

Gln His Ile Arg Glu Leu Thr Arg
1               5

<210> SEQ ID NO 77
<211> LENGTH: 106
<212> TYPE: PRT
<213> ORGANISM: Artificial Sequence
<220> FEATURE:
<223> OTHER INFORMATION: Produced from hybridoma cell line

<400> SEQUENCE: 77

Leu Val Gln Pro Gly Gly Ser Arg Lys Leu Ser Cys Ala Ala Ser Gly
1               5                   10                  15

Phe Thr Phe Ser Asn Phe Gly Met His Trp Val Arg Gln Ala Pro Glu
            20                  25                  30

Lys Gly Leu Glu Trp Val Ala Tyr Ile Ser Ser Gly Ser Asn Thr Ile
        35                  40                  45

Tyr Tyr Ala Asp Thr Val Lys Gly Arg Phe Thr Ile Ser Arg Asp Asn
50                  55                  60

Gly Lys Asn Thr Leu Phe Leu Gln Met Thr Ser Leu Arg Ser Glu Asp
65                  70                  75                  80

Thr Ala Ile Tyr Tyr Cys Ala Ser Tyr Gly Asn Tyr Ala Ala Tyr Trp
                85                  90                  95

Gly Gln Gly Thr Leu Val Thr Val Ser Ala
            100                 105

<210> SEQ ID NO 78
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 78

Gly Phe Thr Phe Ser Asn Phe Gly
1               5

<210> SEQ ID NO 79
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 79

Ile Ser Ser Gly Ser Asn Thr Ile
1               5

<210> SEQ ID NO 80
<211> LENGTH: 9
<212> TYPE: PRT
<213> ORGANISM: Artificial Sequence
<220> FEATURE:
<223> OTHER INFORMATION: Produced from hybridoma cell line

<400> SEQUENCE: 80

Ala Ser Tyr Gly Asn Tyr Ala Ala Tyr
1               5

<210> SEQ ID NO 81
<211> LENGTH: 107
<212> TYPE: PRT

```
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (97)..(97)
<223> OTHER INFORMATION: Xaa can be any naturally occurring amino acid

<400> SEQUENCE: 81

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Xaa Ala Ala Thr Tyr Tyr Cys Gln His Ile Arg
                85                  90                  95

Xaa Ala Tyr Thr Phe Gly Gly Gly Thr Lys Leu
            100                 105

<210> SEQ ID NO 82
<211> LENGTH: 10
<212> TYPE: PRT
<213> ORGANISM: Artificial Sequence
<220> FEATURE:
<223> OTHER INFORMATION: Produced from hybridoma cell line

<400> SEQUENCE: 82

Lys Ser Val Ser Thr Ser Gly Tyr Ser Tyr
1               5                   10

<210> SEQ ID NO 83
<211> LENGTH: 3
<212> TYPE: PRT
<213> ORGANISM: Artificial Sequence
<220> FEATURE:
<223> OTHER INFORMATION: Produced from hybridoma cell line

<400> SEQUENCE: 83

Leu Ala Ser
1

<210> SEQ ID NO 84
<211> LENGTH: 8
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (5)..(5)
<223> OTHER INFORMATION: Xaa can be any naturally occurring amino acid

<400> SEQUENCE: 84

Gln His Ile Arg Xaa Ala Tyr Thr
1               5
```

<210> SEQ ID NO 85
<211> LENGTH: 95
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (57)..(57)
<223> OTHER INFORMATION: Xaa can be any naturally occurring amino acid

<400> SEQUENCE: 85

Leu Ser Ile Thr Cys Thr Val Ser Gly Phe Ser Leu Thr Asp Tyr Gly
1               5                   10                  15

Val Ser Trp Ile Arg Gln Ser Pro Gly Lys Gly Leu Glu Trp Leu Gly
            20                  25                  30

Ile Ile Trp Gly Gly Gly Ser Thr Tyr Tyr Asn Ser Val Leu Lys Ser
        35                  40                  45

Arg Leu Ser Ile Asn Lys Asp Asn Xaa Lys Ser Gln Val Phe Leu Lys
    50                  55                  60

Met Asn Ser Leu Gln Thr Asp Asp Thr Ala Met Tyr Tyr Cys Ala Lys
65                  70                  75                  80

His Arg Gly Asp Trp Gly Gln Gly Thr Leu Val Thr Val Ser Ala
                85                  90                  95

<210> SEQ ID NO 86
<211> LENGTH: 8
<212> TYPE: PRT
<213> ORGANISM: Artificial Sequence
<220> FEATURE:
<223> OTHER INFORMATION: Produced from hybridoma cell line

<400> SEQUENCE: 86

Gly Phe Ser Leu Thr Asp Tyr Gly
1               5

<210> SEQ ID NO 87
<211> LENGTH: 7
<212> TYPE: PRT
<213> ORGANISM: Artificial Sequence
<220> FEATURE:
<223> OTHER INFORMATION: Produced from hybridoma cell line

<400> SEQUENCE: 87

Ile Trp Gly Gly Gly Ser Thr
1               5

<210> SEQ ID NO 88
<211> LENGTH: 6
<212> TYPE: PRT
<213> ORGANISM: Artificial Sequence
<220> FEATURE:
<223> OTHER INFORMATION: Produced from hybridoma cell line

<400> SEQUENCE: 88

Ala Lys His Arg Gly Asp
1               5

<210> SEQ ID NO 89
<211> LENGTH: 108
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature

```
<222> LOCATION: (86)..(86)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid

<400> SEQUENCE: 89

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Xaa Ala Ala Xaa Tyr Tyr Cys Gln His Ile Arg
                85                  90                  95

Glu Leu Thr Arg Ser Glu Gly Gly Pro Ser Trp Lys
            100                 105

<210> SEQ ID NO 90
<211> LENGTH: 10
<212> TYPE: PRT
<213> ORGANISM: Artificial Sequence
<220> FEATURE:
<223> OTHER INFORMATION: Produced from hybridoma cell line

<400> SEQUENCE: 90

Lys Ser Val Ser Thr Ser Gly Tyr Ser Tyr
1               5                   10

<210> SEQ ID NO 91
<211> LENGTH: 3
<212> TYPE: PRT
<213> ORGANISM: Artificial Sequence
<220> FEATURE:
<223> OTHER INFORMATION: Produced from hybridoma cell line

<400> SEQUENCE: 91

Leu Ala Ser
1

<210> SEQ ID NO 92
<211> LENGTH: 7
<212> TYPE: PRT
<213> ORGANISM: Artificial Sequence
<220> FEATURE:
<223> OTHER INFORMATION: Produced from hybridoma cell line

<400> SEQUENCE: 92

Ser Thr Leu Gly Ser Leu His
1               5

<210> SEQ ID NO 93

<400> SEQUENCE: 93

000

<210> SEQ ID NO 94
```

```
<400> SEQUENCE: 94

000

<210> SEQ ID NO 95

<400> SEQUENCE: 95

000

<210> SEQ ID NO 96

<400> SEQUENCE: 96

000

<210> SEQ ID NO 97
<211> LENGTH: 110
<212> TYPE: PRT
<213> ORGANISM: Artificial Sequence
<220> FEATURE:
<223> OTHER INFORMATION: Produced from hybridoma cell line
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (109)..(109)
<223> OTHER INFORMATION: Xaa can be any naturally occurring amino acid

<400> SEQUENCE: 97

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Xaa Ala Ala Thr Tyr Tyr Cys Gln His Ile Arg
                85                  90                  95

Glu Leu Thr Arg Ser Glu Gly Gly Pro Ser Trp Lys Xaa Asn
            100                 105                 110

<210> SEQ ID NO 98
<211> LENGTH: 10
<212> TYPE: PRT
<213> ORGANISM: Artificial Sequence
<220> FEATURE:
<223> OTHER INFORMATION: Produced from hybridoma cell line

<400> SEQUENCE: 98

Lys Ser Val Ser Thr Ser Gly Tyr Ser Tyr
1               5                   10

<210> SEQ ID NO 99
<211> LENGTH: 3
<212> TYPE: PRT
<213> ORGANISM: Artificial Sequence
<220> FEATURE:
<223> OTHER INFORMATION: Produced from hybridoma cell line
```

```
<400> SEQUENCE: 99

Leu Ala Ser
1

<210> SEQ ID NO 100
<211> LENGTH: 7
<212> TYPE: PRT
<213> ORGANISM: Artificial Sequence
<220> FEATURE:
<223> OTHER INFORMATION: Produced from hybridoma cell line

<400> SEQUENCE: 100

Gln His Ile Arg Glu Leu Thr
1               5

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105
<211> LENGTH: 108
<212> TYPE: PRT
<213> ORGANISM: Artificial Sequence
<220> FEATURE:
<223> OTHER INFORMATION: Produced from hybridoma cell line

<400> SEQUENCE: 105

Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Tyr Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105
```

```
<210> SEQ ID NO 106
<211> LENGTH: 10
<212> TYPE: PRT
<213> ORGANISM: Artificial Sequence
<220> FEATURE:
<223> OTHER INFORMATION: Produced from hybridoma cell line

<400> SEQUENCE: 106

Lys Ser Val Ser Thr Ser Gly Tyr Ser Tyr
1               5                   10

<210> SEQ ID NO 107
<211> LENGTH: 3
<212> TYPE: PRT
<213> ORGANISM: Artificial Sequence
<220> FEATURE:
<223> OTHER INFORMATION: Produced from hybridoma cell line

<400> SEQUENCE: 107

Leu Ala Ser
1

<210> SEQ ID NO 108
<211> LENGTH: 9
<212> TYPE: PRT
<213> ORGANISM: Artificial Sequence
<220> FEATURE:
<223> OTHER INFORMATION: Produced from hybridoma cell line

<400> SEQUENCE: 108

Cys Gln His Ile Arg Glu Leu Thr Arg
1               5
```